(12) United States Patent
Wong

(10) Patent No.: US 11,987,619 B2
(45) Date of Patent: *May 21, 2024

(54) SINGLE-CHAIN CHIMERIC POLYPEPTIDES AND USES THEREOF

(71) Applicant: HCW Biologics, Inc., Miramar, FL (US)

(72) Inventor: Hing Wong, Miramar, FL (US)

(73) Assignee: HCW Biologics, Inc., Miramar, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/870,373

(22) Filed: Jul. 21, 2022

(65) Prior Publication Data

US 2023/0039157 A1 Feb. 9, 2023

Related U.S. Application Data

(62) Division of application No. 16/556,040, filed on Aug. 29, 2019, now Pat. No. 11,401,324.

(60) Provisional application No. 62/881,039, filed on Jul. 31, 2019, provisional application No. 62/817,241, filed on Mar. 12, 2019, provisional application No. 62/817,244, filed on Mar. 12, 2019, provisional application No. 62/816,683, filed on Mar. 11, 2019, provisional application No. 62/749,506, filed on Oct. 23, 2018, provisional application No. 62/746,832, filed on Oct. 17, 2018, provisional application No. 62/725,038, filed on Aug. 30, 2018.

(51) Int. Cl.
*C07K 16/18* (2006.01)
*A61P 3/10* (2006.01)
*C07K 16/28* (2006.01)
*C12N 5/0783* (2010.01)
*A61K 39/00* (2006.01)

(52) U.S. Cl.
CPC ............... *C07K 16/18* (2013.01); *A61P 3/10* (2018.01); *C07K 16/2809* (2013.01); *C07K 16/2818* (2013.01); *C07K 16/2866* (2013.01); *C12N 5/0637* (2013.01); *A61K 39/00* (2013.01); *C07K 2317/24* (2013.01); *C07K 2317/56* (2013.01); *C07K 2317/622* (2013.01); *C07K 2319/00* (2013.01); *C12N 2501/998* (2013.01)

(58) Field of Classification Search
None
See application file for complete search history.

(56) References Cited

U.S. PATENT DOCUMENTS

| 6,117,980 | A | 9/2000 | Gonzalez et al. |
|---|---|---|---|
| 7,452,537 | B2 | 11/2008 | Bauer et al. |
| 7,482,436 | B2 | 1/2009 | Sugimura et al. |
| 7,488,802 | B2 | 2/2009 | Collins et al. |
| 7,521,051 | B2 | 4/2009 | Collins et al. |
| 7,612,181 | B2 | 11/2009 | Wu et al. |
| 7,691,380 | B2 * | 4/2010 | Thorpe .............. C07K 16/3015 424/155.1 |
| 7,723,482 | B2 | 5/2010 | Soulillou et al. |
| 7,968,094 | B2 | 6/2011 | Jiao et al. |
| 8,007,795 | B2 | 8/2011 | Jiao et al. |
| 8,133,485 | B2 | 3/2012 | Levi-Schaffer et al. |
| 8,217,149 | B2 | 7/2012 | Irving et al. |
| 8,258,268 | B2 | 9/2012 | Wu et al. |
| 8,475,792 | B2 * | 7/2013 | Dall'Acqua ............ A61P 37/00 530/387.9 |
| 8,552,156 | B2 | 10/2013 | Takayanagi et al. |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |
| 8,741,604 | B2 | 6/2014 | Campbell et al. |
| 8,753,640 | B2 | 6/2014 | Wu et al. |
| 8,759,494 | B2 | 6/2014 | Bachmann et al. |
| 8,822,645 | B2 | 9/2014 | Ghayur et al. |
| 9,035,026 | B2 | 5/2015 | Hoffmann et al. |
| 9,067,997 | B2 | 6/2015 | Romagne et al. |
| 9,085,623 | B2 | 7/2015 | Rother et al. |
| 9,090,684 | B2 | 7/2015 | Borras et al. |
| 9,226,962 | B2 | 1/2016 | Le Gall et al. |
| 9,238,084 | B2 | 1/2016 | Liu et al. |
| 9,273,136 | B2 | 3/2016 | Rader et al. |
| 9,371,395 | B2 | 6/2016 | Takahashi et al. |
| 9,441,034 | B2 | 9/2016 | Sivakumar et al. |
| 9,505,843 | B2 | 11/2016 | Kim et al. |
| 9,617,345 | B2 | 4/2017 | Berne et al. |

(Continued)

FOREIGN PATENT DOCUMENTS

| CN | 102153653 | 8/2011 |
|---|---|---|
| EP | 1245676 | 10/2002 |

(Continued)

OTHER PUBLICATIONS

Teng, Shaolei et al. International journal of computational biology and drug design vol. 3,4 (2010): 334-49 (Year: 2010).*
Stryer, Biochemistry 4th, WH Freeman, New York. 1995 (Year: 1995).*
Zhou, Pengcheng. "Emerging mechanisms and applications of low-dose IL-2 therapy in autoimmunity." Cytokine & Growth Factor Reviews (2022) (Year: 2022).*
Ross, Sarah H, and Doreen A Cantrell. "Signaling and Function of Interleukin-2 in T Lymphocytes." Annual review of immunology vol. 36 (2018): 411-433. doi:10.1146/annurev-immunol-042617-053352 (Year: 2018).*
Tam, James P., Jiaxi Xu, and Khee Dong Eom. "Methods and strategies of peptide ligation." Peptide Science: Original Research on Biomolecules 60.3 (2001): 194-205. (Year: 2001).*

(Continued)

*Primary Examiner* — Michael Szperka
*Assistant Examiner* — Lia E Taylor
(74) *Attorney, Agent, or Firm* — Fish & Richardson P.C.

(57) ABSTRACT

Provided herein are single-chain chimeric polypeptides that include: (i) a first target-binding domain; (ii) a soluble tissue factor domain; and (iii) a second target-binding domain. Also provided here are methods of using these single-chain chimeric polypeptides and nucleic acids encoding these single-chain chimeric polypeptides.

27 Claims, 23 Drawing Sheets

Specification includes a Sequence Listing.

(56) References Cited

U.S. PATENT DOCUMENTS

| | | | |
|---|---|---|---|
| 9,701,758 B2 | 7/2017 | Cooper et al. | |
| 11,672,826 B2 | 6/2023 | Wong | |
| 11,730,762 B2 | 8/2023 | Wong | |
| 11,738,052 B2 | 8/2023 | Wong | |
| 2001/0044427 A1 | 11/2001 | Mazel et al. | |
| 2003/0124678 A1 | 7/2003 | Epstein et al. | |
| 2003/0219441 A1* | 11/2003 | Thorpe | A61K 47/6851 |
| | | | 424/155.1 |
| 2005/0014224 A1 | 1/2005 | Collins et al. | |
| 2006/0159655 A1 | 7/2006 | Collins et al. | |
| 2007/0160579 A1 | 7/2007 | Schmitz et al. | |
| 2009/0148942 A1 | 6/2009 | McDonagh et al. | |
| 2012/0171197 A1 | 7/2012 | Eriksson et al. | |
| 2012/0264920 A1 | 10/2012 | Wang et al. | |
| 2013/0274446 A1 | 10/2013 | Kumagai et al. | |
| 2014/0242077 A1 | 8/2014 | Choi | |
| 2015/0218274 A1 | 8/2015 | Sabatos-Peyton et al. | |
| 2015/0259429 A1 | 9/2015 | Benaroch et al. | |
| 2016/0175397 A1 | 6/2016 | Umana et al. | |
| 2016/0340413 A1 | 11/2016 | Duerner et al. | |
| 2016/0367664 A1 | 12/2016 | Wang et al. | |
| 2017/0051063 A1 | 2/2017 | Baum et al. | |
| 2017/0198042 A1 | 7/2017 | Williams et al. | |
| 2017/0283499 A1 | 10/2017 | Delhem et al. | |
| 2018/0200366 A1 | 7/2018 | Wong | |
| 2019/0078082 A1* | 3/2019 | Amorese | C12N 15/66 |
| 2019/0092846 A1 | 3/2019 | Ibebunjo et al. | |
| 2019/0177406 A1 | 6/2019 | Ledbetter et al. | |
| 2019/0315850 A1 | 10/2019 | Bedinger et al. | |
| 2020/0071374 A1 | 3/2020 | Wong | |
| 2020/0123607 A1 | 4/2020 | Serrano Marugan et al. | |
| 2020/0392221 A1 | 12/2020 | Van Snick et al. | |
| 2020/0399358 A1 | 12/2020 | Shapiro et al. | |
| 2021/0060064 A1 | 3/2021 | Wong | |
| 2021/0061897 A1 | 3/2021 | Ledbetter et al. | |
| 2021/0070825 A1 | 3/2021 | Wong | |
| 2021/0070826 A1 | 3/2021 | Wong | |
| 2021/0100840 A1 | 4/2021 | Wong et al. | |
| 2021/0137981 A1 | 5/2021 | Wong | |
| 2021/0268022 A1 | 9/2021 | Wong et al. | |
| 2021/0277054 A1 | 9/2021 | Wong et al. | |
| 2021/0338724 A1 | 11/2021 | Wong | |
| 2021/0355204 A1 | 11/2021 | Bedinger et al. | |
| 2021/0403545 A1 | 12/2021 | Van Snick et al. | |
| 2022/0073578 A1 | 3/2022 | Wong et al. | |
| 2023/0023389 A1 | 1/2023 | Wong | |
| 2023/0128292 A1 | 4/2023 | Wong | |
| 2023/0174666 A1 | 6/2023 | Wong et al. | |
| 2023/0272027 A1 | 8/2023 | Wong | |
| 2023/0372399 A1 | 11/2023 | Wong | |
| 2023/0372444 A1 | 11/2023 | Wong et al. | |
| 2023/0381238 A1 | 11/2023 | Wong | |

FOREIGN PATENT DOCUMENTS

| | | |
|---|---|---|
| EP | 2537933 | 12/2012 |
| EP | 3029069 | 6/2016 |
| EP | 3348276 | 7/2018 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO 1996/001653 | 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/047299 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Chandrudu S, Simerska P, Toth I. Chemical methods for peptide and protein production. Molecules. 2013;18(4):4373-4388. Published Apr. 12, 2013. doi: 10.3390/molecules18044373 (Year: 2013).*

PCT International Preliminary Report on Patentability in International Appln. No. PCT/US2021/017620, dated Aug. 25, 2022, 12 pages.

PCT International Preliminary Report on Patentability in International Appln. No. PCT/US2021/017621, dated Aug. 25, 2022, 8 pages.

PCT International Preliminary Report on Patentability in International Appln. No. PCT/US2021/017714, dated Aug. 25, 2022, 12 pages.

Li et al., "Transforming Growth Factor-β Regulation of Immune Responses," Annu. Rev. Immunol., 2006, 24:99-146.

McCarron et al., "TGF-β prevents T follicular helper cell accumulation and B cell autoreactivity," J Clin Invest., 2014, 124(10):4375-4386.

Voelker et al., "Anti-TGF-β1 Antibody Therapy in Patients with Diabetic Nephropathy," J Am Soc Nephrol., 2017, 28:953-962.

Wallace et al., "B lymphocytes confer immune tolerance via cell surface GARP-TGF-β complex," JCI Insight., 2018, 3(7):e99863, 19 pages.

Abbott et al., "Genomic organization, exact localization, and tissue expression of the human CD26 (dipeptidyl peptidase IV) gene," Immunogentics, Sep. 1994, 40(5):331-338.

Abdul-Aziz et al., "Acute myeloid leukemia induces protumoral p16INK4a-driven senescence in the bone marrow microenvironment," Blood, Jan. 31, 2019, 133(5):446-456.

Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.

Ait-Oufella el al., "Natural regulatory T cells control the development of atherosclerosis in mice," Nature Medicine, Feb. 5, 2006, 12:178-180.

Akbari, et al., "Design, expression and evaluation of a novel humanized single chain antibody against epidermal growth factor receptor (EGFR)," Protein Expr. Purif., 2016, 127:8-15.

Ali et al., "Regulatory T cells in skin," Immunology, Jul. 12, 2017, 152(3):372-381.

Angevin et al., "First-in-human phase 1 of YS110, a monoclonal antibody directed against CD26 in advanced CD26-expressing cancers," British Journal of Cancer, Mar. 14, 2017, 116(9):1126-1134.

(56) References Cited

OTHER PUBLICATIONS

Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.
Baker, et al., "Clearance of p16Ink4a-positive senescent cells delays ageing-associated disorders," Nature, 2011, 479(7372): 232-236.
Bennett et al., "Erratum: Killing the old: cell senescence in atherosclerosis," Nature Reviews Cardiology, Jan. 12, 2017, 14(3):132.
Bennett et al., "Killing the old: cell senescence in atherosclerosis," Nature Reviews Cardiology, Dec. 12, 2016, 14(1):8-9, 2 pages.
Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.
Bhat et al., "Astrocyte Senescence as a Component of Alzheimer's Disease," PLoS One, Sep. 12, 2012, 7(9):e45069, 10 pages.
Biran et al., "Senescent cells communicate via intercellular protein transfer," Genes & Development, Apr. 8, 2015, 29(8):791-802, 13 pages.
Borea et al., "Pharmacology of Adenosine Receptors: The State of the Art," Physiological Reviews, May 31, 2018, 98(3):1591-1625.
Borgerding et al., "B-lymphoma cells escape rituximab-triggered elimination by NK cells through increased HLA class I expression," Experimental Hematology, Mar. 1, 2010, 38(3):213-21.
Bork, "Powers and Pitfalls in Sequence Analysis: The 70% Hurdle," Genome Research, 2000, 10:398-400.
Bourgeois et al., "Regulation of cellular senescence via the FOXO4-p53 axis," FEBS Lett., 2018, 592(12): 2083-2097.
Bowie et al., "Deciphering the Message in Protein Sequences: Tolerance to Amino Acid Substitutions," Science, 1990, 247:1306-1310.
Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Broxmeyer et al., "Modulation of Hematopoietic Chemokine Effects In Vitro and In Vivo by DPP-4/CD26," Stem Cells and Development, Mar. 4, 2016, 25(8):575-585.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Buhling et al., "Functional role of CD26 on human B lymphocytes," Immunology Letters, Feb. 1995, 45(1-2):47-51.
Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.
Bussian et al., "Clearance of senescent glial cells prevents tau-dependent pathology and cognitive decline," Nature, Sep. 19, 2018, 562(7728):578-582, 21 pages.
Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.

Cao et al., "Expression and characterization of recombinant humanized anti-HER2 single-chain antibody in Pichia pastoris for targeted cancer therapy," Biotechnology Letters, Jul. 1, 2015, 37(7):1347-54.
Cao, "Self-regulation and cross-regulation of pattern-recognition receptor signaling in health and disease," Nature Reviews Immunology, Dec. 29, 2015, 16(1):35-50.
Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin, " Experimental Gerontology. Aug. 2017, 94:78-82.
Chalan et al., "Expression of Lectin-Like Transcript 1, the Ligand for CD161, in Rheumatoid Arthritis," PLoS ONE, 2015, 10(7):e0132436.
Chambers et al., "Can blocking inflammation enhance immunity during aging?," Journal of Allergy and Clinical Immunology, May 2020, 145(5):1323-1331.
Chance et al., "A simple and rapid assay of oxidative phosphorylation," Nature, Jun. 1955, 175(4469):1120-1121.
Chandrudu et al., "Chemical methods for peptide and protein production," Molecules, 2013, 18(4):4373-4388.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chen et al., "Sterile inflammation: sensing and reacting to damage," Nature Reviews Immunology, Nov. 19, 2010, 10(12):826-837.
Chichili et al., "Linkers in the structural biology of protein-protein interactions," Protein Science, Feb. 2013, 22(2):153-67.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chinta, et al., "Cellular senescence is induced by the environmental neurotoxin paraquat and bontributes to neuropathology linked to Parkinson's Disease," Cell Rep., 2018, 22(4): 930-940.
Chong et al., "CD36 initiates the secretory phenotype during the establishment of cellular senescence," EMBO Rep., May 18, 2018, 19(6):e45274, 13 pages.
Ciaglia, et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Clayton et al.,"Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.

(56) References Cited

OTHER PUBLICATIONS

Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl.):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Crews et al., "Molecular mechanisms of neurodegeneration in Alzheimer's disease," Human Molecular Genetics, Apr. 22, 2010, 19(R1):R12-R20, 9 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus," Arthritis Rheumatology, Mar. 2019, 71(3):431-440.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2): 187-98.
De Meyer et al., "Nanobody-based products as research and diagnostic tools," Trends in Biotechnology, May 1, 2014, 32(5):263-70.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healingthrough Secretion of PDGF-AA," Developmental Cell, Dec. 22, 2014, 31(6):722-733.
Deyev et al., "Design of multivalent complexes using the barnase• barstar module," Nature Biotechnology, Dec. 2003, 21(12):1486-92.
Di Ianni et al., "Tregs prevent GVHD and promote immune reconstitution inHLA-haploidentical transplantation," Blood, Apr. 7, 2011, 117(14):3921-3928.
Dietel et al., "Decreased numbers of regulatory T cells are associated with human atherosclerotic lesion vulnerability and inversely correlate with infiltrated mature dendritic cells," Atherosclerosis, Sep. 2013, 230:92-99.
DiGiammarino et al., "Design and generation of DVD-Ig™ molecules for dual-specific targeting," Therapeutic Proteins: Methods and Protocols, Methods in Molecular Biology, 2012, Humana Press, Totowa, NJ., 899:145-516.
Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dinarello, "Interleukin 1 and interleukin 18 as mediators of inflammation and the aging process," The American Journal of Clinical Nutrition, Feb. 1, 2006, 83(2):447S-455S.
Docagne et al., "A soluble transforming growth factor-β (TGF-β) type I receptor mimics TGF-β responses," Journal of Biological Chemistry, Dec. 7, 2001, 276(49):46243-50.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at theIFNGpromoter and CNS-1 is associated with the development of functional IFN-γ memory in human CD4+T lymphocytes," European Journal of Immunology, 2013, 43(3), 793-804.
Dou et al., "Cytoplasmic chromatin triggers inflammation in senescence and cancer," Nature, Oct. 4, 2017, 550(7676):402-406, 21 pages.
Drees, et al., "Soluble production of a biologically active single-chain antibody against murine PD-L1 in *Escherichia coli*," Protein Express. Purif., 2014, 94:60-66.
Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.
Edwardraja et al., "Redesigning of anti-c-met single chain Fv antibody for the cytoplasmic folding and its structural analysis," Biotechnology and Bioengineering, Jun. 15, 2010, 106(3):367-75.
Eisenhut et al., "Ion Channels in Inflammation," Pflugers Archive, Jan. 29, 2011, 461(4):401-421.
Elgueta et al., "Molecular mechanism and function of CD40/CD40L engagement in the immune system," Immunological Reviews, 2009, 229(1):152-172 doi.org/10.1111/j.1600-065X.2009.00782.x.
Elpek et al., "Mature natural killer cells with phenotypic and functional alterations accumulate upon sustained stimulation with IL-15/IL-15Rα complexes," Proceedings of the National Academy of Science, Dec. 14, 2010, 107: 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Farr, et al., "Targeting cellular senescence prevents age-related bone loss in mice," Nat. Med., 2017, 23(9): 1072-1079.
Fehniger et al., "A Phase 1 Trial of CNDO-109—Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.

(56) References Cited

OTHER PUBLICATIONS

Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gibbs et al., "Identification of the factor VIIa binding site on tissue factor by homologous loop swap and alanine scanning mutagenesis," Biochemistry, Nov. 1, 1994, 33(47):14003-10.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Greenspan et al., "Defining epitopes: Its not as easy as it seems," Nature Biotechnology, 1999, 17:936-937.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Guo et al., "Immunobiology of the IL-15-IL-15R complex as an antitumor and antiviral agent," 2017, Cytokine & Growth Factor Reviews, 38:10-21.
Gutschmidt et al., "A quantitative histochemical study of dipeptidyl peptidase IV (DPP IV)," Histochemistry, 1981, 73(2):285-304.
Haile et al., "Soluble CD80 Restores T Cell Activation and Overcomes Tumor Cell Programmed Death Ligand 1—Mediated Immune Suppression," J. Immunol., 2013, 191(5):2829-2836.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145 DOI:1O.1O16/S0022-1759(99)OO220-3.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Heng et al., Sophea, et al. "Multiple soluble TGF-β receptors in addition to soluble endoglin are elevated in preeclamptic serum and they synergistically inhibit TGF-β signalling." Placenta, 2017 57:320 (1 page).
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hombach et al., "Generation of the single chain antibody fragment conserves the idiotypic profile of the anti-CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Hudak et al., "Glycocalyx engineering reveals a Siglec-based mechanism for NK cell immunoevasion," Nature Chemical Biology, Jan. 2014, 10(1), 20 pages.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hughes, et al., "Transfer of a TCR gene derived from a patient with a marked antitumor response conveys highly active T-cell effector functions," Hum. Gene Ther., 2005, 16:457-72.
Hynes et al., "In vitro analysis of cell metabolism using a long-decay pH-sensitive lanthanide probe and extracellular acidification assay," Analytical biochemistry, Jul. 1, 2009, 390(1):21-28.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
Inzucchi et al., "New Drugs for the Treatment of Diabetes, Part II: Incretin-Based Therapy and Beyond," Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Jakob et al., "Structure reveals function of the dual variable domain immunoglobulin (DVD-Ig™) molecule," Mabs, May 1, 2013, Taylor & Francis, 5(3):358-63.
Janeway, "Approaching the Asymptote? Evolution and Revolution in Immunology," Cold Spring Harbor Symposia on Quantitative Biology, 1989, 54 Pt 1:1-13.
Jeannin et al., "Soluble CD86 Is a Costimulatory Moleculefor Human T Lymphocytes," Immunity, 2000, 13(3):303-312.

(56) References Cited

OTHER PUBLICATIONS

Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Kain et al., "The identification of the endogenous ligands of natural killer T cells reveals the presence of mammalian α-linked glycosylceramides," Immunity, Oct. 16, 2014, 41(4):543-54.
Karin et al., "Senescent cell turnover slows with age providing an explanation for the Gompertz law," Nature Communications, 10:5495, 2019, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 2018, 13 pages.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors," Nanomedicine, Jan. 2015, 10(1):161-74.
Kim et al., "Experimental malaria infection triggers early expansion of natural killer cells," Infection and Immunity, Dec. 1, 2008, 76(12):5873-82.
Kim et al., "Identification of senescent cell surface targetable protein DPP4," Genes & Development, 2017, 31(15):1529-1534.
Kim et al., "SCAMP4 enhances the senescent cell secretome," Genes & Development, 2018, 32(13-14):909-914.
Kirchhofer et al., "The tissue factor region that interacts with substrates factor IX and factor X," Biochemistry, Jun. 27, 2000, 39(25):7380-7.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klein et al., "Design and characterization of structured protein linkers with differing flexibilities," Protein Engineering, Design & Selection, 2014, 27(10):325-30.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingenberg et al., "Depletion of FOXP3+ regulatory T cells promotes hypercholesterolemia and atherosclerosis," The Journal of Clinical Investigation, Feb. 15, 2013, 123:1323-1334.
Kondo et al., "Requirements for the functional expression of OX40 ligand on human activated CD4+ and CD8+ T cells," Human Immunology, 2007, 68(7):563-571.
Kovaleva et al., "Shark variable new antigen receptor biologics—a novel technology platform for therapeutic drug development," Expert Opinion on Biological Therapy, Oct. 1, 2014, 14(10):1527-39.
Krah et al., "Single-domain antibodies for biomedical applications," Immunopharmacology and Immunotoxicology, Jan. 2, 2016, 38(1):21-8.
Kritsilis et al., "Ageing, Cellular Senescence and Neurodegenerative Disease," International Journal of Molecular Sciences, Sep. 27, 2018, 19(10):2937, 37 pages.
Krizhanovsky et al., "Senescence of activated stellate cells limits liver fibrosis," Cell, Aug. 22, 2008, 134(4):657-67.
Kumagai et al., "Monitoring of glutamate-induced excitotoxicity by mitochondrial oxygen consumption," Synapse, Jan. 2019, 73(1):e22067, 24 Pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5):1013-1022.
Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lau et al., "RNA-associated autoantigens activate B cells by combined B cell antigen receptor/Toll-like receptor 7 engagement," The Journal of Experimental Medicine, Oct. 31, 2005, 202(9):1171-1177.
Lazar et al., "Transforming Growth Factor Alpha: Mutation of Aspartic Acid 47 and Leucine 48 Results in Different Biological Activities," Mol. Cell. Biol., 1988, 8:1247-1252.
Li et al., "A Novel I L2-based Irrmunotherapeutic Protein Prevents the Development of Atherosclerosis in ApoE-/mice and LDLR-/-mice," Journal of Immunology, May 1, 2020, 204(1):Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1):134-148, 15 pages.
Li et al., "The cGAS-cGAMP-STING pathway connects DNA damage to inflammation, senescence, and cancer," Journal of Experimental Medicine, Apr. 5, 2018, 215(5):1287-1299.
Liton et al., "Cellular senescence in the glaucomatous outflow pathway," Experimental Gerontology, Aug.-Sep. 2005, 40(8-9):745-748.
Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.
Maeda et al., "Original Ligand for LTβR Is LIGHT: Insight into Evolution of the LT/LTβR System," J Immunol., 2018, 201(1):202-214.
Maganto-García et al., "Dynamic Changes in Regulatory T Cells Are Linked to Levels of Diet-Induced Hypercholesterolemia," Circulation, Jun. 20, 2011, 124:185-195.
Mandelboim et al., "Recognition of haemagglutinins on virus-infected cells by NKp46 activates lysis by human NK cells," Nature, Feb. 2001, 409(6823):1055.
Marguet et al., "Enhanced insulin secretion and improved glucose tolerance in mice lacking CD26," Proc. Natl. Acad. Sci. U.S.A., Jun. 6, 2000, 97(12):6874-6879.
Martelli et al., "HLA-haploidentical transplantation with regulatory and conventionalT-cell adoptive immunotherapy prevents acute leukemia relapse," Blood, Jul. 24, 2014, 124(4):638-644.
Masoumi et al., "The role of hypoxia as the driving force for non-erythroid production of globin chains in preeclamptic placentas," Placenta. 2017;57:320.
McHugh et al., "Senescence and aging: Causes, consequences, and therapeutic avenues," Journal of Cellular Biology, Nov. 7, 2017, 217(1):65-77.

(56) References Cited

OTHER PUBLICATIONS

Mehta et al., "Why do trials for Alzheimer's disease drugs keep failing? A discontinued drug perspective for 2010-2015," Expert Opinion on Investigational Drugs, May 2017, 26(6):735-739.
Menshawy et al., "CD58; leucocyte function adhesion-3 (LFA-3) could be used as a differentiating marker between immune and non-immune thyroid disorders," Comparative Clinical Pathology, 2018, 27(3), 721-727, doi.org/10.1007/s00580-018-2657-x.
Mentlein et al., "Dipeptidyl-peptidase IV (CD26)-role in the inactivation of regulatory peptides," Regulatory Peptides, Nov. 30, 1999, 85(1):9-24.
Miah et al., "KIR2DL4 differentially signals downstream functions in human NK cells through distinct structural modules," The Journal of Immunology, Mar. 1, 2008, 180(5):2922-32.
Michelet et al., "Metabolic reprogramming of natural killer cells in obesity limits antitumor responses," Nature Immunology, Nov. 12, 2018, 19(12):1330-1340.
Mikayama et al., "Molecular cloning and functional expression of a cDNA encoding glycosylation-inhibiting factor," Proc. Natl. Acad. Sci. USA, Nov. 1, 1993, 90(21):10056-10060.
Milanovic et al., "Senescence-associated reprogramming promotes cancer stemness," Nature, Dec. 20, 2017, 553(7686):96-100.
Milanovic et al., "The Senescence-Stemness Alliance—A Cancer-Hijacked Regeneration Principle," Trends in Cellular Biology, Dec. 2018, 28(12):1049-1061, 13 pages.
Miller et al., "Soluble CD70: a novel immunotherapeutic agent for experimental glioblastoma," J Neurosurg., 2010, 113(2):280-285.
Miller et al., "Successful adoptive transfer and in vivo expansion of human haploidentical NK cells in patients with cancer," Blood, Apr. 15, 2005, 105(8):3051-3057.
Minamino et al., "A crucial role for adipose tissue p53 in the regulation of insulin resistance," Nature Medicine, Aug. 30, 2009, 15(9):1082-1087.
Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.
Moesta et al., "Targeting CD39 in cancer," Nature Reviews Immunology, Jul. 29, 2020, 20(12):739-755, 17 pages.
Moiseeva et al., "Metformin inhibits the senescence-associated secretory phenotype by interfering with IKK/NF-κB activation," Aging Cell, Mar. 23, 2013, 12(3):489-498.
Molema et al., "The use of bispecific antibodies in tumor cell and tumor vasculature directed immunotherapy," Journal of Controlled Release, 2000, 64(1-3):229-239.
Molgora et al., "Regulatory role of IL-1R8 in immunity and disease," Frontiers in Immunology, Apr. 20, 2016, 7:149.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.
Mujić-Delić et al., "GPCR-targeting nanobodies: attractive research tools, diagnostics, and therapeutics," Trends in Pharmacological Sciences, May 1, 2014, 35(5):247-55.
Muller et al., "Antibody fusions with immunomodulatory proteins for cancer therapy," Pharmacology and Therapeutics, 2015, 154:57-66.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senescence during Mammalian Embryonic Development," Cell, Nov. 21, 2013, 155(5):1104-1118.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Muyldermans et al., "Recognition of antigens by single-domain antibody fragments: the superfluous luxury of paired domains," Trends in Biochemical Sciences, Apr. 1, 2001, 26(4):230-5.
Muyldermans, "Nanobodies: natural single-domain antibodies," Annual Review of Biochemistry, Jun. 2, 2013, 82:775-97.
Muyldermans, "Single domain camel antibodies: current status," Reviews in Molecular Biotechnology, Jun. 1, 2001, 74(4):277-302.
Myung et al., "Evidence of DNA damage in Alzheimer disease: phosphorylation of histone H2AX in astrocytes," Age, Apr. 23, 2008, 30(4):209-215.
Nag et al., "Soluble MHC II-peptide complexes induce antigen-specific apoptosis in T cells," Cellular Immunology, May 25, 1996, 170(1):25-33.
Nayyar et al., "Overcoming Resistance to Natural Killer Cell Based Immunotherapies for Solid Tumors," Frontiers in Oncology, 2019, 9: DOI: 10.3389/fonc.2019.00051.
Nelson et al., "A senescent cell bystander effect: senescence-induced senescence," Aging Cell, Feb. 9, 2012, 11(2):345-349.
Nilsson et al., "Targeted delivery of tissue factor to the ED-B domain of fibronectin, a marker of angiogenesis, mediates the infarction of solid tumors in mice," Cancer Research, American Association for Cancer Researc, Proceddings: AACR 107th Annual Meeting, 2016, Apr. 16-20, 2016, New Orleans, LA 61(2):711-716.
Nishida et al., "CD26 is a potential therapeutic target by humanized monoclonal antibody for the treatment of multiple myeloma," Blood Cancer Journal, Oct. 22, 2018, 8(11):99, 17 pages.
O'Sullivan et al., "Natural Killer Cell Memory," Immunity, Oct. 20, 2015, 43(4):634-645.
Oberle et al., "Rapid Suppression of Cytokine Transcription in Human CD4+CD25– T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.

(56) References Cited

OTHER PUBLICATIONS

Ovadya et al., "Strategies targeting cellular senescence," The Journal of Clinical Investigation, Apr. 2, 2018, 128(4):1247-54.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
PCT International Preliminary Report on Patentability in International Appln. No. PCT/US2019/048881, dated Mar. 11, 2021, 7 pages.
PCT International Preliminary Report on Patentability in International Appln. No. PCT/US2019/048930, dated Mar. 11, 2021, 9 pages.
PCT International Preliminary Report on Patentability in International Appln. No. PCT/US2019/049142, dated Mar. 11, 2021, 11 pages.
PCT International Preliminary Report on Patentability in International Appln. No. PCT/US2019/049158, dated Mar. 11, 2021, 8 pages.
PCT International Preliminary Report on Patentability in International Appln. No. PCT/US2020/038717, dated Dec. 30, 2021, 9 pages.
PCT International Search Report and Written Opinion in International Appln. No. PCT/US2019/048881, dated Nov. 9, 2019, 16 pages.
PCT International Search Report and Written Opinion in International Appln. No. PCT/US2019/048930, dated Nov. 20, 2019, 18 pages.
PCT International Search Report and Written Opinion in International Appln. No. PCT/US2019/04912, dated Jun. 23, 2020, 20 pages.
PCT International Search Report and Written Opinion in International Appln. No. PCT/US2019/049158, dated Jan. 20, 2020, 18 pages.
PCT International Search Report and Written Opinion in International Appln. No. PCT/US2020/035598, dated Feb. 18, 2021, 12 pages.
PCT International Search Report and Written Opinion in International Appln. No. PCT/US2020/038717, dated Oct. 16, 2020, 17 pages.
PCT International Search Report and Written Opinion in International Appln. No. PCT/US2021/017620, dated Aug. 6, 2021, 22 pages.
PCT International Search Report and Written Opinion in International Appln. No. PCT/US2021/017621, dated Jun. 9, 2021, 15 pages.
PCT International Search Report and Written Opinion in International Appln. No. PCT/US2021/017714, dated Aug. 27, 2021, 22 pages.
PCT International Search Report and Written Opinion in International Appln. No. PCT/US2021/029920, dated Oct. 6, 2021, 21 pages.
PCT International Search Report and Written Opinion in International Appln. No. PCT/US2021/035285, dated Oct. 18, 2021, 14 pages.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Pittayapruek et al., "Role of Matrix Metalloproteinases in Photoaging and Photocarcinogenesis," International Journal of Molecular Sciences, 2016, 17(6):868, 20 pages.
Priyanka et al., "Linkers in the structural biology of protein-protein interactions," Protein Sci., 2013, 22(2):153-167.
Purohit et al., "Smad3-dependent regulation of type I collagen in human dermal fibroblasts: Impact on human skin connective tissue aging," Journal of Dermatological Science, Jul. 2016, 83(1):80-83, 4 pages.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovirus disease in immunosuppressed patients," Journal of Clinical Oncology, May 26, 2019, 37(15 Suppl.):7008, 2 pages.
Rahbarizadeh et al., "Nanobody; an old concept and new vehicle for immunotargeting," Immunological Investigations, Jan. 1, 2011, 40(3):299-338.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Ranganathan et al., "Pinpointing the putative heparin/sialic acid-binding residues in the 'sushi' domain 7 of factor H: a molecular modeling study," Biocomputing 2000, 1999, 155-67.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.
Rhein et al., "Characterization of Human and Murine T-Cell Immunoglobulin Mucin Domain 4 (TIM-4) IgV Domain Residues Critical for Ebola Virus Entry," J Virol., 2016, 90(13):6097-6111.
Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.
Rittie et al., "Natural and Sun-Induced Aging of Human Skin," Cold Spring Harbor Perspective in Medicine, 2015, 5(1):a015370, 15 pages.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Rodier et al., "Persistent DNA damage signaling triggers senescence-associated inflammatory cytokine secretion," Nature Cell Biology, Jul. 13, 2009, 11(8): 973-979, 15 pages.
Rogge et al., "Antibodies to the IL-12 receptor β2 chain mark human Th1 but not Th2 cells in vitro and in vivo," The Journal of Immunology, Apr. 1, 1999, 162(7):3926-32.
Roh et al., "Damage-Associated Molecular Patterns in Inflammatory Diseases," Immune Network, Aug. 2018, 18(4):e27, 14 pages.
Romano et al., "Past, Present, and Future of Regulatory T Cell Therapy in Transplantation and Autoimmunity," Frontiers in Immunology, Jan. 1, 2019, 10:43, 14 pages.
Romee et al., "Cytokine activation induces human memory-like NK cells," Blood, Dec. 6, 2012, 120(24):4751-4760.
Rossi et al., "Complex and defined biostructures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Rubinstein et al., "Converting IL-15 to a superagonist by binding to soluble IL-15Rα," Proceedings of the National Academy of Sciences U.S.A., Jun. 13, 2006, 103(24):9166-9171.

(56) References Cited

OTHER PUBLICATIONS

Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistry, Nov. 5, 1992, 267(31):22206-10.
Ruscetti et al., "NK cell-mediated cytotoxicity contributes to tumor control by a cytostatic drug combination," Science, Dec. 21, 2018, 362(6421):1416-1422, 8 pages.
Sagiv et al., "Granule exocytosis mediates immune surveillance of senescent cells," Oncogene, 2013, 32(15):1971-1977.
Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamoto et al., "Phase I clinical trial of autologous NK cell therapy using novel expansion method in patients with advanced digestive cancer," Journal of Translational Medicine, Aug. 25, 2015, 13:277, 13 pages.
Sakamuri et al., "Measurement of respiratory function in isolated cardiac mitochondria using Seahorse XFe24 Analyzer: applications for aging research," Geroscience, Jun. 1, 2018, 40(3):347-356.
Salminen et al., "Emerging role of NF-κB signaling in the induction of senescence-associated secretory phenotype (SASP)," Cellular Signaling, Apr. 2012, 24(4):835-845.
Sandusky et al., "Regulation of 2B4 (CD244)-mediated NK cell activation by ligand-induced receptor modulation," European Journal of Immunology, Dec. 2006, 36(12):3268-76.
Sato et al., "Recombinant soluble murine IL-4 receptor can inhibit or enhance IgE responses in vivo," The Journal of Immunology, Apr. 1, 1993, 150:2717-2723.
Schafer et al., "Cellular senescence mediates fibrotic pulmonary disease," Nat Commun., Feb. 2017, 8:14532, 11 pages.
Schullek et al., "Key ligand interface residues in tissue factor contribute independently to factor VIIa binding," Journal of Biological Chemistry, Jul. 29, 1994, 269(30):19399-403.
Schwoppe et al., "Tissue-factor fusion proteins induce occlusion of tumor vessels," Thrombosis Research, Apr. 1, 2010, 125:S143-S150.
Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.
Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.
Sharma et al., "Regulatory T Cells License Macrophage Pro Resolving Functions During Atherosclerosis Regression," Circulation Research, Apr. 27, 2020, 127:335-353.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment-derived BCMA-targeted Car T cell vector," Molecular Therapy, Jun. 6, 2018, 26(6):1447-56.
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.
Sondel et al., "Combination Therapy with Interleukin-2 and Antitumor Monoclonal Antibodies," Cancer Journal from Scientific American, Jan. 1, 1997, 3(Suppl. 1):S121-S127.
Sone et al., "Pancreatic beta cell senescence contributes to the pathogenesis of type 2 diabetes in high-fat diet-induced diabetic mice," Diabetologia, 2005, 48(1):58-67.
Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.
Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.
Spiess et al., "Alternative molecular formats and therapeutic applications for bispecific antibodies," Molecular Immunology, Oct. 1, 2015, 67(2):95-106.
Stoklasek et al., "Combined IL-15/IL-15Rα Immunotherapy Maximizes IL-15 Activity In Vivo," The Journal of Immunology, Nov. 1, 2006, 177(9):6072-6080.
Storer et al., "Senescence Is a Developmental Mechanism that Contributes to Embryonic Growth and Patterning," Cell, Nov. 21, 2013, 155(5):1119-1130.
Stryer, Biochemistry Fourth Edition, W. H. Freeman and Company, New York, 1995, pp. 18-23, 8 pages.
Swanson et al., "The NLRP3 inflammasome: molecular activation and regulation to therapeutics," Nature Reviews Immunology, Apr. 29, 2019, 19(8):477-489, 13 pages.
Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.
Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.
Takahashi et al., "Downregulation of cytoplasmic DNases is implicated in cytoplasmic DNA accumulation and SASP in senescent cells," Nature Communications, Mar. 28, 2018, 9:1249, 12 pages.
Takahashi et al., "Simple and inexpensive technique for measuring oxygen consumption rate in adherent cultured cells," The Journal of Physiological Sciences, Nov. 2017, 67(6):731-737.
Takeda et al., "Phase I study of YS110, a recombinant humanized monoclonal antibody to CD26, in Japanese patients with advanced malignant pleural mesothelioma," Lung Cancer, Nov. 2019, 137:64-70.
Tam et al., "Methods and strategies of peptide ligation," Peptide Science: Original Research on Biomolecules, 2001, 60(3):194-205.
Tanaka et al., "Cloning and functional expression of the T cell activation antigen CD26," Journal of Immunology, Jul. 15, 1992, 149(2):481-486.
Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Teng et al., "Structural assessment of the effects of amino acid substitutions on protein stability and protein proteininteraction," International journal of computational biology and drug design, Feb. 7, 2011, 3(4):334-349.
Theil et al., "Adoptive transfer of allogeneic regulatory T cells into patients with chronic graft-versus-host disease," Cytotherapy, Apr. 2015, 17(4):473-486, 14 pages.
Thonhoff et al., "Expanded autologous regulatory T-lymphocyte infusions in ALS," Neurology Neuroimmunology Neuroinflammation, May 18, 2018, 5(4):e465, 8 pages.
Tobin et al., "NK cells in childhood obesity are activated, metabolically stressed, and functionally deficient," JCI Insight, Dec. 21, 2017, 2(24):e94939, 9 pages.
Tomala et al., "In Vivo Expansion of Activated Naive CD8+ T Cells and NK Cells Driven by Complexes of IL-2 and Anti-IL-2 Monoclonal Antibody As Novel Approach of Cancer Immunotherapy," The Journal of Immunology, Oct. 15, 2009, 183:4904-4912.

(56) References Cited

OTHER PUBLICATIONS

Tominaga et al., "TGF-β Signaling in Cellular Senescence and Aging-Related Pathology," International Journal of Molecular Sciences, Oct. 10, 2019, 20(20):5002, 18 pages.
Trevani et al., "Extracellular acidification induces human neutrophil activation," The Journal of Immunology, Apr. 15, 1999, 162(8):4849-4857.
Tse et al., "ABT-263: A Potent and Orally Bioavailable Bcl-2 Family Inhibitor," Cancer Research, May 2008, 68(9):3421-3428.
Uryga et al., "Ageing induced vascular smooth muscle cell senescence in atherosclerosis," Journal of Physiology, Apr. 15, 2016, 594(8):2115-2124.
Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Van Deursen, "The role of senescent cells in ageing," Nature, May 21, 2014, 509(7501):439-446.
Vankadari et al., "Emerging COVID-19 coronavirus: glycan shield and structure prediction of spike glycoprotein and its interaction with human CD26," Emerging Microbes and Infection, Mar. 17, 2020, 9(1):601-604.
Vidarsson et al., "IgG subclasses and allotypes: from structure to effector functions," Frontiers in immunology, Oct. 20, 2014, 5:520, 17 Pages.
Vincke et al., "Introduction to heavy chain antibodies and derived Nanobodies," Single Domain Antibodies, Humana Press, Totowa, NJ, 2012, pp. 15-26.
Voet et al., Biochemistry, John Wiley & Sons, Inc., 1990, pp. 126-128 and 228-234, 12 pages.
von Kobbe, "Cellular senescence: a view throughout organismal life," Cellular and Molecular Life Sciences, Jul. 20, 2018, 75:3553-3567, 15 pages.
Waaijer et al., "Do senescence markers correlate in vitro and in situ within individual human donors?," Aging Feb. 2018, 10(2):278-289.
Walsh et al., "Inflammasomes in the CNS," Nature Reviews Neuroscience, Jan. 8, 2014, 15(2):84-97, 14 pages.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565 DOI: 10.1093/jb/mvh065.
Wang et al., "Biomarkers of Cellular Senescence and Skin Aging," Frontiers in Genetics, Aug. 23, 2018, 9:247, 14 pages.
Wang et al., "Loss of lamin B1 is a biomarker to quantify cellular senescence in photoaged skin," Scientific Reports, Nov. 15, 2017, 7(1):15678, 8 pages.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weihermann et al., "Elastin structure and its involvement in skin photoageing," International Journal of Cosmetic Science, Jun. 2017, 39(3):241-247.
Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.
Weiner et al., "Antibody-based immunotherapy of cancer," Cell, Mar. 16, 2012, 148(6):1081-4.
Weiss et al., "Formyl-Peptide Receptors in Infection, Inflammation, and Cancer," Trends in Immunology, Oct. 2018, 39(10):815-829, 15 pages.
Wesolowski et al., "Single domain antibodies: promising experimental and therapeutic tools in infection and immunity," Medical Microbiology and Immunology, Aug. 1, 2009, 198(3):157-74.
Wiemann et al., "Hepatocyte telomere shortening and senescence are general markers of human liver cirrhosis," The FASEB Journal, Jul. 2002, 16(9):935-942.
Wiley et al., "Mitochondrial Dysfunction Induces Senescence with a Distinct Secretory Phenotype," Cell Metabolism, Feb. 9, 2016, 23(2):303-314.
Witkowsa et al., "Soluble intercellular adhesion molecule-1 (sICAM-1): an overview," Eur Cytokine Netw. 2004, 15(2):91-98.
Xiong et al., "Maternal uterine NK cell-activating receptor KIR2DS1 enhances placentation," The Journal of Clinical Investigation, Oct. 1, 2013, 123(10):4264-72.
Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.
Xu et al., "Senolytics improve physical function and increase lifespan in old age," Nature Medicine, Aug. 2018, 24(8):1246, 15 pages.
Xu et al., "Transplanted senescent cells induce an osteoarthritis-like condition in mice," The Journals of Gerontology: Series A, Jun. 1, 2017, 72(6):780-5.
Yamamoto et al., "Measurement of glucose uptake in cultured cells," Curr Protoc Pharmacol, Dec. 2011, Chapter 12:12.14.1-12.14.22.
Yamazaki et al., "Vascular Cell Senescence Contributes to Blood-Brain Barrier Breakdown," Stroke, Feb. 16, 2016, 47(4):1068-1077, 15 pages.
Yan et al., "Obesity- and aging-induced excess of central transforming growth factor-β potentiates diabetic development via an RNA stress response," Nature Medicine, Aug. 3, 2014, 20:1001-1008, 9 pages.
Yanai et al., "Cellular senescence-like features of lung fibroblasts derived from idiopathic pulmonary fibrosis patients," Aging (Albany NY), Sep. 2015, 7(9):664-672.
Yigit et al., "A combination of an anti-SLAMF6 antibody and ibrutinib efficiently abrogates expansion of chronic lymphocytic leukemia cells," Oncotarget, May 3, 2016, 7(18):26346.
Yousefzadeh et al., "An aged immune system drives senescence and ageing of solid organs," Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex structure," Elife, May 5, 2015, 4:e05505, 16 pages.
Yung et al., "A selective transforming growth factor-β ligand trap attenuates pulmonary hypertension," American Journal of Respiratory and Critical Care Medicine, Nov. 1, 2016, 194(9):1140-51.
Zhang et al., "AAED1 modulates proliferation and glycolysis in gastric cancer," Oncology Reports, Aug. 1, 2018, 40(2):1156-1164.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25− T Cells Is Associated with the Expression of CTLA-4 Not FoxP3," The Journal of Immunology, Aug. 1, 2008, 181(3):1683-1691.

(56) References Cited

OTHER PUBLICATIONS

Zhong et al., "A Potential Role for Dendritic Cell/Macrophage-Expressing DPP4 in Obesity-Induced Visceral Inflammation," Diabetes, Jan. 2013, 62(1):149-157.

Zhou et al., "A novel chimeric antigen receptor redirecting T-cell specificity towards CD26cancer cells," Leukemia, Apr. 2020, 35(1):119-129, 11 pages.

Zhu et al., "New agents that target senescent cells: the flavone, fisetin, and the BCL-XL inhibitors, A1331852 and A1155463," Aging (Albany NY), Mar. 2017, 9(3):955-963.

Zhu et al., "Novel Human Interleukin-15 Agonists," The Journal of Immunology, Sep. 15, 2009, 183(6):3598-3607.

Zou et al., "2-NBDG as a fluorescent indicator for direct glucose uptake measurement," Journal of biochemical and biophysical methods, Sep. 30, 2005, 64(3):207-215.

Zwaagstra et al., "Engineering and therapeutic application of single-chain bivalent TGF-β family traps," Molecular Cancer Therapeutics, Jul. 1, 2012, 11(7):1477-87.

Huang et al., "Targeting the vasculature of colorectal carcinoma with a fused protein of (RGD) 3-tTF" The Scientific World Journal, 2013(637086):1-11, 2013.

PCT International Preliminary Report on Patentability in International Appln. No. PCT/US2021/029920, dated Nov. 10, 2022, 11 pages.

International Preliminary Report on Patentability in International Appln. No. PCT/US2020/035598, dated Dec. 6, 2022, 7 pages.

International Preliminary Report on Patentability in International Appln. No. PCT/US2021/035285, dated Dec. 15, 2022, 7 pages.

[No Author Listed], "CN Br-activated Sepharose 4 Fast Flow," 1999, Affinity Chromatography, 4 pages.

Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec. 2015, 14(199):1-12.

Bird et al., "TGFβ inhibition restores a regenerative response in acute liver injury by suppressing paracrine senescence," Science translational medicine, Aug. 15, 2018, 10(454):eaan1230, 15 pages.

Brämer et al., "Membrane adsorber for the fast purification of a monoclonal antibody using protein a chromatography," Membranes, Nov. 27, 2019, 9(12):159, 15 pages.

Cai et al., "Quercetin inhibits transforming growth factor β1-induced epithelial-mesenchymal transition in human retinal pigment epithelial cells via the Smad pathway," Drug design, development and therapy, Dec. 6, 2018, 12:4149-4161.

Chabannon et al., "Manufacturing natural killer cells as medicinal products," Frontiers in Immunology, Nov. 15, 2016, 7(504): 1-9.

Guha et al., "Affinity purification of human tissue factor: interaction of factor VII and tissue factor in detergent micelles," Proceedings of the National Academy of Sciences, Jan. 1986, 83(2):299-302.

Hélie et al., "Application of the Protein Maker as a platform purification system for therapeutic antibody research and development," Computational and Structural Biotechnology Journal, Jan. 1, 2016, 14:238-244.

info.gbiosciences.com [Online], "G-Biosciences, The Basics of Affinity Purification/Affinity Chromatography," Jul. 31, 2018, retrieved on Apr. 18, 2023, retrieved from URL<https://info.gbiosciences.com/blog/the-basics-of-affinity-purification/affinity-chromatography?utm_campaign=G-Bio+Search+Ads&utm_term=&utm_source=adwords&utm_medium=ppc&hsa_src=g&hsa_ver=3&hsa_cam=737902488&hsa_kw=&hsa_ad=621736020174&hsa_tgt=dsa-460355902483&hsa mt-&hsa acc-6752996364&hsa_grp-92226101427&hsa_net-adwords&gclid=CjwKCAjw_ihBhADEiwAXEazJvXifVFgeRGV_W99XbY72eRROhWnHtdd695ydPgyh8qdvTwd9ikGIRoCdecQAvD_BwE>, 5 pages.

Klingemann et al., "Natural killer cells for immunotherapy-advantages of the NK-92 cell line over blood NK cells," Frontiers in immunology, Mar. 14, 2016, 7(91): 1-7.

Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.

Putnam et al., "Clinical grade manufacturing of human alloantigen-reactive regulatory T cells for use in transplantation," American journal of transplantation, Nov. 1, 2013, 13(11):3010-3020.

ThermoFisher.com [Online], "Covalent Immobilization of Affinity Ligands," 2018, retrieved on Apr. 18, 2023, retrieved from <URLhttps://www.thermofisher.com/us/en/home/life-science/protein-biology/protein-biology-learning-center/protein-biology-resource-library/pierce-protein-methods/covalent-immobilization-affinity-ligands.html>, 13 pages.

Uppendahl et al., "Natural killer cell-based immunotherapy in gynecologic malignancy: a review," Frontiers in immunology, Jan. 5, 2018, 8(1825): 1-15.

Urh et al., "Affinity chromatography: general methods," Methods in enzymology, Jan. 1, 2009, 463: 23 pages.

Veluchamy et al., "The rise of allogeneic natural killer cells as a platform for cancer immunotherapy: recent innovations and future developments," Frontiers in immunology, May 31, 2017, 8(631): 1-20.

Fernando et al., "Targeting tumor endothelial marker 8 in the tumor vasculature of colorectal carcinomas in mice," Cancer Research, Jun. 15, 2009, 69(12):5126-5132.

Mortier et al., "Soluble interleukin-15 receptor α (IL-15Rα)-sushi as a selective and potent agonist of IL-15 action through IL-15Rβ/γ: hyperagonist IL-15. IL-15Rα fusion proteins," Journal of Biological Chemistry, Jan. 20, 2006, 281(3):1612-1619.

Wong et al., "Interleukin-15: Interleukin-15 receptor α scaffold for creation of multivalent targeted immune molecules," Protein Engineering, Design & Selection, Apr. 1, 2011, 24(4):373-383.

Chan et al., "Molecular mechanisms of natural killer cell activation in response to cellular stress," Cell Death & Differentiation, Jan. 2014, 21(1):5-14.

Chang et al., "The dock and lock method: a novel platform technology for building multivalent, multifunctional structures of defined composition with retained bioactivity," Clinical cancer research, Sep. 15, 2007, 13(18):5586s-5591s.

Hui et al., "Butyrate inhibit collagen-induced arthritis via Treg/IL-10/Th17 axis," International immunopharmacology, Mar. 1, 2019, 68: Abstract 1 page.

Li et al., "Lipid metabolism fuels cancer's spread," Cell metabolism, Feb. 7, 2017, 25(2):228-230.

Wilchek et al., "Essentials of biorecognition: The (strept) avidin-biotin system as a model for protein-protein and protein-ligand interaction," Immunology letters, Feb. 28, 2006, 103(1): Abstract 2 pages.

Zhang et al., "Depletion of NK cells improves cognitive function in the Alzheimer disease mouse model," The Journal of Immunology, Jul. 15, 2020, 205(2): 10pages.

Chen et al., "A novel idea for establishing Parkinson's disease mouse model by intranasal administration of paraquat," Neurological Research, 43(4):267-277, 2021.

Igarashi et al., "VEGF-C and TGF-β reciprocally regulate mesenchymal stem cell commitment to differentiation into lymphatic endothelial or osteoblastic phenotypes," International Journal of Molecular Medicine, Apr. 1, 2016, 37(4):1005-1013.

Infante-Duarte et al., "New developments in understanding and treating neuroinflammation," Journal of Molecular Medicine, Sep. 2008, 86:975-985.

International Search Report and Written Opinion in International Appln. No. PCT/US2023/065745, dated Jun. 26, 2023, 14 pages.

Janeway et al., "The interaction of the antibody molecule with specific antigen," In Immunobiology: The Immune System in Health and Disease, 5th edition, 5 pages, 2001.

Matsuura et al., "Pole test is a useful method for evaluating the mouse movement disorder caused by striatal dopamine depletion," Journal of Neuroscience Methods, 73(1):45-48, 1997.

Reddy et al., "Linkers in the structural biology of protein-protein interactions," Protein Science, 22(2):153-167, 2013.

(56) References Cited

OTHER PUBLICATIONS

Van Bockstaele et al., "The development of nanobodies for therapeutic applications," Current Opinion in Investigational Drugs, 10(11):1212-1224, 2009.

* cited by examiner

SINGLE-CHAIN CHIMERIC POLYPEPTIDES AND USES THEREOF

CROSS-REFERENCE TO RELATED APPLICATIONS

This application is a divisional application of U.S. patent application Ser. No. 16/556,040, filed Aug. 29, 2019, which claims priority to: U.S. Patent Application Ser. No. 62/725,038, filed Aug. 30, 2018, U.S. Patent Application Ser. No. 62/817,244, filed Mar. 12, 2019; U.S. Patent Application Ser. No. 62/746,832, filed Oct. 17, 2018; U.S. Patent Application Ser. No. 62/749,506, filed Oct. 23, 2018; U.S. Patent Application Ser. No. 62/817,241, filed Mar. 12, 2019; U.S. Patent Application Ser. No. 62/816,683, filed Mar. 11, 2019; and U.S. Patent Application Ser. No. 62/881,039, filed Jul. 31, 2019; each of which is herein incorporated by reference in its entirety.

STATEMENT REGARDING SEQUENCE LISTING

This document includes a sequence listing in electronic format submitted to the United States Patent and Trademark Office via the electronic filing system. The XML file, which is incorporated-by-reference herein, is titled "470390008002ST26.XML," was created on Jul. 21, 2022, and has a size of 180,829 bytes.

TECHNICAL FIELD

The present disclosure relates to the field of biotechnology, and more specifically, to antigen-binding molecules.

BACKGROUND

Tissue factor (TF), a 263 amino acid integral membrane glycoprotein with a molecular weight of ~46 kDa and the trigger protein of the extrinsic blood coagulation pathway, is the primary initiator of coagulation in vivo. Tissue factor, normally not in contact with circulating blood, initiates the coagulation cascade upon exposure to the circulating coagulation serine protease factors. Vascular damage exposes sub-endothelial cells expressing tissue factor, resulting in the formation of a calcium-dependent, high-affinity complex with pre-existing plasma factor VIIa (FVIIa). Binding of the serine protease FVIIa to tissue factor promotes rapid cleavage of FX to FXa and FIX to FIXa. The proteolytic activity of the resulting FXa and an active membrane surface then inefficiently converts a small amount of prothrombin to thrombin. The thrombin generated by FXa initiates platelet activation and activates minute amounts of the pro-cofactors factor V (FV) and factor VIII (FVIII) to become active cofactors, factor Va (FVa) and factor VIIIa (FVIIIa). FIXa complexes with FVIIIa on the platelet surface forming the intrinsic tenase complex, which results in rapid generation of FXa. FXa complexes with FVa to form the pro-thrombinase complex on the activated platelet surface which results in rapid cleavage of prothrombin to thrombin.

In addition to the tissue factor-FVIIa complex, a recent study showed that the tissue factor-FVIIa-FXa complex can activate FVIII, which would provide additional levels of FVIIIa during the initiation phase. The extrinsic pathway is paramount in initiating coagulation via the activation of limited amounts of thrombin, whereas the intrinsic pathway maintains coagulation by dramatic amplification of the initial signal.

Much of the tissue factor expressed on a cell surface is "encrypted," which must be "decrypted" for full participation in coagulation. The mechanism of "decryption" of cell-surface tissue factor is still unclear at this time, however, exposure of anionic phospholipids plays a major role in this process. Healthy cells actively sequester anionic phospholipids such as phosphatidyl serine (PS) to the inner leaflet of the plasma membrane. Following cellular damage, activation, or increased levels of cytosolic $Ca^{2+}$, this bilayer asymmetry is lost, resulting in increased PS exposure on the outer leaflet, which increases the specific activity of cell-surface tissue factor-FVIIa complexes. PS exposure is known to decrease the apparent Km for activation of FIX and FX by tissue factor-FVIIa complexes, but additional mechanisms could include conformational rearrangement of tissue factor or tissue factor-FVIIa and subsequent exposure of substrate binding sites.

SUMMARY

The present invention is based on the discovery that soluble tissue factor can be used as a scaffold for chimeric polypeptides including an antigen-binding domain. Based on this discovery provided herein are single-chain chimeric polypeptides that include: (i) a first target-binding domain; (ii) a soluble tissue factor domain; and (iii) a second target-binding domain. Also provided herein are compositions that include any of the single-chain chimeric polypeptides described herein, nucleic acids that encode any of the single-chain chimeric polypeptides described herein, and cells that include any of the nucleic acids that encode any of the single-chain chimeric polypeptides described herein. Also provided herein are methods of stimulating an immune cell and methods of treating a subject in need thereof that include the use of any of the single-chain chimeric polypeptides described herein. Also provided herein are methods of producing any of the single-chain chimeric polypeptides described herein. Additional uses of any of the single-chain chimeric polypeptides are described herein.

Accordingly, provided herein is a single-chain chimeric polypeptide comprising:
(i) a first target-binding domain;
(ii) a soluble tissue factor domain; and
(iii) a second target-binding domain. In some embodiments, the first target-binding domain and the soluble tissue factor domain directly abut each other. In some embodiments, the single-chain chimeric polypeptide further comprises a linker sequence between the first target-binding domain and the soluble tissue factor domain. In some embodiments, the soluble tissue factor domain and the second target-binding domain directly abut each other. In some embodiments, the single-chain chimeric polypeptide further comprises a linker sequence between the soluble tissue factor domain and the second target-binding domain. In some embodiments, the first target-binding domain and the second target-binding domain directly abut each other. In some embodiments, the single-chain chimeric polypeptide further comprises a linker sequence between the first target-binding domain and the second target-binding domain. In some embodiments, the second target-binding domain and the soluble tissue factor domain directly abut each other. In some embodiments, the single-chain chimeric polypeptide further comprises a linker sequence between the second target-binding domain and the soluble tissue factor domain. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain comprise the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each an antigen-binding domain. In some embodiments, the antigen-binding domain comprises a scFv or a single domain antibody. In some embodiments, one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin, a soluble cytokine protein, or a soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin receptor, a soluble cytokine receptor, or a soluble cell surface receptor. In some embodiments, the soluble interleukin receptor, soluble cytokine receptor, or soluble cell surface receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, the soluble tissue factor domain is a soluble human tissue factor domain. In some embodiments, the soluble human tissue factor domain comprises a sequence that is at least 80% identical to SEQ ID NO: 9. In some embodiments, the soluble human tissue factor domain comprises a sequence that is at least 90% identical to SEQ ID NO: 9. In some embodiments, the soluble human tissue factor domain comprises a sequence that is at least 95% identical to SEQ ID NO: 9. In some embodiments, the single-chain chimeric polypeptide of the soluble human tissue factor domain does not comprise one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding Factor VIIa. In some embodiments, the soluble tissue factor domain does not convert inactive Factor X into Factor Xa. In some embodiments, the single-chain chimeric polypeptide does not stimulate blood coagulation in a mammal. In some embodiments, the single-chain chimeric polypeptide further comprises one or more additional target-binding domains at its N- and/or C-terminus. In some embodiments, the single-chain chimeric polypeptide comprises one or more additional target-binding domains at its N-terminus. In some embodiments, one or more additional target-binding domains directly abuts the first target-binding domain, the second target-binding domain, or the soluble tissue factor domain. In some embodiments, the single-chain chimeric polypeptide further comprises a linker sequence between one of the at least one additional target-binding domains and the first target-binding domain, the second target-binding domain, or the soluble tissue factor domain. In some embodiments, the single-chain chimeric polypeptide comprises one or more additional target-binding domains at its C-terminus. In some embodiments, one of the one or more additional target-binding domains directly abuts the first target-binding domain, the second target-binding domain, or the soluble tissue factor domain. In some embodiments, the single-chain chimeric polypeptide further comprises a linker sequence between one of the at least one additional target-binding domains and the first target-binding domain, the second target-binding domain, or the soluble tissue factor domain. In some embodiments, the single-chain chimeric polypeptide comprises one or more additional target binding domains at its N-terminus and the C-terminus. In some embodiments, one of the one or more additional antigen binding domains at the N-terminus directly abuts the first target-binding domain, the second target-binding domain, or the soluble tissue factor domain. In some embodiments, the single-chain chimeric polypeptide further comprises a linker sequence between one of the one or more additional antigen-binding domains at the N-terminus and the first target-binding domain, the second target-binding domain, or the soluble tissue factor domain. In some embodiments, one of the one or more additional antigen binding domains at the C-terminus directly abuts the first target-binding domain, the second target-binding domain, or the soluble tissue factor domain. In some embodiments, the single-chain chimeric polypeptide further comprises a linker sequence between one of the one or more additional antigen-binding domains at the C-terminus and the first target-binding domain, the second target-binding domain, or the soluble tissue factor domain. In some embodiments, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each comprise the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain comprises a scFv or a single domain antibody. In some embodiments, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or more of the first target-binding domain, the second target-binding domain, and the one or more additional target-binding domains is a soluble interleukin or cytokine protein. In some embodiments, the soluble interleukin or cytokine protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or more of the first target-binding domain, the second target-binding domain, and the one or more additional target-binding domains is a soluble interleukin or cytokine receptor. In some embodiments, the soluble receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, the single-chain chimeric polypeptide further comprises a signal sequence at its N-terminal end. In some embodiments, the single-chain chimeric polypeptide further comprises a peptide tag positioned at the N-terminal end or the C-terminal end of the single-chain chimeric polypeptide.

Also provided herein is a composition comprising any of the single-chain chimeric polypeptides discussed above. In some embodiments, the composition is a pharmaceutical composition. In some embodiments, the single-chain chimeric polypeptides comprise at least one dose of the composition within a kit.

Also provided herein is a method of stimulating an immune cell, the method comprising: contacting an immune cell with an effective amount of any of the single-chain chimeric polypeptides or compositions discussed above. In some embodiments, the method comprises contacting the immune in vitro. In some embodiments, the method comprises obtaining the immune cell from a subject. In some embodiments, the method further comprises obtaining the immune cell from the subject prior to the contacting step. In some embodiments, the method comprises contacting the immune cell in vivo. In some embodiments, the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, and a natural killer cell. In some embodiments, the immune cell has previously been genetically modified to express a chimeric antigen receptor or a recombinant T-cell receptor. In some embodiments, the method further comprises introducing into the immune cell a nucleic acid encoding a chimeric antigen-receptor or a recombinant T-cell receptor after the contacting step. In some embodiments, the method further comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of inducing or increasing proliferation of an immune cell, the method comprising: contacting an immune cell with an effective amount of any of the single-chain chimeric polypeptides or compositions discussed herein. In some embodiments, the method comprises contacting the immune cell in vitro. In some embodiments, the method comprises obtaining the immune cell from a subject. In some embodiments, method further comprises obtaining the immune cell from the subject prior to the contacting step. In some embodiments, the method comprises contacting the immune cell in vivo. In some embodiments, the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, and a natural killer cell. In some embodiments, the immune cell has previously been genetically modified to express a chimeric antigen receptor or a recombinant T-cell receptor. In some embodiments, the method further comprises, after the contacting step, introducing into the immune cell a nucleic acid encoding a chimeric antigen-receptor or a recombinant T-cell receptor. In some embodiments, the method further comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of inducing differentiation of an immune cell into a memory or memory-like immune cell, the method comprising: contacting an immune cell with an effective amount of any of the single-chain chimeric polypeptides or compositions discussed above. In some embodiments, the method comprises contacting the immune cell in vitro. In some embodiments, the method comprises obtaining the immune cell from a subject. In some embodiments, the method further comprises obtaining the immune cell from the subject prior to the contacting step. In some embodiments, the method comprises contacting the immune cell in vivo. In some embodiments, the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments, the method comprises genetically modifying the immune cell to express a chimeric antigen receptor or a recombinant T-cell receptor. In some embodiments, the method further comprises introducing into the immune cell a nucleic acid encoding a chimeric antigen-receptor or a recombinant T-cell receptor after the contacting step. In some embodiments, the method further comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CIVIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of killing a cancer cell, an infected cell, or a senescent cell in a subject in need thereof, the method comprising administering to the subject a therapeutically effective amount of any of the single-chain chimeric polypeptides or compositions discussed above. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method identifying or diagnosing the subject as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Also provided herein is a method of treating a subject in need thereof, the method comprising administering to the subject a therapeutically effective amount of any of the single-chain chimeric polypeptides or compositions discussed above. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CIVIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises identifying or diagnosing the subject as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein are nucleic acids encoding any of the single-chain chimeric polypeptides discussed above. Some embodiments include a vector comprising the nucleic acid discussed above. In some embodiments, the vector is an expression vector.

Some embodiments include a cell comprising the nucleic acid or the vector discussed above.

Also provided herein is a method of producing a single-chain chimeric polypeptide, the method comprising: culturing the cell in a culture medium under conditions sufficient to result in the production of the single-chain chimeric polypeptide; and recovering the single-chain chimeric polypeptide from the cell and/or the culture medium. Some embodiments comprise single-chain chimeric polypeptide produced by the discussed above. In some embodiments of any of the single-chain chimeric polypeptides provided herein, the human soluble tissue factor domain does not initiate blood coagulation. In some embodiments of any of the single-chain chimeric polypeptides provided herein, the soluble tissue factor domain comprises or consists of a soluble wildtype human tissue factor.

In some embodiments, the mutant soluble human tissue factor domain comprises a sequence that is at least 80% identical to SEQ ID NO: 96. In some embodiments, the soluble human tissue factor domain comprises a sequence that is at least 90% identical to SEQ ID NO: 96. In some embodiments, the soluble human tissue factor domain comprises a sequence that is at least 95% identical to SEQ ID NO: 96. In some embodiments, the soluble human tissue factor domain comprises a sequence that is 100% identical to SEQ ID NO: 96. In some embodiments, the soluble human tissue factor domain comprises a sequence that is at least 80% identical to SEQ ID NO: 97. In some embodiments, the soluble human tissue factor domain comprises a sequence that is at least 90% identical to SEQ ID NO: 97. In some embodiments, the soluble human tissue factor domain comprises a sequence that is at least 95% identical to SEQ ID NO: 97. In some embodiments, the soluble human tissue factor domain comprises a sequence that is 100% identical to SEQ ID NO: 97.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., a scFv) and a domain that is derived from a naturally-occurring protein (e.g., a naturally-occurring human protein). In some embodiments, a chimeric polypeptide can include at least two different domains that are synthetic sequences (e.g., two different scFvs).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "single-chain polypeptide" as used herein to refers to a single protein chain.

The term "pair of affinity domains" is two different protein domain(s) that bind specifically to each other with a $K_D$ of less than of less than $1 \times 10^{-7}$ M (e.g., less than $1 \times 10^{-8}$ M, less than $1 \times 10^{-9}$ M, less than $1 \times 10^{-10}$ M, or less than $1 \times 10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

An "immune effector cell" refers to a cell of the immune system of a mammal that is capable, directly or indirectly, of recognizing and/or causing cytostasis or cell death of a pathogenic cell (e.g., a cancer cell) in the mammal. Non-limiting examples of immune effector cells include macrophages, T-lymphocytes (e.g., cytotoxic T-lymphocytes and T-helper cells), natural killer cells, neutrophils, monocytes, and eosinophils. Additional examples of immune effector cells are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 16A shows reduced SDS-PAGE analysis of IL-2/TF/IL-2 before deglycosylation. FIG. 16B shows reduced SDS-PAGE analysis of IL-2/TF/IL-2 after deglycosylation.

FIG. 17A shows spleen weight following treatment with IL-2/TF/IL-2. FIG. 17B shows the percentages of immune cell types following IL-2/TF/IL-2 treatment.

FIG. 20A shows a representative view of atherosclerotic plaques from ApoE$^{-/-}$ mice fed with standard chow or a high fat diet and treated with either PBS control or IL-2/TF/IL-2. FIG. 20B shows the results of quantitative analysis of atherosclerotic plaques of each group.

FIG. 26A shows reduced SDS-PAGE analysis of IL-15/TF/IL-15 before deglycosylation. FIG. 26B shows reduced SDS-PAGE analysis of IL-15/TF/IL-15 after deglycosylation.

FIG. 34A shows pSTAT5 responses in CD4$^+$CD25$^{111}$T$_{reg}$ cells. FIG. 34B shows pSTAT5 responses in CD4+CD25$^-$ T$_{con}$ cells. FIG. 34C shows pSTAT5 responses in CD8$^+$ T$_{con}$ cells.

DETAILED DESCRIPTION

Provided herein are single-chain chimeric polypeptides that include: (i) a first target-binding domain (e.g., any of the target-binding domains described herein or known in the art), (ii) a soluble tissue factor domain (e.g., any of the exemplary soluble tissue factor domains described herein or known in the art), and (iii) as second target-binding domain (e.g., any of the target-binding domains described herein or known in the art).

Also provided herein are compositions that include any of the single-chain chimeric polypeptides described herein, nucleic acids that encode any of the single-chain chimeric polypeptides described herein, and cells that include any of the nucleic acids that encode any of the single-chain chimeric polypeptides described herein. Also provided herein are methods of stimulating an immune cell and methods of treating a subject in need thereof that include the use of any of the single-chain chimeric polypeptides described herein. Also provided herein are methods of producing any of the single-chain chimeric polypeptides described herein.

Figure 1:
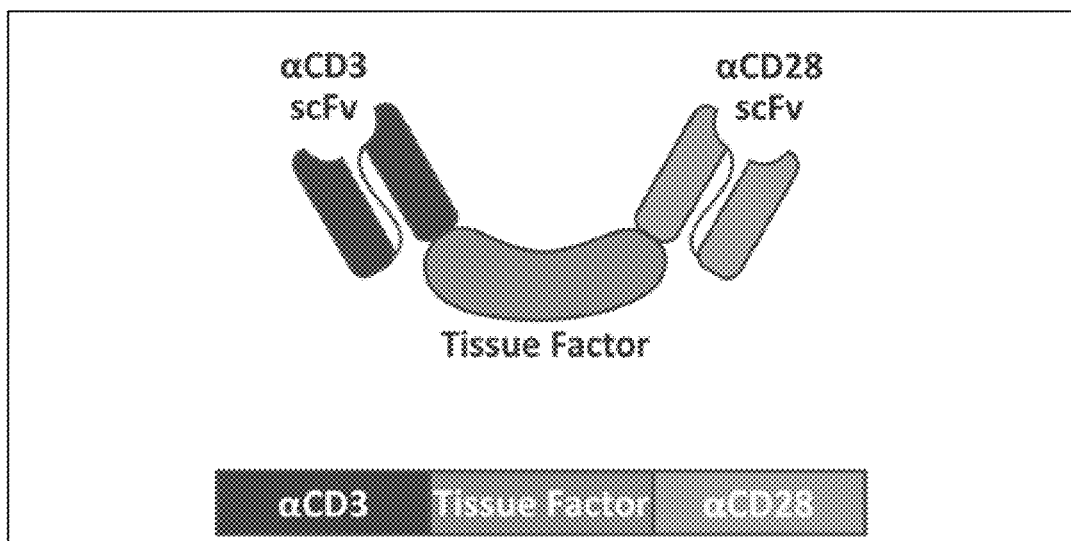
FIG. 1 are schematic diagrams of an exemplary αCD3scFv/TF/αCD28scFv single-chain chimeric polypeptide.

In some examples of any of the single-chain chimeric polypeptides described herein, the single-chain chimeric polypeptide can have a total length of about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids. Diagrams of an exemplary single-chain chimeric polypeptide provided herein are depicted in FIG. 1.

In some embodiments of any of the single-chain chimeric polypeptides described herein, the first target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the soluble tissue factor domain (e.g., any of the exemplary soluble tissue factor domains described herein). In some embodiments of any of the single-chain chimeric polypeptides described herein, the soluble tissue factor domain (e.g., any of the exemplary soluble tissue factor domains described herein) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the soluble tissue factor domain (e.g., any of the exemplary soluble tissue factor domains described herein) and the second target-binding domain (e.g., any of the exemplary target-binding domains described herein or known in the art).

In some embodiments of any of the single-chain chimeric polypeptides described herein, the first target-binding domain (e.g., any of the exemplary target-binding domains described herein or known in the art) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the second target-binding domain (e.g., any of the exemplary target-binding domains described herein or known in the art). In some embodiments of any of the single-chain chimeric polypeptides described herein, the second target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the second target-binding domain (e.g., any of the exemplary target-binding domains described herein or known in the art) and the soluble tissue factor domain (e.g., any of the exemplary soluble tissue factor domains described herein or known in the art).

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to (SEQ ID NO: 1)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINRGGGGSGGGGSGGGGSQVQLQQSGAELARPGASVKMSCKAS

GYTFTRYTMHWVKQRPGQGLEWIGYINPSRGYTNYNQKFKDKATLTTDK

SSSTAYMQLSSLTSEDSAVYYCARYYDDHYCLDYWGQGTTLTVSSSGTT

NTVAAYNLTWKSTNFKTILEWEPKPVNQVYTVQISTKSGDWKSKCFYTT

DTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDL

IYTLYYWKSSSSGKKTAKTNTNEFLIDVDKGENYCFSVQAVIPSRTVNR

KSTDSPVECMGQEKGEFREVQLQQSGPELVKPGASVKMSCKASGYTFTS

YVIQWVKQKPGQGLEWIGSINPYNDYTKYNEKFKGKATLTSDKSSITAY

MEFSSLTSEDSALYYCARWGDGNYWGRGTTLTVSSGGGGSGGGGSGGGG

SDIEMTQSPAIMSASLGERVTMTCTASSSVSSSYFHWYQQKPGSSPKLC

IYSTSNLASGVPPRFSGSGSTSYSLTISSMEAEDAATYFCHQYHRSPTF

GGGTKLETKR.

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 2)
CAGATCGTGCTGACCCAAAGCCCCGCCATCATGAGCGCTAGCCCCGGTG

AGAAGGTGACCATGACATGCTCCGCTTCCAGCTCCGTGTCCTACATGAA

CTGGTATCAGCAGAAAAGCGGAACCAGCCCCAAAAGGTGGATCTACGAC

ACCAGCAAGCTGGCCTCCGGAGTGCCCGCTCATTTCCGGGGCTCTGGAT

-continued
```
CCGGCACCAGCTACTCTTTAACCATTTCCGGCATGGAAGCTGAAGACGC
TGCCACCTACTATTGCCAGCAATGGAGCAGCAACCCCTTCACATTCGGA
TCTGGCACCAAGCTCGAAATCAATCGTGGAGGAGGTGGCAGCGGCGGCG
GTGGATCCGGCGGAGGAGGAAGCCAAGTTCAACTCCAGCAGAGCGGCGC
TGAACTGGCCCGGCCCGGCGCCTCCGTCAAGATGAGCTGCAAGGCTTCC
GGCTATACATTTACTCGTTACACAATGCATTGGGTCAAGCAGAGGCCCG
GTCAAGGTTTAGAGTGGATCGGATATATCAACCCTTCCGGGGCTACAC
CAACTATAACCAAAAGTTCAAGGATAAAGCCACTTTAACCACTGACAAG
AGCTCCTCCACCGCCTACATGCAGCTGTCCTCTTTAACCAGCGAGGACT
CCGCTGTTTACTACTGCGCTAGGTATTACGACGACCACTACTGTTTAGA
CTATTGGGGACAAGGTACCACTTTAACCGTCAGCAGCTCCGGCACCACC
AATACCGTGGCCGCTTATAACCTCACATGGAAGAGCACCAACTTCAAGA
CAATTCTGGAATGGGAACCCAAGCCCGTCAATCAAGTTTACACCGTGCA
GATCTCCACCAAATCCGGAGACTGGAAGAGCAAGTGCTTCTACACAACA
GACACCGAGTGTGATTTAACCGACGAAATCGTCAAGGACGTCAAGCAAA
CCTATCTGGCTCGGGTCTTTTCCTACCCCGCTGGCAATGTCGAGTCCAC
CGGCTCCGCTGGCGAGCCTCTCTACGAGAATTCCCCCGAATTCACCCCT
TATTTAGAGACCAATTTAGGCCAGCCTACCATCCAGAGCTTCGAGCAAG
TTGGCACCAAGGTGAACGTCACCGTCGAGGATGAAAGGACTTTAGTGCG
GCGGAATAACACATTTTTATCCCTCCGGGATGTGTTCGGCAAAGACCTC
ATCTACACACTGTACTATTGGAAGTCCAGCTCCTCCGGCAAAAAGACCG
CTAAGACCAACACCAACGAGTTTTTAATTGACGTGGACAAAGGCGAGAA
CTACTGCTTCAGCGTGCAAGCCGTGATCCCTTCTCGTACCGTCAACCGG
AAGAGCACAGATTCCCCCGTTGAGTGCATGGGCCAAGAAAAGGGCGAGT
TCCGGGAGGTCCAGCTGCAGCAGAGCGGACCCGAACTCGTGAAACCCGG
TGCTTCCGTGAAAATGTCTTGTAAGGCCAGCGGATACACCTTCACCTCC
TATGTGATCCAGTGGGTCAAACAGAAGCCCGGACAAGGTCTCGAGTGGA
TCGGCAGCATCAACCCTTACAACGACTATACCAAATACAACGAGAAGTT
TAAGGGAAAGGCTACTTTAACCTCCGACAAAAGCTCCATCACAGCCTAC
ATGGAGTTCAGCTCTTTAACATCCGAGGACAGCGCTCTGTACTATTGCG
CCCGGTGGGGCGACGGCAATTACTGGGGACGGGGCACAACACTGACCGT
GAGCAGCGGAGGCGGAGGCTCCGGCGGAGGCGGATCTGGCGGTGGCGGC
TCCGACATCGAGATGACCCAGTCCCCCGCTATCATGTCCGCCTCTTTAG
GCGAGCGGGTCACAATGACTTGTACAGCCTCCTCCAGCGTCTCCTCCTC
CTACTTCCATTGGTACCAACAGAAACCCGGAAGCTCCCCTAAACTGTGC
ATCTACAGCACCAGCAATCTCGCCAGCGGCGTGCCCCCTAGGTTTTCCG
GAAGCGGAAGCACCAGCTACTCTTTAACCATCTCCTCCATGGAGGCTGA
GGATGCCGCCACCTACTTTGTCACCAGTACCACCGGTCCCCCACCTTC
GGAGGCGGCACCAAACTGGAGACAAAGAGG.
```

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to

```
                                           (SEQ ID NO: 3)
MKWVTFISLLFLFSSAYSQIVLTQSPAIMSASPGEKVTMTCSASSSVSY
MNWYQQKSGTSPKRWIYDTSKLASGVPAHFRGSGSGTSYSLTISGMEAE
DAATYYCQQWSSNPFTFGSGTKLEINRGGGGSGGGGSGGGGSQVQLQQS
GAELARPGASVKMSCKASGYTFTRYTMHWVKQRPGQGLEWIGYINPSRG
YTNYNQKFKDKATLTTDKSSSTAYMQLSSLTSEDSAVYYCARYYDDHYC
LDYWGQGTTLTVSSSGTTNTVAAYNLTWKSTNFKTILEWEPKPVNQVYT
VQISTKSGDWKSKCFYTTDTECDLTDEIVKDVKQTYLARVFSYPAGNVE
STGSAGEPLYENSPEFTPYLETNLGQPTIQSFEQVGTKVNVTVEDERTL
VRRNNTFLSLRDVFGKDLIYTLYYWKSSSSGKKTAKTNTNEFLIDVDKG
ENYCFSVQAVIPSRTVNRKSTDSPVECMGQEKGEFREVQLQQSGPELVK
PGASVKMSCKASGYTFTSYVIQWVKQKPGQGLEWIGSINPYNDYTKYNE
KFKGKATLTSDKSSITAYMEFSSLTSEDSALYYCARWGDGNYWGRGTTL
TVSSGGGGSGGGGSGGGGSDIEMTQSPAIMSASLGERVTMTCTASSSVS
SSYFHWYQQKPGSSPKLCIYSTSNLASGVPPRFSGSGSTSYSLTISSME
AEDAATYFCHQYHRSPTFGGGTKLETKR.
```

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to

```
                                            (SEQ ID NO: 4)
ATGAAGTGGGTGACCTTCATCAGCTTATTATTTTTATTCAGCTCCGCCT
ATTCCCAGATCGTGCTGACCCAAAGCCCCGCCATCATGAGCGCTAGCCC
CGGTGAGAAGGTGACCATGACATGCTCCGCTTCCAGCTCCGTGTCCTAC
ATGAACTGGTATCAGCAGAAAAGCGGAACCAGCCCCAAAAGGTGGATCT
ACGACACCAGCAAGCTGGCCTCCGGAGTGCCCGCTCATTTCCGGGGCTC
TGGATCCGGCACCAGCTACTCTTTAACCATTTCCGGCATGGAAGCTGAA
GACGCTGCCACCTACTATTGCCAGCAATGGAGCAGCAACCCCTTCACAT
TCGGATCTGGCACCAAGCTCGAAATCAATCGTGGAGGAGGTGGCAGCGG
CGGCGGTGGATCCGGCGGAGGAGGAAGCCAAGTTCAACTCCAGCAGAGC
GGCGCTGAACTGGCCCGGCCCGGCGCCTCCGTCAAGATGAGCTGCAAGG
CTTCCGGCTATACATTTACTCGTTACACAATGCATTGGGTCAAGCAGAG
GCCCGGTCAAGGTTTAGAGTGGATCGGATATATCAACCCTTCCGGGGC
TACACCAACTATAACCAAAAGTTCAAGGATAAAGCCACTTTAACCACTG
ACAAGAGCTCCTCCACCGCCTACATGCAGCTGTCCTCTTTAACCAGCGA
GGACTCCGCTGTTTACTACTGCGCTAGGTATTACGACGACCACTACTGT
TTAGACTATTGGGGACAAGGTACCACTTTAACCGTCAGCAGCTCCGGCA
CCACCAATACCGTGGCCGCTTATAACCTCACATGGAAGAGCACCAACTT
CAAGACAATTCTGGAATGGGAACCCAAGCCCGTCAATCAAGTTTACACC
```

```
GTGCAGATCTCCACCAAATCCGGAGACTGGAAGAGCAAGTGCTTCTACA

CAACAGACACCGAGTGTGATTTAACCGACGAAATCGTCAAGGACGTCAA

GCAAACCTATCTGGCTCGGGTCTTTTCCTACCCCGCTGGCAATGTCGAG

TCCACCGGCTCCGCTGGCGAGCCTCTCTACGAGAATTCCCCCGAATTCA

CCCCTTATTTAGAGACCAATTTAGGCCAGCCTACCATCCAGAGCTTCGA

GCAAGTTGGCACCAAGGTGAACGTCACCGTCGAGGATGAAAGGACTTTA

GTGCGGCGGAATAACACATTTTTATCCCTCCGGGATGTGTTCGGCAAAG

ACCTCATCTACACACTGTACTATTGGAAGTCCAGCTCCTCCGGCAAAAA

GACCGCTAAGACCAACACCAACGAGTTTTTAATTGACGTGGACAAAGGC

GAGAACTACTGCTTCAGCGTGCAAGCCGTGATCCCTTCTCGTACCGTCA

ACCGGAAGAGCACAGATTCCCCCGTTGAGTGCATGGGCCAAGAAAGGG

CGAGTTCCGGGAGGTCCAGCTGCAGCAGAGCGGACCCGAACTCGTGAAA

CCCGGTGCTTCCGTGAAAATGTCTTGTAAGGCCAGCGGATACACCTTCA

CCTCCTATGTGATCCAGTGGGTCAAACAGAAGCCCGGACAAGGTCTCGA

GTGGATCGGCAGCATCAACCCTTACAACGACTATACCAAATACAACGAG

AAGTTTAAGGGAAAGGCTACTTTAACCTCCGACAAAAGCTCCATCACAG

CCTACATGGAGTTCAGCTCTTTAACATCCGAGGACAGCGCTCTGTACTA

TTGCGCCCGGTGGGGCGACGGCAATTACTGGGGACGGGGCACAACACTG

ACCGTGAGCAGCGGAGGCGGAGGCTCCGGCGGAGGCGGATCTGGCGGTG

GCGGCTCCGACATCGAGATGACCCAGTCCCCCGCTATCATGTCCGCCTC

TTTAGGCGAGCGGGTCACAATGACTTGTACAGCCTCCTCCAGCGTCTCC

TCCTCCTACTTCCATTGGTACCAACAGAAACCCGGAAGCTCCCCTAAAC

TGTGCATCTACAGCACCAGCAATCTCGCCAGCGGCGTGCCCCCTAGGTT

TTCCGGAAGCGGAAGCACCAGCTACTCTTTAACCATCTCCTCCATGGAG

GCTGAGGATGCCGCCACCTACTTTTGTCACCAGTACCACCGGTCCCCCA

CCTTCGGAGGCGGCACCAAACTGGAGACAAAGAGG.
```

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to

```
                                          (SEQ ID NO: 5)
VQLQQSGPELVKPGASVKMSCKASGYTFTSYVIQWVKQPGQGLEWIGS

INPYNDYTKYNEKFKGKATLTSDKSSITAYMEFSSLTSEDSALYYCARW

GDGNYWGRGTTLTVSSGGGGSGGGGSGGGGSDIEMTQSPAIMSASLGER

VTMTCTASSSVSSSYFHWYQQKPGSSPKLCIYSTSNLASGVPPRFSGSG

STSYSLTISSMEAEDAATYFCHQYHRSPTFGGGTKLETKRSGTTNTVAA

YNLTWKSTNFKTILEWEPKPVNQVYTVQISTKSGDWKSKCFYTTDTECD

LTDEIVKDVKQTYLARVFSYPAGNVESTGSAGEPLYENSPEFTPYLETN

LGQPTIQSFEQVGTKVNVTVEDERTLVRRNNTFLSLRDVFGKDLIYTLY

YWKSSSSGKKTAKTNTNEFLIDVDKGENYCFSVQAVIPSRTVNRKSTDS

PVECMGQEKGEFREQIVLTQSPAIMSASPGEKVTMTCSASSSVSYMNWY

QQKSGTSPKRWIYDTSKLASGVPAHFRGSGSGTSYSLTISGMEAEDAAT

YYCQQWSSNPFTFGSGTKLEINRGGGGSGGGGSGGGGSQVQLQQSGAEL

ARPGASVKMSCKASGYTFTRYTMHWVKQRPGQGLEWIGYINPSRGYTNY

NQKFKDKATLTTDKSSSTAYMQLSSLTSEDSAVYYCARYYDDHYCLDYW

GQGTTLTVSS.
```

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to

```
                                          (SEQ ID NO: 6)
GTGCAGCTGCAGCAGTCCGGACCCGAACTGGTCAAGCCCGGTGCCTCCG

TGAAAATGTCTTGTAAGGCTTCTGGCTACACCTTTACCTCCTACGTCAT

CCAATGGGTGAAGCAGAAGCCCGGTCAAGGTCTCGAGTGGATCGGCAGC

ATCAATCCCTACAACGATTACACCAAGTATAACGAAAAGTTTAAGGGCA

AGGCCACTCTGACAAGCGACAAGAGCTCCATTACCGCCTACATGGAGTT

TTCCTCTTTAACTTCTGAGGACTCCGCTTTATACTATTGCGCTCGTTGG

GGCGATGGCAATTATTGGGGCCGGGGAACTACTTTAACAGTGAGCTCCG

GCGGCGGCGGAAGCGGAGGTGGAGGATCTGGCGGTGGAGGCAGCGACAT

CGAGATGACACAGTCCCCCGCTATCATGAGCGCCTCTTTAGGAGAACGT

GTGACCATGACTTGTACAGCTTCCTCCAGCGTGAGCAGCTCCTATTTCC

ACTGGTACCAGCAGAAACCCGGCTCCTCCCCTAAACTGTGTATCTACTC

CACAAGCAATTTAGCTAGCGGCGTGCCTCCTCGTTTTAGCGGCTCCGGC

AGCACCTCTTACTCTTTAACCATTAGCTCTATGGAGGCCGAAGATGCCG

CCACATACTTTTGCCATCAGTACCACCGGTCCCCTACCTTTGGCGGAGG

CACAAAGCTGGAGACCAAGCGGAGCGGCACCACCAACACAGTGGCCGCC

TACAATCTGACTTGGAAATCCACCAACTTCAAGACCATCCTCGAGTGGG

AGCCCAAGCCCGTTAATCAAGTTTATACCGTGCAGATTTCCACCAAGAG

CGGCGACTGGAAATCCAAGTGCTTCTATACCACAGACACCGAGTGCGAT

CTCACCGACGAGATCGTCAAAGACGTGAAGCAGACATATTTAGCTAGGG

TGTTCTCCTACCCCGCTGGAAACGTGGAGAGCACCGGATCCGCTGGAGA

GCCTTTATACGAGAACTCCCCCGAATTCACCCCCTATCTGGAAACCAAT

TTAGGCCAGCCCACCATCCAGAGCTTCGAACAAGTTGGCACAAAGGTGA

ACGTCACCGTCGAAGATGAGAGGACTTTAGTGCGGAGGAACAATACATT

TTTATCCTTACGTGACGTCTTCGGCAAGGATTTAATCTACACACTGTAT

TACTGGAAGTCTAGCTCCTCCGGCAAGAAGACCGCCAAGACCAATACCA

ACGAATTTTAATTGACGTGGACAAGGGCGAGAACTACTGCTTCTCCGT

GCAAGCTGTGATCCCCTCCCGGACAGTGAACCGGAAGTCCACCGACTCC

CCCGTGGAGTGCATGGGCCAAGAAGGGAGAGTTTCGTGAGCAGATCG

TGCTGACCCAGTCCCCCGCTATTATGAGCGCTAGCCCCGGTGAAAAGGT

GACTATGACATGCAGCGCCAGCTCTTCCGTGAGCTACATGAACTGGTAT
```

CAGCAGAAGTCCGGCACCAGCCCTAAAAGGTGGATCTACGACACCAGCA

AGCTGGCCAGCGGCGTCCCCGCTCACTTTCGGGGCTCCGGCTCCGGAAC

AAGCTACTCTCTGACCATCAGCGGCATGGAAGCCGAGGATGCCGCTACC

TATTACTGTCAGCAGTGGAGCTCCAACCCCTTCACCTTTGGATCCGGCA

CCAAGCTCGAGATTAATCGTGGAGGCGGAGGTAGCGGAGGAGGCGGATC

CGGCGGTGGAGGTAGCCAAGTTCAGCTCCAGCAAAGCGGCGCCGAACTC

GCTCGGCCCGGCGCTTCCGTGAAGATGTCTTGTAAGGCCTCCGGCTATA

CCTTCACCCGGTACACAATGCACTGGGTCAAGCAACGGCCCGGTCAAGG

TTTAGAGTGGATTGGCTATATCAACCCCTCCCGGGGCTATACCAACTAC

AACCAGAAGTTCAAGGACAAAGCCACCCTCACCACCGACAAGTCCAGCA

GCACCGCTTACATGCAGCTGAGCTCTTTAACATCCGAGGATTCCGCCGT

GTACTACTGCGCTCGGTACTACGACGATCATTACTGCCTCGATTACTGG

GGCCAAGGTACCACCTTAACAGTCTCCTCC.

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to (SEQ ID NO: 7)
MKWVTFISLLFLFSSAYSVQLQQSGPELVKPGASVKMSCKASGYTFTSY

VIQWVKQKPGQGLEWIGSINPYNDYTKYNEKFKGKATLTSDKSSITAYM

EFSSLTSEDSALYYCARWGDGNYWGRGTTLTVSSGGGGSGGGGSGGGGS

DIEMTQSPAIMSASLGERVTMTCTASSSVSSSYFHWYQQKPGSSPKLCI

YSTSNLASGVPPRFSGSGSTSYSLTISSMEAEDAATYFCHQYHRSPTFG

GGTKLETKRSGTTNTVAAYNLTWKSTNFKTILEWEPKPVNQVYTVQIST

KSGDWKSKCFYTTDTECDLTDEIVKDVKQTYLARVFSYPAGNVESTGSA

GEPLYENSPEFTPYLETNLGQPTIQSFEQVGTKVNVTVEDERTLVRRNN

TFLSLRDVFGKDLIYTLYYWKSSSSGKKTAKTNTNEFLIDVDKGENYCF

SVQAVIPSRTVNRKSTDSPVECMGQEKGEFREQIVLTQSPAIMSASPGE

KVTMTCSASSSVSYMNWYQQKSGTSPKRWIYDTSKLASGVPAHFRGSGS

GTSYSLTISGMEAEDAATYYCQQWSSNPFTFGSGTKLEINRGGGGSGGG

GSGGGGSQVQLQQSGAELARPGASVKMSCKASGYTFTRYTMHWVKQRPG

QGLEWIGYINPSRGYTNYNQKFKDKATLTTDKSSSTAYMQLSSLTSEDS

AVYYCARYYDDHYCLDYWGQGTTLTVSS.

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 8)
ATGAAATGGGTCACCTTCATCTCTTTACTGTTTTTATTTAGCAGCGCCT

ACAGCGTGCAGCTGCAGCAGTCCGGACCCGAACTGGTCAAGCCCGGTGC

CTCCGTGAAAATGTCTTGTAAGGCTTCTGGCTACACCTTTACCTCCTAC

GTCATCCAATGGGTGAAGCAGAAGCCCGGTCAAGGTCTCGAGTGGATCG

GCAGCATCAATCCCTACAACGATTACACCAAGTATAACGAAAAGTTTAA

GGGCAAGGCCACTCTGACAAGCGACAAGAGCTCCATTACCGCCTACATG

GAGTTTTCCTCTTTAACTTCTGAGGACTCCGCTTTATACTATTGCGCTC

GTTGGGGCGATGGCAATTATTGGGCCGGGGAACTACTTTAACAGTGAG

CTCCGGCGGCGGCGGAAGCGGAGGTGGAGGATCTGGCGGTGGAGGCAGC

GACATCGAGATGACACAGTCCCCCGCTATCATGAGCGCCTCTTTAGGAG

AACGTGTGACCATGACTTGTACAGCTTCCTCCAGCGTGAGCAGCTCCTA

TTTCCACTGGTACCAGCAGAAACCCGGCTCCTCCCCTAAACTGTGTATC

TACTCCACAAGCAATTTAGCTAGCGGCGTGCCTCCTCGTTTTAGCGGCT

CCGGCAGCACCTCTTACTCTTTAACCATTAGCTCTATGGAGGCCGAAGA

TGCCGCCACATACTTTTGCCATCAGTACCACCGGTCCCCTACCTTTGGC

GGAGGCACAAAGCTGGAGACCAAGCGGAGCGGCACCACCAACACAGTGG

CCGCCTACAATCTGACTTGGAAATCCACCAACTTCAAGACCATCCTCGA

GTGGGAGCCCAAGCCCGTTAATCAAGTTTATACCGTGCAGATTTCCACC

AAGAGCGGCGACTGGAAATCCAAGTGCTTCTATACCACAGACACCGAGT

GCGATCTCACCGACGAGATCGTCAAAGACGTGAAGCAGACATATTTAGC

TAGGGTGTTCTCCTACCCCGCTGGAAACGTGGAGAGCACCGGATCCGCT

GGAGAGCCTTTATACGAGAACTCCCCCGAATTCACCCCCTATCTGGAAA

CCAATTTAGGCCAGCCCACCATCCAGAGCTTCGAACAAGTTGGCACAAA

GGTGAACGTCACCGTCGAAGATGAGAGGACTTTAGTGCGGAGGAACAAT

ACATTTTTATCCTTACGTGACGTCTTCGGCAAGGATTTAATCTACACAC

TGTATTACTGGAAGTCTAGCTCCTCCGGCAAGAAGACCGCCAAGACCAA

TACCAACGAATTTTTAATTGACGTGGACAAGGGCGAGAACTACTGCTTC

TCCGTGCAAGCTGTGATCCCCTCCCGGACAGTGAACCGGAAGTCCACCG

ACTCCCCCGTGGAGTGCATGGGCCAAGAGAAGGGAGAGTTTCGTGAGCA

GATCGTGCTGACCCAGTCCCCCGCTATTATGAGCGCTAGCCCCGGTGAA

AAGGTGACTATGACATGCAGCGCCAGCTCTTCCGTGAGCTACATGAACT

GGTATCAGCAGAAGTCCGGCACCAGCCCTAAAAGGTGGATCTACGACAC

CAGCAAGCTGGCCAGCGGCGTCCCCGCTCACTTTCGGGGCTCCGGCTCC

GGAACAAGCTACTCTCTGACCATCAGCGGCATGGAAGCCGAGGATGCCG

CTACCTATTACTGTCAGCAGTGGAGCTCCAACCCCTTCACCTTTGGATC

CGGCACCAAGCTCGAGATTAATCGTGGAGGCGGAGGTAGCGGAGGAGGC

GGATCCGGCGGTGGAGGTAGCCAAGTTCAGCTCCAGCAAAGCGGCGCCG

AACTCGCTCGGCCCGGCGCTTCCGTGAAGATGTCTTGTAAGGCCTCCGG

CTATACCTTCACCCGGTACACAATGCACTGGGTCAAGCAACGGCCCGGT

CAAGGTTTAGAGTGGATTGGCTATATCAACCCCTCCCGGGGCTATACCA

-continued
ACTACAACCAGAAGTTCAAGGACAAAGCCACCCTCACCACCGACAAGTC

CAGCAGCACCGCTTACATGCAGCTGAGCTCTTTAACATCCGAGGATTCC

GCCGTGTACTACTGCGCTCGGTACTACGACGATCATTACTGCCTCGATT

ACTGGGGCCAAGGTACCACCTTAACAGTCTCCTCC.

Non-limiting aspects of these chimeric polypeptides, nucleic acids, vectors, cells, and methods are described below, and can be used in any combination without limitation. Additional aspects of these chimeric polypeptides, nucleic acids, vectors, cells, and methods are known in the art.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the Ile-$^{154}$-Arg$^{152}$ bond in the short linker region between the EGF2 and the protease domain. This cleavage results in the light and heavy chains being held together by a single disulfide bond of Cys$^{135}$ and Cys$^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of His$^{193}$, Asp$^{242}$, and Ser$^{344}$, and binding of a single $Ca^{2+}$ ion within the FVIIa protease domain is critical for its catalytic activity. Proteolytic activation of FVII to FVIIa frees the newly formed amino terminus at Ile$^{153}$ to fold back and be inserted into the activation pocket forming a salt bridge with the carboxylate of Asp$^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues Arg$^{135}$ and Phe$^{140}$ located on the protruding B-C loop provide an independent contact with FVIIa. Leu$^{133}$ is located at the base of the fingerlike structure and packed into the cleft between the two modules. This provides continuity to a major cluster of important binding residues consisting of Lys$^{20}$, Thr$^{60}$, Asp$^{58}$, and Ile$^{22}$. Thr$^{60}$ is only partially solvent-exposed and may play a local structural role rather than making a significant contact with ligand. The binding site extends onto the concave side of the intermodule angle involving Glu$^{24}$ and Gln$^{110}$, and potentially the more distant residue Val$^{207}$. The binding region extends from Asp$^{58}$ onto a convex surface area formed by Lys$^{48}$, Lys$^{46}$, Gln$^{37}$, Asp$^{44}$, and Trp$^{45}$. Trp$^{45}$ and Asp$^{44}$ do not interact independently with FVIIa, indicating that the mutational effect at the Trp$^{45}$ position may reflect a structural importance of this side chain for the local packing of the adjacent Asp$^{44}$ and Gln$^{37}$ side chain. The interactive area further includes two surface-exposed aromatic residues, Phe$^{76}$ and Tyr$^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues Lys$^{165}$ and Lys$^{166}$ have also been demonstrated to be important for substrate recognition and binding. Mutation of either of these residues to alanine results in a significant decrease in the tissue factor co-factor function. Lys$^{165}$ and Lys$^{166}$ face away from each other, with Lys$^{165}$ pointing towards FVIIa in most tissue factor-FVIIa structures, and Lys$^{166}$ pointing into the substrate binding exosite region in the crystal structure. Putative salt bridge formation between Lys$^{165}$ of and Gla$^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Soluble Tissue Factor Domain

In some embodiments of any of the single-chain chimeric polypeptides, compositions, or methods described herein, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

Exemplary Soluble Human Tissue Factor Domain
(SEQ ID NO: 9)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

Exemplary Nucleic Acid Encoding Soluble Human Tissue Factor Domain
(SEQ ID NO: 10)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG

Exemplary Soluble Mouse Tissue Factor Domain
(SEQ ID NO: 11)
agipekafnltwistdfktilewqpkptnytytvqisdrsrnwknkcfs ttdtecdltdeivkdvtwayeakvlsvprrnsvhgdgdqlvihgeeppf tnapkflpyrdtnlgqpviqqfeqdgrklnvvvkdsltlvrkngtfltl rqvfgkdlgyiityrkgsstgkktnitntnefsidveegvsycffvqam ifsrktnqnspgsstveteqwksflge Exemplary Soluble Rat Tissue Factor Domain
(SEQ ID NO: 12)
Agtppgkafnltwistdfktilewqpkptnytytvqisdrsrnwkykct gttdtecdltdeivkdvnwtyearvlsvpwrnsthgketlfgthgeepp ftnarkflpyrdtkigqpviqkyeqggtklkvtvkdsftlvrkngtflt lrqvfgndlgyiltyrkdsstgrktntthtneflidvekgvsycffaqa vifsrktnhkspesitkcteqwksvlge -continued Exemplary Mutant Soluble Human Tissue Factor
Domain
(SEQ ID NO: 96)
SGTTNTVAAYNLTWKSTNFATALEWEPKPVNQVYTVQISTKSGDWKSKC

FYTTDTECALTDEIVKDVKQTYLARVFSYPAGNVESTGSAGEPLYENSP

EFTPYLETNLGQPTIQSFEQVGTKVNVTVEDERTLVARNNTALSLRDVF

GKDLIYTLYYWKSSSSGKKTAKTNTNEFLIDVDKGENYCFSVQAVIPSR

TVNRKSTDSPVECMGQEKGEFRE

Exemplary Mutant Soluble Human Tissue Factor
Domain
(SEQ ID NO: 97)
SGTTNTVAAYNLTWKSTNFATALEWEPKPVNQVYTVQISTKSGDAKSKC

FYTTDTECALTDEIVKDVKQTYLARVFSYPAGNVESTGSAGEPLAENSP

EFTPYLETNLGQPTIQSFEQVGTKVNVTVEDERTLVARNNTALSLRDVF

GKDLIYTLYYWKSSSSGKKTAKTNTNEFLIDVDKGENYCFSVQAVIPSR

TVNRKSTDSPVECMGQEKGEFRE

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 9, 11, 12, 96, or 97. In some embodiments, a soluble tissue factor domain can include a sequence of SEQ ID NO: 9, 11, 12, 96, or 97 with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples of any of the single-chain chimeric polypeptides described herein, the soluble tissue factor domain is not capable of binding to Factor VIIa. In some examples of any of the single-chain chimeric polypeptides described herein, the soluble tissue factor domain does not convert inactive Factor X into Factor Xa. In some embodiments of any of the single-chain chimeric polypeptides described herein, the single-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 96 or SEQ ID NO: 97.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 10.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

In some embodiments, the soluble tissue factor domain can comprise or consist of a soluble wildtype human tissue factor (or any sequence therefrom).

Linker Sequences

In some embodiments, the linker sequence can be a flexible linker sequence. Non-limiting examples of linker sequences that can be used are described in Klein et al., Protein Engineering, Design & Selection Vol. 27, No. 10, pp. 325-330, 2014; Priyanka et al., Protein Sci., 2013 February; 22(2):153-167. In some examples, the linker sequence is a synthetic linker sequence.

In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art). In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) sequences, e.g., 1, 2, 3, 4, 5, 6, 7, 8, 9, or 10 or more GGGS sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker has one or more Gly-Gly-Ser-Gly (GGSG) sequences, e.g., 1, 2, 3, 4, 5, 6, 7, 8, 9, or 10 or more GGSG sequences.

In some embodiments, the linker sequence can comprise or consist of GGGGSGGGGSGGGGS (SEQ ID NO: 13). In some embodiments, the linker sequence can be encoded by a nucleic acid comprising or consisting of: GGCGGTGGAGGATCCGGAGGAGGTGGCTCCGGCGGCGGAGGATCT (SEQ ID NO: 14). In some embodiments, the linker sequence can comprise or consist of: GGGSGGGS (SEQ ID NO: 15).

Target-Binding Domains

In some embodiments of any of the single-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein), and a soluble interleukin or cytokine receptor (e.g., any of the exemplary soluble interleukin receptors or soluble cytokine receptors described herein).

In some embodiments of any of the single-chain chimeric polypeptides described herein, one or more of the first target-binding domain (e.g., any of the exemplary first target binding domains described herein or known in the art), the second target-binding domain (e.g., any of the exemplary second target binding domains described herein or known in the art), and the one or more additional target binding domains can each, independently, bind specifically to a target selected from the group of: bind specifically to a target selected from the group consisting of: CD16a, CD28, CD3 (e.g., one or more of CD3α, CD3β, CD3δ, CD3 ε, and CD3γ), CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16- binding protein (e.g., ULBP1, ULBP2, ULBP3, ULBP4, ULBP5, and ULBP6), HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1 \times 10^{-7}$ M, less than $1 \times 10^{-8}$M, less than $1 \times 10^{-9}$M, less than $1 \times 10^{-10}$ M less than $1 \times 10^{-11}$M, less than $1 \times 10^{-12}$M, or less than $1 \times 10^{-13}$M. In some embodiments, the antigen-binding protein construct provided herein can bind to an identifying antigen with a $K_D$ of about $1 \times 10^{-3}$M to about $1 \times 10^{-5}$ M, about $1 \times 10^{-4}$ M to about $1 \times 10^{-6}$ M, about $1 \times 10^{-5}$M to about $1 \times 10^{-7}$ M, about $1 \times 10^{-6}$M to about $1 \times 10^{-8}$M, about $1 \times 10^{-7}$ M to about $1 \times 10^{-9}$M, about $1 \times 10^{-8}$M to about $1 \times 10^{-10}$ M, or about $1 \times 10^{-9}$M to about $1 \times 10^{-11}$M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 30 nM, about 30 pM to about 25 nM, about 30 pM to about 30 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 30 nM, about 60 pM to about 25 nM, about 60 pM to about 30 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 30 nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about 25 nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the single-chain chimeric polypeptides described herein, the first target-binding domain and the second target-binding domain bind specifically to the same antigen. In some embodiments of these single-chain chimeric polypeptides, the first target-binding domain and the second target-binding domain bind specifically to the same epitope. In some embodiments of these single-chain chimeric polypeptides, the first target-binding domain and the second target-binding domain include the same amino acid sequence.

In some embodiments of any of the single-chain chimeric polypeptides described herein, the first target-binding domain and the second target-binding domain bind specifically to different antigens.

In some embodiments of any of the single-chain chimeric polypeptides described herein, one or both of the first target-binding domain and the second target-binding domain is an antigen-binding domain. In some embodiments of any of the single-chain chimeric polypeptides described herein, the first target-binding domain and the second target-binding domain are each an antigen-binding domain.

In some embodiments of any of the single-chain chimeric polypeptides described herein, the antigen-binding domain includes or is a scFv or a single domain antibody (e.g., a $V_HH$ or a $V_{NAR}$ domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif.* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11(4): 121-129, 2002), IL-8 (see, e.g., those described in U.S. Pat. No. 6,117,980), TNFα (see, e.g., those described in Geng et al., *Immunol. Res.* 62(3):377-385, 2015), CD26a (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48(5):497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUC5AC (see, e.g., those described in U.S. Pat. No. 9,238,084), Trop-2 (see, e.g., those described in WO 2013/068946), CMET (see, e.g., those described in Edwardraj a et al., *Biotechnol. Bioeng.* 106(3):367-375, 2010), EGFR (see, e.g., those described in Akbari et al., *Protein Expr. Purif.* 127:8-15, 2016), HER1 (see, e.g., those described in U.S. Patent Application Publication No. 2013/0274446), HER2 (see, e.g., those described in Cao et al., *Biotechnol. Lett.* 37(7):1347-1354, 2015), HER3 (see, e.g., those described in U.S. Pat. No. 9,505,843), PSMA (see, e.g., those described in Parker et al., *Protein Expr. Purif.* 89(2):136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26(6):1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14(2):123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), or PDGFDD (see, e.g., those described in U.S. Pat. No. 9,441,034).

The antigen-binding domains present in any of the single-chain chimeric polypeptides described herein are each independently selected from the group consisting of: a VHH domain, a VNAR domain, and a scFv.

In some embodiments, the first target binding domain, the second target-binding domain, and/or one or more of the one or more additional antigen-binding domains can be an anti-CD3 scFv. In some embodiments, the anti-CD3 scFv can include a heavy chain variable domain including a sequence that is at least 70% identical (e.g., at least 75% identical, at least 80% identical, at least 85% identical, at least 90% identical, at least 95% identical, at least 99% identical, or 100% identical) to (SEQ ID NO: 16)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSS and/or a light chain variable domain including a sequence that is at least 70% identical (e.g., at least 75% identical, at least 80% identical, at least 85% identical, at least 90% identical, at least 95% identical, at least 99% identical, or 100% identical) to (SEQ ID NO: 17)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINR.

In some embodiments, a scFv (e.g., any of the scFvs described herein) can include a linker sequence (e.g., any of the exemplary linker sequences described herein or known in the art) between the heavy chain variable domain and the light chain variable domain. In some embodiments, the anti-CD3 scFv can include a heavy chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to (SEQ ID NO: 18)
CAAGTTCAGCTCCAGCAAAGCGGCGCCGAACTCGCTCGGCCCGGCGCTTC

CGTGAAGATGTCTTGTAAGGCCTCCGGCTATACCTTCACCCGGTACACAA

TGCACTGGGTCAAGCAACGGCCCGGTCAAGGTTTAGAGTGGATTGGCTAT

ATCAACCCCTCCCGGGGCTATACCAACTACAACCAGAAGTTCAAGGACAA

AGCCACCCTCACCACCGACAAGTCCAGCAGCACCGCTTACATGCAGCTGA

GCTCTTTAACATCCGAGGATTCCGCCGTGTACTACTGCGCTCGGTACTAC

GACGATCATTACTGCCTCGATTACTGGGGCCAAGGTACCACCTTAACAGT

CTCCTCC, and/or a light chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to (SEQ ID NO: 19)
CAGATCGTGCTGACCCAGTCCCCCGCTATTATGAGCGCTAGCCCCGGTGA

AAAGGTGACTATGACATGCAGCGCCAGCTCTTCCGTGAGCTACATGAACT

GGTATCAGCAGAAGTCCGGCACCAGCCCTAAAAGGTGGATCTACGACACC

AGCAAGCTGGCCAGCGGCGTCCCCGCTCACTTTCGGGGCTCCGGCTCCGG

AACAAGCTACTCTCTGACCATCAGCGGCATGGAAGCCGAGGATGCCGCTA

CCTATTACTGTCAGCAGTGGAGCTCCAACCCCTTCACCTTTGGATCCGGC

ACCAAGCTCGAGATTAATCGT.

In some embodiments, an anti-CD3 scFv can include a sequence that is at least 70% identical (e.g., at least 75% identical, at least 80% identical, at least 85% identical, at least 90% identical, at least 95% identical, at least 99% identical, or 100% identical) to (SEQ ID NO: 20)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSS.

In some embodiments, an anti-CD3 scFv can include the six CDRs present in SEQ ID NO: 20.

In some embodiments, an anti-CD3 scFv can include a sequence encoded by a nucleic acid sequence that is at least 70% identical (e.g., at least 75% identical, at least 80% identical, at least 85% identical, at least 90% identical, at least 95% identical, at least 99% identical, or 100% identical) to (SEQ ID NO: 21)
CAGATCGTGCTGACCCAGTCCCCCGCTATTATGAGCGCTAGCCCCGGTGA

AAAGGTGACTATGACATGCAGCGCCAGCTCTTCCGTGAGCTACATGAACT

GGTATCAGCAGAAGTCCGGCACCAGCCCTAAAAGGTGGATCTACGACACC

AGCAAGCTGGCCAGCGGCGTCCCCGCTCACTTTCGGGGCTCCGGCTCCGG

```
AACAAGCTACTCTCTGACCATCAGCGGCATGGAAGCCGAGGATGCCGCTA

CCTATTACTGTCAGCAGTGGAGCTCCAACCCCTTCACCTTTGGATCCGGC

ACCAAGCTCGAGATTAATCGTGGAGGCGGAGGTAGCGGAGGAGGCGGATC

CGGCGGTGGAGGTAGCCAAGTTCAGCTCCAGCAAAGCGGCGCCGAACTCG

CTCGGCCCGGCGCTTCCGTGAAGATGTCTTGTAAGGCCTCCGGCTATACC

TTCACCCGGTACACAATGCACTGGGTCAAGCAACGGCCCGGTCAAGGTTT

AGAGTGGATTGGCTATATCAACCCCTCCCGGGGCTATACCAACTACAACC

AGAAGTTCAAGGACAAAGCCACCCTCACCACCGACAAGTCCAGCAGCACC

GCTTACATGCAGCTGAGCTCTTTAACATCCGAGGATTCCGCCGTGTACTA

CTGCGCTCGGTACTACGACGATCATTACTGCCTCGATTACTGGGGCCAAG

GTACCACCTTAACAGTCTCCTCC.
```

In some embodiments, the first target binding domain, the second target-binding domain, and/or one or more of the one or more additional antigen-binding domains can be an anti-CD28 scFv. In some embodiments, the anti-CD28 scFv can include a heavy chain variable domain including a sequence that is at least 70% identical (e.g., at least 75% identical, at least 80% identical, at least 85% identical, at least 90% identical, at least 95% identical, at least 99% identical, or 100% identical) to

```
                                       (SEQ ID NO: 22)
DIEMTQSPAIMSASLGERVTMTCTASSSVSSSYFHWYQQKPGSSPKLCIY

STSNLASGVPPRFSGSGSTSYSLTISSMEAEDAATYFCHQYHRSPTFGGG

TKLETKR
``` and/or a light chain variable domain including a sequence that is at least 70% identical (e.g., at least 75% identical, at least 80% identical, at least 85% identical, at least 90% identical, at least 95% identical, at least 99% identical, or 100% identical) to

```
                                       (SEQ ID NO: 23)
VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSS.
```

In some embodiments, the anti-CD28 scFv can include a heavy chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to

```
                                       (SEQ ID NO: 24)
GACATCGAGATGACACAGTCCCCCGCTATCATGAGCGCCTCTTTAGGAGA

ACGTGTGACCATGACTTGTACAGCTTCCTCCAGCGTGAGCAGCTCCTATT

TCCACTGGTACCAGCAGAAACCCGGCTCCTCCCCTAAACTGTGTATCTAC

TCCACAAGCAATTTAGCTAGCGGCGTGCCTCCTCGTTTTAGCGGCTCCGG

CAGCACCTCTTACTCTTTAACCATTAGCTCTATGGAGGCCGAAGATGCCG

CCACATACTTTTGCCATCAGTACCACCGGTCCCCTACCTTTGGCGGAGGC

ACAAAGCTGGAGACCAAGCGG,
``` and/or a light chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to

```
                                       (SEQ ID NO: 25)
GTGCAGCTGCAGCAGTCCGGACCCGAACTGGTCAAGCCCGGTGCCTCCGT

GAAAATGTCTTGTAAGGCTTCTGGCTACACCTTTACCTCCTACGTCATCC

AATGGGTGAAGCAGAAGCCCGGTCAAGGTCTCGAGTGGATCGGCAGCATC

AATCCCTACAACGATTACACCAAGTATAACGAAAAGTTTAAGGGCAAGGC

CACTCTGACAAGCGACAAGAGCTCCATTACCGCCTACATGGAGTTTTCCT

CTTTAACTTCTGAGGACTCCGCTTTATACTATTGCGCTCGTTGGGGCGAT

GGCAATTATTGGGCCGGGGAACTACTTTAACAGTGAGCTCC.
```

In some embodiments, an anti-CD28 scFv can include a sequence that is at least 70% identical (e.g., at least 75% identical, at least 80% identical, at least 85% identical, at least 90% identical, at least 95% identical, at least 99% identical, or 100% identical) to

```
                                       (SEQ ID NO: 26)
VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSSGGGGSGGGGSGGGGSDIEMTQSPAIMSASLGERVTM

TCTASSSVSSSYFHWYQQKPGSSPKLCIYSTSNLASGVPPRFSGSGSTSY

SLTISSMEAEDAATYFCHQYHRSPTFGGGTKLETKR.
```

In some embodiments, an anti-CD28 scFv can include the six CDRs present in SEQ ID NO: 26.

In some embodiments, an anti-CD28 scFv can include a sequence encoded by a nucleic acid sequence that is at least 70% identical (e.g., at least 75% identical, at least 80% identical, at least 85% identical, at least 90% identical, at least 95% identical, at least 99% identical, or 100% identical) to

```
                                       (SEQ ID NO: 27)
GTGCAGCTGCAGCAGTCCGGACCCGAACTGGTCAAGCCCGGTGCCTCCGT

GAAAATGTCTTGTAAGGCTTCTGGCTACACCTTTACCTCCTACGTCATCC

AATGGGTGAAGCAGAAGCCCGGTCAAGGTCTCGAGTGGATCGGCAGCATC

AATCCCTACAACGATTACACCAAGTATAACGAAAAGTTTAAGGGCAAGGC

CACTCTGACAAGCGACAAGAGCTCCATTACCGCCTACATGGAGTTTTCCT

CTTTAACTTCTGAGGACTCCGCTTTATACTATTGCGCTCGTTGGGGCGAT

GGCAATTATTGGGCCGGGGAACTACTTTAACAGTGAGCTCCGGCGGCGG

CGGAAGCGGAGGTGGAGGATCTGGCGGTGGAGGCAGCGACATCGAGATGA

CACAGTCCCCCGCTATCATGAGCGCCTCTTTAGGAGAACGTGTGACCATG
```

```
                                              -continued
ACTTGTACAGCTTCCTCCAGCGTGAGCAGCTCCTATTTCCACTGGTACCA

GCAGAAACCCGGCTCCTCCCCTAAACTGTGTATCTACTCCACAAGCAATT

TAGCTAGCGGCGTGCCTCCTCGTTTTAGCGGCTCCGGCAGCACCTCTTAC

TCTTTAACCATTAGCTCTATGGAGGCCGAAGATGCCGCCACATACTTTTG

CCATCAGTACCACCGGTCCCCTACCTTTGGCGGAGGCACAAAGCTGGAGA

CCAAGCGG.
```

In some embodiments, any of the antigen-binding domains described herein is a BiTe, a (scFv)₂, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the single-chain chimeric polypeptide are known in the art.

A VHH domain is a single monomeric variable antibody domain that can be found in camelids. A $V_{NAR}$ domain is a single monomeric variable antibody domain that can be found in cartilaginous fish. Non-limiting aspects of VHH domains and $V_{NAR}$ domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the single-chain chimeric polypeptides described herein are both VHH domains, or at least one antigen-binding domain is a VHH domain. In some embodiments, each of the antigen-binding domains in the single-chain chimeric polypeptides described herein are both VNAR domains, or at least one antigen-binding domain is a VNAR domain. In some embodiments, each of the antigen-binding domains in the single-chain chimeric polypeptides described herein are both scFv domains, or at least one antigen-binding domain is a scFv domain. DARTs are described in, e.g., Garber, *Nature Reviews Drug Discovery* 13:799-801, 2014.

In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the single-chain chimeric polypeptides described herein, one or both of the first target-binding domain and the second target-binding domain can be a soluble interleukin protein, soluble cytokine protein, or soluble cell surface protein. In some embodiments, the soluble interleukin or soluble cytokine protein, is selected from the group of: IL-2, IL-3, IL-7, IL-8, IL-10, IL-12, IL-15, IL-17, IL-18, IL-21, PDGF-DD, SCF, FLT3L. Non-limiting examples of soluble IL-2, IL-3, IL-7, IL-8, IL-10, IL-15, IL-17, IL-18, IL-21, PDGF-DD, SCF, and FLT3L are provided below.

```
Human Soluble IL-2
                                              (SEQ ID NO: 28)
aptssstkkt qlqlehllld lqmilnginn yknpkltrml tfkfympkka telkhlqcle eelkpleevl nlaqsknfhl rprdlisnin vivlelkgse ttfmceyade tativeflnr witfcqsiis tlt Human Soluble IL-3
                                              (SEQ ID NO: 29)
apmtqttplkt swvncsnmid eiithlkqpp plldfnnln gedqdilmen nlrrpnleaf nravkslqna saiesilknl lpclplataa ptrhpihikd gdwnefrrkl tfylktlena qaqqttlsla if Human Soluble IL-7
                                              (SEQ ID NO: 30)
dcdiegkdgkqyesv lmvsidqlld smkeigsncl nnefnffkrh icdankegmf lfraarklrq flkmnstgdf dlhllkvseg ttillnctgq vkgrkpaalg eaqptkslee nkslkeqkkl ndlcflkrll qeiktcwnki lmgtkeh Human Soluble IL-8
                                              (SEQ ID NO: 31)
egavlprsak elrcqcikty skpfhpkfik elrviesgph canteiivkl sdgrelcldp kenwvqrvve kflkraens
```

-continued

Human Soluble IL-10
(SEQ ID NO: 32)
spgqgtqsensc thfpgnlpnm lrdlrdafsr vktffqmkdq ldnlllkesl ledfkgylgc qalsemiqfy leevmpqaen qdpdikahvn slgenlktlr lrlrrchrfl pcenkskave qvknafnklq ekgiykamse fdifinyiea ymtmkirn Human Soluble IL-12β (p40)
(SEQ ID NO: 33)
IWELKKDVYVVELDWYPDAPGEMVVLTCDTPEEDGITWTLDQSSEVLGSGKTLT

IQVKEFGDAGQYTCHKGGEVLSHSLLLLHKKEDGIWSTDILKDQKEPKNKTFLR

CEAKNYSGRFTCWWLTTISTDLTFSVKSSRGSSDPQGVTCGAATLSAERVRGDNK

EYEYSVECQEDSACPAAEESLPIEVMVDAVHKLKYENYTSSFFIRDIIKPDPPKNL

QLKPLKNSRQVEVSWEYPDTWSTPHSYFSLTFCVQVQGKSKREKKDRVFTDKTS

ATVICRKNASISVRAQDRYYSSSWSEWASVPCS

Nucleic Acid Encoding Human Soluble IL-12β (p40)
(SEQ ID NO: 34)
ATTTGGGAACTGAAGAAGGACGTCTACGTGGTCGAACTGGACTGGTATCCCGA

TGCTCCCGGCGAAATGGTGGTGCTCACTTGTGACACCCCCGAAGAAGACGGC

ATCACTTGGACCCTCGATCAGAGCAGCGAGGTGCTGGGCTCCGGAAAGACCC

TCACAATCCAAGTTAAGGAGTTCGGAGACGCTGGCCAATACACATGCCACAA

GGGAGGCGAGGTGCTCAGCCATTCCTTATTATTATTACACAAGAAGGAAGACG

GAATCTGGTCCACCGACATTTTAAAAGATCAGAAGGAGCCCAAGAATAAGAC

CTTTTTAAGGTGTGAGGCCAAAAACTACAGCGGTCGTTTCACTTGTTGGTGGC

TGACCACCATTTCCACCGATTTAACCTTCTCCGTGAAAAGCAGCCGGGGAAGC

TCCGACCCTCAAGGTGTGACATGTGGAGCCGCTACCCTCAGCGCTGAGAGGG

TTCGTGGCGATAACAAGGAATACGAGTACAGCGTGGAGTGCCAAGAAGATAG

CGCTTGTCCCGCTGCCGAAGAATCTTTACCCATTGAGGTGATGGTGGACGCCG

TGCACAAACTCAAGTACGAGAACTACACCTCCTCCTTCTTTATCCGGGACATCA

TTAAGCCCGATCCTCCTAAGAATTTACAGCTGAAGCCTCTCAAAAATAGCCGG

CAAGTTGAGGTCTCTTGGGAATATCCCGACACTTGGAGCACACCCCACAGCTA

CTTCTCTTTAACCTTTTGTGTGCAAGTTCAAGGTAAAAGCAAGCGGGAGAAGA

AAGACCGGGTGTTTACCGACAAAACCAGCGCCACCGTCATCTGTCGGAAGAA

CGCCTCCATCAGCGTGAGGGCTCAAGATCGTTATTACTCCAGCAGCTGGTCCG

AGTGGGCCAGCGTGCCTTGTTCC

Human Soluble IL-12α (p35)
(SEQ ID NO: 35)
RNLPVATPDPGMFPCLHHSQNLLRAVSNMLQKARQTLEFYPCTSEEIDHEDITKD

KTSTVEACLPLELTKNESCLNSRETSFITNGSCLASRKTSFMMALCLSSIYEDLKM

YQVEFKTMNAKLLMDPKRQIFLDQNMLAVIDELMQALNFNSETVPQKSSLEEPD

FYKTKIKLCILLHAFRIRAVTIDRVMSYLNAS

Nucleic Acid Encoding Human Soluble IL-12α (p35)
(SEQ ID NO: 36)
CGTAACCTCCCCGTGGCTACCCCCGATCCCGGAATGTTCCCTTGTTTACACCAC

AGCCAGAATTTACTGAGGGCCGTGAGCAACATGCTGCAGAAAGCTAGGCAGA

CTTTAGAATTTTACCCTTGCACCAGCGAGGAGATCGACCATGAAGATATCACCA

AGGACAAGACATCCACCGTGGAGGCTTGTTTACCTCTGGAGCTGACAAAGAA

-continued

```
CGAGTCTTGTCTCAACTCTCGTGAAACCAGCTTCATCACAAATGGCTCTTGTTT

AGCTTCCCGGAAGACCTCCTTTATGATGGCTTTATGCCTCAGCTCCATCTACGA

GGATTTAAAGATGTACCAAGTGGAGTTCAAGACCATGAACGCCAAGCTGCTCA

TGGACCCTAAACGGCAGATCTTTTTAGACCAGAACATGCTGGCTGTGATTGAT

GAGCTGATGCAAGCTTTAAACTTCAACTCCGAGACCGTCCCTCAGAAGTCCTC

CCTCGAGGAGCCCGATTTTTACAAGACAAAGATCAAACTGTGCATTTTACTCC

ACGCCTTTAGGATCCGGGCCGTGACCATTGACCGGGTCATGAGCTATTTAAAC

GCCAGC
```

Exemplary Human Soluble IL-12
(SEQ ID NO: 37)
```
IWELKKDVYVVELDWYPDAPGEMVVLTCDTPEEDGITWTLDQSSEVLGSGKTLT

IQVKEFGDAGQYTCHKGGEVLSHSLLLLHKKEDGIWSTDILKDQKEPKNKTFLR

CEAKNYSGRFTCWWLTTISTDLTFSVKSSRGSSDPQGVTCGAATLSAERVRGDN

KEYEYSVECQEDSACPAAEESLPIEVMVDAVHKLKYENYTSSFFIRDIIKPDPPKN

LQLKPLKNSRQVEVSWEYPDTWSTPHSYFSLTFCVQVQGKSKREKKDRVFTDKT

SATVICRKNASISVRAQDRYYSSSWSEWASVPCSGGGGSGGGGSGGGGSRNLPV

ATPDPGMFPCLHHSQNLLRAVSNMLQKARQTLEFYPCTSEEIDHEDITKDKTSTV

EACLPLELTKNESCLNSRETSFITNGSCLASRKTSFMMALCLSSIYEDLKMYQVEF

KTMNAKLLMDPKRQIFLDQNMLAVIDELMQALNFNSETVPQKSSLEEPDFYKTK

IKLCILLHAFRIRAVTIDRVMSYLNAS
```

Nucleic Acid Encoding Exemplary Human Soluble IL-12
(SEQ ID NO: 38)
```
ATTTGGGAACTGAAGAAGGACGTCTACGTGGTCGAACTGGACTGGTATCCCG

ATGCTCCCGGCGAAATGGTGGTGCTCACTTGTGACACCCCCGAAGAAGACGG

CATCACTTGGACCCTCGATCAGAGCAGCGAGGTGCTGGGCTCCGGAAAGACC

CTCACAATCCAAGTTAAGGAGTTCGGAGACGCTGGCCAATACACATGCCACA

AGGGAGGCGAGGTGCTCAGCCATTCCTTATTATTATTACACAAGAAGGAAGA

CGGAATCTGGTCCACCGACATTTTAAAAGATCAGAAGGAGCCCAAGAATAAG

ACCTTTTTAAGGTGTGAGGCCAAAAACTACAGCGGTCGTTTCACTTGTTGGTG

GCTGACCACCATTTCCACCGATTTAACCTTCTCCGTGAAAAGCAGCCGGGGA

AGCTCCGACCCTCAAGGTGTGACATGTGGAGCCGCTACCCTCAGCGCTGAGA

GGGTTCGTGGCGATAACAAGGAATACGAGTACAGCGTGGAGTGCCAAGAAG

ATAGCGCTTGTCCCGCTGCCGAAGAATCTTTACCCATTGAGGTGATGGTGGAC

GCCGTGCACAAACTCAAGTACGAGAACTACACCTCCTCCTTCTTTATCCGGGA

CATCATTAAGCCCGATCCTCCTAAGAATTTACAGCTGAAGCCTCTCAAAAATA

GCCGGCAAGTTGAGGTCTCTTGGGAATATCCCGACACTTGGAGCACACCCCA

CAGCTACTTCTCTTTAACCTTTTGTGTGCAAGTTCAAGGTAAAAGCAAGCGGG

AGAAGAAAGACCGGGTGTTTACCGACAAAACCAGCGCCACCGTCATCTGTCG

GAAGAACGCCTCCATCAGCGTGAGGGCTCAAGATCGTTATTACTCCAGCAGC

TGGTCCGAGTGGGCCAGCGTGCCTTGTTCCGGCGGTGGAGGATCCGGAGGAG

GTGGCTCCGGCGGCGGAGGATCTCGTAACCTCCCCGTGGCTACCCCCGATCC

CGGAATGTTCCCTTGTTTACACCACAGCCAGAATTTACTGAGGGCCGTGAGC
```

-continued

```
AACATGCTGCAGAAAGCTAGGCAGACTTTAGAATTTTACCCTTGCACCAGCG

AGGAGATCGACCATGAAGATATCACCAAGGACAAGACATCCACCGTGGAGG

CTTGTTTACCTCTGGAGCTGACAAAGAACGAGTCTTGTCTCAACTCTCGTGAA

ACCAGCTTCATCACAAATGGCTCTTGTTTAGCTTCCCGGAAGACCTCCTTTAT

GATGGCTTTATGCCTCAGCTCCATCTACGAGGATTTAAAGATGTACCAAGTGG

AGTTCAAGACCATGAACGCCAAGCTGCTCATGGACCCTAAACGGCAGATCTT

TTTAGACCAGAACATGCTGGCTGTGATTGATGAGCTGATGCAAGCTTTAAACT

TCAACTCCGAGACCGTCCCTCAGAAGTCCTCCCTCGAGGAGCCCGATTTTTAC

AAGACAAAGATCAAACTGTGCATTTTACTCCACGCCTTTAGGATCCGGGCCG

TGACCATTGACCGGGTCATGAGCTATTTAAACGCCAGC
```

Human Soluble IL-15
(SEQ ID NO: 39)
Nwvnvisdlkki edliqsmhid atlytesdvh psckvtamkc fllelqvisl esgdasihdt venliilann slssngnvte sgckeceele eknikeflqs fvhivqmfin ts Human Soluble IL-17
(SEQ ID NO: 40)
gitiprn pgcpnsedkn fprtvmvnln ihnrntntnp krssdyynrs tspwnlhrne dperypsviw eakcrhlgci nadgnvdyhm nsvpiqqeil vlrrepphcp nsfrlekilv svgctcvtpi vhhva Human Soluble IL-18
(SEQ ID NO: 41)
YFGKLESKLSVIRNLNDQVLFIDQGNRPLFEDMTDSDCRDNAPRTIFIISMYKDSQPRG

MAVTISVKCEKISTLSCENKIISFKEMNPPDNIKDTKSDIIFFQRSVPGHDNKMQFESS

SYEGYFLACEKERDLFKLILKKEDELGDRSIMFTVQNED

Nucleic Acid Encoding Human Soluble IL-18
(SEQ ID NO: 42)
```
TACTTCGGCAAACTGGAATCCAAGCTGAGCGTGATCCGGAATTTAAACGACCA

AGTTCTGTTTATCGATCAAGGTAACCGGCCTCTGTTCGAGGACATGACCGACT

CCGATTGCCGGGACAATGCCCCCCGGACCATCTTCATTATCTCCATGTACAAGG

ACAGCCAGCCCCGGGGCATGGCTGTGACAATTAGCGTGAAGTGTGAGAAAAT

CAGCACTTTATCTTGTGAGAACAAGATCATCTCCTTTAAGGAAATGAACCCCC

CCGATAACATCAAGGACACCAAGTCCGATATCATCTTCTTCCAGCGGTCCGTGC

CCGGTCACGATAACAAGATGCAGTTCGAATCCTCCTCCTACGAGGGCTACTTTT

TAGCTTGTGAAAAGGAGAGGGATTTATTCAAGCTGATCCTCAAGAAGGAGGA

CGAGCTGGGCGATCGTTCCATCATGTTCACCGTCCAAAACGAGGAT
```

Human Soluble IL-21
(SEQ ID NO: 43)
QGQDRHMIRMRQLIDIVDQLKNYVNDLVPEFLPAPEDVETNCEWSAFSCFQKAQ

LKSANTGNNERIINVSIKKLKRKPPSTNAGRRQKHRLTCPSCDSYEKKPPKEFLER

FKSLLQKMIHQHLSSRTHGSEDS

Nucleic Acid Encoding Human Soluble IL-21
(SEQ ID NO: 44)
```
CAGGGCCAGGACAGGCACATGATCCGGATGAGGCAGCTCATCGACATCGTCG

ACCAGCTGAAGAACTACGTGAACGACCTGGTGCCCGAGTTTCTGCCTGCCCC

CGAGGACGTGGAGACCAACTGCGAGTGGTCCGCCTTCTCCTGCTTTCAGAAG

GCCCAGCTGAAGTCCGCCAACACCGGCAACAACGAGCGGATCATCAACGTGA
```

```
GCATCAAGAAGCTGAAGCGGAAGCCTCCCTCCACAAACGCCGGCAGGAGGC

AGAAGCACAGGCTGACCTGCCCCAGCTGTGACTCCTACGAGAAGAAGCCCCC

CAAGGAGTTCCTGGAGAGGTTCAAGTCCCTGCTGCAGAAGATGATCCATCAG

CACCTGTCCTCCAGGACCCACGGCTCCGAGGACTCC
```

Human Soluble PDGF-DD
(SEQ ID NO: 45)
```
rdtsatpqsasi kalrnanlrr desnhltdly rrdetiqvkg ngyvqsprfp nsyprnlllt wrlhsqentr iqlvfdnqfg leeaendicr ydfvevedis etstiirgrw cghkevppri ksrtnqikit fksddyfvak pgfkiyysll edfqpaaase tnwesvtssi sgvsynspsv tdptliadal dkkiaefdtv edllkyfnpe swqedlenmy ldtpryrgrs yhdrkskvdl drinddakry sctprnysvn ireelklanv vffprcllvq rcggncgcgt vnwrsctcns gktvkkyhev lqfepghikr rgraktmalv diqldhherc dcicssrppr
```

Human Soluble SCF
(SEQ ID NO: 46)
```
egicrnrvtnnvkdv tklvanlpkd ymitikyvpg mdvlpshcwi semvvqlsds ltdlldkfsn iseglsnysi idklvnivdd lvecvkenss kdlkksfksp eprlftpeef frifnrsida fkdfvvaset sdcvvsstls pekdsrvsvt kpfmlppvaa sslrndsssss nrkaknppgd sslhwaamal palfsliigf afgalywkkr qpsltraven iqineednei smlqekeref qev
```

Human Soluble FLT3L
(SEQ ID NO: 47)
```
tqdcsfqhspissd favkirelsd yllqdypvtv asnlqdeelc gglwrlvlaq rwmerlktva gskmqgller vnteihfvtk cafqpppscl rfvqtnisrl lqetseqlva lkpwitrqnf srclelqcqp dsstlpppws prpleatapt apqppllllll llpvglllla aawclhwqrt rrrtprpgeq vppvpspqdl llveh
```

Exemplary soluble cell surface proteins include soluble MICA, MICB, and a ULP16 binding protein (e.g., ULBP1, ULBP2, ULBP3, ULBP4, ULBP5, or ULBP6). Exemplary sequences for soluble MICA, MICB, ULBP1, ULBP2, ULBP3, ULBP4, ULBP5, and ULBP6 are listed below.

Human Soluble MICA
(SEQ ID NO: 48)
```
ephslry nltvlswdgs vqsgfltevh lgqpflrcd rqkcrakpqg qwaedvlgnk twdretrdlt gngkdlrmtl ahikdqkegl hslqeirvce ihednstrss qhfyydgelf lsqnletkew tmpqssraqt lamnvrnflk edamktkthy hamhadclqe lrrylksgvv lrrtvppmvn vtrseasegn itvtcrasgf ypwnitlswr qdgvslshdt qqwgdvlpdg ngtyqtwvat ricqgeeqrf tcymehsgnh sthpvpsgkv lvlqshwqtf hvsavaaaai fviiifyvrc ckkktsaaeg pelvslqvld qhpvgtsdhr datqlgfqpl msdlgstgst ega
```

Human Soluble MICB
(SEQ ID NO: 49)
```
aephslry nlmvlsqdes vqsgflaegh ldgqpflryd rqkrrakpqg qwaedvlgak twdtetedlt engqdlrrtl thikdqkggl hslqeirvce ihedsstrgs rhfyydgelf lsqnletqes tvpqssraqt lamnvtnfwk edamktkthy ramqadclqk lqrylksgva irrtvppmvn vtcsevsegn itvtcrassf yprnitltwr qdgvslshnt qqwgdvlpdg ngtyqtwvat rirqgeeqrf tcymehsgnh gthpvpsgkv lvlqsqrtdf pyvsaampcf viiiilcvpc ckkktsaaeg pelvslqvld qhpvgtgdhr daaqlgfqpl msatgstgst ega
```

Human Soluble ULBP1
(SEQ ID NO: 50)
```
wvdthclcydfiit pksrpepqwc evqglvderp flhydcvnhk akafaslgkk vnvtktweeq tetlrdvvdf lkgqlldiqv
```

-continued enlipiepit lqarmscehe ahghgrgswq flfngqkfll fdsnnrkwta lhpgakkmte kweknrdvtm ffqkislgdc kmwleeflmy weqmldptkp pslapg Human Soluble ULBP2
(SEQ ID NO: 51)
gradphslcyditvi pkfrpgprwc avqgqvdekt flhydcgnkt vtpvsplgkk lnvttawkaq npvlrevvdi lteqlrdiql enytpkeplt lqarmsceqk aeghssgswq fsfdgqifll fdsekrmwtt vhpgarkmke kwendkvvam sfhyfsmgdc igwledflmg mdstlepsag aplams Human Soluble ULBP3
(SEQ ID NO: 52)
dahslwynfti ihlprhgqqw cevqsqvdqk nflsydcgsd kvlsmghlee qlyatdawgk qlemlrevgq rlrleladte ledftpsgpl tlqvrmscec eadgyirgsw qfsfdgrkfl lfdsnnrkwt vvhagarrmk ekwekdsglt tffkmvsmrd ckswlrdflm hrkkrlepta pptmapg Human Soluble ULBP4
(SEQ ID NO: 53)
hslcfnftik slsrpgqpwc eaqvflnknl flqynsdnnm vkplgllgkk vyatstwgel tqtlgevgrd lrmllcdikp qiktsdpstl qvemfcqrea erctgaswqf atngeksllf damnmtwtvi nheaskiket wkkdrgleky frklskgdcd hwlreflghw eampeptvsp vnasdihwss sslpdrwiil gafillvlmg ivlicvwwqn gewqaglwpl rts Human Soluble ULBP5
(SEQ ID NO: 54)
gladp hslcyditvi pkfrpgprwc avqgqvdekt flhydcgskt vtpvsplgkk lnvttawkaq npvlrevvdi lteqlldiql enyipkeplt lqarmsceqk aeghgsgswq lsfdgqifll fdsenrmwtt vhpgarkmke kwendkdmtm sfhyismgdc tgwledflmg mdstlepsag apptmssg Human Soluble ULBP6
(SEQ ID NO: 55)
rrddp hslcyditvi pkfrpgprwc avqgqvdekt flhydcgnkt vtpvsplgkk lnvtmawkaq npvlrevvdi lteqlldiql enytpkeplt lqarmsceqk aeghssgswq fsidgqtfll fdsekrmwtt vhpgarkmke kwendkdvam sfhyismgdc igwledflmg mdstlepsag aplamssg In some embodiments, a soluble IL-12 protein can include a first sequence that is at least 70% identical (e.g., at least 75% identical, at least 80% identical, at least 85% identical, at least 90% identical, at least 95% identical, at least 99% identical, or 100% identical) to SEQ ID NO: 33, and a second sequence that is at least 70% identical (e.g., at least 75% identical, at least 80% identical, at least 85% identical, at least 90% identical, at least 95% identical, at least 99% identical, or 100% identical) to SEQ ID NO: 35. In some embodiments, the soluble IL-12 can further include a linker sequence (e.g., any of the exemplary linker sequences described herein or known in the art) between the first sequence and the second sequence.

In some embodiments, a soluble IL-12 protein is encoded by a first nucleic acid encoding a first sequence at least 70% identical (e.g., at least 75% identical, at least 80% identical, at least 85% identical, at least 90% identical, at least 95% identical, at least 99% identical, or 100% identical) to SEQ ID NO: 34, and a second nucleic acid sequence encoding a second sequence that is at least 70% identical (e.g., at least 75% identical, at least 80% identical, at least 85% identical, at least 90% identical, at least 95% identical, at least 99% identical, or 100% identical) to SEQ ID NO: 36. In some embodiments, the nucleic acid encoding a soluble IL-12 protein further includes a nucleic acid sequence encoding a linker sequence (e.g., any of the exemplary linker sequences described herein or known in the art) between the first nucleic acid and the second nucleic acid.

In some embodiments, a soluble IL-12 protein includes a sequence that is at least 70% identical (e.g., at least 75% identical, at least 80% identical, at least 85% identical, at least 90% identical, at least 95% identical, at least 99% identical, or 100% identical) to SEQ ID NO: 37. In some embodiments, a soluble IL-12 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 38.

In some embodiments, a soluble IL-18 protein can include a sequence that is at least 70% identical (e.g., at least 75% identical, at least 80% identical, at least 85% identical, at least 90% identical, at least 95% identical, at least 99% identical, or 100% identical) to SEQ ID NO: 41. In some embodiments, a soluble IL-18 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 42.

In some embodiments, a soluble IL-21 protein can include a sequence that is at least 70% identical (e.g., at least 75% identical, at least 80% identical, at least 85% identical, at least 90% identical, at least 95% identical, at least 99% identical, or 100% identical) to SEQ ID NO: 43. In some embodiments, a soluble IL-21 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 44.

Additional examples of soluble interleukin proteins and soluble cytokine proteins are known in the art.

Soluble Receptor

In some embodiments of any of the single-chain chimeric polypeptides described herein, one or both of the first target-binding domain and the second target-binding domain is a soluble interleukin receptor, a soluble cytokine receptor, or a soluble cell surface receptor. In some embodiments, the soluble receptor is a soluble TGF-β receptor II (TGF-βRII) (see, e.g., those described in Yung et al., *Am. J. Resp. Crit. Care Med.* 194(9):1140-1151, 2016), a soluble TGF-βRIII (see, e.g., those described in Heng et al., *Placenta* 57:320, 2017), or a soluble NKG2D (see, e.g., Cosman et al., *Immunity* 14(2):123-133, 2001; Costa et al., *Front. Immunol.*, Vol. 9, Article 1150, May 29, 2018; doi: 10.3389/fimmu.2018.01150). In some embodiments, the soluble cell surface receptor is a soluble NKp30 (see, e.g., Costa et al., *Front. Immunol.*, Vol. 9, Article 1150, May 29, 2018; doi: 10.3389/fimmu.2018.01150), a soluble NKp44 (see, e.g., those described in Costa et al., *Front. Immunol.*, Vol. 9, Article 1150, May 29, 2018; doi: 10.3389/fimmu.2018.01150), a soluble NKp46 (see, e.g., Mandelboim et al., *Nature* 409:1055-1060, 2001; Costa et al., *Front. Immunol.*, Vol. 9, Article 1150, May 29, 2018; doi: 10.3389/fimmu.2018.01150), a soluble DNAM1 (see, e.g., those described in Costa et al., *Front. Immunol.*, Vol. 9, Article 1150, May 29, 2018; doi: 10.3389/fimmu.2018.01150), a scMHCI (see, e.g., those described in Washburn et al., *PLoS One* 6(3):e18439, 2011), a scMHCII (see, e.g., those described in Bishwajit et al., *Cellular Immunol.* 170(1):25-33, 1996), a scTCR (see, e.g., those described in Weber et al., *Nature* 356(6372):793-796, 1992), a soluble CD155 (see, e.g., those described in Tahara-Hanaoka et al., *Int. Immunol.* 16(4):533-538, 2004), or a soluble CD28 (see, e.g., Hebbar et al., *Clin. Exp. Immunol.* 136:388-392, 2004).

In some embodiments, a soluble TGFβRII receptor can include a first sequence that is at least 70% identical (e.g., at least 75% identical, at least 80% identical, at least 85% identical, at least 90% identical, at least 95% identical, at least 99% identical, or 100% identical) to:

(SEQ ID NO: 56)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD, and a second sequence that is at least 70% identical (e.g., at least 75% identical, at least 80% identical, at least 85% identical, at least 90% identical, at least 95% identical, at least 99% identical, or 100% identical) to:

(SEQ ID NO: 56)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments, the soluble TGFβRII receptor can further include a linker sequence (e.g., any of the exemplary linker sequences described herein or known in the art) between the first sequence and the second sequence.

In some embodiments, a soluble TGFβRII receptor is encoded by a first nucleic acid encoding a first sequence at least 70% identical (e.g., at least 75% identical, at least 80% identical, at least 85% identical, at least 90% identical, at least 95% identical, at least 99% identical, or 100% identical) to:

(SEQ ID NO: 57)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT, and a second nucleic acid sequence encoding a second sequence that is at least 70% identical (e.g., at least 75% identical, at least 80% identical, at least 85% identical, at least 90% identical, at least 95% identical, at least 99% identical, or 100% identical) to:

(SEQ ID NO: 57)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments, the nucleic acid encoding a soluble TGFβRII receptor further includes a nucleic acid sequence encoding a linker sequence (e.g., any of the exemplary linker sequences described herein or known in the art) between the first nucleic acid and the second nucleic acid.

In some embodiments, a soluble TGFβRII receptor includes a sequence that is at least 70% identical (e.g., at least 75% identical, at least 80% identical, at least 85% identical, at least 90% identical, at least 95% identical, at least 99% identical, or 100% identical) to:

(SEQ ID NO: 60)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments, a soluble TGFβRII receptor is encoded by a nucleic acid including a sequence at least 70% identical (e.g., at least 75% identical, at least 80% identical, at least 85% identical, at least 90% identical, at least 95% identical, at least 99% identical, or 100% identical) to:

(SEQ ID NO: 61)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

-continued

```
AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCACA

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.
```

Additional examples of soluble interleukin receptors and soluble cytokine receptors are known in the art.

Additional Antigen-Binding Domains

Some embodiments of any of the single-chain chimeric polypeptides described herein can further include one or more (e.g., two, three, four, five, six, seven, eight, nine, or ten) additional target-binding domains (e.g., any of the exemplary target-binding domains described herein or known in the art) at its N- and/or C-terminus.

In some embodiments, the single-chain chimeric polypeptides can include one or more (e.g., two, three, four, five, six, seven, eight, nine, or ten) additional target-binding domains (e.g., any of the exemplary target-binding domains described herein or known in the art) at its N-terminus. In some embodiments, one of the one or more additional target-binding domains (e.g., any of the exemplary target-binding domains described herein or known in the art) at the N-terminus of the single-chain chimeric polypeptide can directly abut the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the at least one additional target-binding domains (e.g., any of the exemplary target-binding domains described herein or known in the art) at the N-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide includes one or more (e.g., two, three, four, five, six, seven, eight, nine, or ten) additional target-binding domains (e.g., any of the exemplary target-binding domains described herein or known in the art) at its C-terminus. In some embodiments, one of the one or more additional target-binding domains (e.g., any of the exemplary target-binding domains described herein or known in the art) at the C-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein or known in the art). In some embodiments, the single-chain chimeric polypeptide further comprises a linker sequence (e.g., any of the exemplary linker sequences described herein or known in the art) between one of the at least one additional target-binding domains (e.g., any of the exemplary target-binding domains described herein or known in the art) at the C-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide comprises one or more (e.g., two, three, four, five, six, seven, eight, nine, or ten) additional target binding domains (e.g., any of the exemplary target-binding domains described herein or known in the art) at its N-terminus and its C-terminus. In some embodiments, one of the one or more additional antigen binding domains (e.g., any of the exemplary target-binding domains described herein or known in the art) at the N-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the N-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, one of the one or more additional antigen binding domains (e.g., any of the exemplary target-binding domains described herein or known in the art) at the C-terminus directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the C-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same antigen. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same epitope. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) include the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same antigen. In some embodiments, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same epitope. In some embodiments, the first target-binding domain, the second target-binding domain, and the one or more (e.g., two, three, four, five, six, seven, eight, nine, or ten) additional target-binding domains each comprise the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) bind specifically to different antigens.

In some embodiments of any of the single-chain chimeric polypeptides, one or more of the first target-binding domain, the second target-binding domain, and the one or more target-binding domains is an antigen-binding domain (e.g., any of the exemplary antigen-binding domains described herein or known in the art). In some embodiments of any of the single-chain chimeric polypeptides described herein, the first target-binding domain, the second target-binding domain, and the one or more additional target-binding domains are each an antigen-binding domain (e.g., any of the exemplary antigen-binding domains described herein or known in the art). In some embodiments, the antigen-binding domain can include a scFv or a single domain antibody.

In some embodiments of any of the single-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more target-binding domains (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin, a soluble cytokine protein, or a soluble cell surface protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, SCF, and FLT3L. Non-limiting examples of soluble cell surface proteins include: MICA, MICB, and a ULP16-binding protein.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin receptor, a soluble cytokine receptor, or a soluble cell surface receptor. Non-limiting examples of soluble interleukin receptors and soluble cytokine receptors include: a soluble TGF-β receptor II (TGF-βRII) and a soluble TGF-βRIII Non-limiting examples of soluble cell surface receptors include: a soluble NKG2D, a soluble NK30, a soluble NKp44, a soluble NKp46, a soluble DNAM1, a scMHCI, a scMHCII, a scTCR, a soluble CD155, a soluble CD122, a soluble CD3, and a soluble CD28.

Signal Sequence

In some embodiments, a single-chain chimeric polypeptide includes a signal sequence at its N-terminal end. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a single-chain chimeric polypeptide includes a signal sequence having an amino acid sequence MKWVTFISLLFLFSSAYS (SEQ ID NO: 62). In some embodiments, a single chain chimeric polypeptide includes a signal sequence encoded by the nucleic acid sequence

ATGAAATGGGTGACCTTTATTTCTTTACTGTTCCTCTTTAGCAGCGCCTA CTCC, (SEQ ID NO: 63)

ATGAAGTGGGTCACATTTATCTCTTTACTGTTCCTCTTCTCCAGCGCCTA CAGC, (SEQ ID NO: 64)

or

ATGAAATGGGTGACCTTTATTTCTTTACTGTTCCTCTTTAGCAGCGCCTA CTCC. (SEQ ID NO: 65)

In some embodiments, a single-chain chimeric polypeptide includes a signal sequence having an amino acid sequence MKCLLYLAFLFLGVNC (SEQ ID NO: 66). In some embodiments, a single-chain chimeric polypeptide includes a signal sequence having an amino acid sequence MGQIVTMFEALPHIIDEVINIVIIVLIIITSIKAVYN-FATCGILALVSFLFLAGRSCG (SEQ ID NO: 67). In some embodiments, a single-chain chimeric polypeptide includes a signal sequence having an amino acid sequence MPNHQSGSPTGSSDLLLSGKKQRPHLALRRKRRRE-MRKINRKVRRMNLAPIKEK TAWQHLQALISE-AEEVLKTSQTPQNSLTLFLALLSVLGPPVTG (SEQ ID NO: 68). In some embodiments, a single-chain chimeric polypeptide includes a signal sequence having an amino acid sequence MDSKGSSQKGSRLLLLLVVSNLLLCQGVVS (SEQ ID NO: 69). Those of ordinary skill in the art will be aware of other appropriate signal sequences for use in a single-chain chimeric polypeptide.

In some embodiments, a single-chain chimeric polypeptide includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKWVTFISLL-FLFSSAYS (SEQ ID NO: 62) can include one or more additional amino acids at the N-terminus or C-terminus, while still retaining the ability to direct the single-chain chimeric polypeptide to the secretory pathway.

In some embodiments, a single-chain chimeric polypeptide includes a signal sequence that directs the single-chain chimeric polypeptide into the extracellular space. Such embodiments are useful in producing single-chain chimeric polypeptides that are relatively easy to be isolated and/or purified.

Peptide Tags

In some embodiments, a single-chain chimeric polypeptide includes a peptide tag (e.g., at the N-terminal end or the C-terminal end of the single-chain chimeric polypeptide). In some embodiments, a single-chain chimeric polypeptide includes two or more peptide tags.

Exemplary peptide tags that can be included in a single-chain chimeric polypeptide include, without limitation, Avi-Tag (GLNDIFEAQKIEWHE; SEQ ID NO: 70), a calmodulin-tag (KRRWKKNFIAVSAANRFKKISSSGAL; SEQ ID NO: 71), a polyglutamate tag (EEEEEE; SEQ ID NO: 72), an E-tag (GAPVPYPDPLEPR; SEQ ID NO: 73), a FLAG-tag (DYKDDDDK; SEQ ID NO: 74), an HA-tag, a peptide from hemagglutinin (YPYDVPDYA; SEQ ID NO: 75), a his-tag (HHHHH (SEQ ID NO: 76); HHHHHH (SEQ ID NO: 77); HHHHHHH (SEQ ID NO: 78); HHHHHHHH (SEQ ID NO: 79); HHHHHHHH (SEQ ID NO: 80); or HHHHHHHHHH (SEQ ID NO: 81)), a myc-tag (EQKLISEEDL; SEQ ID NO: 82), NE-tag (TKENPRSNQEESYDDNES; SEQ ID NO: 83), S-tag, (KETAAAKFERQHMDS; SEQ ID NO: 84), SBP-tag (MDEKTTGWRGGHVVEGLAGELEQLRARLEHHPQGQREP; SEQ ID NO: 85), Softag 1 (SLAELLNAGLGGS; SEQ ID NO: 86), Softag 3 (TQDPSRVG; SEQ ID NO: 87), Spot-tag (PDRVRAVSHWSS; SEQ ID NO: 88), Strep-tag (WSHPQFEK; SEQ ID NO: 89), TC tag (CCPGCC; SEQ ID NO: 90), Ty tag (EVHTNQDPLD; SEQ ID NO: 91), V5 tag (GKPIPNPLLGLDST; SEQ ID NO: 92), VSV-tag (YTDIEMNRLGK; SEQ ID NO: 93), and Xpress tag (DLYDDDDK; SEQ ID NO: 94). In some embodiments, tissue factor protein is a peptide tag.

Peptide tags that can be included in a single-chain chimeric polypeptide can be used in any of a variety of applications related to the single-chain chimeric polypeptide. For example, a peptide tag can be used in the purification of a single-chain chimeric polypeptide. As one non-limiting example, a single-chain chimeric polypeptide can include a myc tag; and can be purified using an antibody that recognizes the myc tag(s). One non-limiting example of an antibody that recognizes a myc tag is 9E10, available from the non-commercial Developmental Studies Hybridoma Bank. As another non-limiting example, a single-chain chimeric polypeptide can include a histidine tag, and can be purified using a nickel or cobalt chelate. Those of ordinary skill in the art will be aware of other suitable tags and agent that bind those tags for use in purifying a single-chain chimeric polypeptide. In some embodiments, a peptide tag is removed from the single-chain chimeric polypeptide after purification. In some embodiments, a peptide tag is not removed from the single-chain chimeric polypeptide after purification.

Peptide tags that can be included in a single-chain chimeric polypeptide can be used, for example, in immunoprecipitation of the single-chain chimeric polypeptide, imaging of the single-chain chimeric polypeptide (e.g., via Western blotting, ELISA, flow cytometry, and/or immunocytochemistry), and/or solubilization of the single-chain chimeric polypeptide.

In some embodiments, a single-chain chimeric polypeptide includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a single-chain chimeric polypeptide can be of any suitable length. For example, peptide tags can be 5, 6, 7, 8, 9, 10, 11, 12, 13, 14, 15, 16, 17, 18, 19, 20, or more amino acids in length. In embodiments in which a single-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 82) can include one or more additional amino acids (e.g., at the N-terminus and/or the C-terminus of the peptide tag), while still retaining the ability to be bound by an antibody (e.g., 9E10).

Exemplary Embodiments of Single-Chain Chimeric Polypeptides—Type A

In some embodiments of any of the single-chain chimeric polypeptides described herein, the first target-binding domain and/or the second target-binding domain can independently bind specifically to CD3 (e.g., human CD3) or CD28 (e.g., human CD28). In some embodiments, the first target-binding domain binds specifically to CD3 (e.g., human CD3) and the second target-binding domain binds specifically to CD28 (e.g., human CD28). In some embodiments, the first target-binding domain binds specifically to CD28 (e.g., human CD28) and the second target-binding domain binds specifically to CD3 (e.g., human CD3).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, one or both of the first target-binding domain and the second target-binding domain is an antigen-binding domain. In some embodiments of these single-chain chimeric polypeptides, the first target-binding domain and the second target-binding domain are each an antigen-binding domain (e.g., any of the exemplary antigen-binding domains described herein). In some embodiments of these single-chain chimeric polypeptides, the antigen-binding domain includes a scFv or a single domain antibody.

A non-limiting example of an scFv that binds specifically to CD3 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 20)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSS.
```

In some embodiments, an scFv that binds specifically to CD3 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 99)
CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGTGGAGGAGGTGGCAGCGGCGGCGGTGGATC

CGGCGGAGGAGGAAGCCAAGTTCAACTCCAGCAGAGCGGCGCTGAACTGG

CCCGGCCCGGCGCCTCCGTCAAGATGAGCTGCAAGGCTTCCGGCTATACA

TTTACTCGTTACACAATGCATTGGGTCAAGCAGAGGCCCGGTCAAGGTTT

AGAGTGGATCGGATATATCAACCCTTCCCGGGGCTACACCAACTATAACC

AAAAGTTCAAGGATAAAGCCACTTTAACCACTGACAAGAGCTCCTCCACC

GCCTACATGCAGCTGTCCTCTTTAACCAGCGAGGACTCCGCTGTTTACTA

CTGCGCTAGGTATTACGACGACCACTACTGTTTAGACTATTGGGACAAG

GTACCACTTTAACCGTCAGCAGC.
```

A non-limiting example of an scFv that binds specifically to CD28 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 26)
VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD
```

```
GNYWGRGTTLTVSSGGGGSGGGGSGGGGSDIEMTQSPAIMSASLGERVTM

TCTASSSVSSSYFHWYQQKPGSSPKLCIYSTSNLASGVPPRFSGSGSTSY

SLTISSMEAEDAATYFCHQYHRSPTFGGGTKLETKR.
```

In some embodiments, an scFv that binds specifically to CD28 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 101)
GTCCAGCTGCAGCAGAGCGGACCCGAACTCGTGAAACCCGGTGCTTCCGT

GAAAATGTCTTGTAAGGCCAGCGGATACACCTTCACCTCCTATGTGATCC

AGTGGGTCAAACAGAAGCCCGGACAAGGTCTCGAGTGGATCGGCAGCATC

AACCCTTACAACGACTATACCAAATACAACGAGAAGTTTAAGGGAAAGGC

TACTTTAACCTCCGACAAAAGCTCCATCACAGCCTACATGGAGTTCAGCT

CTTTAACATCCGAGGACAGCGCTCTGTACTATTGCGCCCGGTGGGGCGAC

GGCAATTACTGGGACGGGGCACAACACTGACCGTGAGCAGCGGAGGCGG

AGGCTCCGGCGGAGGCGGATCTGGCGGTGGCGGCTCCGACATCGAGATGA

CCCAGTCCCCCGCTATCATGTCCGCCTCTTTAGGCGAGCGGGTCACAATG

ACTTGTACAGCCTCCTCCAGCGTCTCCTCCTCCTACTTCCATTGGTACCA

ACAGAAACCCGGAAGCTCCCCTAAACTGTGCATCTACAGCACCAGCAATC

TCGCCAGCGGCGTGCCCCCTAGGTTTTCCGGAAGCGGAAGCACCAGCTAC

TCTTTAACCATCTCCTCCATGGAGGCTGAGGATGCCGCCACCTACTTTTG

TCACCAGTACCACCGGTCCCCCACCTTCGGAGGCGGCACCAAACTGGAGA

CAAAGAGG.
```

In some embodiments of these single-chain chimeric polypeptides, the first target-binding domain and/or the second target-binding domain is a soluble receptor (e.g., a soluble CD28 receptor or a soluble CD3 receptor). In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 1)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSSSGTTNTVAA

YNLTWKSTNFKTILEWEPKPVNQVYTVQISTKSGDWKSKCFYTTDTECDL
```

TDEIVKDVKQTYLARVFSYPAGNVESTGSAGEPLYENSPEFTPYLETNLG
QPTIQSFEQVGTKVNVTVEDERTLVRRNNTFLSLRDVFGKDLIYTLYYWK
SSSSGKKTAKTNTNEFLIDVDKGENYCFSVQAVIPSRTVNRKSTDSPVEC
MGQEKGEFREVQLQQSGPELVKPGASVKMSCKASGYTFTSYVIQWVKQKP
GQGLEWIGSINPYNDYTKYNEKFKGKATLTSDKSSITAYMEFSSLTSEDS
ALYYCARWGDGNYWGRGTTLTVSSGGGGSGGGGSGGGGSDIEMTQSPAIM
SASLGERVTMTCTASSSVSSSYFHWYQQKPGSSPKLCIYSTSNLASGVPP
RFSGSGSTSYSLTISSMEAEDAATYFCHQYHRSPTFGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 2)
CAGATCGTGCTGACCCAAAGCCCCGCCATCATGAGCGCTAGCCCCGGTGA
GAAGGTGACCATGACATGCTCCGCTTCCAGCTCCGTGTCCTACATGAACT
GGTATCAGCAGAAAAGCGGAACCAGCCCCAAAGGTGGATCTACGACACC
AGCAAGCTGGCCTCCGGAGTGCCCGCTCATTTCCGGGGCTCTGGATCCGG
CACCAGCTACTCTTTAACCATTTCCGGCATGGAAGCTGAAGACGCTGCCA
CCTACTATTGCCAGCAATGGAGCAGCAACCCCTTCACATTCGGATCTGGC
ACCAAGCTCGAAATCAATCGTGGAGGAGGTGGCAGCGGCGGCGGTGGATC
CGGCGGAGGAGGAAGCCAAGTTCAACTCCAGCAGAGCGGCGCTGAACTGG
CCCGGCCCGGCGCCTCCGTCAAGATGAGCTGCAAGGCTTCCGGCTATACA
TTTACTCGTTACACAATGCATTGGGTCAAGCAGAGGCCCGGTCAAGGTTT
AGAGTGGATCGGATATATCAACCCTTCCCGGGGCTACACCAACTATAACC
AAAAGTTCAAGGATAAAGCCACTTTAACCACTGACAAGAGCTCCTCCACC
GCCTACATGCAGCTGTCCTCTTTAACCAGCGAGGACTCCGCTGTTTACTA
CTGCGCTAGGTATTACGACGACCACTACTGTTTAGACTATTGGGGACAAG
GTACCACTTTAACCGTCAGCAGCTCCGGCACCACCAATACCGTGGCCGCT
TATAACCTCACATGGAAGAGCACCAACTTCAAGACAATTCTGGAATGGGA
ACCCAAGCCCGTCAATCAAGTTTACACCGTGCAGATCTCCACCAAATCCG
GAGACTGGAAGAGCAAGTGCTTCTACACAACAGACACCGAGTGTGATTTA
ACCGACGAAATCGTCAAGGACGTCAAGCAAACCTATCTGGCTCGGGTCTT
TTCCTACCCCGCTGGCAATGTCGAGTCCACCGGCTCCGCTGGCGAGCCTC
TCTACGAGAATTCCCCCGAATTCACCCCTTATTTAGAGACCAATTTAGGC
CAGCCTACCATCCAGAGCTTCGAGCAAGTTGGCACCAAGGTGAACGTCAC
CGTCGAGGATGAAAGGACTTTAGTGCGGCGGAATAACACATTTTTATCCC
TCCGGGATGTGTTCGGCAAAGACCTCATCTACACACTGTACTATTGGAAG
TCCAGCTCCTCCGGCAAAAAGACCGCTAAGACCAACACCAACGAGTTTTT
AATTGACGTGGACAAAGGCGAGAACTACTGCTTCAGCGTGCAAGCCGTGA
TCCCCTTCTCGTACCGTCAACCGGAAGAGCACAGATTCCCCCGTTGAGTGC
ATGGGCCAAGAAAAGGGCGAGTTCCGGGAGGTCCAGCTGCAGCAGAGCGG
ACCCGAACTCGTGAAACCCGGTGCTTCCGTGAAAATGTCTTGTAAGGCCA
GCGGATACACCTTCACCTCCTATGTGATCCAGTGGGTCAAACAGAAGCCC
GGACAAGGTCTCGAGTGGATCGGCAGCATCAACCCTTACAACGACTATAC
CAAATACAACGAGAAGTTTAAGGGAAAGGCTACTTTAACCTCCGACAAAA
GCTCCATCACAGCCTACATGGAGTTCAGCTCTTTAACATCCGAGGACAGC
GCTCTGTACTATTGCGCCCGGTGGGGCGACGGCAATTACTGGGGACGGGG
CACAACACTGACCGTGAGCAGCGGAGGCGGAGGCTCCGGCGGAGGCGGAT
CTGGCGGTGGCGGCTCCGACATCGAGATGACCCAGTCCCCCGCTATCATG
TCCGCCTCTTTAGGCGAGCGGGTCACAATGACTTGTACAGCCTCCTCCAG
CGTCTCCTCCTCCTACTTCCATTGGTACCAACAGAAACCCGGAAGCTCCC
CTAAACTGTGCATCTACAGCACCAGCAATCTCGCCAGCGGCGTGCCCCCT
AGGTTTTCCGGAAGCGGAAGCACCAGCTACTCTTTAACCATCTCCTCCAT
GGAGGCTGAGGATGCCGCCACCTACTTTGTCACCAGTACCACCGGTCCC
CCACCTTCGGAGGCGGCACCAAACTGGAGACAAAGAGG.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 3)
MKWVTFISLLFLFSSAYSQIVLTQSPAIMSASPGEKVTMTCSASSSVSYM
NWYQQKSGTSPKRWIYDTSKLASGVPAHFRGSGSGTSYSLTISGMEAEDA
ATYYCQQWSSNPFTFGSGTKLEINRGGGGSGGGGSGGGGSQVQLQQSGAE
LARPGASVKMSCKASGYTFTRYTMHWVKQRPGQGLEWIGYINPSRGYTNY
NQKFKDKATLTTDKSSSTAYMQLSSLTSEDSAVYYCARYYDDHYCLDYWG
QGTTLTVSSSGTTNTVAAYNLTWKSTNFKTILEWEPKPVNQVYTVQISTK
SGDWKSKCFYTTDTECDLTDEIVKDVKQTYLARVFSYPAGNVESTGSAGE
PLYENSPEFTPYLETNLGQPTIQSFEQVGTKVNVTVEDERTLVRRNNTFL
SLRDVFGKDLIYTLYYWKSSSSGKKTAKTNTNEFLIDVDKGENYCFSVQA
VIPSRTVNRKSTDSPVECMGQEKGEFREVQLQQSGPELVKPGASVKMSCK
ASGYTFTSYVIQWVKQKPGQGLEWIGSINPYNDYTKYNEKFKGKATLTSD
KSSITAYMEFSSLTSEDSALYYCARWGDGNYWGRGTTLTVSSGGGGSGGG
GSGGGGSDIEMTQSPAIMSASLGERVTMTCTASSSVSSSYFHWYQQKPGS
SPKLCIYSTSNLASGVPPRFSGSGSTSYSLTISSMEAEDAATYFCHQYHR
SPTFGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 4)
ATGAAGTGGGTGACCTTCATCAGCTTATTATTTTTATTCAGCTCCGCCTA

TTCCCAGATCGTGCTGACCCAAAGCCCCGCCATCATGAGCGCTAGCCCCG

GTGAGAAGGTGACCATGACATGCTCCGCTTCCAGCTCCGTGTCCTACATG

AACTGGTATCAGCAGAAAAGCGGAACCAGCCCCAAAAGGTGGATCTACGA

CACCAGCAAGCTGGCCTCCGGAGTGCCCGCTCATTTCCGGGGCTCTGGAT

CCGGCACCAGCTACTCTTTAACCATTTCCGGCATGGAAGCTGAAGACGCT

GCCACCTACTATTGCCAGCAATGGAGCAGCAACCCCTTCACATTCGGATC

TGGCACCAAGCTCGAAATCAATCGTGGAGGAGGTGGCAGCGGCGGCGGTG

GATCCGGCGGAGGAGGAAGCCAAGTTCAACTCCAGCAGAGCGGCGCTGAA

CTGGCCCGGCCCGGCGCCTCCGTCAAGATGAGCTGCAAGGCTTCCGGCTA

TACATTTACTCGTTACACAATGCATTGGGTCAAGCAGAGGCCCGGTCAAG

GTTTAGAGTGGATCGGATATATCAACCCTTCCCGGGGCTACACCAACTAT

AACCAAAAGTTCAAGGATAAAGCCACTTTAACCACTGACAAGAGCTCCTC

CACCGCCTACATGCAGCTGTCCTCTTTAACCAGCGAGGACTCCGCTGTTT

ACTACTGCGCTAGGTATTACGACGACCACTACTGTTTAGACTATTGGGGA

CAAGGTACCACTTTAACCGTCAGCAGCTCCGGCACCACCAATACCGTGGC

CGCTTATAACCTCACATGGAAGAGCACCAACTTCAAGACAATTCTGGAAT

GGGAACCCAAGCCCGTCAATCAAGTTTACACCGTGCAGATCTCCACCAAA

TCCGGAGACTGGAAGAGCAAGTGCTTCTACACAACAGACACCGAGTGTGA

TTTAACCGACGAAATCGTCAAGGACGTCAAGCAAACCTATCTGGCTCGGG

TCTTTTCCTACCCCGCTGGCAATGTCGAGTCCACCGGCTCCGCTGGCGAG

CCTCTCTACGAGAATTCCCCCGAATTCACCCCTTATTTAGAGACCAATTT

AGGCCAGCCTACCATCCAGAGCTTCGAGCAAGTTGGCACCAAGGTGAACG

TCACCGTCGAGGATGAAAGGACTTTAGTGCGGCGGAATAACACATTTTTA

TCCCTCCGGGATGTGTTCGGCAAGACCTCATCTACACACTGTACTATTG

GAAGTCCAGCTCCTCCGGCAAAAAGACCGCTAAGACCAACACCAACGAGT

TTTTAATTGACGTGGACAAAGGCGAGAACTACTGCTTCAGCGTGCAAGCC

GTGATCCCTTCTCGTACCGTCAACCGGAAGAGCACAGATTCCCCCGTTGA

GTGCATGGGCCAAGAAAAGGGCGAGTTCCGGGAGGTCCAGCTGCAGCAGA

GCGGACCCGAACTCGTGAAACCCGGTGCTTCCGTGAAAATGTCTTGTAAG

GCCAGCGGATACACCTTCACCTCCTATGTGATCCAGTGGGTCAAACAGAA

GCCCGGACAAGGTCTCGAGTGGATCGGCAGCATCAACCCTTACAACGACT

ATACCAAATACAACGAGAAGTTTAAGGGAAAGGCTACTTTAACCTCCGAC

AAAAGCTCCATCACAGCCTACATGGAGTTCAGCTCTTTAACATCCGAGGA

CAGCGCTCTGTACTATTGCGCCCGGTGGGGCGACGGCAATTACTGGGGAC

GGGGCACAACACTGACCGTGAGCAGCGGAGGCGGAGGCTCCGGCGGAGGC

GGATCTGGCGGTGGCGGCTCCGACATCGAGATGACCCAGTCCCCCGCTAT

CATGTCCGCCTCTTTAGGCGAGCGGGTCACAATGACTTGTACAGCCTCCT

CCAGCGTCTCCTCCTCCTACTTCCATTGGTACCAACAGAAACCCGGAAGC

TCCCCTAAACTGTGCATCTACAGCACCAGCAATCTCGCCAGCGGCGTGCC

CCCTAGGTTTTCCGGAAGCGGAAGCACCAGCTACTCTTTAACCATCTCCT

CCATGGAGGCTGAGGATGCCGCCACCTACTTTTGTCACCAGTACCACCGG

TCCCCCACCTTCGGAGGCGGCACCAAACTGGAGACAAAGAGG.

Exemplary Embodiments of Single-Chain Chimeric Polypeptides—Type B

In some embodiments of any of the single-chain chimeric polypeptides described herein, the first target-binding domain and/or the second target-binding domain can independently bind specifically to an IL-2 receptor (e.g., human IL-2 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-2 protein. A non-limiting example of an IL-2 protein that binds specifically to an IL-2 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 28)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 106)
GCACCTACTTCAAGTTCTACAAAGAAAACACAGCTACAACTGGAGCATTT

ACTGCTGGATTTACAGATGATTTTGAATGGAATTAATAATTACAAGAATC

CCAAACTCACCAGGATGCTCACATTTAAGTTTTACATGCCCAAGAAGGCC

ACAGAACTGAAACATCTTCAGTGTCTAGAAGAAGAACTCAAACCTCTGGA

GGAAGTGCTAAATTTAGCTCAAAGCAAAAACTTTCACTTAAGACCCAGGG

ACTTAATCAGCAATATCAACGTAATAGTTCTGGAACTAAAGGGATCTGAA

ACAACATTCATGTGTGAATATGCTGATGAGACAGCAACCATTGTAGAATT

TCTGAACAGATGGATTACCTTTTGTCAAAGCATCATCTCAACACTAACT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 107)
GCCCCCACCTCCTCCTCCACCAAGAAGACCCAGCTGCAGCTGGAGCATTT

ACTGCTGGATTTACAGATGATTTTAAACGGCATCAACAACTACAAGAACC

CCAAGCTGACTCGTATGCTGACCTTCAAGTTCTACATGCCCAAGAAGGCC

ACCGAGCTGAAGCATTTACAGTGTTTAGAGGAGGAGCTGAAGCCCCTCGA

GGAGGTGCTGAATTTAGCCCAGTCCAAGAATTTCCATTTAAGGCCCCGGG

ATTTAATCAGCAACATCAACGTGATCGTTTTAGAGCTGAAGGGCTCCGAG

ACCACCTTCATGTGCGAGTACGCCGACGAGACCGCCACCATCGTGGAGTT

TTTAAATCGTTGGATCACCTTCTGCCAGTCCATCATCTCCACTTTAACC

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 108)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTSGTTNTVAAYNLTWKST

NFKTILEWEPKPVNQVYTVQISTKSGDWKSKCFYTTDTECDLTDEIVKDV

KQTYLARVFSYPAGNVESTGSAGEPLYENSPEFTPYLETNLGQPTIQSFE

QVGTKVNVTVEDERTLVRRNNTFLSLRDVFGKDLIYTLYYWKSSSSGKKT

AKTNTNEFLIDVDKGENYCFSVQAVIPSRTVNRKSTDSPVECMGQEKGEF

REAPTSSSTKKTQLQLEHLLLDLQMILNGINNYKNPKLTRMLTFKFYMPK

KATELKHLQCLEEELKPLEEVLNLAQSKNFHLRPRDLISNINVIVLELKG

SETTFMCEYADETATIVEFLNRWITFCQSIISTLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 109)
GCCCCCACCTCCTCCTCCACCAAGAAGACCCAGCTGCAGCTGGAGCATTT

ACTGCTGGATTTACAGATGATTTTAAACGGCATCAACAACTACAAGAACC

CCAAGCTGACTCGTATGCTGACCTTCAAGTTCTACATGCCCAAGAAGGCC

ACCGAGCTGAAGCATTTACAGTGTTTAGAGGAGGAGCTGAAGCCCCTCGA

GGAGGTGCTGAATTTAGCCCAGTCCAAGAATTTCCATTTAAGGCCCCGGG

ATTTAATCAGCAACATCAACGTGATCGTTTTAGAGCTGAAGGGCTCCGAG

ACCACCTTCATGTGCGAGTACGCCGACGAGACCGCCACCATCGTGGAGTT

TTTAAATCGTTGGATCACCTTCTGCCAGTCCATCATCTCCACTTTAACCA

GCGGCACAACCAACACAGTCGCTGCCTATAACCTCACTTGGAAGAGCACC

AACTTCAAAACCATCCTCGAATGGGAACCCAAACCCGTTAACCAAGTTTA

CACCGTGCAGATCAGCACCAAGTCCGGCGACTGGAAGTCCAAATGTTTCT

ATACCACCGACACCGAGTGCGATCTCACCGATGAGATCGTGAAAGATGTG

AAACAGACCTACCTCGCCCGGGTGTTTAGCTACCCCGCCGGCAATGTGGA

GAGCACTGGTTCCGCTGGCGAGCCTTTATACGAGAACAGCCCCGAATTTA

CCCCTTACCTCGAGACCAATTTAGGACAGCCCACCATCCAAAGCTTTGAG

CAAGTTGGCACAAAGGTGAATGTGACAGTGGAGGACGAGCGGACTTTAGT

GCGGCGGAACAACACCTTTCTCAGCCTCCGGGATGTGTTCGGCAAAGATT

TAATCTACACACTGTATTACTGGAAGTCCTCTTCCTCCGGCAAGAAGACA

GCTAAAACCAACACAAACGAGTTTTTAATCGACGTGGATAAAGGCGAAAA

CTACTGTTTCAGCGTGCAAGCTGTGATCCCCTCCCGGACCGTGAATAGGA

AAAGCACCGATAGCCCCGTTGAGTGCATGGGCCAAGAAAAGGGCGAGTTC

CGGGAGGCACCTACTTCAAGTTCTACAAAGAAAACACAGCTACAACTGGA

GCATTTACTGCTGGATTTACAGATGATTTTGAATGGAATTAATAATTACA

AGAATCCCAAACTCACCAGGATGCTCACATTTAAGTTTTACATGCCCAAG

AAGGCCACAGAACTGAAACATCTTCAGTGTCTAGAAGAAGAACTCAAACC

TCTGGAGGAAGTGCTAAATTTAGCTCAAAGCAAAAACTTTCACTTAAGAC

CCAGGGACTTAATCAGCAATATCAACGTAATAGTTCTGGAACTAAAGGGA

TCTGAAACAACATTCATGTGTGAATATGCTGATGAGACAGCAACCATTGT

AGAATTTCTGAACAGATGGATTACCTTTTGTCAAAGCATCATCTCAACAC

TAACT.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 110)
MKWVTFISLLFLFSSAYSAPTSSSTKKTQLQLEHLLLDLQMILNGINNYK

NPKLTRMLTFKFYMPKKATELKHLQCLEEELKPLEEVLNLAQSKNFHLRP

RDLISNINVIVLELKGSETTFMCEYADETATIVEFLNRWITFCQSIISTL

TSGTTNTVAAYNLTWKSTNFKTILEWEPKPVNQVYTVQISTKSGDWKSKC

-continued

FYTTDTECDLTDEIVKDVKQTYLARVFSYPAGNVESTGSAGEPLYENSPE

FTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVN

RKSTDSPVECMGQEKGEFREAPTSSSTKKTQLQLEHLLLDLQMILNGINN

YKNPKLTRMLTFKFYMPKKATELKHLQCLEEELKPLEEVLNLAQSKNFHL

RPRDLISNINVIVLELKGSETTFMCEYADETATIVEFLNRWITFCQSIIS

TLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 111)
ATGAAGTGGGTGACCTTCATCAGCCTGCTGTTCCTGTTCTCCAGCGCCTA

CTCCGCCCCCACCTCCTCCTCCACCAAGAAGACCCAGCTGCAGCTGGAGC

ATTTACTGCTGGATTTACAGATGATTTTAAACGGCATCAACAACTACAAG

AACCCCAAGCTGACTCGTATGCTGACCTTCAAGTTCTACATGCCCAAGAA

GGCCACCGAGCTGAAGCATTTACAGTGTTTAGAGGAGGAGCTGAAGCCCC

TCGAGGAGGTGCTGAATTTAGCCCAGTCCAAGAATTTCCATTTAAGGCCC

CGGGATTTAATCAGCAACATCAACGTGATCGTTTTAGAGCTGAAGGGCTC

CGAGACCACCTTCATGTGCGAGTACGCCGACGAGACCGCCACCATCGTGG

AGTTTTTAAATCGTTGGATCACCTTCTGCCAGTCCATCATCTCCACTTTA

ACCAGCGGCACAACCAACACAGTCGCTGCCTATAACCTCACTTGGAAGAG

CACCAACTTCAAAACCATCCTCGAATGGGAACCCAAACCCGTTAACCAAG

TTTACACCGTGCAGATCAGCACCAAGTCCGGCGACTGGAAGTCCAAATGT

TTCTATACCACCGACACCGAGTGCGATCTCACCGATGAGATCGTGAAAGA

TGTGAAACAGACCTACCTCGCCCGGGTGTTTAGCTACCCCGCCGGCAATG

TGGAGAGCACTGGTTCCGCTGGCGAGCCTTTATACGAGAACAGCCCCGAA

TTTACCCCTTACCTCGAGACCAATTTAGGACAGCCCACCATCCAAAGCTT

TGAGCAAGTTGGCACAAAGGTGAATGTGACAGTGGAGGACGAGCGGACTT

TAGTGCGGCGGAACAACACCTTTCTCAGCCTCCGGGATGTGTTCGGCAAA

GATTTAATCTACACACTGTATTACTGGAAGTCCTCTTCCTCCGGCAAGAA

GACAGCTAAAACCAACACAAACGAGTTTTTAATCGACGTGGATAAAGGCG

AAAACTACTGTTTCAGCGTGCAAGCTGTGATCCCCTCCCGGACCGTGAAT

AGGAAAAGCACCGATAGCCCCGTTGAGTGCATGGGCCAAGAAAAGGGCGA

GTTCCGGGAGGCACCTACTTCAAGTTCTACAAAGAAAACACAGCTACAAC

TGGAGCATTTACTGCTGGATTTACAGATGATTTTGAATGGAATTAATAAT

TACAAGAATCCCAAACTCACCAGGATGCTCACATTTAAGTTTTACATGCC

CAAGAAGGCCACAGAACTGAAACATCTTCAGTGTCTAGAAGAAGAACTCA

AACCTCTGGAGGAAGTGCTAAATTTAGCTCAAAGCAAAAACTTTCACTTA

AGACCCAGGGACTTAATCAGCAATATCAACGTAATAGTTCTGGAACTAAA

-continued

GGGATCTGAAACAACATTCATGTGTGAATATGCTGATGAGACAGCAACCA

TTGTAGAATTTCTGAACAGATGGATTACCTTTTGTCAAAGCATCATCTCA

ACACTAACT.

Exemplary Embodiments of Single-Chain Chimeric Polypeptides—Type C

In some embodiments of any of the single-chain chimeric polypeptides described herein, the first target-binding domain and/or the second target-binding domain can independently bind specifically to an IL-15 receptor (e.g., a human IL-15 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-15 protein. A non-limiting example of an IL-15 protein that binds specifically to an IL-15 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 39)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS.

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
AACTGGGTGAACGTGATCAGCGATTTAAAGAAGATCGAGGATTTAATCCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGC.

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSSGTTNTVAAYNLTWKSTNFKTILEWEPKPVNQVYTV

QISTKSGDWKSKCFYTTDTECDLTDEIVKDVKQTYLARVFSYPAGNVEST

GSAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENYC

FSVQAVIPSRTVNRKSTDSPVECMGQEKGEFRENWVNVISDLKKIEDLIQ

SMHIDATLYTESDVHPSCKVTAMKCFLLELQVISLESGDASIHDTVENLI

ILANNSLSSNGNVTESGCKECEELEEKNIKEFLQSFVHIVQMFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
AACTGGGTGAACGTGATCAGCGATTTAAAGAAGATCGAGGATTTAATCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGCAGCGGCAC

AACCAACACAGTCGCTGCCTATAACCTCACTTGGAAGAGCACCAACTTCA

AAACCATCCTCGAATGGGAACCCAAACCCGTTAACCAAGTTTACACCGTG

CAGATCAGCACCAAGTCCGGCGACTGGAAGTCCAAATGTTTCTATACCAC

CGACACCGAGTGCGATCTCACCGATGAGATCGTGAAAGATGTGAAACAGA

CCTACCTCGCCCGGGTGTTTAGCTACCCCGCCGGCAATGTGGAGAGCACT

GGTTCCGCTGGCGAGCCTTTATACGAGAACAGCCCCGAATTTACCCCTTA

CCTCGAGACCAATTTAGGACAGCCCACCATCCAAAGCTTTGAGCAAGTTG

GCACAAAGGTGAATGTGACAGTGGAGGACGAGCGGACTTTAGTGCGGCGG

AACAACACCTTTCTCAGCCTCCGGGATGTGTTCGGCAAAGATTTAATCTA

CACACTGTATTACTGGAAGTCCTCTTCCTCCGGCAAGAAGACAGCTAAAA

CCAACACAAACGAGTTTTTAATCGACGTGGATAAAGGCGAAAACTACTGT

TTCAGCGTGCAAGCTGTGATCCCCTCCCGGACCGTGAATAGGAAAAGCAC

CGATAGCCCCGTTGAGTGCATGGGCCAAGAAAAGGGCGAGTTCCGGGAGA

ACTGGGTGAACGTCATCAGCGATTTAAAGAAGATCGAAGATTTAATTCAG

TCCATGCATATCGACGCCACTTTATACACAGAATCCGACGTGCACCCCTC

TTGTAAGGTGACCGCCATGAAATGTTTTTACTGGAGCTGCAAGTTATCT

CTTTAGAGAGCGGAGACGCTAGCATCCACGACACCGTGGAGAATTTAATC

ATTTTAGCCAATAACTCTTTATCCAGCAACGGCAACGTGACAGAGTCCGG

CTGCAAGGAGTGCGAAGAGCTGGAGGAGAAGAACATCAAGGAGTTTCTGC

AATCCTTTGTGCACATTGTCCAGATGTTCATCAATACCTCC.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 116)
MKWVTFISLLFLFSSAYSNWVNVISDLKKIEDLIQSMHIDATLYTESDVH

PSCKVTAMKCFLLELQVISLESGDASIHDTVENLIILANNSLSSNGNVTE

SGCKECEELEEKNIKEFLQSFVHIVQMFINTSSGTTNTVAAYNLTWKSTN

FKTILEWEPKPVNQVYTVQISTKSGDWKSKCFYTTDTECDLTDEIVKDVK

QTYLARVFSYPAGNVESTGSAGEPLYENSPEFTPYLETNLGQPTIQSFEQ

VGTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEFR

-continued

ENWVNVISDLKKIEDLIQSMHIDATLYTESDVHPSCKVTAMKCFLLELQV

ISLESGDASIHDTVENLIILANNSLSSNGNVTESGCKECEELEEKNIKEF

LQSFVHIVQMFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 117)
ATGAAGTGGGTGACCTTCATCAGCCTGCTGTTCCTGTTCTCCAGCGCCTA

CTCCAACTGGGTGAACGTGATCAGCGATTTAAAGAAGATCGAGGATTTAA

TCCAGAGCATGCACATCGACGCCACTCTGTACACTGAGAGCGACGTGCAC

CCTAGCTGCAAGGTGACTGCCATGAAGTGCTTTTTACTGGAGCTGCAAGT

TATCTCTTTAGAGAGCGGCGATGCCAGCATCCACGACACTGTGGAGAATT

TAATCATTTTAGCCAACAACTCTTTAAGCAGCAACGGCAACGTGACAGAG

AGCGGCTGCAAGGAGTGCGAGGAGCTGGAGGAGAAGAACATCAAGGAGTT

TTTACAGAGCTTCGTGCACATCGTGCAGATGTTCATCAACACTAGCAGCG

GCACAACCAACACAGTCGCTGCCTATAACCTCACTTGGAAGAGCACCAAC

TTCAAAACCATCCTCGAATGGGAACCCAAACCCGTTAACCAAGTTTACAC

CGTGCAGATCAGCACCAAGTCCGGCGACTGGAAGTCCAAATGTTTCTATA

CCACCGACACCGAGTGCGATCTCACCGATGAGATCGTGAAAGATGTGAAA

CAGACCTACCTCGCCCGGGTGTTTAGCTACCCCGCCGGCAATGTGGAGAG

CACTGGTTCCGCTGGCGAGCCTTTATACGAGAACAGCCCCGAATTTACCC

CTTACCTCGAGACCAATTTAGGACAGCCCACCATCCAAAGCTTTGAGCAA

GTTGGCACAAAGGTGAATGTGACAGTGGAGGACGAGCGGACTTTAGTGCG

GCGGAACAACACCTTTCTCAGCCTCCGGGATGTGTTCGGCAAAGATTTAA

TCTACACACTGTATTACTGGAAGTCCTCTTCCTCCGGCAAGAAGACAGCT

AAAACCAACACAAACGAGTTTTTAATCGACGTGGATAAAGGCGAAAACTA

CTGTTTCAGCGTGCAAGCTGTGATCCCCTCCCGGACCGTGAATAGGAAAA

GCACCGATAGCCCCGTTGAGTGCATGGGCCAAGAAAAGGGCGAGTTCCGG

GAGAACTGGGTGAACGTCATCAGCGATTTAAAGAAGATCGAAGATTTAAT

TCAGTCCATGCATATCGACGCCACTTTATACACAGAATCCGACGTGCACC

CCTCTTGTAAGGTGACCGCCATGAAATGTTTTTTACTGGAGCTGCAAGTT

ATCTCTTTAGAGAGCGGAGACGCTAGCATCCACGACACCGTGGAGAATTT

AATCATTTTAGCCAATAACTCTTTATCCAGCAACGGCAACGTGACAGAGT

CCGGCTGCAAGGAGTGCGAAGAGCTGGAGGAGAAGAACATCAAGGAGTTT

CTGCAATCCTTTGTGCACATTGTCCAGATGTTCATCAATACCTCC.

Compositions/Kits

Also provided herein are compositions (e.g., pharmaceutical compositions) that include at least one of any single-chain chimeric polypeptides, any of the cells, or any of the nucleic acids described herein. In some embodiments, the compositions include at least one of any of the single-chain chimeric polypeptides described herein. In some embodiments, the compositions include any of the immune cells (e.g., any of the immune cells described herein, e.g., any of the immune cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent or ameliorate conditions, diseases or symptoms.

Also provided herein are kits that include any of the single-chain chimeric polypeptides, compositions, nucleic acids, or cells (e.g., immune cells) described herein. In some embodiments, the kits can include instructions for performing any of the methods described herein. In some embodiments, the kits can include at least one dose of any of the pharmaceutical compositions described herein.

Nucleic Acids/Vectors

Also provided herein are nucleic acids that encode any of the single-chain chimeric polypeptides described herein. Also provided herein are vectors that include any of the nucleic acids encoding any of the single-chain chimeric polypeptides described herein.

Any of the vectors described herein can be an expression vector. For example, an expression vector can include a promoter sequence operably linked to the sequence encoding the single-chain chimeric polypeptide.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, e.g., include sufficient cis-acting elements for expression; other elements for expression can be supplied by the host mammalian cell or in an in vitro expression system. Skilled practitioners will be capable of selecting suitable vectors and mammalian cells for making any of the single-chain chimeric polypeptides described herein.

Cells

Also provided herein are cells (e.g., any of the exemplary cells described herein or known in the art) comprising any of the nucleic acids described herein that encode any of the single-chain chimeric polypeptides described herein.

Also provided herein are cells (e.g., any of the exemplary cells described herein or known in the art) that include any of the vectors described herein that encode any of the single-chain chimeric polypeptides described herein.

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., an eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Single-Chain Chimeric Polypeptides

Also provided herein are methods of producing any of the single-chain chimeric polypeptides described herein that include culturing any of the cells described herein in a culture medium under conditions sufficient to result in the production of the single-chain chimeric polypeptide; and recovering the single-chain chimeric polypeptide from the cell and/or the culture medium.

The recovery of the single-chain chimeric polypeptide from a culture medium or a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Methods of culturing cells are well known in the art. Cells can be maintained in vitro under conditions that favor proliferation, differentiation and growth. Briefly, cells can be cultured by contacting a cell (e.g., any cell) with a cell culture medium that includes the necessary growth factors and supplements to support cell viability and growth.

Also provided herein are single-chain chimeric polypeptides (e.g., any of the single-chain chimeric polypeptides described herein) produced by any of the methods described herein.

Methods of Stimulating an Immune Cell

Also provided herein are methods of stimulating an immune cell (e.g., any of the exemplary immune cells described herein or known in the art) that include contacting an immune cell with an effective amount of any of the single-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Activation of an immune cell can be determined using methods known in the art. For example, activation of an immune cell can be determined by detecting the levels of cytokines and chemokines that are secreted upon activation of an immune cell. Non-limiting examples of cytokines, chemokines, and regulatory molecules that are secreted or upregulated upon activation of an immune cell include: IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, RORγT, FOXP3, STAT6, and GATA3. The detection of these cytokines and chemokines or regulatory molecules can be performed using an immunoassay (e.g., an enzyme-linked immunosorbent assay) or quantitative PCR. For example, activation of an immune cell can result in an increase of about 1% to about 800% (e.g., about 1% to about 750%, about 1% to about 700%, about 1% to about 650%, about 1% to about 600%, about 1% to about 550%, about 1% to about 500%, about 1% to about 450%, about 1% to about 400%, about 1% to about 350%, about 1% to about 300%, about 1% to about 280%, about 1% to about 260%, about 1% to about 240%, about 1% to about 220%, about 1% to about 200%, about 1% to about 180%, about 1% to about 160%, about 1% to about 140%, about 1% to about 120%, about 1% to about 100%, about 1% to about 90%, about 1% to about 80%, about 1% to about 70%, about 1% to about 60%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 800%, about 5% to about 750%, about 5% to about 700%, about 5% to about 650%, about 5% to about 600%, about 5% to about 550%, about 5% to about 500%, about 5% to about 450%, about 5% to about 400%, about 5% to about 350%, about 5% to about 300%, about 5% to about 280%, about 5% to about 260%, about 5% to about 240%, about 5% to about 220%, about 5% to about 200%, about 5% to about 180%, about 5% to about 160%, about 5% to about 140%, about 5% to about 120%, about 5% to about 100%, about 5% to about 90%, about 5% to about 80%, about 5% to about 70%, about 5% to about 60%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 800%, about 10% to about 750%, about 10% to about 700%, about 10% to about 650%, about 10% to about 600%, about 10% to about 550%, about 10% to about 500%, about 10% to about 450%, about 10% to about 400%, about 10% to about 350%, about 10% to about 300%, about 10% to about 280%, about 10% to about 260%, about 10% to about 240%, about 10% to about 220%, about 10% to about 200%, about 10% to about 180%, about 10% to about 160%, about 10% to about 140%, about 10% to about 120%, about 10% to about 100%, about 10% to about 90%, about 10% to about 80%, about 10% to about 70%, about 10% to about 60%, about 10% to about 50%, about 10% to about 45%, about 10% to about 40%, about 10% to about 35%, about 10% to about 30%, about 10% to about 25%, about 10% to about 20%, about 10% to about 15%, about 15% to about 800%, about 15% to about 750%, about 15% to about 700%, about 15% to about 650%, about 15% to about 600%, about 15% to about 550%, about 15% to about 500%, about 15% to about 450%, about 15% to about 400%, about 15% to about 350%, about 15% to about 300%, about 15% to about 280%, about 15% to about 260%, about 15% to about 240%, about 15% to about 220%, about 15% to about 200%, about 15% to about 180%, about 15% to about 160%, about 15% to about 140%, about 15% to about 120%, about 15% to about 100%, about 15% to about 90%, about 15% to about 80%, about 15% to about 70%, about 15% to about 60%, about 15% to about 50%, about 15% to about 45%, about 15% to about 40%, about 15% to about 35%, about 15% to about 30%, about 15% to about 25%, about 15% to about 20%, about 20% to about 800%, about 20% to about 750%, about 20% to about 700%, about 20% to about 650%, about 20% to about 600%, about 20% to about 550%, about 20% to about 500%, about 20% to about 450%, about 20% to about 400%, about 20% to about 350%, about 20% to about 300%, about 20% to about 280%, about 20% to about 260%, about 20% to about 240%, about 20% to about 220%, about 20% to about 200%, about 20% to about 180%, about 20% to about 160%, about 20% to about 140%, about 20% to about 120%, about 20% to about 100%, about 20% to about 90%, about 20% to about 80%, about 20% to about 70%, about 20% to about 60%, about 20% to about 50%, about 20% to about 45%, about 20% to about 40%, about 20% to about 35%, about 20% to about 30%, about 20% to about 25%, about 25% to about 800%, about 25% to about 750%, about 25% to about 700%, about 25% to about 650%, about 25% to about 600%, about 25% to about 550%, about 25% to about 500%, about 25% to about 450%, about 25% to about 400%, about 25% to about 350%, about 25% to about 300%, about 25% to about 280%, about 25% to about 260%, about 25% to about 240%, about 25% to about 220%, about 25% to about 200%, about 25% to about 180%, about 25% to about 160%, about 25% to about 140%, about 25% to about 120%, about 25% to about 100%, about 25% to about 90%, about 25% to about 80%, about 25% to about 70%, about 25% to about 60%, about 25% to about 50%, about 25% to about 45%, about 25% to about 40%, about 25% to about 35%, about 35% to about 800%, about 35% to about 750%, about 35% to about 700%, about 35% to about 650%, about 35% to about 600%, about 35% to about 550%, about 35% to about 500%, about 35% to about 450%, about 35% to about 400%, about 35% to about 350%, about 35% to about 300%, about 35% to about 280%, about 35% to about 260%, about 35% to about 240%, about 35% to about 220%, about 35% to about 200%, about 35% to about 180%, about 35% to about 160%, about 35% to about 140%, about 35% to about 120%, about 35% to about 100%, about 35% to about 90%, about 35% to about 80%, about 35% to about 70%, about 35% to about 60%, about 35% to about 50%, about 35% to about 45%, about 35% to about 40%, about 40% to about 800%, about 40% to about 750%, about 40% to about 700%, about 40% to about 650%, about 40% to about 600%, about 40% to about 550%, about 40% to about 500%, about 40% to about 450%, about 40% to about 400%, about 40% to about 350%, about 40% to about 300%, about 40% to about 280%, about 40% to about 260%, about 40% to about 240%, about 40% to about 220%, about 40% to about 200%, about 40% to about 180%, about 40% to about 160%, about 40% to about 140%, about 40% to about 120%, about 40% to about 100%, about 40% to about 90%, about 40% to about 80%, about 40% to about 70%, about 40% to about 60%, about 40% to about 50%, about 40% to about 45%, about 45% to about 800%, about 45% to about 750%, about 45% to about 700%, about 45% to about 650%, about 45% to about 600%, about 45% to about 550%, about 45% to about 500%, about 45% to about 450%, about 45% to about 400%, about 45% to about 350%, about 45% to about 300%, about 45% to about 280%, about 45% to about 260%, about 45% to about 240%, about 45% to about 220%, about 45% to about 200%, about 45% to about 180%, about 45% to about 160%, about 45% to about 140%, about 45% to about 120%, about 45% to about 100%, about 45% to about 90%, about 45% to about 80%, about 45% to about 70%, about 45% to about 60%, about 45% to about 50%, about 50% to about 800%, about 50% to about 750%, about 50% to about 700%, about 50% to about 650%, about 50% to about 600%, about 50% to about 550%, about 50% to about 500%, about 50% to about 450%, about 50% to about 400%, about 50% to about 350%, about 50% to about 300%, about 50% to about 280%, about 50% to about 260%, about 50% to about 240%, about 50% to about 220%, about 50% to about 200%, about 50% to about 180%, about 50% to about 160%, about 50% to about 140%, about 50% to about 120%, about 50% to about 100%, about 50% to about 90%, about 50% to about 80%, about 50% to about 70%, about 50% to about 60%, about 60% to about 800%, about 60% to about 750%, about 60% to about 700%, about 60% to about 650%, about 60% to about 600%, about 60% to about 550%, about 60% to about 500%, about 60% to about 450%, about 60% to about 400%, about 60% to about 350%, about 60% to about 300%, about 60% to about 280%, about 60% to about 260%, about 60% to about 240%, about 60% to about 220%, about 60% to about 200%, about 60% to about 180%, about 60% to about 160%, about 60% to about 140%, about 60% to about 120%, about 60% to about 100%, about 60% to about 90%, about 60% to about 80%, about 60% to about 70%, about 70% to about 800%, about 70% to about 750%, about 70% to about 700%, about 70% to about 650%, about 70% to about 600%, about 70% to about 550%, about 70% to about 500%, about 70% to about 450%, about 70% to about 400%, about 70% to about 350%, about 70% to about 300%, about 70% to about 280%, about 70% to about 260%, about 70% to about 240%, about 70% to about 220%, about 70% to about 200%, about 70% to about 180%, about 70% to about 160%, about 70% to about 140%, about 70% to about 120%, about 70% to about 100%, about 70% to about 90%, about 70% to about 80%, about 80% to about 800%, about 80% to about 750%, about 80% to about 700%, about 80% to about 650%, about 80% to about 600%, about 80% to about 550%, about 80% to about 500%, about 80% to about 450%, about 80% to about 400%, about 80% to about 350%, about 80% to about 300%, about 80% to about 280%, about 80% to about 260%, about 80% to about 240%, about 80% to about 220%, about 80% to about 200%, about 80% to about 180%, about 80% to about 160%, about 80% to about 140%, about 80% to about 120%, about 80% to about 100%, about 80% to about 90%, about 90% to about 800%, about 90% to about 750%, about 90% to about 700%, about 90% to about 650%, about 90% to about 600%, about 90% to about 550%, about 90% to about 500%, about 90% to about 450%, about 90% to about 400%, about 90% to about 350%, about 90% to about 300%, about 90% to about 280%, about 90% to about 260%, about 90% to about 240%, about 90% to about 220%, about 90% to about 200%, about 90% to about 180%, about 90% to about 160%, about 90% to about 140%, about 90% to about 120%, about 90% to about 100%, about 100% to about 800%, about 100% to about 750%, about 100% to about 700%, about 100% to about 650%, about 100% to about 600%, about 100% to about 550%, about 100% to about 500%, about 100% to about 450%, about 100% to about 400%, about 100% to about 350%, about 100% to about 300%, about 100% to about 280%, about 100% to about 260%, about 100% to about 240%, about 100% to about 220%, about 100% to about 200%, about 100% to about 180%, about 100% to about 160%, about 100% to about 140%, about 100% to about 120%, about 120% to about 800%, about 120% to about 750%, about 120% to about 700%, about 120% to about 650%, about 120% to about 600%, about 120% to about 550%, about 120% to about 500%, about 120% to about 450%, about 120% to about 400%, about 120% to about 350%, about 120% to about 300%, about 120% to about 280%, about 120% to about 260%, about 120% to about 240%, about 120% to about 220%, about 120% to about 200%, about 120% to about 180%, about 120% to about 160%, about 120% to about 140%, about 140% to about 800%, about 140% to about 750%, about 140% to about 700%, about 140% to about 650%, about 140% to about 600%, about 140% to about 550%, about 140% to about 500%, about 140% to about 450%, about 140% to about 400%, about 140% to about 350%, about 140% to about 300%, about 140% to about 280%, about 140% to about 260%, about 140% to about 240%, about 140% to about 220%, about 140% to about 200%, about 140% to about 180%, about 140% to about 160%, about 160% to about 800%, about 160% to about 750%, about 160% to about 700%, about 160% to about 650%, about 160% to about 600%, about 160% to about 550%, about 160% to about 500%, about 160% to about 450%, about 160% to about 400%, about 160% to about 350%, about 160% to about 300%, about 160% to about 280%, about 160% to about 260%, about 160% to about 240%, about 160% to about 220%, about 160% to about 200%, about 160% to about 180%, about 180% to about 800%, about 180% to about 750%, about 180% to about 700%, about 180% to about 650%, about 180% to about 600%, about 180% to about 550%, about 180% to about 500%, about 180% to about 450%, about 180% to about 400%, about 180% to about 350%, about 180% to about 300%, about 180% to about 280%, about 180% to about 260%, about 180% to about 240%, about 180% to about 220%, about 180% to about 200%, about 200% to about 800%, about 200% to about 750%, about 200% to about 700%, about 200% to about 650%, about 200% to about 600%, about 200% to about 550%, about 200% to about 500%, about 200% to about 450%, about 200% to about 400%, about 200% to about 350%, about 200% to about 300%, about 200% to about 280%, about 200% to about 260%, about 200% to about 240%, about 200% to about 220%, about 220% to about 800%, about 220% to about 750%, about 220% to about 700%, about 220% to about 650%, about 220% to about 600%, about 220% to about 550%, about 220% to about 500%, about 220% to about 450%, about 220% to about 400%, about 220% to about 350%, about 220% to about 300%, about 220% to about 280%, about 220% to about 260%, about 240% to about 800%, about 240% to about 750%, about 240% to about 700%, about 240% to about 650%, about 240% to about 600%, about 240% to about 550%, about 240% to about 500%, about 240% to about 450%, about 240% to about 400%, about 240% to about 350%, about 240% to about 300%, about 240% to about 280%, about 240% to about 260%, about 260% to about 800%, about 260% to about 750%, about 260% to about 700%, about 260% to about 650%, about 260% to about 600%, about 260% to about 550%, about 260% to about 500%, about 260% to about 450%, about 260% to about 400%, about 260% to about 350%, about 260% to about 300%, about 260% to about 280%, about 280% to about 800%, about 280% to about 750%, about 280% to about 700%, about 280% to about 650%, about 280% to about 600%, about 280% to about 550%, about 280% to about 500%, about 280% to about 450%, about 280% to about 400%, about 280% to about 350%, about 300% to about 800%, about 300% to about 750%, about 300% to about 700%, about 300% to about 650%, about 300% to about 600%, about 300% to about 550%, about 300% to about 500%, about 300% to about 450%, about 300% to about 400%, about 300% to about 350%, about 350% to about 800%, about 350% to about 750%, about 350% to about 700%, about 350% to about 650%, about 350% to about 600%, about 350% to about 550%, about 350% to about 500%, about 350% to about 450%, about 350% to about 400%, about 400% to about 800%, about 400% to about 750%, about 400% to about 700%, about 400% to about 650%, about 400% to about 600%, about 400% to about 550%, about 400% to about 500%, about 400% to about 450%, about 450% to about 800%, about 450% to about 750%, about 450% to about 700%, about 450% to about 650%, about 450% to about 600%, about 450% to about 550%, about 450% to about 500%, about 500% to about 800%, about 500% to about 750%, about 500% to about 700%, about 500% to about 650%, about 500% to about 600%, about 500% to about 550%, about 550% to about 800%, about 550% to about 750%, about 550% to about 700%, about 550% to about 650%, about 550% to about 600%, about 600% to about 800%, about 600% to about 750%, about 600% to about 700%, about 600% to about 650%, about 650% to about 800%, about 650% to about 750%, about 650% to about 700%, about 700% to about 800%, about 700% to about 750%, or about 750% to about 800%) of one or more of any of the cytokines or chemokines or regulatory molecules described herein (e.g., one or more of any of IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, RORγT, FOXP3, STAT6, and GATA3) (e.g., as compared to the level of the one or more cytokines and chemokines in a control not contacted with any of the single-chain chimeric polypeptides described herein).

Methods of Inducing or Increasing Proliferation of an Immune Cell

Also provided herein are methods of inducing or increasing proliferation of an immune cell (e.g., any of the exemplary immune cells described herein or known in the art) that include contacting an immune cell with an effective amount of any of the single-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Detection of the proliferation of an immune cell can be performed using methods known in the art, e.g., cytometry (e.g., fluorescence-assisted flow cytometry), microscopy, and immunofluorescence microscopy, e.g., by comparing the rate of increase in the concentration of the immune cell in a sample not contacted with a single-chain chimeric polypeptide to the rate of increase in the concentration of the immune cell in a similar sample contacted with any of the single-chain chimeric polypeptides described herein).

In other examples, the proliferation of an immune cell can be indirectly detected by detecting an increase in the level of one or more cytokines or chemokines secreted or regulatory molecules by proliferating immune cells (e.g., one or more of IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, RORγT, FOXP3, STAT6, and GATA3) (e.g., as compared to the level of the one or more cytokines and chemokines in a control not contacted with any of the single-chain chimeric polypeptides described herein).

In some embodiments, the methods provided herein can result in an increase (e.g., about 1% to about 800% increase, or any of the subranges of this range described herein) in the rate of increase in the concentration of the immune cell in a sample contacted with any of the single-chain chimeric polypeptides described herein as compared to the rate of increase in a similar control sample not contacted with any of the single-chain chimeric polypeptides described herein.

Methods of Inducing Differentiation of an Immune Cell

Also provided herein are method of inducing differentiation of an immune cell (e.g., any of the exemplary immune cells described herein or known in the art) into a memory or memory-like immune cell that include contacting an immune cell with an effective amount of any of the single-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

In some examples, the immune cell is a NK cell, and the detection of a memory NK cell can include, e.g., the detection of the increased level of one or more of CD25, CD69, CD62L, IL-12, IL-18, IL-33, STAT4, STAT5, Zbtb32, DNAM-1, NKp30, NKp40, NKp46, BIM, Noxa, SOCS1, BNIP3, BNIP3L, IFN-γ, CXCL16, CXCR6, NKG2D, TRAIL, CD49, Ly49D, CD49b, and Ly79H. A description of NK memory cells and methods of detecting the same is described in O'Sullivan et al., *Immunity* 43:634-645, 2015.

In some examples, the immune cell is a T cell, and the detection of memory T cells can include, e.g., the detection of the level of expression of one or more of CD45RO, CCR7, L-selectin (CD62L), CD44, CD45RA, integrin αeβ7, CD43, CD27, CD28, IL-7Rα, CD95, IL-2Rβ, CXCR3, and LFA-1. In some examples, the immune cell is a B cell and the detection of memory B cells can include, e.g., the detection of the level of expression of CD27. Other types and markers of memory or memory-like immune cells are known in the art.

Methods of Treatment

Also provided herein are methods of treating a subject in need thereof (e.g., any of the exemplary subjects described herein or known in the art) that include administering to the subject a therapeutically effective amount of any of the single-chain chimeric polypeptides described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, these methods can result in a reduction in the number, severity, or frequency of one or more symptoms of the cancer in the subject (e.g., as compared to the number, severity, or frequency of the one or more symptoms of the cancer in the subject prior to treatment). In some embodiments, these methods can result in a reduction (e.g., about 1% reduction to about 99% reduction, about 1% reduction to about 95% reduction, about 1% reduction to about 90% reduction, about 1% reduction to about 85% reduction, about 1% reduction to about 80% reduction, about 1% reduction to about 75% reduction, about 1% reduction to about 70% reduction, about 1% reduction to about 65% reduction, about 1% reduction to about 60% reduction, about 1% reduction to about 55% reduction, about 1% reduction to about 50% reduction, about 1% reduction to about 45% reduction, about 1% reduction to about 40% reduction, about 1% reduction to about 35% reduction, about 1% reduction to about 30% reduction, about 1% reduction to about 25% reduction, about 1% reduction to about 20% reduction, about 1% reduction to about 15% reduction, about 1% reduction to about 10% reduction, about 1% reduction to about 5% reduction, about 5% reduction to about 99% reduction, about 5% reduction to about 95% reduction, about 5% reduction to about 90% reduction, about 5% reduction to about 85% reduction, about 5% reduction to about 80% reduction, about 5% reduction to about 75% reduction, about 5% reduction to about 70% reduction, about 5% reduction to about 65% reduction, about 5% reduction to about 60% reduction, about 5% reduction to about 55% reduction, about 5% reduction to about 50% reduction, about 5% reduction to about 45% reduction, about 5% reduction to about 40% reduction, about 5% reduction to about 35% reduction, about 5% reduction to about 30% reduction, about 5% reduction to about 25% reduction, about 5% reduction to about 20% reduction, about 5% reduction to about 15% reduction, about 5% reduction to about 10% reduction, about 10% reduction to about 99% reduction, about 10% reduction to about 95% reduction, about 10% reduction to about 90% reduction, about 10% reduction to about 85% reduction, about 10% reduction to about 80% reduction, about 10% reduction to about 75% reduction, about 10% reduction to about 70% reduction, about 10% reduction to about 65% reduction, about 10% reduction to about 60% reduction, about 10% reduction to about 55% reduction, about 10% reduction to about 50% reduction, about 10% reduction to about 45% reduction, about 10% reduction to about 40% reduction, about 10% reduction to about 35% reduction, about 10% reduction to about 30% reduction, about 10% reduction to about 25% reduction, about 10% reduction to about 20% reduction, about 10% reduction to about 15% reduction, about 15% reduction to about 99% reduction, about 15% reduction to about 95% reduction, about 15% reduction to about 90% reduction, about 15% reduction to about 85% reduction, about 15% reduction to about 80% reduction, about 15% reduction to about 75% reduction, about 15% reduction to about 70% reduction, about 15% reduction to about 65% reduction, about 15% reduction to about 60% reduction, about 15% reduction to about 55% reduction, about 15% reduction to about 50% reduction, about 15% reduction to about 45% reduction, about 15% reduction to about 40% reduction, about 15% reduction to about 35% reduction, about 15% reduction to about 30% reduction, about 15% reduction to about 25% reduction, about 15% reduction to about 20% reduction, about 20% reduction to about 99% reduction, about 20% reduction to about 95% reduction, about 20% reduction to about 90% reduction, about 20% reduction to about 85% reduction, about 20% reduction to about 80% reduction, about 20% reduction to about 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 20% reduction to about 30% reduction, about 20% reduction to about 25% reduction, about 25% reduction to about 99% reduction, about 25% reduction to about 95% reduction, about 25% reduction to about 90% reduction, about 25% reduction to about 85% reduction, about 25% reduction to about 80% reduction, about 25% reduction to about 75% reduction, about 25% reduction to about 70% reduction, about 25% reduction to about 65% reduction, about 25% reduction to about 60% reduction, about 25% reduction to about 55% reduction, about 25% reduction to about 50% reduction, about 25% reduction to about 45% reduction, about 25% reduction to about 40% reduction, about 25% reduction to about 35% reduction, about 25% reduction to about 30% reduction, about 30% reduction to about 99% reduction, about 30% reduction to about 95% reduction, about 30% reduction to about 90% reduction, about 30% reduction to about 85% reduction, about 30% reduction to about 80% reduction, about 30% reduction to about 75% reduction, about 30% reduction to about 70% reduction, about 30% reduction to about 65% reduction, about 30% reduction to about 60% reduction, about 30% reduction to about 55% reduction, about 30% reduction to about 50% reduction, about 30% reduction to about 45% reduction, about 30% reduction to about 40% reduction, about 30% reduction to about 35% reduction, about 35% reduction to about 99% reduction, about 35% reduction to about 95% reduction, about 35% reduction to about 90% reduction, about 35% reduction to about 85% reduction, about 35% reduction to about 80% reduction, about 35% reduction to about 75% reduction, about 35% reduction to about 70% reduction, about 35% reduction to about 65% reduction, about 35% reduction to about 60% reduction, about 35% reduction to about 55% reduction, about 35% reduction to about 50% reduction, about 35% reduction to about 45% reduction, about 35% reduction to about 40% reduction, about 40% reduction to about 99% reduction, about 40% reduction to about 95% reduction, about 40% reduction to about 90% reduction, about 40% reduction to about 85% reduction, about 40% reduction to about 80% reduction, about 40% reduction to about 75% reduction, about 40% reduction to about 70% reduction, about 40% reduction to about 65% reduction, about 40% reduction to about 60% reduction, about 40% reduction to about 55% reduction, about 40% reduction to about 50% reduction, about 40% reduction to about 45% reduction, about 45% reduction to about 99% reduction, about 45% reduction to about 95% reduction, about 45% reduction to about 90% reduction, about 45% reduction to about 85% reduction, about 45% reduction to about 80% reduction, about 45% reduction to about 75% reduction, about 45% reduction to about 70% reduction, about 45% reduction to about 65% reduction, about 45% reduction to about 60% reduction, about 45% reduction to about 55% reduction, about 45% reduction to about 50% reduction, about 50% reduction to about 99% reduction, about 50% reduction to about 95% reduction, about 50% reduction to about 90% reduction, about 50% reduction to about 85% reduction, about 50% reduction to about 80% reduction, about 50% reduction to about 75% reduction, about 50% reduction to about 70% reduction, about 50% reduction to about 65% reduction, about 50% reduction to about 60% reduction, about 50% reduction to about 55% reduction, about 55% reduction to about 99% reduction, about 55% reduction to about 95% reduction, about 55% reduction to about 90% reduction, about 55% reduction to about 85% reduction, about 55% reduction to about 80% reduction, about 55% reduction to about 75% reduction, about 55% reduction to about 70% reduction, about 55% reduction to about 65% reduction, about 55% reduction to about 60% reduction, about 60% reduction to about 99% reduction, about 60% reduction to about 95% reduction, about 60% reduction to about 90% reduction, about 60% reduction to about 85% reduction, about 60% reduction to about 80% reduction, about 60% reduction to about 75% reduction, about 60% reduction to about 70% reduction, about 60% reduction to about 65% reduction, about 65% reduction to about 99% reduction, about 65% reduction to about 95% reduction, about 65% reduction to about 90% reduction, about 65% reduction to about 85% reduction, about 65% reduction to about 80% reduction, about 65% reduction to about 75% reduction, about 65% reduction to about 70% reduction, about 70% reduction to about 99% reduction, about 70% reduction to about 95% reduction, about 70% reduction to about 90% reduction, about 70% reduction to about 85% reduction, about 70% reduction to about 80% reduction, about 70% reduction to about 75% reduction, about 75% reduction to about 99% reduction, about 75% reduction to about 95% reduction, about 75% reduction to about 90% reduction, about 75% reduction to about 85% reduction, about 75% reduction to about 80% reduction, about 80% reduction to about 99% reduction, about 80% reduction to about 95% reduction, about 80% reduction to about 90% reduction, about 80% reduction to about 85% reduction, about 85% reduction to about 99% reduction, about 85% reduction to about 95% reduction, about 85% reduction to about 90% reduction, about 90% reduction to about 99% reduction, about 90% reduction to about 95% reduction, or about 95% reduction to about 99% reduction) in the volume of one or more solid tumors in the subject (e.g., as compared to the volume of the one or more solid tumors prior to treatment or at the start of treatment). In some embodiments, the these methods can reduce (e.g., about 1% reduction to about 99% reduction, or any of the subranges of this range described herein) the risk of developing a metastasis or developing one or more additional metastasis in a subject (e.g., as compared to the risk of developing a metastasis or developing one or more additional metastasis in a subject prior to treatment or in a similar subject or a population of subjects administered a different treatment).

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples, these methods can result in a reduction in the number, severity, or frequency of one or more symptoms of the aging-related disease or condition in the subject (e.g., as compared to the number, severity, or frequency of the one or more symptoms of the aging-related disease or condition in the subject prior to treatment). In some examples, the methods can result in a decrease (e.g., about 1% decrease to about 99% decrease, an about 1% decrease to about 95% decrease, about 1% decrease to about 90% decrease, about 1% decrease to about 85% decrease, about 1% decrease to about 80% decrease, about 1% decrease to about 75% decrease, about 1% to about 70% decrease, about 1% decrease to about 65% decrease, about 1% decrease to about 60% decrease, about 1% decrease to about 55% decrease, about 1% decrease to about 50% decrease, about 1% decrease to about 45% decrease, about 1% decrease to about 40% decrease, about 1% decrease to about 35% decrease, about 1% decrease to about 30% decrease, about 1% decrease to about 25% decrease, about 1% decrease to about 20% decrease, about 1% decrease to about 15% decrease, about 1% decrease to about 10% decrease, about 1% decrease to about 5% decrease, about 5% decrease to about 99% decrease, an about 5% decrease to about 95% decrease, about 5% decrease to about 90% decrease, about 5% decrease to about 85% decrease, about 5% decrease to about 80% decrease, about 5% decrease to about 75% decrease, about 5% to about 70% decrease, about 5% decrease to about 65% decrease, about 5% decrease to about 60% decrease, about 5% decrease to about 55% decrease, about 5% decrease to about 50% decrease, about 5% decrease to about 45% decrease, about 5% decrease to about 40% decrease, about 5% decrease to about 35% decrease, about 5% decrease to about 30% decrease, about 5% decrease to about 25% decrease, about 5% decrease to about 20% decrease, about 5% decrease to about 15% decrease, about 5% decrease to about 10% decrease, about 10% decrease to about 99% decrease, an about 10% decrease to about 95% decrease, about 10% decrease to about 90% decrease, about 10% decrease to about 85% decrease, about 10% decrease to about 80% decrease, about 10% decrease to about 75% decrease, about 10% to about 70% decrease, about 10% decrease to about 65% decrease, about 10% decrease to about 60% decrease, about 10% decrease to about 55% decrease, about 10% decrease to about 50% decrease, about 10% decrease to about 45% decrease, about 10% decrease to about 40% decrease, about 10% decrease to about 35% decrease, about 10% decrease to about 30% decrease, about 10% decrease to about 25% decrease, about 10% decrease to about 20% decrease, about 10% decrease to about 15% decrease, about 15% decrease to about 99% decrease, an about 15% decrease to about 95% decrease, about 15% decrease to about 90% decrease, about 15% decrease to about 85% decrease, about 15% decrease to about 80% decrease, about 15% decrease to about 75% decrease, about 15% to about 70% decrease, about 15% decrease to about 65% decrease, about 15% decrease to about 60% decrease, about 15% decrease to about 55% decrease, about 15% decrease to about 50% decrease, about 15% decrease to about 45% decrease, about 15% decrease to about 40% decrease, about 15% decrease to about 35% decrease, about 15% decrease to about 30% decrease, about 15% decrease to about 25% decrease, about 15% decrease to about 20% decrease, about 20% decrease to about 99% decrease, an about 20% decrease to about 95% decrease, about 20% decrease to about 90% decrease, about 20% decrease to about 85% decrease, about 20% decrease to about 80% decrease, about 20% decrease to about 75% decrease, about 20% to about 70% decrease, about 20% decrease to about 65% decrease, about 20% decrease to about 60% decrease, about 20% decrease to about 55% decrease, about 20% decrease to about 50% decrease, about 20% decrease to about 45% decrease, about 20% decrease to about 40% decrease, about 20% decrease to about 35% decrease, about 20% decrease to about 30% decrease, about 20% decrease to about 25% decrease, about 25% decrease to about 99% decrease, an about 25% decrease to about 95% decrease, about 25% decrease to about 90% decrease, about 25% decrease to about 85% decrease, about 25% decrease to about 80% decrease, about 25% decrease to about 75% decrease, about 25% to about 70% decrease, about 25% decrease to about 65% decrease, about 25% decrease to about 60% decrease, about 25% decrease to about 55% decrease, about 25% decrease to about 50% decrease, about 25% decrease to about 45% decrease, about 25% decrease to about 40% decrease, about 25% decrease to about 35% decrease, about 25% decrease to about 30% decrease, about 30% decrease to about 99% decrease, an about 30% decrease to about 95% decrease, about 30% decrease to about 90% decrease, about 30% decrease to about 85% decrease, about 30% decrease to about 80% decrease, about 30% decrease to about 75% decrease, about 30% to about 70% decrease, about 30% decrease to about 65% decrease, about 30% decrease to about 60% decrease, about 30% decrease to about 55% decrease, about 30% decrease to about 50% decrease, about 30% decrease to about 45% decrease, about 30% decrease to about 40% decrease, about 30% decrease to about 35% decrease, about 35% decrease to about 99% decrease, an about 35% decrease to about 95% decrease, about 35% decrease to about 90% decrease, about 35% decrease to about 85% decrease, about 35% decrease to about 80% decrease, about 35% decrease to about 75% decrease, about 35% to about 70% decrease, about 35% decrease to about 65% decrease, about 35% decrease to about 60% decrease, about 35% decrease to about 55% decrease, about 35% decrease to about 50% decrease, about 35% decrease to about 45% decrease, about 35% decrease to about 40% decrease, about 40% decrease to about 99% decrease, an about 40% decrease to about 95% decrease, about 40% decrease to about 90% decrease, about 40% decrease to about 85% decrease, about 40% decrease to about 80% decrease, about 40% decrease to about 75% decrease, about 40% to about 70% decrease, about 40% decrease to about 65% decrease, about 40% decrease to about 60% decrease, about 40% decrease to about 55% decrease, about 40% decrease to about 50% decrease, about 40% decrease to about 45% decrease, about 45% decrease to about 99% decrease, an about 45% decrease to about 95% decrease, about 45% decrease to about 90% decrease, about 45% decrease to about 85% decrease, about 45% decrease to about 80% decrease, about 45% decrease to about 75% decrease, about 45% to about 70% decrease, about 45% decrease to about 65% decrease, about 45% decrease to about 60% decrease, about 45% decrease to about 55% decrease, about 45% decrease to about 50% decrease, about 50% decrease to about 99% decrease, an about 50% decrease to about 95% decrease, about 50% decrease to about 90% decrease, about 50% decrease to about 85% decrease, about 50% decrease to about 80% decrease, about 50% decrease to about 75% decrease, about 50% to about 70% decrease, about 50% decrease to about 65% decrease, about 50% decrease to about 60% decrease, about 50% decrease to about 55% decrease, about 55% decrease to about 99% decrease, an about 55% decrease to about 95% decrease, about 55% decrease to about 90% decrease, about 55% decrease to about 85% decrease, about 55% decrease to about 80% decrease, about 55% decrease to about 75% decrease, about 55% to about 70% decrease, about 55% decrease to about 65% decrease, about 55% decrease to about 60% decrease, about 60% decrease to about 99% decrease, an about 60% decrease to about 95% decrease, about 60% decrease to about 90% decrease, about 60% decrease to about 85% decrease, about 60% decrease to about 80% decrease, about 60% decrease to about 75% decrease, about 60% to about 70% decrease, about 60% decrease to about 65% decrease, about 65% decrease to about 99% decrease, an about 65% decrease to about 95% decrease, about 65% decrease to about 90% decrease, about 65% decrease to about 85% decrease, about 65% decrease to about 80% decrease, about 65% decrease to about 75% decrease, about 65% to about 70% decrease, about 70% decrease to about 99% decrease, an about 70% decrease to about 95% decrease, about 70% decrease to about 90% decrease, about 70% decrease to about 85% decrease, about 70% decrease to about 80% decrease, about 70% decrease to about 75% decrease, about 75% decrease to about 99% decrease, an about 75% decrease to about 95% decrease, about 75% decrease to about 90% decrease, about 75% decrease to about 85% decrease, about 75% decrease to about 80% decrease, about 80% decrease to about 99% decrease, an about 80% decrease to about 95% decrease, about 80% decrease to about 90% decrease, about 80% decrease to about 85% decrease, about 85% decrease to about 99% decrease, an about 85% decrease to about 95% decrease, about 85% decrease to about 90% decrease, about 90% decrease to about 99% decrease, an about 90% decrease to about 95% decrease, or about 95% decrease to about 99% decrease) in the number of senescent cells in the subject (e.g., a decrease in the number of senescent cells in one or more specific tissues involved and/or implicated in the aging-related disease or disorder in the subject), e.g., as compared to the number of senescent cells in the subject prior to treatment.

In some examples of these methods, the subject has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus. In some embodiments, these methods can result in a decrease in the infectious titer (e.g., viral titer) in a subject (e.g., as compared to the infectious titer in the subject prior to treatment). In some embodiments, these methods can result in a reduction in the number, severity, or frequency of one or more symptoms of the infectious disease (e.g., viral infection) in the subject (e.g., as compared to the number, severity, or frequency of the one or more symptoms of the infectious disease in the subject prior to treatment).

The term "subject" refers to any mammal. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine or primate animals) may be employed.

Methods of Killing a Cancer Cell, an Infected Cell, or a Senescent Cell

Also provided herein are methods of killing a cancer cell (e.g., any of the exemplary types of cancer described herein or known in the art), an infected cell (e.g., a cell infected with any of the exemplary viruses described herein or known in the art), or a senescent cell (e.g., a senescent cancer cell, a senescent fibroblast, or a senescent endothelial cell) in a subject in need thereof (e.g., any of the exemplary subjects described herein or known in the art) that include administering to the subject a therapeutically effective amount of any of the single-chain chimeric polypeptides described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. Non-limiting examples of an infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Senescent Cells

Senescence is a form of irreversible growth arrest accompanied by phenotypic changes, resistance to apoptosis and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence the tissue hemostasis, disease and aging through their secretory phenotype. Senescence is considered as a physiologic process and is important in promoting wound healing, tissue homeostasis, regeneration, and fibrosis regulation. For instance, transient induction of senescent cells is observed during would healing and contributes to wound resolution. Perhaps one of the most important roles of senescence is its role in tumor suppression. However, the accumulation of senescent cells also drives aging- and aging-related diseases and conditions. The senescent phenotype also can trigger chronic inflammatory responses and consequently augment chronic inflammatory conditions to promote tumor growth. The connection between senescence and aging was initially based on observations that senescent cells accumulate in aged tissue. The use of transgenic models has enabled the detection of senescent cells systematically in many age-related pathologies. Strategies to selectively eliminate senescent cells has demonstrated that senescent cells can indeed play a causal role in aging and related pathologies.

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p16INK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, *J Clin Invest.* 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, Oncogene 32(15): 1971-1977, 2013), hepatocellular carcinoma (Iannello, *J Exp Med* 210(10): 2057-2069, 2013), multiple myeloma (Soriani, *Blood* 113 (15): 3503-3511, 2009), and glioma cells stressed by dysfunction of the mevalonate pathway (Ciaglia, *Int J Cancer* 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, *Elife* 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80+ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, *Cell* 134(4): 657-667, 2008). Studies have described various models to study senescence including liver fibrosis (Krizhanovsky, *Cell* 134(4): 657-667, 2008), osteoarthritis (Xu, *J Gerontol A Blot Sci Med Sci* 72(6): 780-785, 2017), and Parkinson's disease (Chinta, *Cell Rep* 22(4): 930-940, 2018). Animal models for studying senescent cells are described in: Krizhanovsky, Cell 134(4): 657-667, 2008; Baker, *Nature* 479(7372): 232-236, 2011; Farr, *Nat Med* 23(9): 1072-1079, 2017; Bourgeois, *FEBS Lett* 592(12): 2083-2097, 2018; Xu, *Nat Med* 24(8): 1246-1256, 2018).

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as a single-chain chimeric polypeptide (e.g., any of the single-chain chimeric polypeptides described herein) or an immune cell (e.g., administered as a single formulation or two or more formulations to the subject). In some embodiments, one or more additional therapeutic agents can be administered to the subject prior to administration of a single-chain chimeric polypeptide (e.g., any of the single-chain chimeric polypeptides described herein) or an immune cell. In some embodiments, one or more additional therapeutic agents can be administered to the subject after administration of a single-chain chimeric polypeptide (e.g., any of the single-chain chimeric polypeptides described herein) or an immune cell to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include antimetabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

Non-limiting examples of activating receptor agonists include any agonists for activating receptors which activate and enhance the cytotoxicity of NK cells, including anti-CD16 antibodies (e.g., anti-CD16/CD30 bispecific monoclonal antibody (BiMAb)) and Fc-based fusion proteins. Non-limiting examples of checkpoint inhibitors include anti-PD-1 antibodies (e.g., MEDI0680), anti-PD-L1 antibodies (e.g., BCD-135, BGB-A333, CBT-502, CK-301, CS1001, FAZ053, KN035, MDX-1105, MSB2311, SHR-1316, anti-PD-L1/CTLA-4 bispecific antibody KN046, anti-PD-L1/TGFβRII fusion protein M7824, anti-PD-L1/TIM-3 bispecific antibody LY3415244, atezolizumab, or avelumab), anti-TIM3 antibodies (e.g., TSR-022, Sym023, or MBG453) and anti-CTLA-4 antibodies (e.g., AGEN1884, MK-1308, or an anti-CTLA-4/OX40 bispecific antibody ATOR-1015). Non-limiting examples of agents for blocking HLA-specific inhibitory receptors include monalizumab (e.g., an anti-HLA-E NKG2A inhibitory receptor monoclonal antibody). Non-limiting examples of GSK3 inhibitor include tideglusib or CHIR99021. Non-limiting examples of antibodies that can be used as additional therapeutic agents include anti-CD26 antibodies (e.g., YS110), anti-CD36 antibodies, and any other antibody or antibody construct that can bind to and activate an Fc receptor (e.g., CD16) on a NK cell. In some embodiments, an additional therapeutic agent can be insulin or metformin.

EXAMPLES

The invention is further described in the following examples, which do not limit the scope of the invention described in the claims.

Example 1. Production of an Exemplary Single-Chain Chimeric Polypeptides

An exemplary single-chain chimeric polypeptide including a first target-binding domain that is an anti-CD3 scFv, a soluble human tissue factor domain, and a second target-binding domain that is an anti-CD28 scFv was generated (αCD3scFv/TF/αCD28scFv) (FIG. 1). The nucleic acid and amino acid sequences of this single-chain chimeric polypeptide are shown below.

Nucleic Acid Encoding Exemplary Single-Chain
Chimeric Polypeptide (αCD3scFv/TF/αCD28scFv)
(SEQ ID NO: 4)
(Signal peptide)
ATGAAGTGGGTGACCTTCATCAGCTTATTATTTTTATTCAGCTCCGCCTA

TTCC (αCD3 light chain variable region)
CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGT (Linker)
GGAGGAGGTGGCAGCGGCGGCGGTGGATCCGGCGGAGGAGGAAGC (αCD3 heavy chain variable region)
CAAGTTCAACTCCAGCAGAGCGGCGCTGAACTGGCCCGGCCCGGCGCCTC

CGTCAAGATGAGCTGCAAGGCTTCCGGCTATACATTTACTCGTTACACAA

TGCATTGGGTCAAGCAGAGGCCCGGTCAAGGTTTAGAGTGGATCGGATAT

ATCAACCCTTCCCGGGGCTACACCAACTATAACCAAAAGTTCAAGGATAA

AGCCACTTTAACCACTGACAAGAGCTCCTCCACCGCCTACATGCAGCTGT

CCTCTTTAACCAGCGAGGACTCCGCTGTTTACTACTGCGCTAGGTATTAC

GACGACCACTACTGTTTAGACTATTGGGGACAAGGTACCACTTTAACCGT

CAGCAGC (Human tissue factor 219 form)
TCCGGCACCACCAATACCGTGGCCGCTTATAACCTCACATGGAAGAGCAC

CAACTTCAAGACAATTCTGGAATGGGAACCCAAGCCCGTCAATCAAGTTT

ACACCGTGCAGATCTCCACCAAATCCGGAGACTGGAAGAGCAAGTGCTTC

TACACAACAGACACCGAGTGTGATTTAACCGACGAAATCGTCAAGGACGT

CAAGCAAACCTATCTGGCTCGGGTCTTTTCCTACCCCGCTGGCAATGTCG

AGTCCACCGGCTCCGCTGGCGAGCCTCTCTACGAGAATTCCCCCGAATTC

ACCCCTTATTTAGAGACCAATTTAGGCCAGCCTACCATCCAGAGCTTCGA

GCAAGTTGGCACCAAGGTGAACGTCACCGTCGAGGATGAAAGGACTTTAG

TGCGGCGGAATAACACATTTTTATCCCTCCGGGATGTGTTCGGCAAAGAC

CTCATCTACACACTGTACTATTGGAAGTCCAGCTCCTCCGGCAAAAAGAC

CGCTAAGACCAACACCAACGAGTTTTTAATTGACGTGGACAAAGGCGAGA

ACTACTGCTTCAGCGTGCAAGCCGTGATCCCTTCTCGTACCGTCAACCGG

AAGAGCACAGATTCCCCCGTTGAGTGCATGGGCCAAGAAAAGGGCGAGTT

CCGGGAG (αCD28 light chain variable region)
GTCCAGCTGCAGCAGAGCGGACCCGAACTCGTGAAACCCGGTGCTTCCGT

GAAAATGTCTTGTAAGGCCAGCGGATACACCTTCACCTCCTATGTGATCC

AGTGGGTCAAACAGAAGCCCGGACAAGGTCTCGAGTGGATCGGCAGCATC

AACCCTTACAACGACTATACCAAATACAACGAGAAGTTTAAGGGAAAGGC

TACTTTAACCTCCGACAAAAGCTCCATCACAGCCTACATGGAGTTCAGCT

CTTTAACATCCGAGGACAGCGCTCTGTACTATTGCGCCCGGTGGGGCGAC

GGCAATTACTGGGGACGGGCACAACACTGACCGTGAGCAGC

-continued (Linker)
GGAGGCGGAGGCTCCGGCGGAGGCGGATCTGGCGGTGGCGGCTCC (αCD28 light chain variable region)
GACATCGAGATGACCCAGTCCCCCGCTATCATGTCCGCCTCTTTAGGCGA

GCGGGTCACAATGACTTGTACAGCCTCCTCCAGCGTCTCCTCCTCCTACT

TCCATTGGTACCAACAGAAACCCGGAAGCTCCCCTAAACTGTGCATCTAC

AGCACCAGCAATCTCGCCAGCGGCGTGCCCCCTAGGTTTTCCGGAAGCGG

AAGCACCAGCTACTCTTTAACCATCTCCTCCATGGAGGCTGAGGATGCCG

CCACCTACTTTTGTCACCAGTACCACCGGTCCCCCACCTTCGGAGGCGGC

ACCAAACTGGAGACAAAGAGG

Exemplary Single-Chain Chimeric Polypeptide
(αCD3scFv/TF/αCD28scFv)
(SEQ ID NO: 3)
(Signal peptide)
MKWVTFISLLFLFSSAYS (αCD3 light chain variable region)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINR (Linker)
GGGGSGGGGSGGGGS (αCD3 heavy chain variable region)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS (Human tissue factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (αCD28 light chain variable region)
VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCIY

STSNLASGVPPRFSGSGSTSYSLTISSMEAEDAATYFCHQYHRSPTFGGG

TKLETKR

Figure 2:
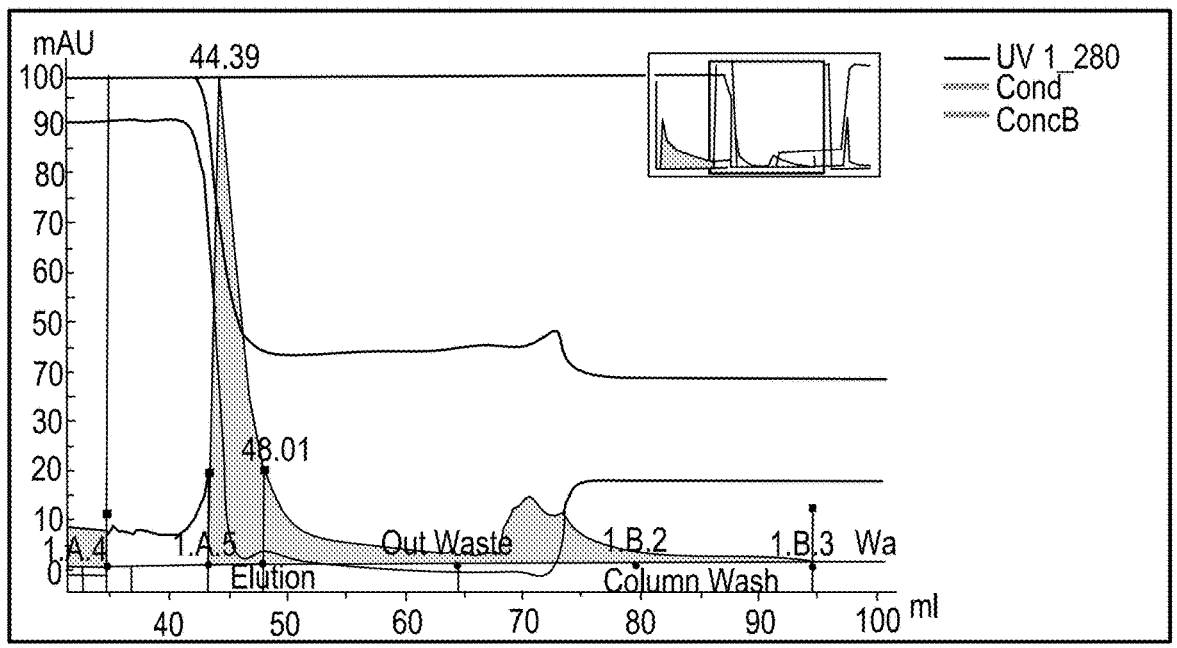
FIG. 2 is a chromatograph showing the elution of an exemplary αCD3scFv/TF/αCD28scFv single-chain chimeric polypeptide from an anti-tissue factor antibody affinity column.

A second exemplary single-chain chimeric polypeptide including a first target-binding domain that is an anti-CD28 scFv, a soluble human tissue factor domain, and a second target-binding domain that is an anti-CD3 scFv was generated (αCD28scFv/TF/αCD3scFv) (FIG. 2). The nucleic acid and amino acid sequences of this single-chain chimeric polypeptide are shown below.

Nucleic Acid Encoding Exemplary Single-Chain
Chimeric Polypeptide (αCD28scFv/TF/αCD3scFv)
(SEQ ID NO: 8)
(Signal peptide)
ATGAAATGGGTCACCTTCATCTCTTTACTGTTTTTATTTAGCAGCGCCTA

CAGC (αCD28 light chain variable region)
GTGCAGCTGCAGCAGTCCGGACCCGAACTGGTCAAGCCCGGTGCCTCCGT

GAAAATGTCTTGTAAGGCTTCTGGCTACACCTTTACCTCCTACGTCATCC

AATGGGTGAAGCAGAAGCCCGGTCAAGGTCTCGAGTGGATCGGCAGCATC

AATCCCTACAACGATTACACCAAGTATAACGAAAAGTTTAAGGGCAAGGC

CACTCTGACAAGCGACAAGAGCTCCATTACCGCCTACATGGAGTTTTCCT

CTTTAACTTCTGAGGACTCCGCTTTATACTATTGCGCTCGTTGGGGCGAT

GGCAATTATTGGGGCCGGGGAACTACTTTAACAGTGAGCTCC (Linker)
GGCGGCGGCGGAAGCGGAGGTGGAGGATCTGGCGGTGGAGGCAGC (αCD28 heavy chain variable region)
GACATCGAGATGACACAGTCCCCCGCTATCATGAGCGCCTCTTTAGGAGA

ACGTGTGACCATGACTTGTACAGCTTCCTCCAGCGTGAGCAGCTCCTATT

TCCACTGGTACCAGCAGAAACCCGGCTCCTCCCCTAAACTGTGTATCTAC

TCCACAAGCAATTTAGCTAGCGGCGTGCCTCCTCGTTTTAGCGGCTCCGG

CAGCACCTCTTACTCTTTAACCATTAGCTCTATGGAGGCCGAAGATGCCG

CCACATACTTTTGCCATCAGTACCACCGGTCCCCTACCTTTGGCGGAGGC

ACAAAGCTGGAGACCAAGCGG (Human tissue factor 219 form)
AGCGGCACCACCAACACAGTGGCCGCCTACAATCTGACTTGGAAATCCAC

CAACTTCAAGACCATCCTCGAGTGGGAGCCCAAGCCCGTTAATCAAGTTT

ATACCGTGCAGATTTCCACCAAGAGCGGCGACTGGAAATCCAAGTGCTTC

TATACCACAGACACCGAGTGCGATCTCACCGACGAGATCGTCAAAGACGT

GAAGCAGACATATTTAGCTAGGGTGTTCTCCTACCCCGCTGGAAACGTGG

AGAGCACCGGATCCGCTGGAGAGCCTTTATACGAGAACTCCCCCGAATTC

ACCCCCTATCTGGAAACCAATTTAGGCCAGCCCACCATCCAGAGCTTCGA

ACAAGTTGGCACAAAGGTGAACGTCACCGTCGAAGATGAGAGGACTTTAG

TGCGGAGGAACAATACATTTTTATCCTTACGTGACGTCTTCGGCAAGGAT

TTAATCTACACACTGTATTACTGGAAGTCTAGCTCCTCCGGCAAGAAGAC

CGCCAAGACCAATACCAACGAATTTTTAATTGACGTGGACAAGGGCGAGA

ACTACTGCTTCTCCGTGCAAGCTGTGATCCCCTCCCGGACAGTGAACCGG

AAGTCCACCGACTCCCCCGTGGAGTGCATGGGCCAAGAGAAGGGAGAGTT

TCGTGAG (αCD3 light chain variable region)
CAGATCGTGCTGACCCAGTCCCCCGCTATTATGAGCGCTAGCCCCGGTGA

AAAGGTGACTATGACATGCAGCGCCAGCTCTTCCGTGAGCTACATGAACT

GGTATCAGCAGAAGTCCGGCACCAGCCCTAAAAGGTGGATCTACGACACC

```
-continued
AGCAAGCTGGCCAGCGGCGTCCCCGCTCACTTTCGGGGCTCCGGCTCCGG

AACAAGCTACTCTCTGACCATCAGCGGCATGGAAGCCGAGGATGCCGCTA

CCTATTACTGTCAGCAGTGGAGCTCCAACCCCTTCACCTTTGGATCCGGC

ACCAAGCTCGAGATTAATCGT (Linker)
GGAGGCGGAGGTAGCGGAGGAGGCGGATCCGGCGGTGGAGGTAGC (αCD3 heavy chain variable region)
CAAGTTCAGCTCCAGCAAAGCGGCGCCGAACTCGCTCGGCCCGGCGCTTC

CGTGAAGATGTCTTGTAAGGCCTCCGGCTATACCTTCACCCGGTACACAA

TGCACTGGGTCAAGCAACGGCCCGGTCAAGGTTTAGAGTGGATTGGCTAT

ATCAACCCCTCCCGGGGCTATACCAACTACAACCAGAAGTTCAAGGACAA

AGCCACCCTCACCACCGACAAGTCCAGCAGCACCGCTTACATGCAGCTGA

GCTCTTTAACATCCGAGGATTCCGCCGTGTACTACTGCGCTCGGTACTAC

GACGATCATTACTGCCTCGATTACTGGGGCCAAGGTACCACCTTAACAGT

CTCCTCC

Exemplary Single-Chain Chimeric Polypeptide
(αCD28scFv/TF/αCD3scFv)
                                        (SEQ ID NO: 7)
(Signal peptide)
MKWVTFISLLFLFSSAYS (αCD28 light chain variable region)
VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCIY

STSNLASGVPPRFSGSGSTSYSLTISSMEAEDAATYFCHQYHRSPTFGGG

TKLETKR (Human tissue factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (αCD3 light chain variable region)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINR (Linker)
GGGGSGGGGSGGGGS (αCD3 heavy chain variable region)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS
```

The nucleic acid encoding αCD3scFv/TF/αCD28scFv was cloned into a modified retrovirus expression vectors as described previously (Hughes et al., *Hum Gene Ther* 16:457-72, 2005). The expression vector encoding αCD3scFv/TF/αCD28scFv was transfected into CHO-K1 cells. Expression of the expression vector in CHO-K1 cells allowed for secretion of the soluble αCD3scFv/TF/αCD28scFv single-chain chimeric polypeptide (referred to as 3t28), which can be purified by anti-TF antibody affinity and other chromatography methods.

An anti-tissue factor antibody affinity column was used to purify the αCD3scFv/TF/αCD28scFv single-chain chimeric polypeptide. The anti-tissue factor antibody affinity column was connected to a GE Healthcare AKTA Avant system. A flow rate of 4 mL/min was used for all steps except the elution step, which was 2 mL/min.

Cell culture harvest including αCD3scFv/TF/αCD28scFv single-chain chimeric polypeptide was adjusted to pH 7.4 with 1M Tris base and loaded onto the anti-TF antibody affinity column (described above) which was equilibrated with 5 column volumes of PBS. After sample loading, the column was washed with 5 column volumes PBS, followed by elution with 6 column volumes 0.1 M acetic acid, pH 2.9. An A280 elution peak was collected and then neutralized to pH 7.5-8.0 by adding 1 M Tris base. The neutralized sample was then buffer exchanged into PBS using Amicon centrifugal filters with a 30 kDa molecular weight cutoff. The data in FIG. 2 show that the anti-tissue factor antibody affinity column can bind the αCD3scFv/TF/αCD28scFv single-chain chimeric polypeptide, which contains a human soluble tissue factor domain. The buffer-exchanged protein sample was stored at 2-8° C. for further biochemical analysis and biological activity testing.

After each elution, the anti-tissue factor antibody affinity column was stripped using 6 column volumes of 0.1 M glycine, pH 2.5. The column was then neutralized using 10 column volumes of PBS, 0.05% $NaN_3$, and stored at 2-8° C.

Figure 3:
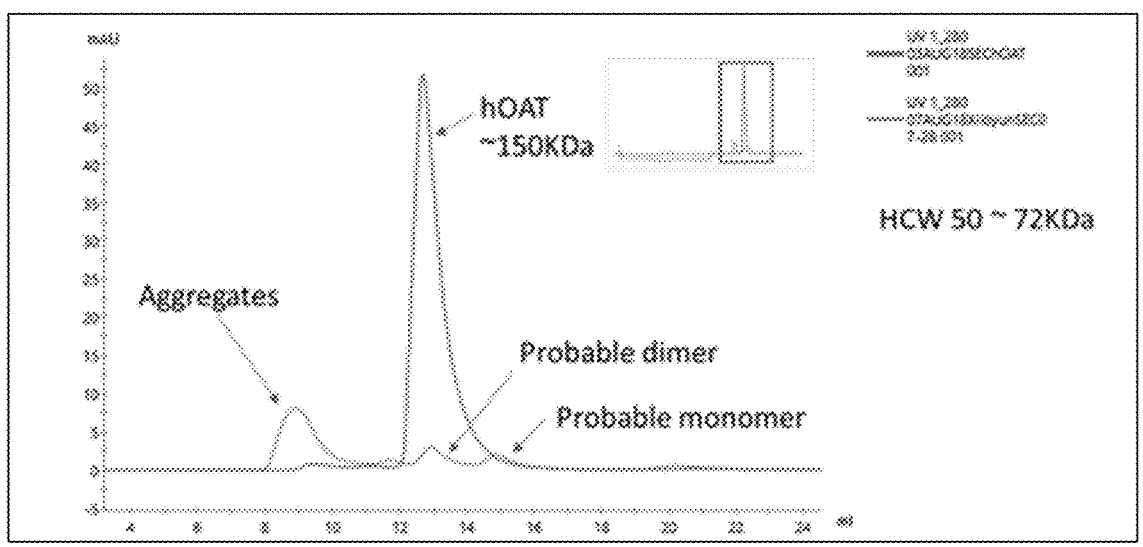
FIG. 3 is a chromatograph showing the elution of a Superdex 200 Increase 10/300 GL gel filtration column loaded with an exemplary αCD3scFv/TF/αCD28scFv single-chain chimeric polypeptide.

Analytical size exclusion chromatography (SEC) was performed on the αCD3scFv/TF/αCD28scFv single-chain chimeric polypeptide using a Superdex 200 Increase 10/300 GL gel filtration column (from GE Healthcare) connected to an AKTA Avant system (from GE Healthcare). The column was equilibrated with 2 column volumes of PBS. A flow rate of 0.8 mL/min was used. Two hundred μL of αCD3scFv/TF/αCD28scFv single-chain chimeric polypeptide (1 mg/mL) was injected onto the column using a capillary loop. After injection of the single-chain chimeric polypeptide, 1.25 column volumes of PBS were flowed into the column. The SEC chromatograph is shown in FIG. 3. The data show that there are 3 protein peaks, likely representing a monomer and dimer or other different forms of the αCD3scFv/TF/αCD28scFv single-chain chimeric polypeptide.

Figure 4:
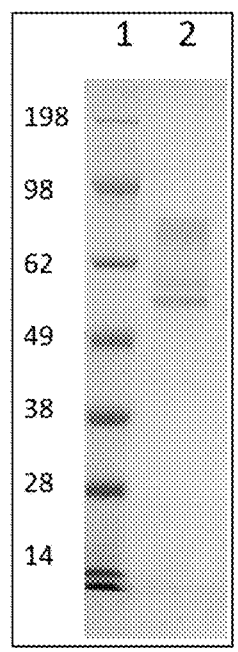
FIG. 4 is a sodium dodecyl sulfate polyacrylamide gel (4-12% NuPage Bis-Tris gel) of an exemplary αCD3scFv/TF/αCD28scFv single-chain chimeric polypeptide purified using an anti-tissue factor antibody affinity column.

To determine the purity and protein molecular weight of the αCD3scFv/TF/αCD28scFv single-chain chimeric polypeptide, the purified αCD3scFv/TF/αCD28scFv protein sample from anti-tissue factor antibody affinity column was analyzed by standard sodium dodecyl sulfate polyacrylamide gel (4-12% NuPage Bis-Tris gel) electrophoresis (SDS-PAGE) method under reduced conditions. The gel was stained with InstantBlue for about 30 minutes and destained overnight with purified water. FIG. 4 shows the SDS gel of the αCD3scFv/TF/αCD28scFv single-chain chimeric polypeptide purified using an anti-tissue factor antibody affinity column. The results show that the purified αCD3scFv/TF/αCD28scFv single-chain chimeric polypeptide has the expected molecular weight (72 kDa) in reduced SDS gel.

Figure 5:
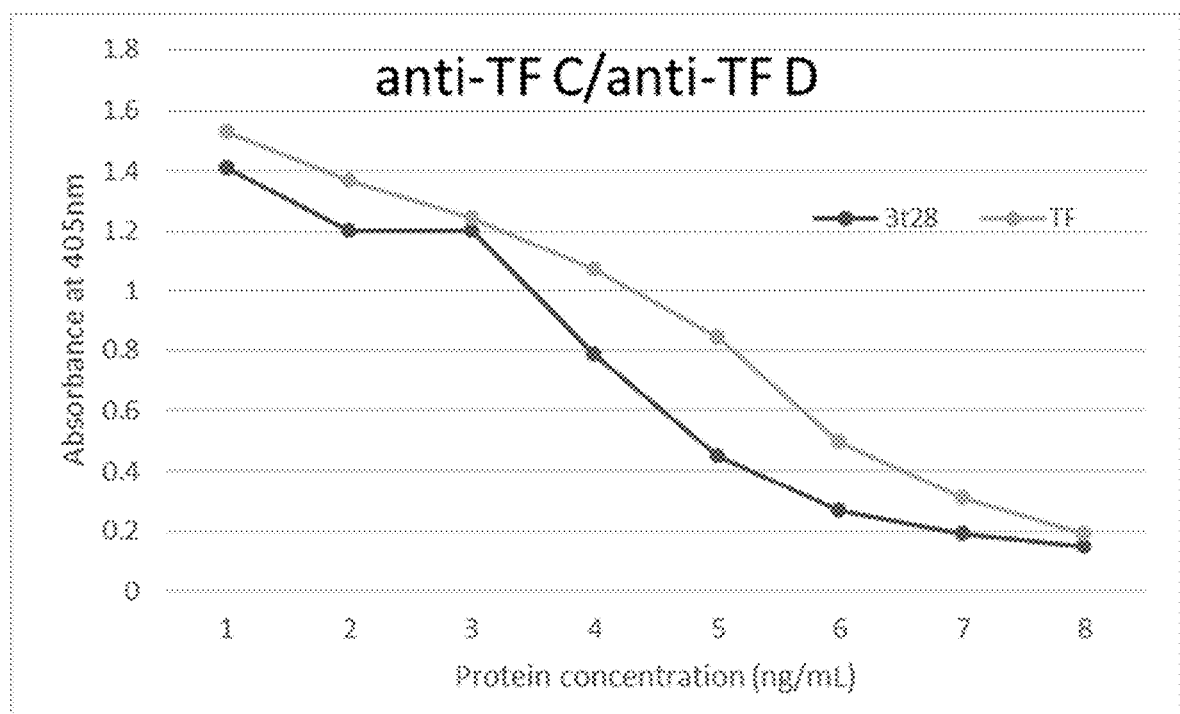
FIG. 5 is a graph showing the ELISA quantitation of an exemplary αCD3scFv/TF/αCD28scFv single-chain chimeric polypeptide performed using the methods described in Example 1. Purified tissue factor was used as the control.
Figure 6:
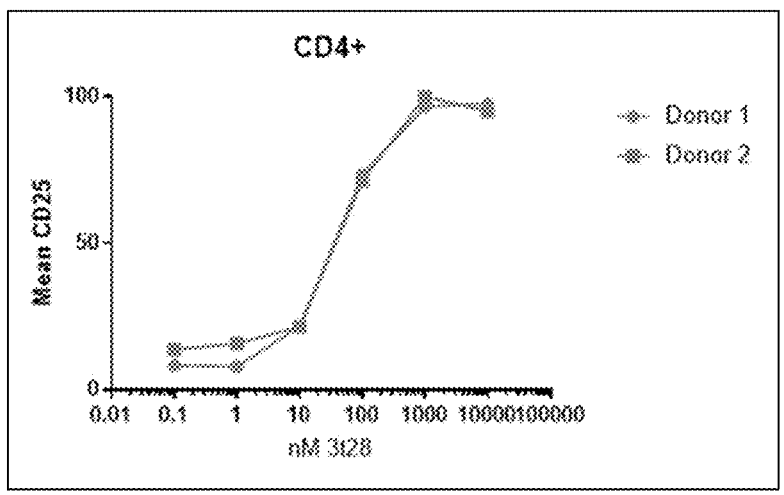
FIG. 6 is a graph showing the ability of an exemplary αCD3scFv/TF/αCD28scFv single-chain chimeric polypeptide to stimulate CD25 expression in CD4+ T-cells isolated from blood from two donors. The experiments were performed as described in Example 2.
Figure 7:
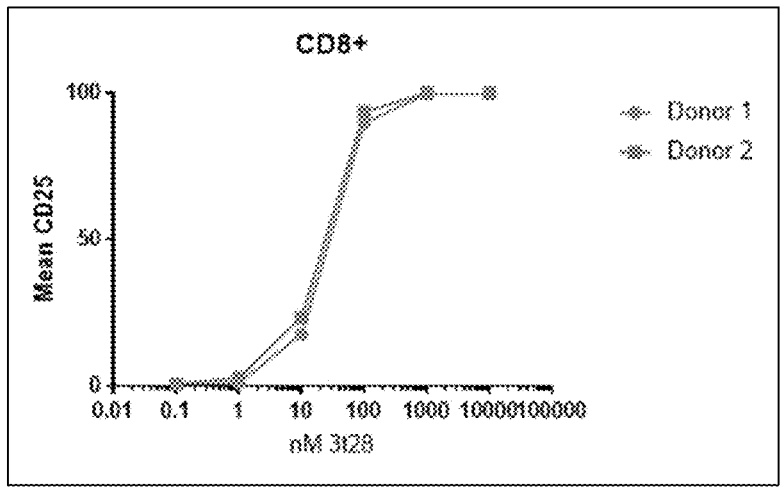
FIG. 7 is a graph showing the ability of an exemplary αCD3scFv/TF/αCD28scFv single-chain chimeric polypeptide to stimulate CD25 expression in CD8+ T-cells isolated from blood from two donors. The experiments were performed as described in Example 2.
Figure 8:
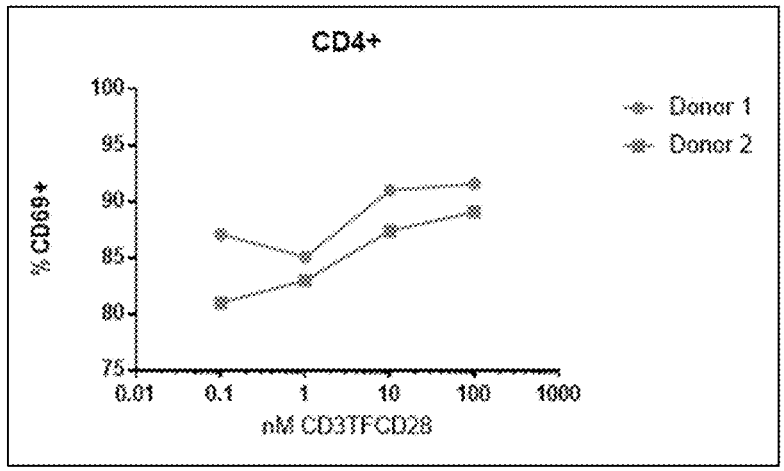
FIG. 8 is a graph showing the ability of an exemplary αCD3scFv/TF/αCD28scFv single-chain chimeric polypeptide to stimulate CD69 expression in CD4+ T-cells isolated from blood from two donors. The experiments were performed as described in Example 2.
Figure 9:
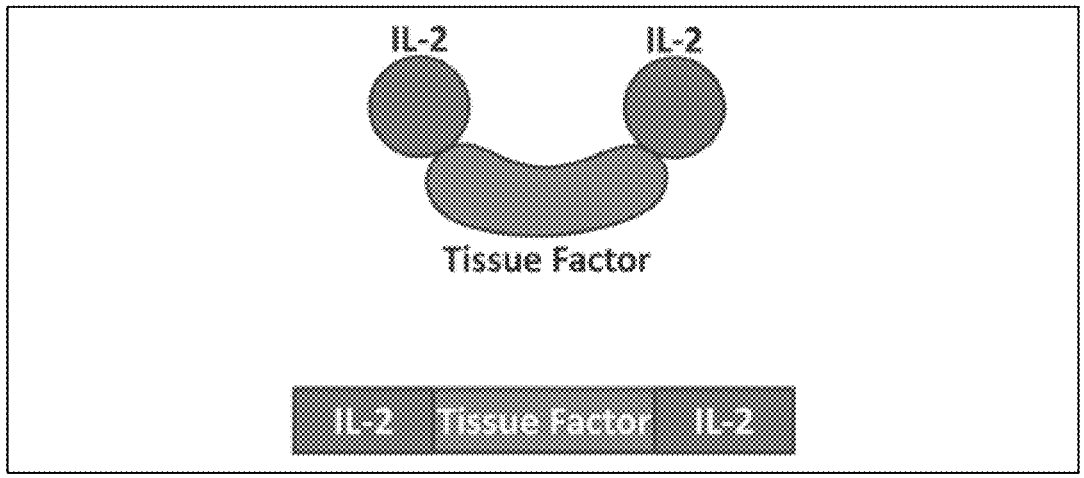
FIG. 9 are schematic diagrams of an exemplary IL-2/TF/IL-2 single-chain chimeric polypeptide.

Example 2. Functional Characterization of αCD3scFv/TF/αCD28scFv Single-Chain Chimeric Polypeptide ELISA-based methods confirmed the formation of the αCD3scFv/TF/αCD28scFv single-chain chimeric polypeptide. The αCD3scFv/TF/αCD28scFv single-chain chimeric polypeptide was detected using ELISA with one anti-TF monoclonal antibody for capture and a different anti-TF monoclonal antibody for detection (FIG. 5). A purified tissue factor protein with a similar concentration was used as a control.

A further in vitro experiment was performed to determine whether the αCD3scFv/TF/αCD28scFv single-chain chimeric polypeptide is capable of activating human peripheral blood mononuclear cells (PBMCs). Fresh human leukocytes were obtained from the blood bank and peripheral blood mononuclear cells (PBMC) were isolated using density gradient Histopaque (Sigma). The cells were counted and resuspended in $0.2\times10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with αCD3scFv/TF/αCD28scFv single-chain chimeric polypeptide from 0.01 nM to 1000 nM for 3 days at 37° C., 5% $CO_2$. After 72 hours, the cells were harvested and surface stained for CD4-488, CD8-PerCP Cy5.5, CD25-BV421, CD69-APCFire750, CD62L-PE Cy7, and CD44-PE (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data in FIGS. 6 and 7 show that the αCD3scFv/TF/αCD28scFv single-chain chimeric polypeptide is able to stimulate both $CD8^+$ and $CD4^+$ T-cells.

A further experiment was performed, in which PBMCs isolated from blood using Histopaque (Sigma) were counted and resuspended in $0.2\times10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were then stimulated with the αCD3scFv/TF/αCD28scFv single-chain chimeric polypeptide from 0.01 nM to 1000 nM for 3 days at 37° C., 5% $CO_2$. After 72 hours, the cells were harvested and surface stained for CD4-488, CD8-PerCP Cy5.5, CD25-BV421, CD69-APC-Fire750, CD62L-PE Cy7, and CD44-PE (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data again show that the αCD3scFv/TF/αCD28scFv single-chain chimeric polypeptide was able to stimulate activation of $CD4^+$ T cells (FIG. 8).

Example 3. Production and Characterization of the Exemplary Single-Chain Chimeric Polypeptide IL-2/TF/IL-2

An exemplary single-chain chimeric polypeptide including a first target-binding domain that binds to an IL-2 receptor, a soluble human tissue factor domain, and a second target-binding domain that binds to an IL-2 receptor was generated (IL-2/TF/IL-2) (FIG. 9). The nucleic acid and amino acid sequences of this single-chain chimeric polypeptide are shown below.

```
Nucleic Acid Encoding Exemplary Single-Chain
Chimeric Polypeptide (IL-2/TF/IL-2)
                                  (SEQ ID NO: 111)
(Signal peptide)
ATGAAGTGGGTGACCTTCATCAGCCTGCTGTTCCTGTTCTCCAGCGCCTA

CTCC (First IL-2 fragment)
GCCCCCACCTCCTCCTCCACCAAGAAGACCCAGCTGCAGCTGGAGCATTT

ACTGCTGGATTTACAGATGATTTTAAACGGCATCAACAACTACAAGAACC

CCAAGCTGACTCGTATGCTGACCTTCAAGTTCTACATGCCCAAGAAGGCC

ACCGAGCTGAAGCATTTACAGTGTTTAGAGGAGGAGCTGAAGCCCCTCGA

GGAGGTGCTGAATTTAGCCCAGTCCAAGAATTTCCATTTAAGGCCCCGGG

ATTTAATCAGCAACATCAACGTGATCGTTTTAGAGCTGAAGGGCTCCGAG

ACCACCTTCATGTGCGAGTACGCCGACGAGACCGCCACCATCGTGGAGTT

TTTAAATCGTTGGATCACCTTCTGCCAGTCCATCATCTCCACTTTAACC (Human tissue factor 219 form)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Second IL-2 fragment)
GCACCTACTTCAAGTTCTACAAAGAAAACACAGCTACAACTGGAGCATTT

ACTGCTGGATTTACAGATGATTTTGAATGGAATTAATAATTACAAGAATC

CCAAACTCACCAGGATGCTCACATTTAAGTTTTACATGCCCAAGAAGGCC

ACAGAACTGAAACATCTTCAGTGTCTAGAAGAAGAACTCAAACCTCTGGA

GGAAGTGCTAAATTTAGCTCAAAGCAAAAACTTTCACTTAAGACCCAGGG

ACTTAATCAGCAATATCAACGTAATAGTTCTGGAACTAAAGGGATCTGAA

ACAACATTCATGTGTGAATATGCTGATGAGACAGCAACCATTGTAGAATT

TCTGAACAGATGGATTACCTTTTGTCAAAGCATCATCTCAACACTAACT
```

-continued
Exemplary Single-Chain Chimeric Polypeptide
(IL-2/TF/IL-2)
(SEQ ID NO: 110)
(Signal peptide)
MKWVTFISLLFLFSSAYS (Human IL-2)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-2)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT

The nucleic acid encoding IL-2/TF/IL-2 was cloned into a modified retrovirus expression vector as described previously (Hughes et al., Hum Gene Ther 16:457-72, 2005). The expression vector encoding IL-2/TF/IL-2 was transfected into CHO-K1 cells. Expression of the expression vector in CHO-K1 cells allowed for secretion of the soluble IL-2/TF/IL-2 single-chain chimeric polypeptide (referred to as 2t2), which can be purified by anti-TF antibody affinity and other chromatography methods.

Figure 10:
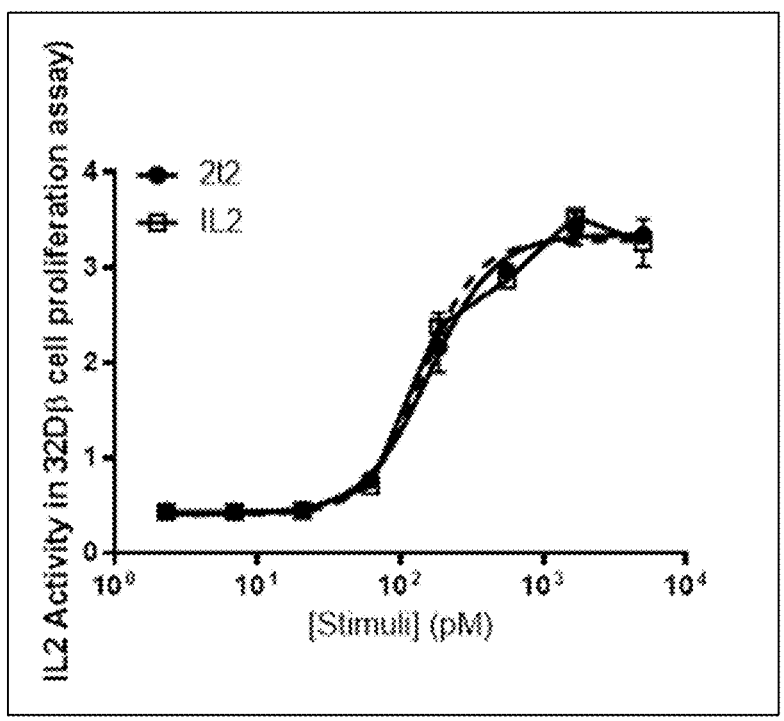
FIG. 10 shows IL-2 activity in IL-2/TF/IL-2 as compared to recombinant IL-2 using a 32Dβ cell proliferation assay.

IL-2 and IL-2/TF/IL-2 Promoted IL-2Rβ and Common γ Chain Containing 32Dβ Cell Proliferation in a Similar Manner To evaluate the IL-2 activity of IL-2/TF/IL-2, IL-2/TF/IL-2 was compared with recombinant IL-2 for promoting proliferation of 32Dβ cells that express IL-2Rβ and common γ chain. IL-2 dependent 32Dβ cells were washed 5 times with IMDM-10% FBS and seeded to the wells at $2 \times 10^4$ cells/well. Serial dilutions of IL-2/TF/IL-2 or IL-2 were added to the cells (FIG. 10). Cells were incubated in a $CO_2$ incubator at 37° C. for 3 days. Cell proliferation was detected by adding 10 µl of WST1 to each well on day 3 and incubating for an additional 3 hours in a $CO_2$ incubator at 37° C. The amount of formazan dye produced was analyzed by measuring the absorbance at 450 nm. As shown in FIG. 10, IL-2/TF/IL-2 and IL-2 activated 32Dβ cells in a similar manner. The $EC_{50}$ of IL-2/TF/IL-2 and IL-2 was 158.1 pM and 140 pM, respectively.

IL-2/TF/IL-2 Showed Improved Ability to Promote IL-2Rαβγ Containing CTLL-2 Cell Proliferation as Compared to IL-2

Figure 11:
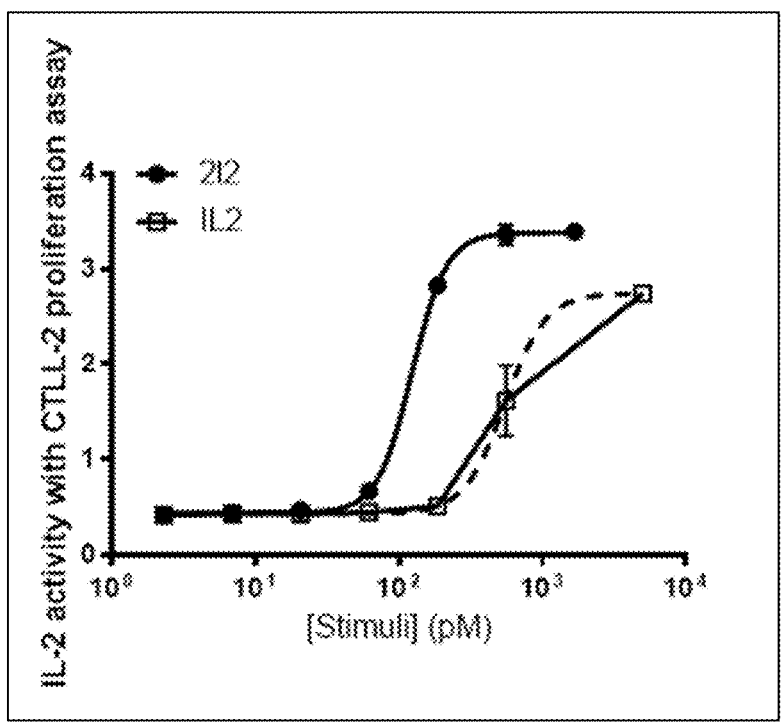
FIG. 11 shows IL-2 activity in IL-2/TF/IL-2 as compared to recombinant IL-2 using a CTLL-2 cell proliferation assay.

To evaluate the IL-2 activity of IL-2/TF/IL-2, IL-2/TF/IL-2 was compared with recombinant IL-2 for promoting proliferation of CTLL-2 cells that express IL-2Rα, IL-2Rβ and common γ chain. IL-2 dependent CTLL-2 cells were washed 5 times with IMDM-10% FBS and seeded to the wells at $2 \times 10^4$ cells/well. Serial dilutions of IL-2/TF/IL-2 or IL-2 were added to the cells (FIG. 11). Cells were incubated in a $CO_2$ incubator at 37° C. for 3 days. Cell proliferation was detected by adding 10 µl of WST1 to each well in the day 3 and incubating for an additional 3 hours in a $CO_2$ incubator at 37° C. The amount of formazan dye produced was analyzed by measuring the absorbance at 450 nm. As shown in FIG. 3, IL-2/TF/IL-2 promoted CTLL-2 cell proliferation 4-5-fold stronger than IL-2. The $EC_{50}$ of IL-2/TF/IL-2 was 123.2 pM and IL-2 was 548.2 pM.

Figure 12:
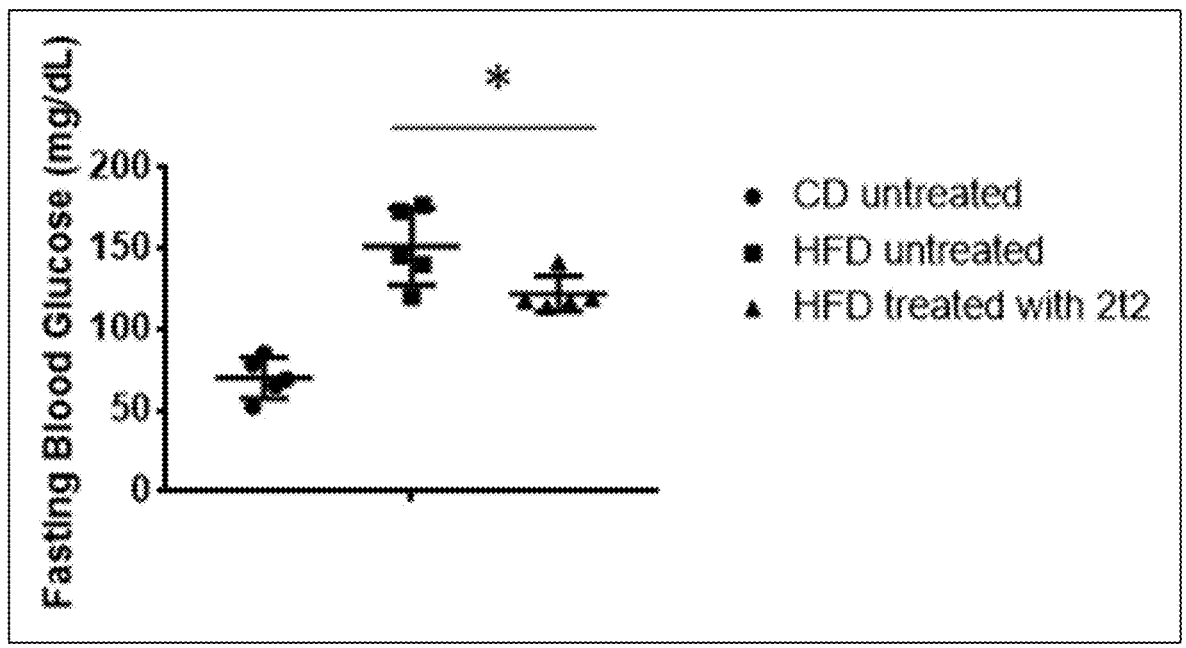
FIG. 12 shows the fasting blood glucose levels in ApoE$^{-/-}$ mice fed with standard chow or a high fat diet and treated with a PBS control (untreated) or with IL-2/TF/IL-2.

IL-2/TF/IL-2 Suppressed the Increase of the High Fat-Induced Hyperglycemia in ApoE$^{-/-}$ Mice Six-week-old female ApoE$^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with high fat diet were randomly assigned into the control group and treatment group. Mice then received either IL-2/TF/IL-2 (treatment group) or PBS (chow diet group and control group) per subcutaneous injection at a dosage of 3 mg/kg. Three days post dosing, the mice were fasted overnight, and blood samples were collected through retro-orbital venous plexus puncture. Overnight fasting glucose levels were measured using a OneTouch Glucometer. As shown in FIG. 12, the results showed that IL-2/TF/IL-2 injection effectively suppresses the increase of glucose levels in ApoE$^{-/-}$ mice.

Figure 13:
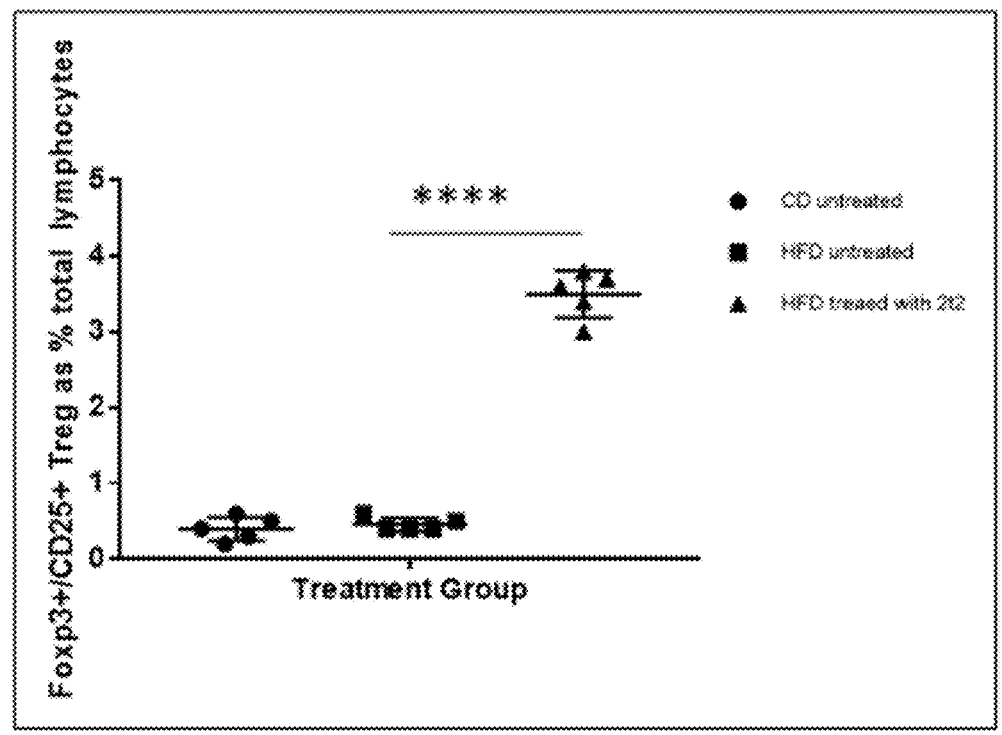
FIG. 13 shows the ratio of CD4$^+$CD25$^+$FoxP3$^+$ T regulatory cells in blood lymphocytes from ApoE-/- mice fed with standard chow or a high fat diet and treated with a PBS control (untreated) or with IL-2/TF/IL-2.

IL-2/TF/IL-2 Significantly Upregulate the Ratio of CD4$^+$CD25$^+$FoxP3$^+$ T Regulatory (Treg) Cells in Blood Lymphocytes Six-week-old female ApoE$^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with the high fat diet were randomly assigned into control group and treatment group. Mice then received either IL-2/TF/IL-2 (treatment group) or PBS (chow diet group and control group) per subcutaneous injection at a dosage of 3 mg/kg. Three days after the dosing, overnight fasting blood samples were collected through retro-orbital venous plexus puncture and incubated with ACK lysing buffer (Thermo Fisher Scientific) at 37° C. for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer followed by centrifugation at 1500 RPM for 5 minutes at room temperature. The cells were analyzed by flow cytometry (Celesta-BD Bioscience). As shown in FIG. 13, IL-2/TF/IL-2 treatment significantly increased Treg populations in blood lymphocytes (3.5%±0.32) compared to the untreated groups (0.4%±0.16 for chow diet group and 0.46%±0.09 for high fat diet group).

Figure 14:
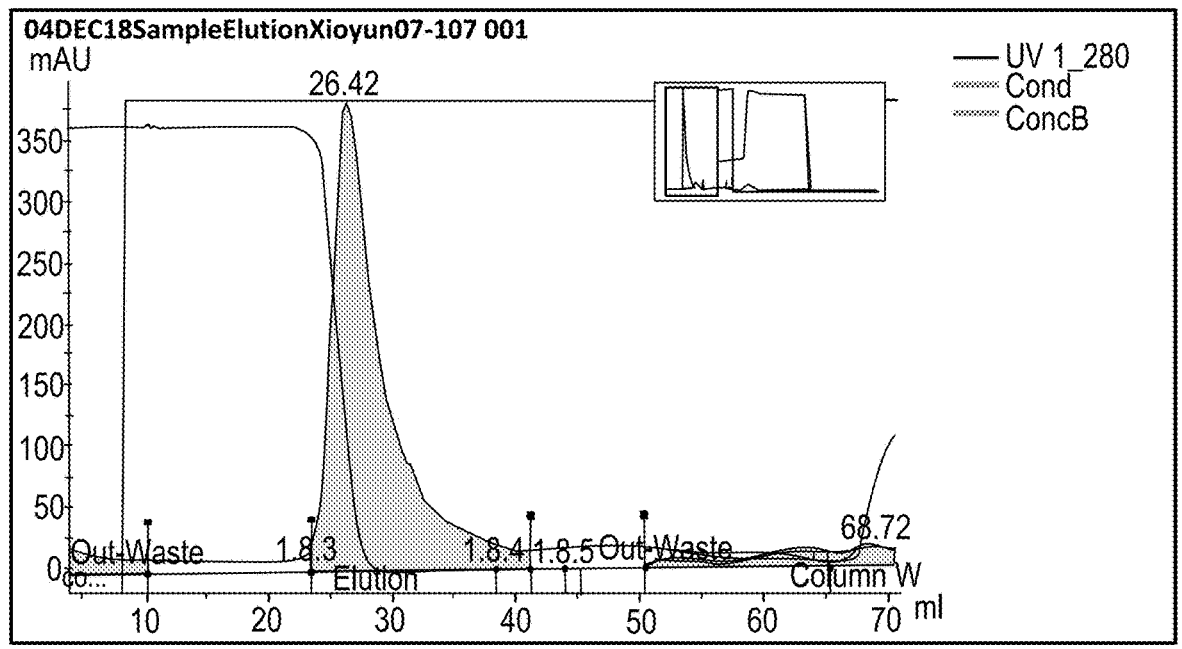
FIG. 14 is a line graph showing the chromatographic profile of IL-2/TF/IL-2 protein containing cell culture supernatant following binding and elution on anti-TF antibody resin.

Purification Elution Chromatograph of IL-2/TF/IL-2 from Anti-TF Antibody Affinity Column IL-2/TF/IL-2 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid, pH 2.9. A280 elution peak was collected and then neutralized to pH 7.5-8.0 with 1M Tris base. The neutralized sample was then buffer exchanged into PBS using Amicon centrifugal filters with a 30 kDa molecular weight cutoff. As shown in FIG. 14, the anti-TF antibody affinity column bound to IL-2/TF/IL-2 which contains TF as a fusion domain. The buffer-exchanged protein sample was stored at 2-8° C. for further biochemical analyses and biological activity tests. After each elution, the anti-TF antibody affinity column was stripped using 6 column volumes of 0.1M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of IL-2/TF/IL-2

Figure 15:
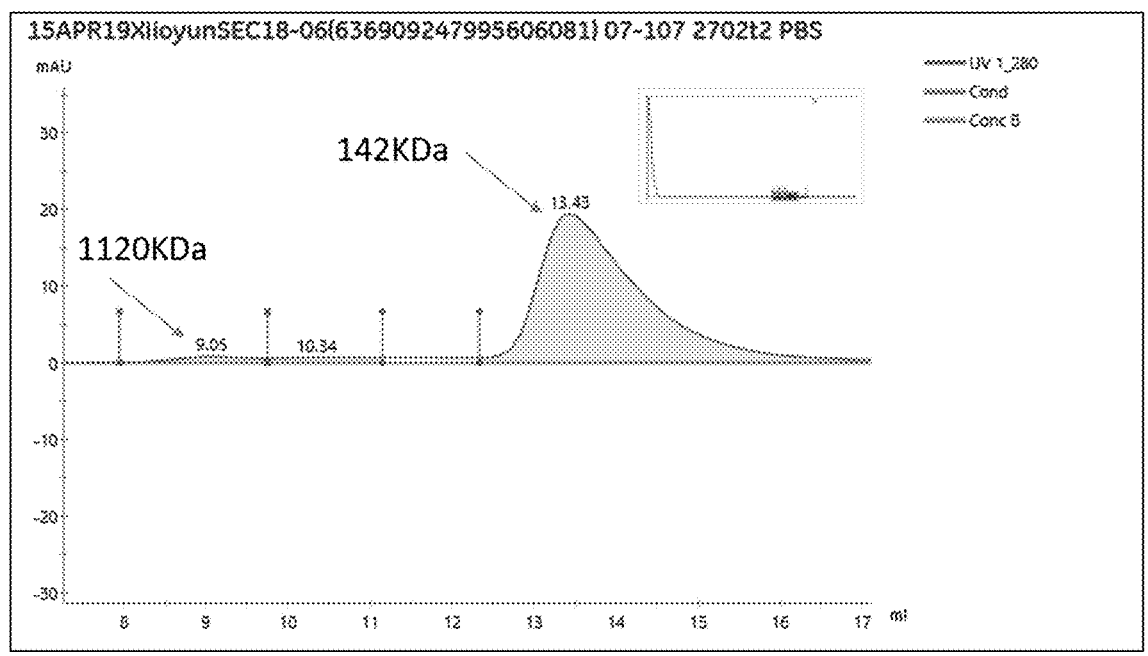
FIG. 15 shows an analytical SEC profile of IL-2/TF/IL-2.

To analyze IL-2/TF/IL-2 using analytical size exclusion chromatography (SEC), a Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing IL-2/TF/IL-2 in PBS was injected into the Superdex 200 column using a capillary loop, and analyzed by SEC. The SEC chromatograph of the sample is shown in FIG. 15. The SEC results indicated two protein peaks for IL-2/TF/IL-2.

Reduced SDS PAGE of IL-2/TF/IL-2

To determine the purity and molecular weight of the protein, IL-2/TF/IL-2 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 16A:
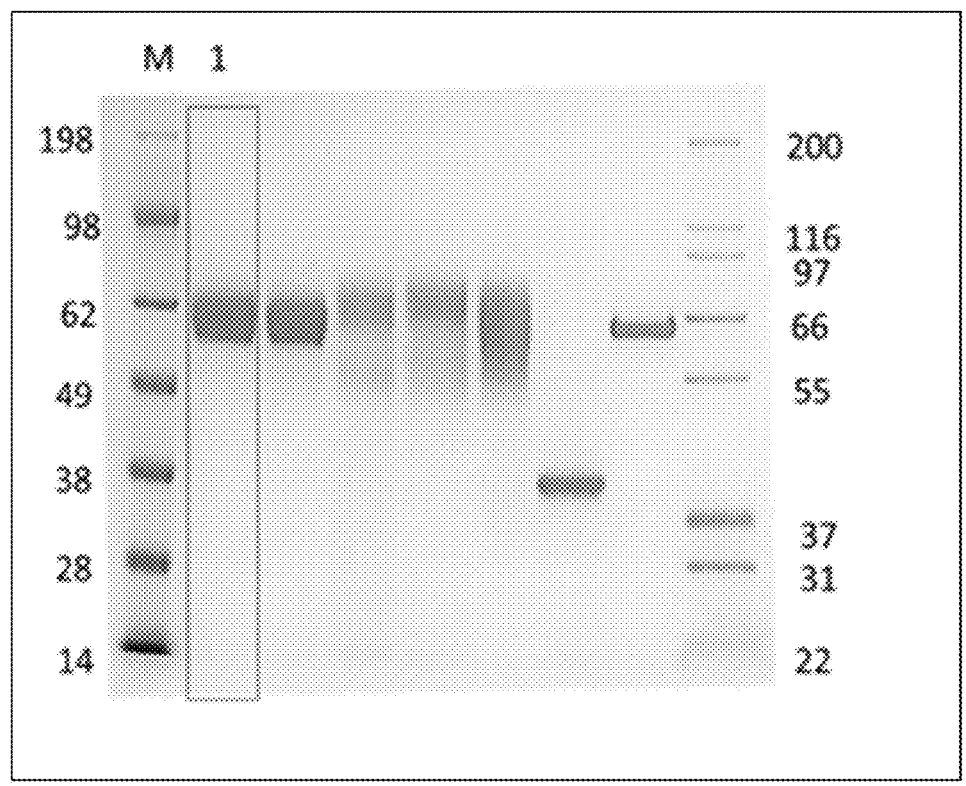
FIGS. 16A and 16B show reduced SDS-PAGE analysis of IL-2/TF/IL-2 before and after deglycosylation.
Figure 16B:
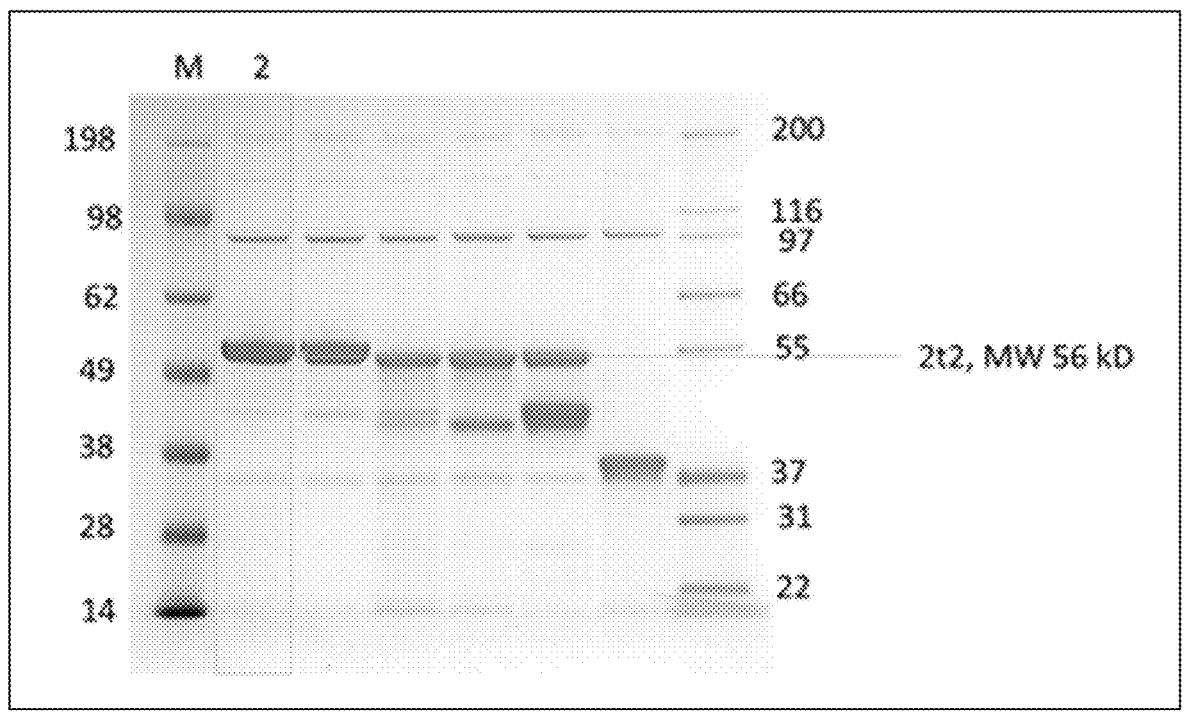

To verify that the IL-2/TF/IL-2 protein undergoes glycosylation after translation in CHO cells, a deglycosylation experiment was conducted using the Protein Deglycosylation Mix II kit from New England Biolabs according to the manufacturer's instructions. FIGS. 16A and 16B show the reduced SDS-PAGE analysis of the sample in non-deglycosylated (lane 1 in red outline) and deglycosylated (lane 2 in yellow outline) state. The results show that the IL-2/TF/IL-2 protein is glycosylated when expressed in CHO cells. After deglycosylation, the purified sample ran with expected molecular weights (56 kDa) in reduced SDS gel. Lane M was loaded with 10 µL of SeeBlue Plus2 Prestained Standard.

In Vivo Characterization of IL-2/TF/IL-2

Figure 17A:
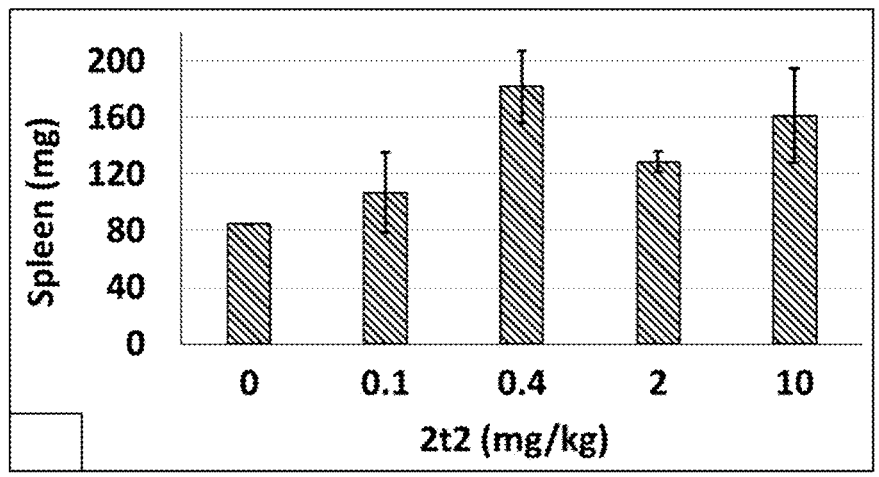
FIGS. 17A and 17B show results of immunostimulation in C57BL/6 mice using IL-2/TF/IL-2.
Figure 17B:
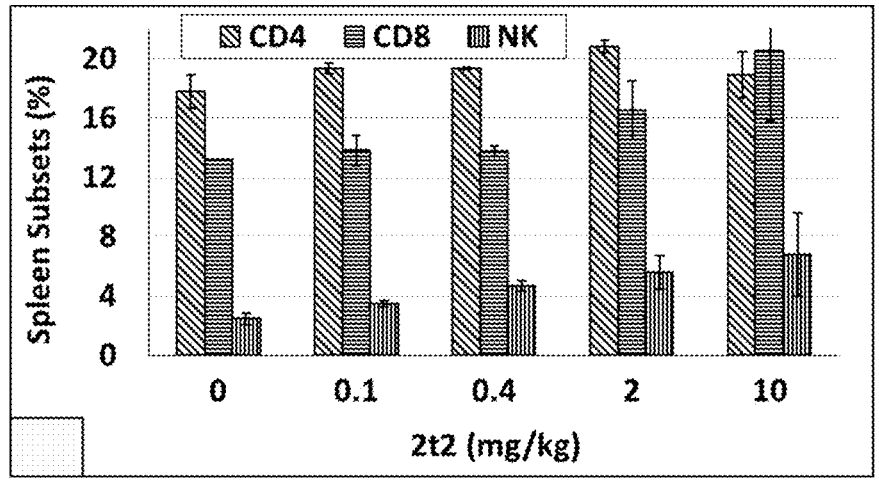

IL-2/TF/IL-2 was subcutaneously injected into C57BL/6 mice at various doses to determine the immunostimulatory activity of IL-2/TF/IL-2 in vivo. Mice were subcutaneously treated with control solution (PBS) or IL-2/TF/IL-2 at 0.1, 0.4, 2 and 10 mg/kg. The treated mice were euthanized day 3 post treatment. The mouse spleens were collected and weighed day 3 post treatment. Single splenocyte suspensions were prepared, and the prepared splenocytes were stained for CD4$^+$ T cells, CD8$^+$ T cells and NK cells (with fluorochrome-conjugated anti-CD4, -CD8, and —NK1.1 antibodies), and analyzed by flow cytometry. The results showed that IL-2/TF/IL-2 was effective at expanding splenocytes based on spleen weight (FIG. 17A) especially at 0.1-10 mg/kg. The percentage of CD8$^+$ T cells were higher compared to control-treated mice (FIG. 17B) at 2 and 10 mg/kg. The percentage of NK cells were higher compared to control-treated mice (FIG. 17B) at all doses tested.

Figure 18:
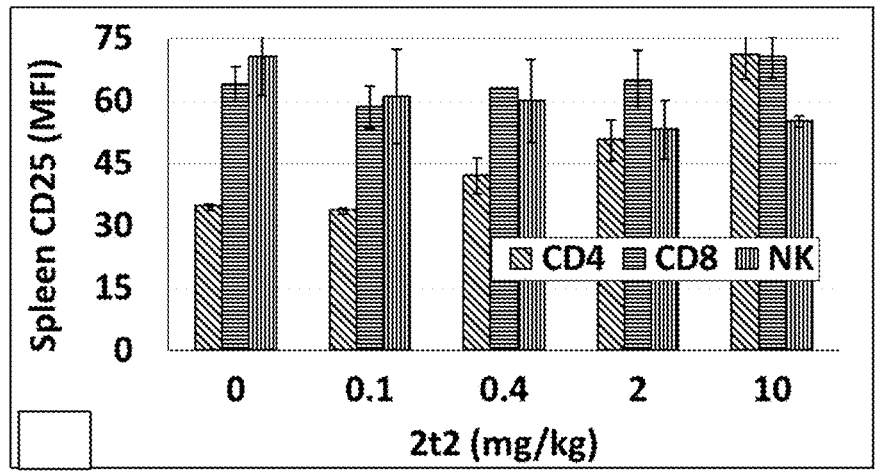
FIG. 18 shows upregulation of CD25 expression of CD4$^+$ T cells in mice treated with IL-2/TF/IL-2.

It has been known that IL-2 upregulates CD25 expression by immunocytes. We therefore accessed CD25 expression of CD4$^+$ T cells, CD8$^+$ T cells and NK cells in the IL-2/TF/IL-2 treated mice. C57BL/6 mice were subcutaneously treated with IL-2/TF/IL-2 as described in the paragraph above. The splenocytes were stained with fluorochrome-conjugated anti-CD4, -CD8, CD25 and NK1.1 monoclonal antibodies. The CD25 expression (MFI) of splenocyte subsets was analyzed by flow cytometry. As shown in FIG. 18, at the doses and time point (day 3) tested, IL-2/TF/IL-2 significantly upregulated CD25 expression by CD4$^+$ T cells but not CD8+ T cells or NK cells.

Figure 19:
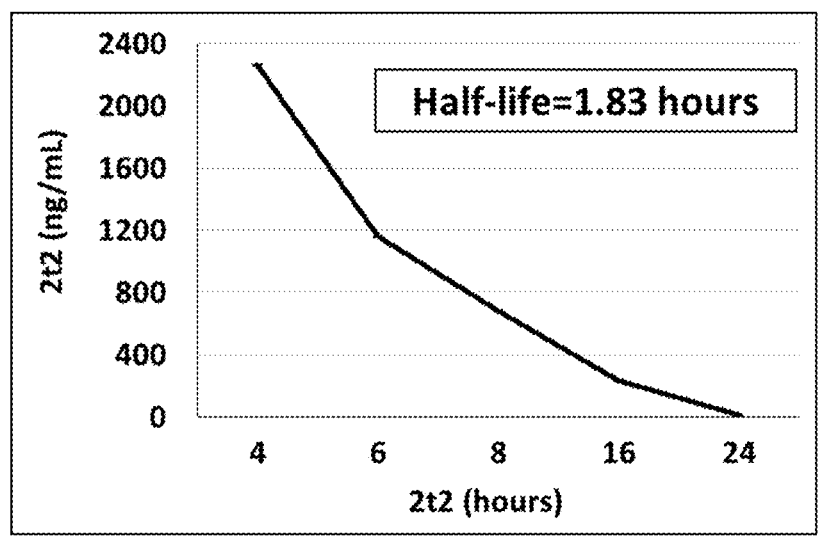
FIG. 19 shows the pharmacokinetics of IL-2/TF/IL-2 in C57BL/6 mice.

The pharmacokinetics of IL-2/TF/IL-2 in C57BL/6 mice was also investigated. IL-2/TF/IL-2 was subcutaneously injected into C57BL/6 mice at 1 mg/kg. The mouse blood was drawn from tail vein at various time points as shown in FIG. 19 and the serum was prepared. IL-2/TF/IL-2 concentrations were determined with ELISA (Capture: anti-tissue factor antibody; Detection: biotinylated anti-human IL-2 antibody followed by SA-HRP and ABTS substrate). The half-life of IL-2/TF/IL-2 was 1.83 hours calculated with PK Solutions 2.0 (Summit Research Services).

Figure 20A:
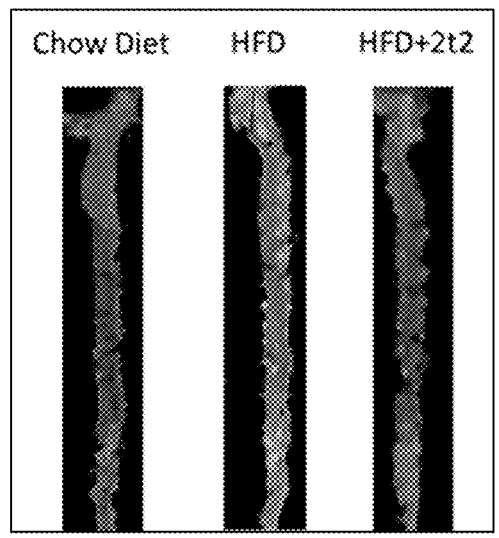
FIGS. 20A and 20B show effects of IL-2/TF/IL-2 in attenuating the formation of high fat-induced atherosclerotic plaques in ApoE$^{-/-}$ mice.
Figure 20B:
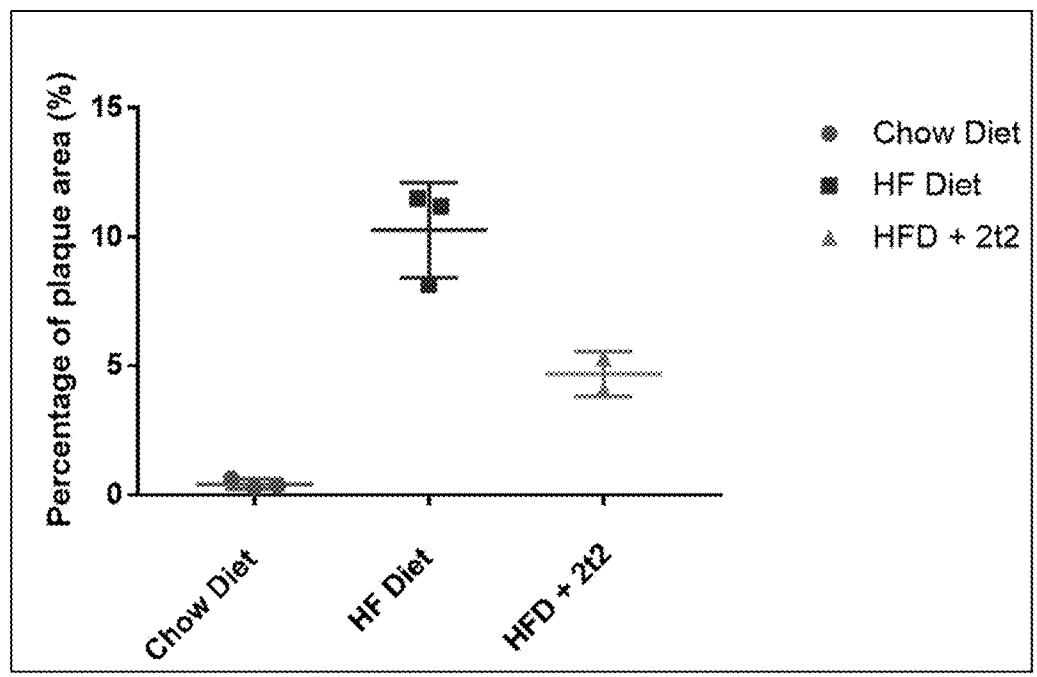
Figure 21:
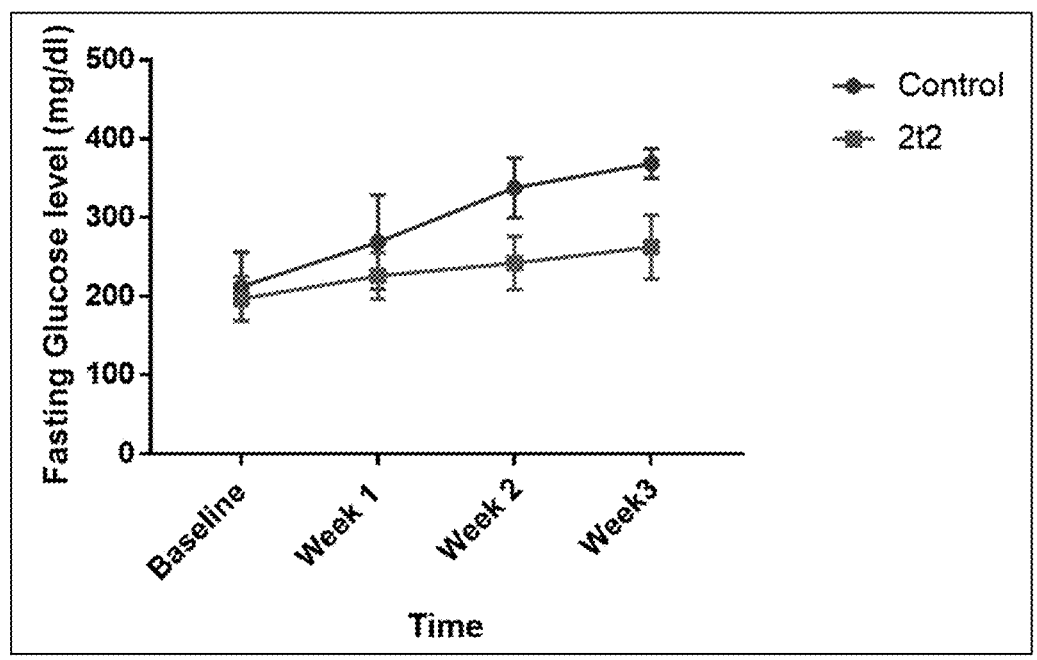
FIG. 21 shows fasting glucose levels in IL-2/TF/IL-2 treated-mice as compared to control-treated mice.

IL-2/TF/IL-2 Attenuated the Formation of High Fat-Induced Atherosclerotic Plaques in ApoE$^{-/-}$ Mice Six-week-old female ApoE$^{-/-}$ mice (The Jackson Laboratory) were fed with standard chow diet or high diet fat (21% fat, 0.15% cholesterol, 34.1% sucrose, 19.5% casein, and 15% starch) (TD88137, Harlan Laboratories) and maintained in the standard conditions. At week 7, mice fed with high fat diet (HFD) were randomly assigned into control group and treatment group. Mice were then administrated either IL-2/TF/IL-2 (treatment group) or PBS (chow diet group and control group) subcutaneously at a dosage of 3 mg/kg weekly for 4 weeks. At week 12, all mice were euthanized by isoflurane. Aortas were collected, opened longitudinally and stained with Sudan IV solution (0.5%) using en face method. The percentage of plaque area (red color as shown in FIG. 20A) relative to total aorta area was then quantified with Image J software. FIG. 20A shows a representative view of atherosclerotic plaques from each group. FIG. 20B shows the results of quantitative analysis of atherosclerotic plaques of each group. The percentage of plaque areas in control group (HF Diet) was much higher than the treatment group (HFD+IL-2/TF/IL-2), being 10.28% vs 4.68%.

IL-2/TF/IL-2 Suppresses the Progression of Type 2 Diabetes

Male BKS.Cg-Dock7$^m$+/+Lepr$^{db}$/J (db/db (Jackson Lab)) mice were fed with standard chow diet and received drinking water ad libitum. At the age of six weeks, mice were randomly assigned into control group and treatment group. The treatment group received IL-2/TF/IL-2 by subcutaneous injection at 3 mg/kg bi-weekly, while control group received vehicle (PBS) only. Overnight fasting glucose levels were measure weekly using a OneTouch Glucometer. The results showed that IL-2/TF/IL-2 effectively suppressed the increase of glucose levels in BKS.Cg-Dock7$^m$+/+Lepr$^{db}$/J mice.

Figure 22:
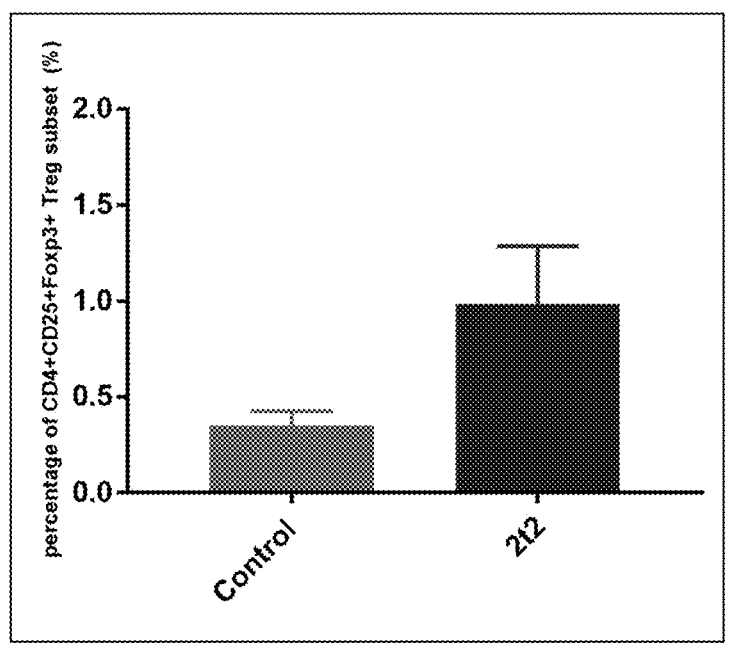
FIG. 22 shows the percentage of CD4$^+$CD25$^+$FoxP3$^+$ Tregs in blood lymphocytes from mice treated with IL-2/TF/IL-2 and control-treated mice.

IL-2/TF/IL-2 Significantly Upregulates the Ratio of CD4$^+$ CD25$^+$FoxP3$^+$ T Regulatory Cells in Blood Lymphocytes after the First Injection Male BKS.Cg-Dock7$^m$+/+Lepr$^{db}$/J (db/db) (The Jackson Laboratory) mice were fed with standard chow diet and received drinking water ad libitum. At the age of six weeks, mice were randomly assigned into control group and treatment group. The treatment group received IL-2/TF/IL-2 by subcutaneous injection at 3 mg/kg bi-weekly, while the control group received vehicle (PBS) only. Four days after the first drug injection, overnight fasting blood samples were collected and incubated with ACK lysing buffer (Thermo Fisher Scientific) at 37° C. for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer and were analyzed by flow cytometry (Celesta-BD Bioscience). The percentage of CD4$^+$CD25$^+$FoxP3$^+$ Tregs in blood lymphocytes were measured. As shown in FIG. 22, the results showed that IL-2/TF/IL-2 significantly upregulated the ratio of Tregs in blood lymphocytes. *p<0.05

Example 4. Production and Characterization of the Exemplary Single-Chain Chimeric Polypeptide IL-15/TF/IL-15

Figure 23:
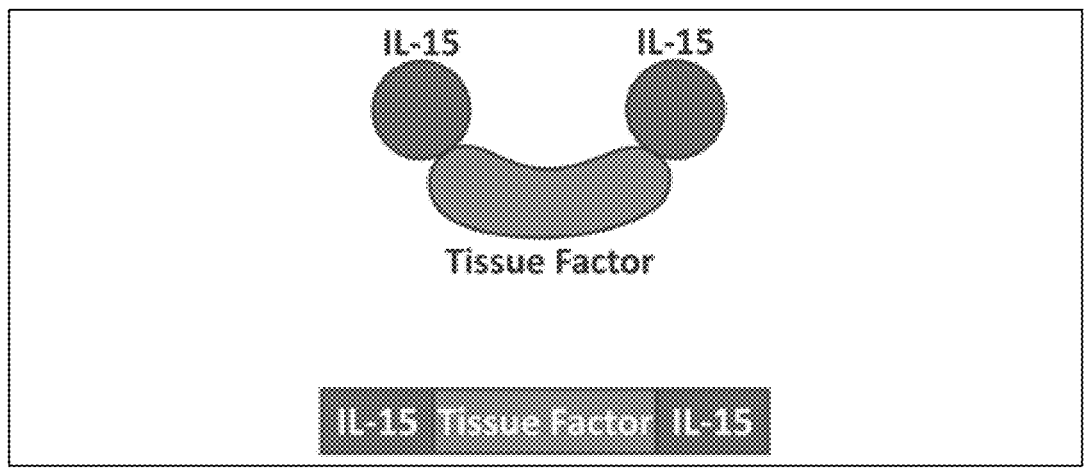
FIG. 23 are schematic diagrams of an exemplary IL-15/TF/IL-15 single-chain chimeric polypeptide.

A second exemplary single-chain chimeric polypeptide including a first target-binding domain that binds to an IL-15 receptor, a soluble human tissue factor domain, and a second target-binding domain that binds to an IL-15 receptor was generated (IL-15/TF/IL-15 or IL-15/TF/IL-15) (FIG. 23). The nucleic acid and amino acid sequences of this single-chain chimeric polypeptide are shown below.

```
Nucleic Acid Encoding Exemplary Single-Chain
Chimeric Polypeptide (IL-15/TF/IL-15)
                                       (SEQ ID NO: 117)
(Signal peptide)
ATGAAGTGGGTGACCTTCATCAGCCTGCTGTTCCTGTTCTCCAGCGCCTA

CTCC (First IL-15 fragment)
AACTGGGTGAACGTGATCAGCGATTTAAAGAAGATCGAGGATTTAATCCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGC (Human tissue factor 219 form)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Second IL-15 fragment)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

Exemplary Single-Chain Chimeric Polypeptide
(IL-15/TF/IL-15)
                                       (SEQ ID NO: 116)
(Signal peptide)
MKWVTFISLLFLSSAYS (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

The nucleic acid encoding IL-15/TF/IL-15 was cloned into a modified retrovirus expression vector as described previously (Hughes et al., *Hum Gene Ther* 16:457-72, 2005). The expression vector encoding IL-15/TF/IL-15 was transfected into CHO-K1 cells. Expression of the expression vector in CHO-K1 cells allowed for secretion of the soluble IL-15/TF/IL-15 single-chain chimeric polypeptide (referred to as 15t15), which can be purified by anti-TF antibody affinity and other chromatography methods.

Figure 24:
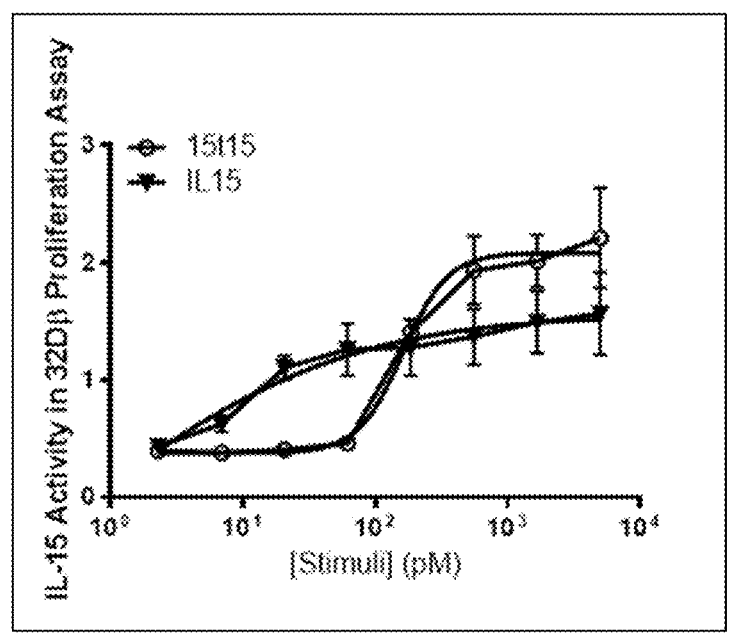
FIG. 24 shows the IL-15 activity of IL-15/TF/IL-15 as compared to recombinant IL-15 in a 32Dβ cell proliferation assay.

IL-15/TF/IL-15 Promotes IL-2Rβ and Common γ Chain Containing 32Dβ Cell Proliferation IL-15 activity of IL-15/TF/IL-15 was compared with recombinant IL-15 in IL2Rβ and common γ chain expressed 32Dβ cells. IL-15 dependent 32Dβ cells were washed five times with IMDM-10% FBS and seeded to the wells at 2×10$^4$ cells/well. Serial dilutions of IL-15/TF/IL-15 or IL-15 were added to the cells (FIG. 24). Cells were incubated in a $CO_2$ incubator at 37° C. for 3 days. Cell proliferation was detected by adding 10 μl of WST1 to each well in the day 3 and incubating for an additional 3 hours in a $CO_2$ incubator at 37° C. The amount of formazan dye produced was analyzed by measuring the absorbance at 450 nm. As shown in FIG. 24, IL-15/TF/IL-15 promoted 32Dβ cell proliferation less efficiently as compared to IL-15. The EC$_{50}$ of IL-15/TF/IL-15 and IL-15 was 161.4 pM and 1.6 pM. respectively.

Figure 25:
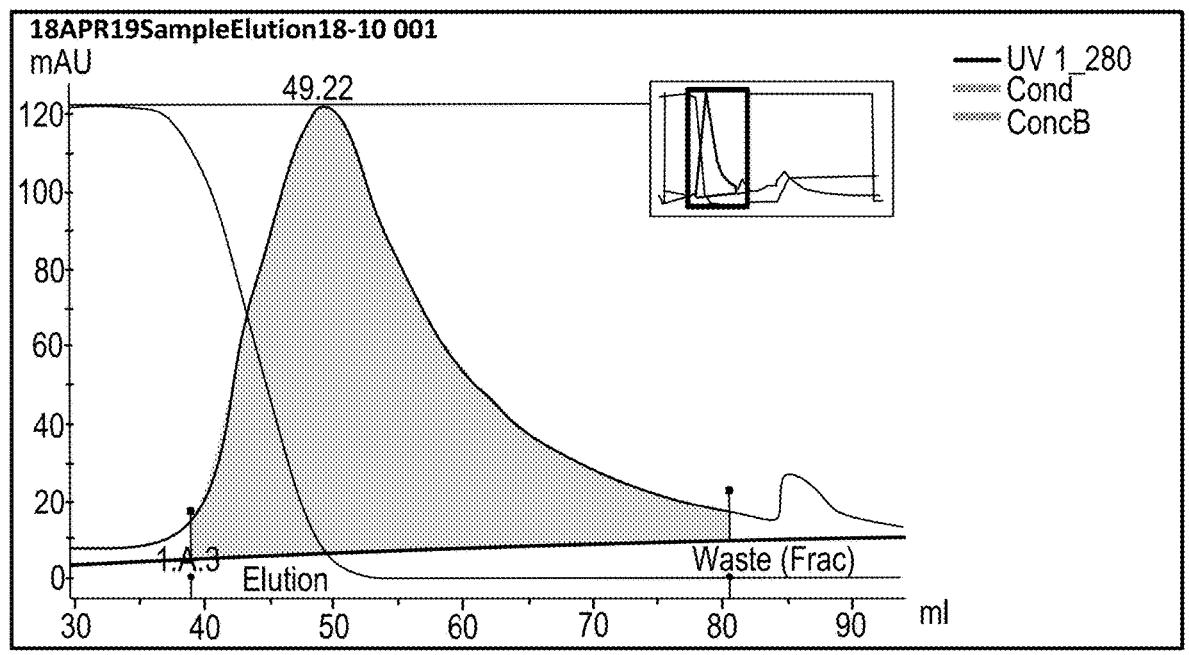
FIG. 25 is a line graph showing the chromatographic profile of IL-15/TF/IL-15 protein containing cell culture supernatant following binding and elution on anti-TF antibody resin.

Purification Elution Chromatograph of IL-15/TF/IL-15 from Anti-TF Antibody Affinity Column IL-15/TF/IL-15 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid, pH 2.9. A280 elution peak was collected and then neutralized to pH 7.5-8.0 with 1M Tris base. The neutralized sample was then buffer exchanged into PBS using Amicon centrifugal filters with a 30 kDa molecular weight cutoff. As shown in FIG. 25, the anti-TF antibody affinity column bound to IL-15/TF/IL-15 which contains TF as a fusion domain. The buffer-exchanged protein sample was stored at 2-8° C. for further biochemical analyses and biological activity tests. After each elution, the anti-TF antibody affinity column was stripped using 6 column volumes of 0.1M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of IL-15/TF/IL-15

To determine the purity and molecular weight of the protein, IL-15/TF/IL-15 (15t15) protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 26A:
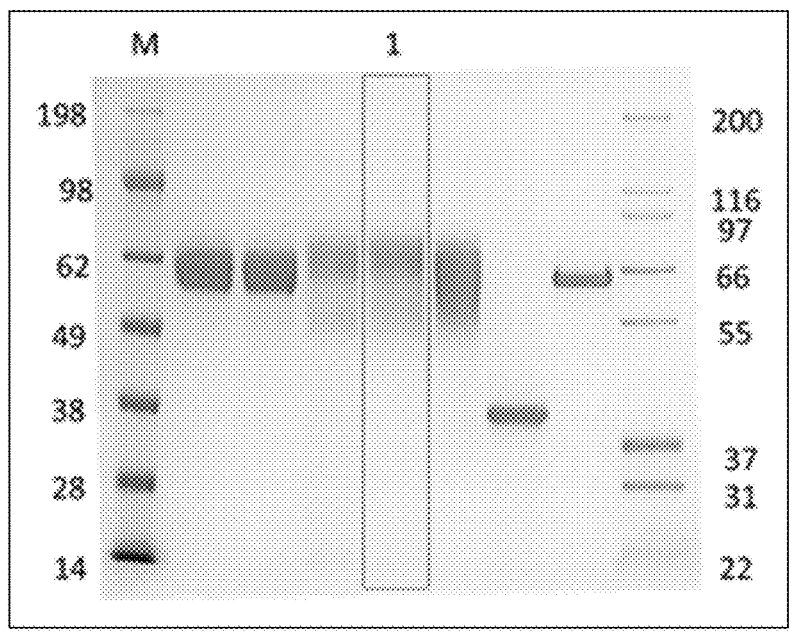
FIGS. 26A and 26B show reduced SDS-PAGE analysis of IL-15/TF/IL-15 before and after deglycosylation.
Figure 26B:
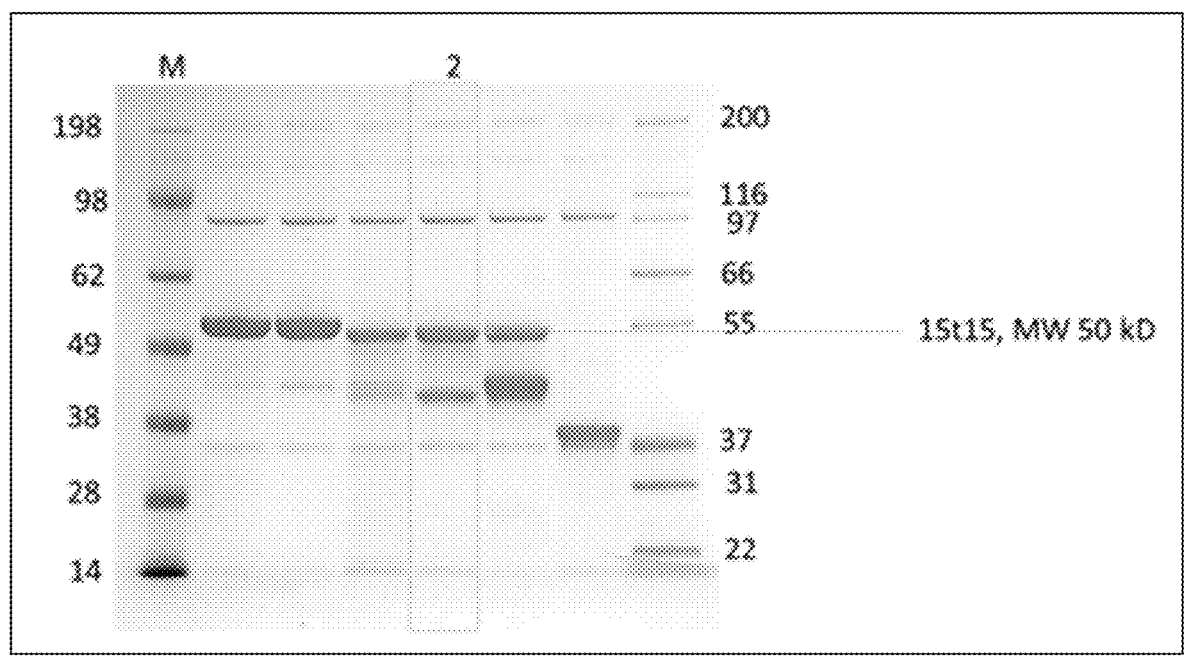

To verify that the IL-15/TF/IL-15 protein undergoes glycosylation after translation in CHO cells, a deglycosylation experiment was conducted using the Protein Deglycosylation Mix II kit from New England Biolabs and the manufacturer's instructions. FIGS. 26A and 26B show the reduced SDS-PAGE analysis of the sample in non-deglycosylated (lane 1 in red outline) and deglycosylated (lane 2 in yellow outline) state. The results showed that the IL-15/TF/IL-15 protein is glycosylated when expressed in CHO cells. After deglycosylation, the purified sample ran with expected molecular weights (50 kDa) in reduced SDS gel. Lane M was loaded with 10 µL of SeeBlue Plus2 Prestained Standard.

Example 5: Stimulation of NK Cells In Vivo by IL-2/TF/IL-2 (2t2)

Figure 27A:
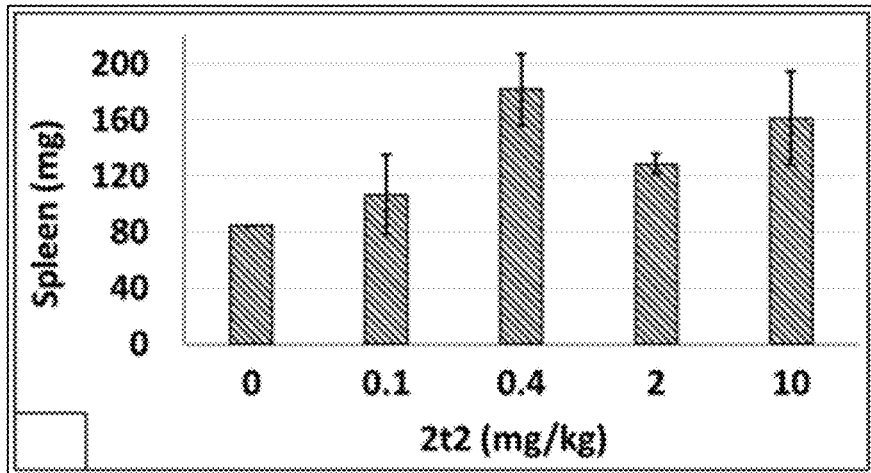
FIGS. 27A-27C is a set of graphs showing immunostimulation in C57BL/6 mice following treatment with 2t2.
Figure 27B:
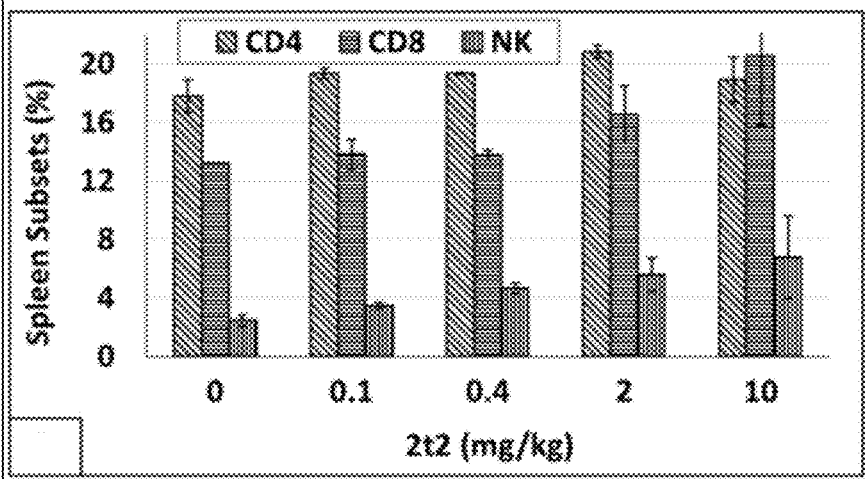
Figure 27C:
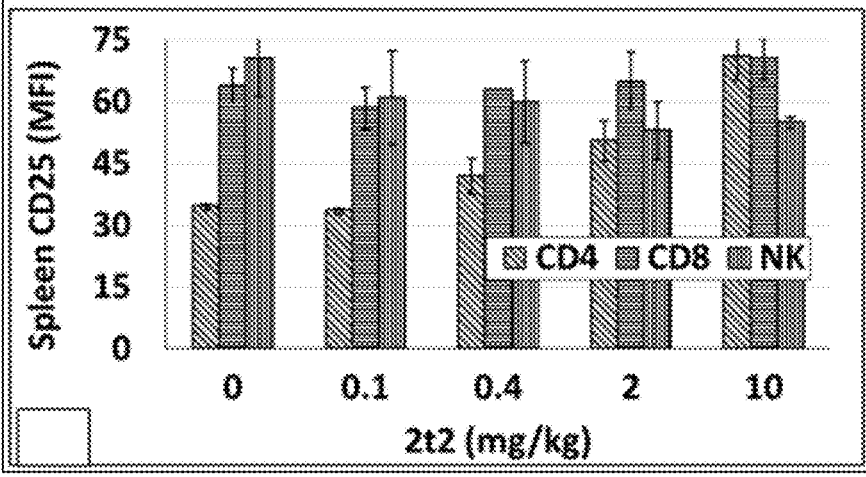

A set of experiments was performed to determine the effect of the 2t2 construct on immune stimulation in C57BL/6 mice. In these experiments, C57BL/6 mice were subcutaneously treated with control solution (PBS) or 2t2 at 0.1, 0.4, 2, and 10 mg/kg. Treated mice were euthanized 3 days post-treatment. Spleen weight was measured and single splenocyte suspensions were prepared. Splenocytes suspensions were stained with conjugated anti-CD4, anti-CD8, and anti-NK1.1 (NK) antibodies. The percentage of CD4$^+$ T cells, CD8$^+$ T cells, and NK cells, and CD25 expression on lymphocyte subsets were analyzed by flow cytometry. FIG. 27A shows that 2t2 was effective at expanding splenocytes based on spleen weight especially at a dose level of 0.1-10 mg/kg. Following treatment, the percentage of CD8$^+$ T cells were higher in 2t2-treated mice compared to control-treated mice at 2 and 10 mg/kg (FIG. 27B). The percentage of NK cells were also higher in 2t2-treated mice compared to control-treated mice at all doses of 2t2 tested (FIG. 27B). Additionally, 2t2 significantly upregulated CD25 expression by CD4$^+$ T cells, but not CD8$^+$ T cells and NK cells following treatment at 0.4 to 10 mg/kg (FIG. 27C).

Figure 28A:
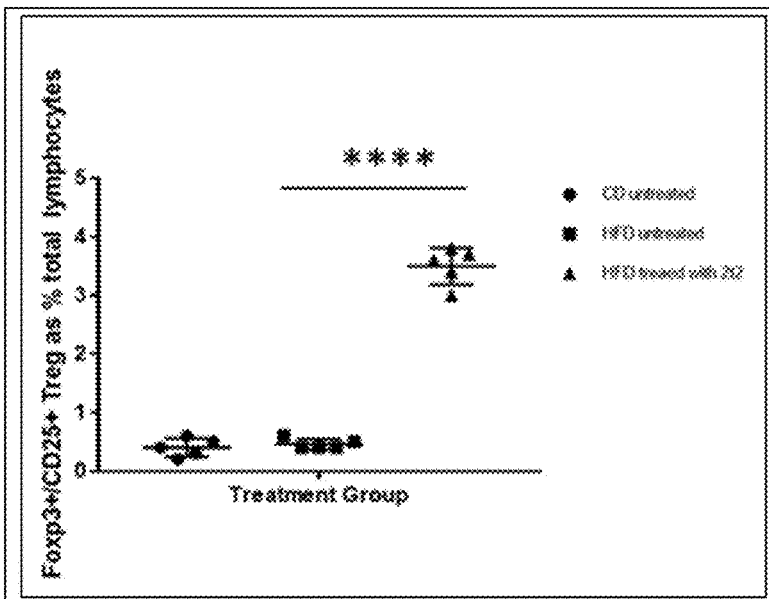
FIGS. 28A-28C is a set of graphs showing in vivo stimulation of Tregs, NK cells, and CD8$^+$ T cells in ApoE$^{-/-}$ mice fed with a Western diet and treated with 2t2.
Figure 28B:
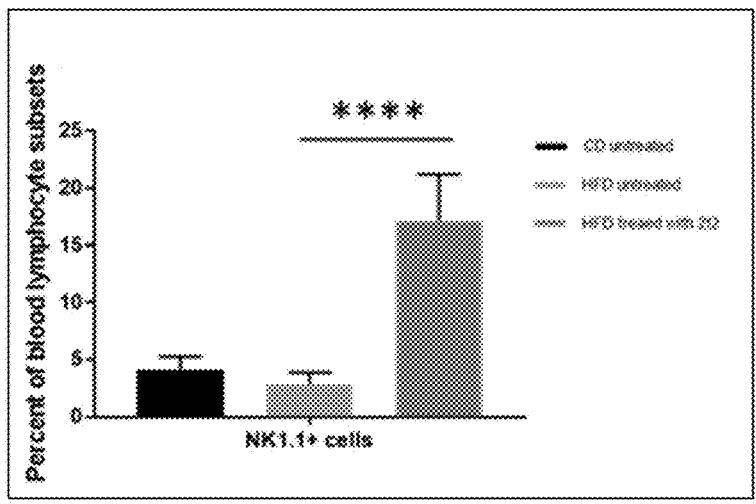
Figure 28C:
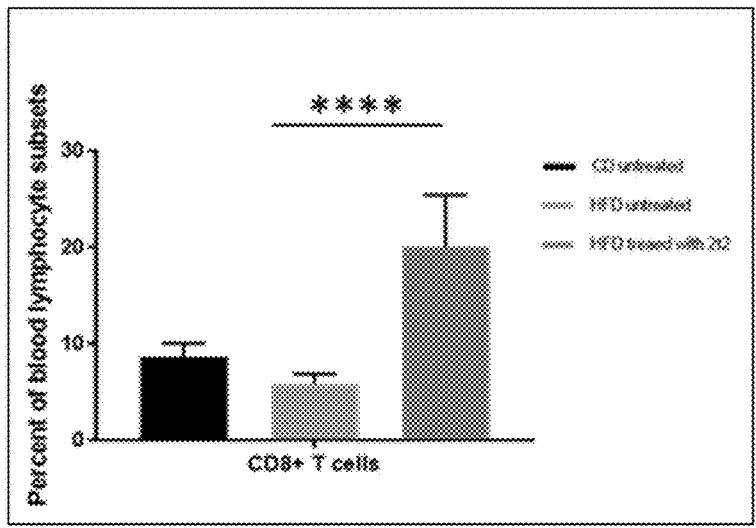

A set of experiments was performed to determine the effect of the 2t2 construct on immune stimulation in ApoE$^{-/-}$ mice fed with a Western diet. In these experiments, 6-week old female B6.129P2-ApoE$^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with 2t2 at 3 mg/kg. Three days post treatment, mice were fasted for 16 hours and then blood samples were collected through retro-orbital venous plexus puncture. The blood was mixed with 10 µL 0.5 M EDTA, and 20 µL blood was taken for lymphocyte subsets analysis. The red blood cells were lysed with ACK (0.15 M NH$_4$Cl, 1.0 mM KHCO$_3$, 0.1 mM Na$_2$EDTA, pH 7.4) and the lymphocytes were stained with anti-mouse CD8a and anti-mouse NK1.1 antibodies for 30 minutes at 4° C. in FACS staining buffer (1% BSA in PBS). The cells were washed once and analyzed with a BD FACS Celesta. For Treg staining, ACK treated blood lymphocytes were stained with anti-mouse CD4 and anti-mouse CD25 antibodies for 30 minutes at 4° C. in FACS staining buffer. The cells were washed once and resuspended in fixation/permeabilization working solution and incubated at room temperature for 60 minutes. The cells were washed once and resuspended in permeabilization buffer. The samples were centrifuged at 300-400×g for 5 minutes at room temperature and the supernatant was then discarded. The cell pellet was resuspended in residual volume and the volume adjusted to about 100 µL with 1× permeabilization buffer. Anti-Foxp3 antibody was added to the cells, and the cells were incubated for 30 minutes at room temperature. Permeabilization buffer (200 µL) was added to the cells, and the cells were centrifuged at 300-400×g for 5 minutes at room temperature. The cells were resuspended in flow cytometry staining buffer and analyzed on a flow cytometer. FIGS. 28B-28C show that treatment with 2t2 increased the percentage of NK cells and CD8$^+$ T cells in ApoE$^{-/-}$ mice fed with Western diet. FIG. 28A shows that treatment with 2t2 also increased the percentage of Treg cells.

Example 6: Induction of Proliferation of Immune Cells In Vivo

Figure 29A:
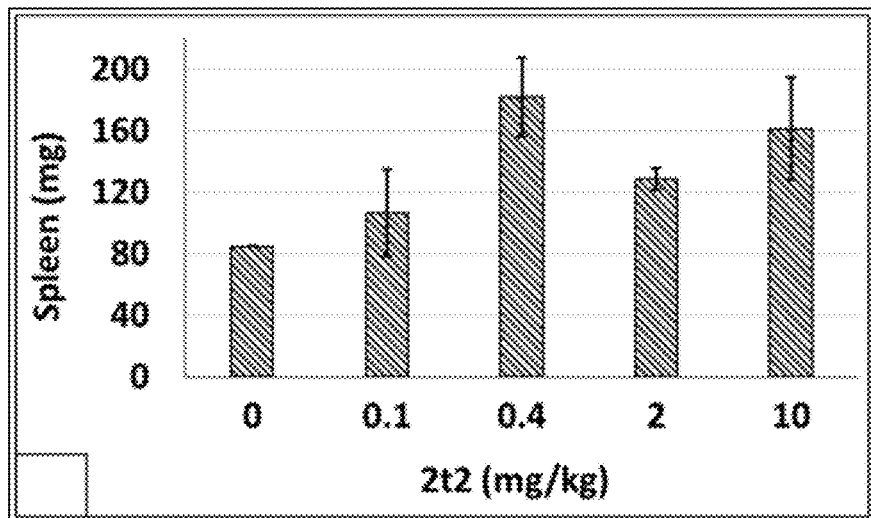
FIGS. 29A and 29B is a set of graphs showing induction of splenocyte proliferation by 2t2 in C57BL/6 mice.
Figure 29B:
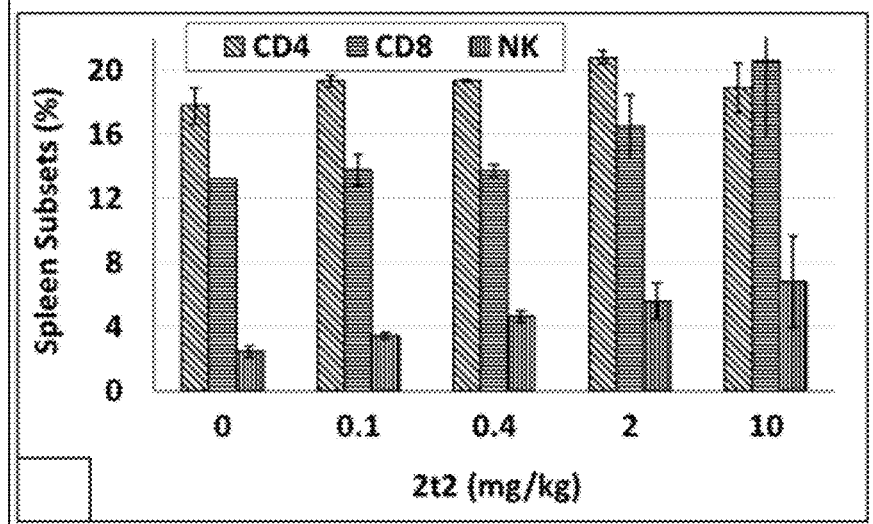

A set of experiments was performed to determine the effect of the 2t2 construct on immune cell stimulation in C57BL/6 mice. In these experiments, C57BL/6 mice were subcutaneously treated with control solution (PBS) or 2t2 at 0.1, 0.4, 2, and 10 mg/kg. Treated mice were euthanized 3 days post-treatment. Spleen weight was measured and single splenocyte suspensions were prepared. The splenocyte suspensions were stained with conjugated anti-CD4, anti-CD8, and anti-NK1.1 (NK) antibodies. The percentage of CD4$^+$ T cells, CD8$^+$ T cells, and NK cells were analyzed by flow cytometry. FIG. 29A shows that 2t2 treatment was effective at expanding splenocytes based on spleen weight especially at 0.1-10 mg/kg. The percentage of CD8$^+$ T cells was higher compared to control-treated mice at 2 and 10 mg/kg (FIG. 29B). The percentage of NK cells was higher compared to control-treated mice at all doses of 2t2 tested (FIG. 29B). These results demonstrate that 2t2 treatment was able to induce proliferation of CD8$^+$ T cells and NK cells in C57BL/6 mice.

Figure 30A:
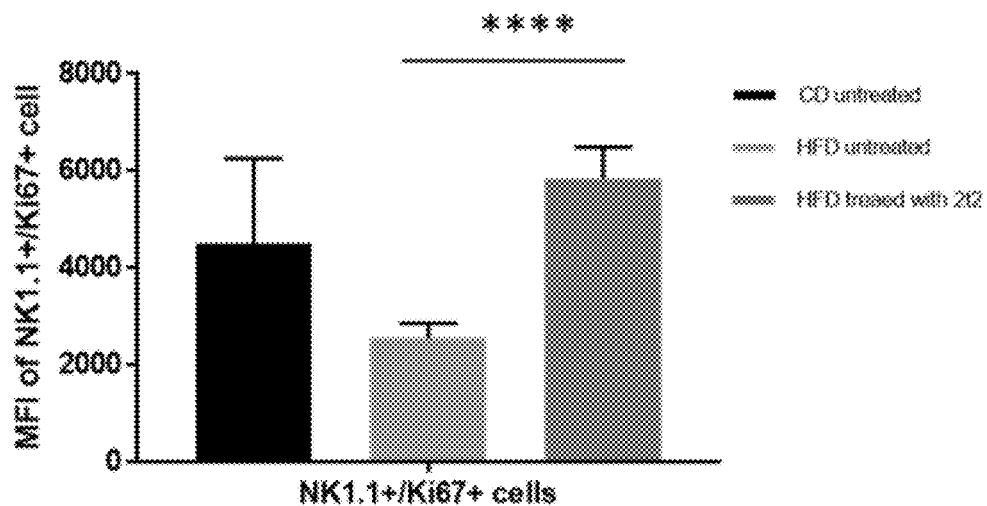
FIGS. 30A and 30B is a set of graphs showing in vivo induction of proliferation of NK cells and CD8$^+$ T cells in ApoE$^{-/-}$ mice fed with a Western diet and treated with 2t2.
Figure 30B:
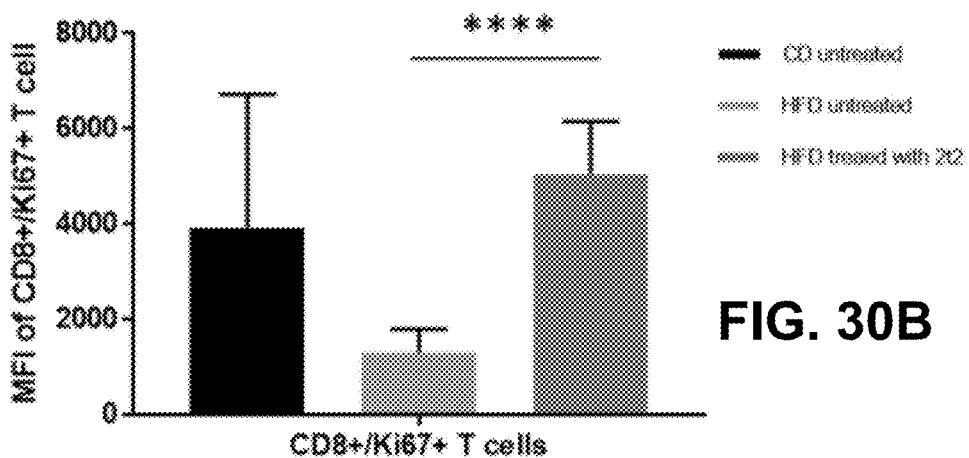

A set of experiments was performed to determine the effect of the 2t2 construct on immune stimulation in ApoE$^{-/-}$ mice fed with a Western diet. In these experiments, 6-week old female B6.129P2-ApoE$^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-week of the Western diet, the mice were injected subcutaneously with 2t2 at 3 mg/kg. Three days post-treatment, the mice were fasted for 16 hours and then blood samples were collected through retro-orbital venous plexus puncture. The blood was mixed with 10 µL 0.5 M EDTA and 20 µL blood was taken for lymphocyte subsets analysis. The red blood cells were lysed with ACK (0.15 M NH$_4$Cl, 1.0 mM KHCO$_3$, 0.1 mM Na$_2$EDTA, pH 7.4) and the lymphocytes were stained with anti-mouse CD8a and anti-mouse NK1.1 antibodies for 30 minutes at 4° C. in FACS staining buffer (1% BSA in PBS). The cells were washed once and resuspended in Fixation Buffer (BioLegend Cat #420801) for 20 minutes at room temperature. The cells were centrifuged at 350×g for 5 minutes, the fixed cells were resuspended in Intracellular Staining Permeabilization Wash Buffer (BioLegend Cat #421002) and then centrifuged at 350×g for 5 minutes. The cells were then stained with anti-Ki67 antibody for 20 minutes at RT. The cells were washed twice with Intracellular Staining Permeabilization Wash Buffer and centrifuged at 350×g for 5 minutes. The cells were then resuspended in FACS staining buffer. Lymphocyte subsets were analyzed with a BD FACS Celesta. FIGS. 30A and 30B shows treatment of ApoE$^{-/-}$ mice with 2t2 also induced proliferation (Ki67-positive staining) in NK and CD8$^+$ T cells.

Example 7: Treatment of Diabetes

Figure 31A:
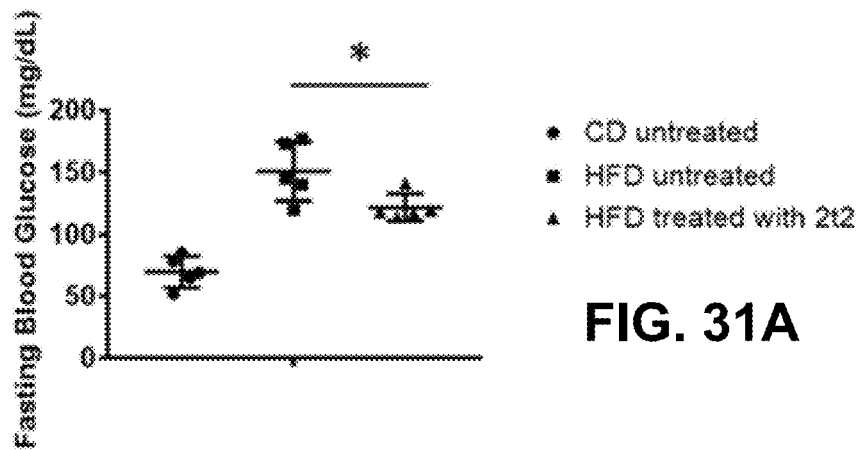
FIGS. 31A-31C is a set of graphs showing amelioration of the Western diet-induced hyperglycemia in ApoE$^{-/-}$ mice by 2t2.
Figure 31B:
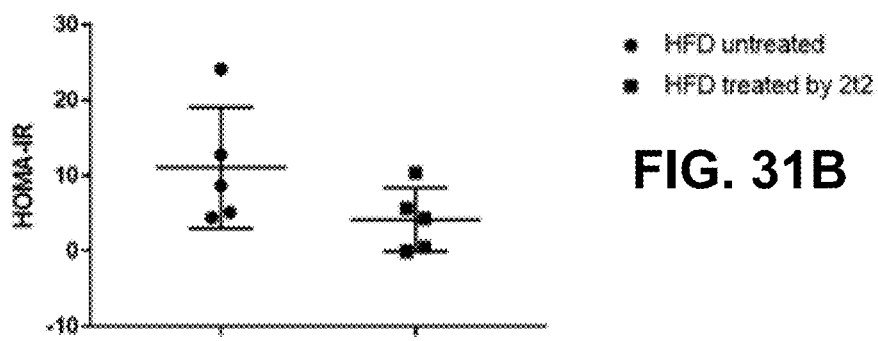
Figure 31C:
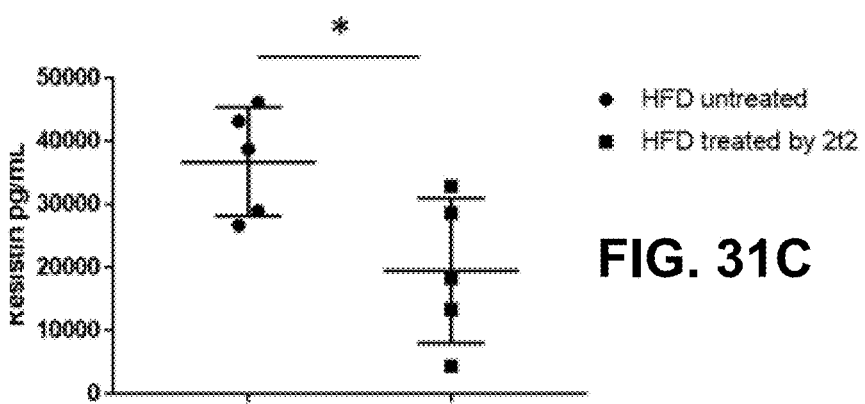

A set of experiments was performed to investigate amelioration of Western diet-induced hyperglycemia in ApoE$^{-/-}$ mice by 2t2. In these experiments, 6-week old female B6.129P2-ApoE$^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with 2t2 at 3 mg/kg. Three days post-treatment, the mice were fasted for 16 hours and then blood samples were collected through retro-orbital venous plexus puncture. Blood glucose was detected with a glucose meter (OneTouch UltraMini) and GenUltimated test strips using a drop of fresh blood. As shown in FIG. 31A, 2t2 treatment significantly reduced hyperglycemia induced by the Western diet (p<0.04). The plasma insulin and resistin levels were analyzed with Mouse Rat Metabolic Array by Eve Technologies. HOMA-IR was calculated using the following formula: homeostatic model assessment-insulin resistance=Glucose (mg/dL)*Insulin (mU/mL)/405. As shown in FIG. 31B, 2t2 treatment reduced insulin resistance compared to the untreated group. 2t2 (p<0.02) reduced resistin levels significantly compared to the untreated group as shown in FIG. 31C, which may relate to the reduced insulin resistance induced by 2t2 (FIG. 31B).

Example 8. Upregulation of CD44 Memory T Cells

Figure 32:
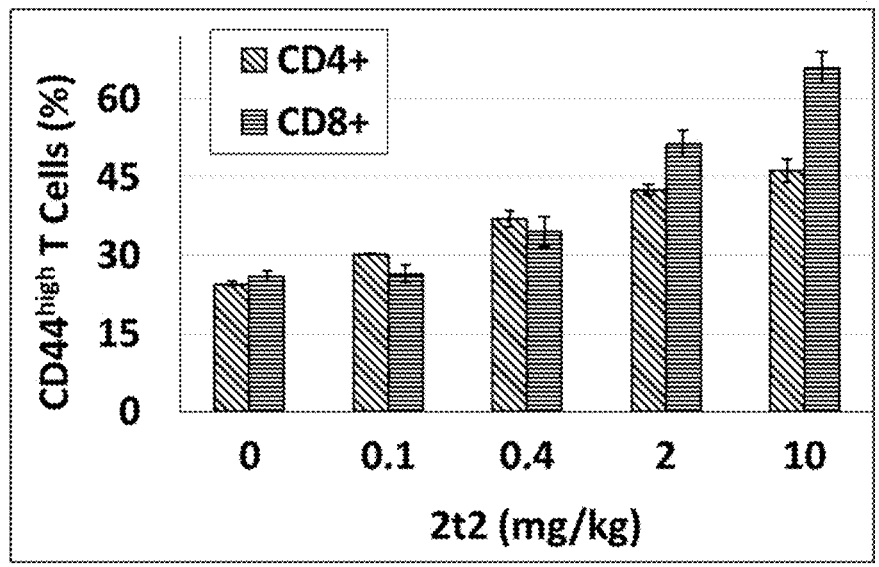
FIG. 32 shows upregulation of CD44 memory T cells upon treatment with 2t2.

C57BL/6 mice were subcutaneously treated with 2t2. The treated mice were euthanized and the single splenocyte suspensions were prepared 4 days (TGFRt15-TGFRs) or 3 days (2t2) following the treatment. The prepared splenocytes were stained with fluorochrome-conjugated anti-CD4, anti-CD8 and anti-CD44 antibodies and the percentages of CD44$^{high}$ T cells in CD4$^+$ T cells or CD8$^+$ T cells were analyzed by flow cytometry. The results show that 2t2 upregulated expression of the memory marker CD44 on CD4$^+$ and CD8$^+$ T cells (FIG. 32). These findings indicate that 2t2 was able to induce mouse T cells to differentiate into memory T cells.

Example 9. Tissue Factor Coagulation Assays Following Treatment with Single-Chain or Multi-Chain Chimeric Polypeptides A set of experiments was performed to assess blood coagulation following treatment with single-chain or multi-chain chimeric polypeptides. To initiate the blood coagulation cascade pathway, tissue factor (TF) binds to Factor VIIa (FVIIa) to form a TF/FVIIa complex. The TF/FVIIa complex then binds Factor X (FX) and converts FX to FXa.

An assay to measure blood coagulation involves measuring activation of Factor X (FX). Briefly, TF/VIIa activates blood coagulation Factor X (FX) to Factor Xa (FXa) in the presence of calcium and phospholipids. TF$_{243}$, which contains the transmembrane domain of TF, has much higher activity in activating FX to FXa than TF$_{219}$, which does not contain the transmembrane domain. TF/VIIa dependent activation of FX is determined by measuring FXa activity using an FXa-specific chromogenic substrate S-2765 (Diapharma, West Chester, OH). The color change of S-2765 can be monitored spectrophotometrically and is proportional to the proteolytic activity of FXa.

Figure 33:
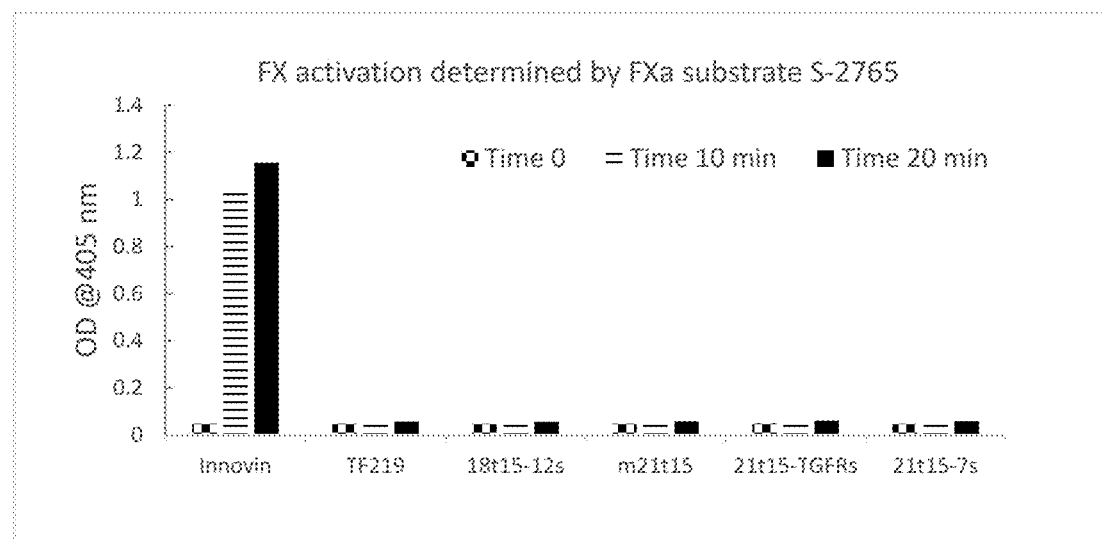
FIG. 33 shows a graph of Factor X (FX) activation following treatment with single-chain or multi-chain chimeric polypeptides.

In these experiments, FX activation with a multi-chain chimeric polypeptide (18t15-12s, mouse (m)21t15, 21t15-TGFRs, and 21t15-7s) was compared with a positive control (Innovin) or TF$_{219}$. TF$_{219}$ (or TF$_{219}$-containing multi-chain chimeric polypeptides)/FVIIa complexes were mixed at an equal molar concentration (0.1 nM each) in a volume of 50 µL in round bottom wells of a 96-well ELISA plate, after which 10 µL of 180 nM FX was added. After 15 minutes of incubation at 37° C., during which time FX was converted to FXa, 8 µL of 0.5 M EDTA (which chelates calcium and thus terminates FX activation by TF/VIIa) was added to each well to stop FX activation. Next, 10 µL of 3.2 mM S-2765 substrate was added to the reaction mixture. Immediately, the plate absorbance was measured at 405 nm and was recorded as the absorbance at time 0. The plate was then incubated for 10-20 minutes at 37° C. The color change was monitored by reading absorbance at 405 nm following the incubation. Results of FX activation as measured by FXa activity using chromogenic substrate S-2765 are shown in FIG. 33. In this experiment, Innovin, which is a commercial prothrombin reagent containing lipidated recombinant human TF$_{243}$, was used as a positive control for FX activation. Innovin was reconstituted with purified water to about 10 nM of TF$_{243}$. Next, 0.1 nM TF/VIIa complex was made by mixing an equal volume of 0.2 nM of FVIIa with 0.2 nM of Innovin. Innovin demonstrated very potent FX activation activity, while TF$_{219}$ and TF$_{219}$-containing multi-chain chimeric polypeptides had very low FX activation activity, confirming that TF$_{219}$ is not active in a TF/FVIIa complex for activating natural substrate FX in vivo.

Example 10: Induction of Treg Cells by 2t2

Figure 34A:
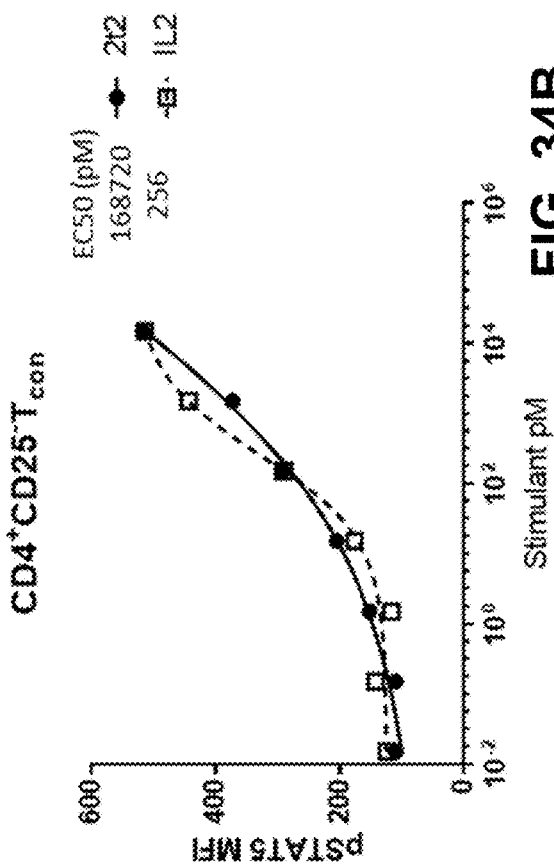
FIG. 34A-34C show human blood lymphocyte pStat5a responses in CD4$^+$CD25$^{hi}$T$_{reg}$ cells, CD4$^+$CD25$^-$ T$_{con}$ cells, or in CD8$^+$ T$_{con}$ cells in response to 2t2 or IL2 treatment.
Figure 34B:
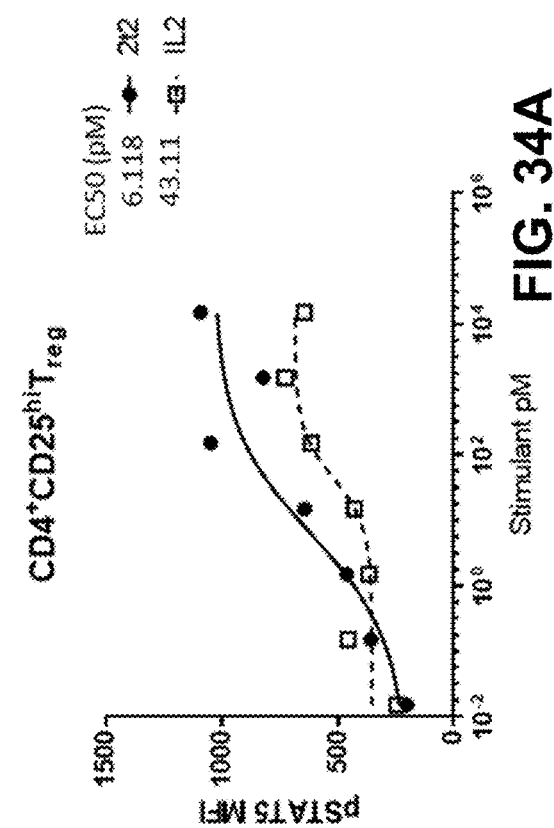
Figure 34C:
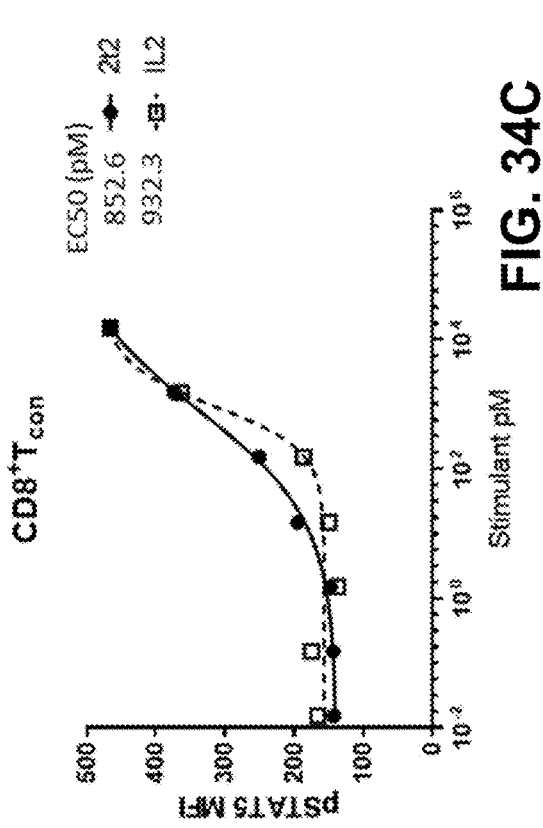

The peripheral blood mononuclear cells (PBMC) of a heathy donor (Donor 163) were isolated from 5 mL of whole blood buffy coats by Ficoll Paque Plus (GE17144003). The PBMC were then lysed with ACK to remove red blood cells. Cells were washed with IMDM-10% FBS and counted. 1.8×10$^6$ cells (100 µL/tube) were seeded to the flow tubes and incubated with 50 µL of descending 2t2 or IL2 (15000, 1500, 150, 15, 1.5, 0.15, or 0 pM) and 50 μL of pre-staining antibodies (anti-CD8-BV605 and anti-CD127-AF647). Cells were incubated for 30 min at 37° C. in water bath. 200 μL of pre-warmed BD Phosflow Fix Buffer I (Cat #557870, Becton Dickinson Biosciences) was added for 10 min at 37° C. in water bath to stop the stimulation. Cells ($4.5 \times 10^5$ cells/100 μL) were transferred to a V-shape 96-well plate and were spun down followed by permeabilization with 100 μL of −20° C. pre-cooled BD Phosflow Perm Buffer III (Cat #BD Biosciences) for 30 min on ice. The cells were then extensively washed ×2 with 200 μL of FACS buffer and stained with a panel of fluorescent antibodies (anti-CD25-PE, CD4-PerCP-Cy5.5, CD56-BV421, CD45RA-PE-Cy7 and pSTAT5a-AF488) to distinguish between different lymphocyte subpopulations and evaluate the pSTAT5a status. Cells were spun down and resuspended in 200 μL of FACS buffer for FACSCelesta analysis. As shown in Figure C1A, 6 pM of 2t2 was sufficient to induce the phosphorylation of Stat5a in $CD4^+CD25^{hi}$ $T_{reg}$ cells while 43.11 pM of IL-2 was required to induce phosphorylation of Stat5a in the same population of lymphocytes. In contrast, 2t2 was less active (FIG. 34B) or equally active (FIG. 34C) as compared to IL2 in inducing phosphorylation of Stat5a in $CD4^+CD25^-$ $T_{con}$ and $CD8^+$ $T_{con}$ cells. These results suggest that 2t2 is superior as compared to IL2 in activating $T_{reg}$ in human PBMC, and that 2t2 demonstrates increased $T_{reg}$ selectivity compared to IL-2 in human blood lymphocyte pStat5a responses.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

A. Exemplary Embodiments

Embodiment A1. A single-chain chimeric polypeptide comprising:
(i) a first target-binding domain;
(ii) a soluble tissue factor domain; and
(iii) a second target-binding domain.

Embodiment A2. The single-chain chimeric polypeptide of embodiment A1, wherein the first target-binding domain and the soluble tissue factor domain directly abut each other.

Embodiment A3. The single-chain chimeric polypeptide of embodiment A1, wherein the single-chain chimeric polypeptide further comprises a linker sequence between the first target-binding domain and the soluble tissue factor domain.

Embodiment A4. The single-chain chimeric polypeptide of any one of embodiments A1-A3, wherein the soluble tissue factor domain and the second target-binding domain directly abut each other.

Embodiment A5. The single-chain chimeric polypeptide of any one of embodiments A1-A3, wherein the single-chain chimeric polypeptide further comprises a linker sequence between the soluble tissue factor domain and the second target-binding domain.

Embodiment A6. The single-chain chimeric polypeptide of embodiment A1, wherein the first target-binding domain and the second target-binding domain directly abut each other.

Embodiment A7. The single-chain chimeric polypeptide of embodiment A1, wherein the single-chain chimeric polypeptide further comprises a linker sequence between the first target-binding domain and the second target-binding domain.

Embodiment A8. The single-chain chimeric polypeptide of embodiment A6 or A7, wherein the second target-binding domain and the soluble tissue factor domain directly abut each other.

Embodiment A9. The single-chain chimeric polypeptide of embodiment A6 or A7, wherein the single-chain chimeric polypeptide further comprises a linker sequence between the second target-binding domain and the soluble tissue factor domain.

Embodiment A10. The single-chain chimeric polypeptide of any one of embodiments A1-A9, wherein the first target-binding domain and the second target-binding domain bind specifically to the same antigen.

Embodiment A11. The single-chain chimeric polypeptide of embodiment A10, wherein the first target-binding domain and the second target-binding domain bind specifically to the same epitope.

Embodiment A12. The single-chain chimeric polypeptide of embodiment A11, wherein the first target-binding domain and the second target-binding domain comprise the same amino acid sequence.

Embodiment A13. The single-chain chimeric polypeptide of any one of embodiments A1-A9, wherein the first target-binding domain and the second target-binding domain bind specifically to different antigens.

Embodiment A14. The single-chain chimeric polypeptide of any one of embodiments A1-A13, wherein one or both of the first target-binding domain and the second target-binding domain is an antigen-binding domain.

Embodiment A15. The single-chain chimeric polypeptide of embodiment A14, wherein the first target-binding domain and the second target-binding domain are each an antigen-binding domain.

Embodiment A16. The single-chain chimeric polypeptide of embodiment A13, wherein antigen-binding domain comprises a scFv or a single domain antibody.

Embodiment A17. The single-chain chimeric polypeptide of any one of embodiments A1-A16, wherein one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A18. The single-chain chimeric polypeptide of any one of embodiments A1-A16, wherein one or both of the first target-binding domain and the second target-binding domain is a soluble interleukin, a soluble cytokine protein, or a soluble cell surface protein.

Embodiment A19. The single-chain chimeric polypeptide of embodiment A18, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment A20. The single-chain chimeric polypeptide of any one of embodiments A1-A16, wherein one or both of the first target-binding domain and the second target-binding domain is a soluble interleukin receptor, a soluble cytokine receptor, or a soluble cell surface receptor.

Embodiment A21. The single-chain chimeric polypeptide of embodiment A20, wherein the soluble interleukin receptor, soluble cytokine receptor, or soluble cell surface receptor is a soluble TGF-βreceptor II (TGF-βRII), a soluble TGF-βRIII, a soluble NKG2D, a soluble NK30, a soluble NKp44, a soluble NKp46, a soluble DNAM1, a scMHCI, a scMHCII, a scTCR, a soluble CD155, or a soluble CD28.

Embodiment A22. The single-chain chimeric polypeptide of any one of embodiments A1-A21, wherein the soluble tissue factor domain is a soluble human tissue factor domain.

Embodiment A23. The single-chain chimeric polypeptide of embodiment A22, wherein the soluble human tissue factor domain comprises a sequence that is at least 80% identical to SEQ ID NO: 9.

Embodiment A24. The single-chain chimeric polypeptide of embodiment A23, wherein the soluble human tissue factor domain comprises a sequence that is at least 90% identical to SEQ ID NO: 9.

Embodiment A25. The single-chain chimeric polypeptide of embodiment A24, wherein the soluble human tissue factor domain comprises a sequence that is at least 95% identical to SEQ ID NO: 9.

Embodiment A26. The single-chain chimeric polypeptide of any one of embodiments A22-A25, wherein the soluble human tissue factor domain does not comprise one or more of:
  a lysine at an amino acid position that corresponds to amino acid position 20 of mature wildtype human tissue factor protein;
  an isoleucine at an amino acid position that corresponds to amino acid position 22 of mature wildtype human tissue factor protein;
  a tryptophan at an amino acid position that corresponds to amino acid position 45 of mature wildtype human tissue factor protein;
  an aspartic acid at an amino acid position that corresponds to amino acid position 58 of mature wildtype human tissue factor protein;
  a tyrosine at an amino acid position that corresponds to amino acid position 94 of mature wildtype human tissue factor protein;
  an arginine at an amino acid position that corresponds to amino acid position 135 of mature wildtype human tissue factor protein; and
  a phenylalanine at an amino acid position that corresponds to amino acid position 140 of mature wildtype human tissue factor protein.

Embodiment A27. The single-chain chimeric polypeptide of embodiment A26, wherein the soluble human tissue factor domain does not comprise any of:
  a lysine at an amino acid position that corresponds to amino acid position 20 of mature wildtype human tissue factor protein;
  an isoleucine at an amino acid position that corresponds to amino acid position 22 of mature wildtype human tissue factor protein;
  a tryptophan at an amino acid position that corresponds to amino acid position 45 of mature wildtype human tissue factor protein;
  an aspartic acid at an amino acid position that corresponds to amino acid position 58 of mature wildtype human tissue factor protein;
  a tyrosine at an amino acid position that corresponds to amino acid position 94 of mature wildtype human tissue factor protein;
  an arginine at an amino acid position that corresponds to amino acid position 135 of mature wildtype human tissue factor protein; and
  a phenylalanine at an amino acid position that corresponds to amino acid position 140 of mature wildtype human tissue factor protein.

Embodiment A28. The single-chain chimeric polypeptide of any one of embodiments A1-A27, wherein the soluble tissue factor domain is not capable of binding Factor VIIa.

Embodiment A29. The single-chain chimeric polypeptide of any one of embodiments A1-A28, wherein the soluble tissue factor domain does not convert inactive Factor X into Factor Xa.

Embodiment A30. The single-chain chimeric polypeptide of any one of embodiments A1-A29, wherein the single-chain chimeric polypeptide does not blood stimulate coagulation in a mammal.

Embodiment A31. The single-chain chimeric polypeptide of any one of embodiments A1-A30, wherein the single-chain chimeric polypeptide further comprises one or more additional target-binding domains at its N- and/or C-terminus.

Embodiment A32. The single-chain chimeric polypeptide of embodiment A31, wherein the single-chain chimeric polypeptide comprises one or more additional target-binding domains at its N-terminus.

Embodiment A33. The single-chain chimeric polypeptide of embodiment A32, wherein one or more additional target-binding domains directly abuts the first target-binding domain, the second target-binding domain, or the soluble tissue factor domain.

Embodiment A34. The single-chain chimeric polypeptide of embodiment A33, wherein the single-chain chimeric polypeptide further comprises a linker sequence between one of the at least one additional target-binding domains and the first target-binding domain, the second target-binding domain, or the soluble tissue factor domain.

Embodiment A35. The single-chain chimeric polypeptide of embodiment A31, wherein the single-chain chimeric polypeptide comprises one or more additional target-binding domains at its C-terminus.

Embodiment A36. The single-chain chimeric polypeptide of embodiment A35, wherein one of the one or more additional target-binding domains directly abuts the first target-binding domain, the second target-binding domain, or the soluble tissue factor domain.

Embodiment A37. The single-chain chimeric polypeptide of embodiment A35, wherein the single-chain chimeric polypeptide further comprises a linker sequence between one of the at least one additional target-binding domains and the first target-binding domain, the second target-binding domain, or the soluble tissue factor domain.

Embodiment A38. The single-chain chimeric polypeptide of embodiment A31, wherein the single-chain chimeric polypeptide comprises one or more additional target binding domains at its N-terminus and the C-terminus.

Embodiment A39. The single-chain chimeric polypeptide of embodiment A38, wherein one of the one or more additional antigen binding domains at the N-terminus directly abuts the first target-binding domain, the second target-binding domain, or the soluble tissue factor domain.

Embodiment A40. The single-chain chimeric polypeptide of embodiment A38, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment A41. The single-chain chimeric polypeptide of embodiment A38, wherein one of the one or more additional antigen binding domains at the C-terminus directly abuts the first target-binding domain, the second target-binding domain, or the soluble tissue factor domain.

Embodiment A42. The single-chain chimeric polypeptide of embodiment A38, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment A43. The single-chain chimeric polypeptide of any one of embodiments A31-A42, wherein two or more of the first target-binding domain, the second target-binding domain, and the one or more additional target-binding domains bind specifically to the same antigen.

Embodiment A44. The single-chain chimeric polypeptide of embodiment A43, wherein two or more of the first target-binding domain, the second target-binding domain, and the one or more additional target-binding domains bind specifically to the same epitope.

Embodiment A45. The single-chain chimeric polypeptide of embodiment A44, wherein two or more of the first target-binding domain, the second target-binding domain, and the one or more additional target-binding domains comprise the same amino acid sequence.

Embodiment A46. The single-chain chimeric polypeptide of embodiment A43, wherein the first target-binding domain, the second target-binding domain, and the one or more additional target-binding domains each bind specifically to the same antigen.

Embodiment A47. The single-chain chimeric polypeptide of embodiment A46, wherein the first target-binding domain, the second target-binding domain, and the one or more additional target-binding domains each bind specifically to the same epitope.

Embodiment A48. The single-chain chimeric polypeptide of embodiment A47, wherein the first target-binding domain, the second target-binding domain, and the one or more additional target-binding domains each comprise the same amino acid sequence.

Embodiment A49. The single-chain chimeric polypeptide of any one of embodiments A31-A42, wherein the first target-binding domain, the second target-binding domain, and the one or more additional target-binding domains bind specifically to different antigens.

Embodiment A50. The single-chain chimeric polypeptide of any one of embodiments A31-A49, wherein one or more of the first target-binding domain, the second target-binding domain, and the one or more target-binding domains is an antigen-binding domain.

Embodiment A51. The single-chain chimeric polypeptide of embodiment A50, wherein the first target-binding domain, the second target-binding domain, and the one or more additional target-binding domains are each an antigen-binding domain.

Embodiment A52. The single-chain chimeric polypeptide of embodiment A51, wherein antigen-binding domain comprises a scFv or a single domain antibody.

Embodiment A53. The single-chain chimeric polypeptide of any one of embodiments A31-A52, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A54. The single-chain chimeric polypeptide of any one of embodiments A31-A52, wherein one or more of the first target-binding domain, the second target-binding domain, and the one or more additional target-binding domains is a soluble interleukin, a soluble cytokine protein, or a soluble cell surface protein.

Embodiment A55. The single-chain chimeric polypeptide of embodiment A54, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment A56. The single-chain chimeric polypeptide of any one of embodiments A31-A52, wherein one or more of the first target-binding domain, the second target-binding domain, and the one or more additional target-binding domains is a soluble interleukin receptor, a soluble cytokine receptor, or a soluble cell surface receptor.

Embodiment A57. The single-chain chimeric polypeptide of embodiment A56, wherein the soluble receptor is a soluble TGF-β receptor II (TGF-βRII), a soluble TGF-βRIII, a soluble NKG2D, a soluble NK30, a soluble NKp44, a soluble NKp46, a soluble DNAM1, a scMHCI, a scMHCII, a scTCR, a soluble CD155, a soluble CD122, a soluble CD3, or a soluble CD28.

Embodiment A58. The single-chain chimeric polypeptide of any one of embodiments A1-A57, wherein the single-chain chimeric polypeptide further comprises a signal sequence at its N-terminal end.

Embodiment A59. The single-chain chimeric polypeptide of any one of embodiments A1-A58, wherein the single-chain chimeric polypeptide further comprises a peptide tag positioned at the N-terminal end or the C-terminal end of the single-chain chimeric polypeptide.

Embodiment A60. A composition comprising any of the single-chain chimeric polypeptides of embodiments A1-A59.

Embodiment A61. The composition of embodiment A60, wherein the composition is a pharmaceutical composition.

Embodiment A62. A kit comprising at least one dose of the composition of embodiment A60 or A61.

Embodiment A63. A method of stimulating an immune cell, the method comprising:

contacting an immune cell with an effective amount of any of the single-chain chimeric polypeptides of embodiments A1-A59 or the composition of embodiment A60 or A61.

Embodiment A64. The method of embodiment A63, wherein the immune cell is contacted in vitro.

Embodiment A65. The method of embodiment A64, wherein the immune cell was previously obtained from a subject.

Embodiment A66. The method of embodiment A65, wherein the method further comprises obtaining the immune cell from the subject prior to the contacting step.

Embodiment A67. The method of embodiment A63, wherein the immune cell is contacted in vivo.

Embodiment A68. The method of any one of embodiments A63-A67, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment A69. The method of any one of embodiments A63-A68, wherein the immune cell has previously been genetically modified to express a chimeric antigen receptor or a recombinant T-cell receptor.

Embodiment A70. The method of any one of embodiments A63-A68, wherein the method further comprises, after the contacting step, introducing into the immune cell a nucleic acid encoding a chimeric antigen-receptor or a recombinant T-cell receptor.

Embodiment A71. The method of any one of embodiments A63-A70, wherein the method further comprises administering the immune cell to a subject in need thereof.

Embodiment A72. The method of embodiment A71, wherein the subject has been identified or diagnosed as having an age-related disease or condition.

Embodiment A73. The method of embodiment A72, wherein the age-related disease or condition is selected from the group consisting of: Alzheimer's disease, aneurysm, cystic fibrosis, fibrosis in panceatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A74. The method of embodiment A71, wherein the subject has been identified or diagnosed as having a cancer.

Embodiment A75. The method of embodiment A74, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A76. The method of embodiment A71, wherein the subject has been diagnosed or identified as having an infectious disease.

Embodiment A77. The method of embodiment A76, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A78. A method of inducing or increasing proliferation of an immune cell, the method comprising:

contacting an immune cell with an effective amount of any of the single-chain chimeric polypeptides of embodiments A1-A59 or the composition of embodiment A60 or A61.

Embodiment A79. The method of embodiment A88, wherein the immune cell is contacted in vitro.

Embodiment A80. The method of embodiment A79, wherein the immune cell was previously obtained from a subject.

Embodiment A81. The method of embodiment A80, wherein the method further comprises obtaining the immune cell from the subject prior to the contacting step.

Embodiment A82. The method of embodiment A78, wherein the immune cell is contacted in vivo.

Embodiment A83. The method of any one of embodiments A78-A82, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment A84. The method of any one of embodiments A78-A83, wherein the immune cell has previously been genetically modified to express a chimeric antigen receptor or a recombinant T-cell receptor.

Embodiment A85. The method of any one of embodiments A78-A83, wherein the method further comprises, after the contacting step, introducing into the immune cell a nucleic acid encoding a chimeric antigen-receptor or a recombinant T-cell receptor.

Embodiment A86. The method of any one of embodiments A78-A85, wherein the method further comprises administering the immune cell to a subject in need thereof.

Embodiment A87. The method of embodiment A86, wherein the subject has been identified or diagnosed as having an age-related disease or condition.

Embodiment A88. The method of embodiment A87, wherein the age-related disease or condition is selected from the group consisting of: Alzheimer's disease, aneurysm, cystic fibrosis, fibrosis in panceatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A89. The method of embodiment A86, wherein the subject has been identified or diagnosed as having a cancer.

Embodiment A90. The method of embodiment A89, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A91. The method of embodiment A86, wherein the subject has been diagnosed or identified as having an infectious disease.

Embodiment A92. The method of embodiment A86, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A93. A method of inducing differentiation of an immune cell into a memory or memory-like immune cell, the method comprising:

contacting an immune cell with an effective amount of any of the single-chain chimeric polypeptides of embodiments A1-A59 or the composition of embodiment A60 or A61.

Embodiment A94. The method of embodiment A93, wherein the immune cell is contacted in vitro.

Embodiment A95. The method of embodiment A94, wherein the immune cell was previously obtained from a subject.

Embodiment A96. The method of embodiment A95, wherein the method further comprises obtaining the immune cell from the subject prior to the contacting step.

Embodiment A97. The method of embodiment A93, wherein the immune cell is contacted in vivo.

Embodiment A98. The method of any one of embodiments A93-A97, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment A99. The method of any one of embodiments A93-A98, wherein the immune cell has previously been genetically modified to express a chimeric antigen receptor or a recombinant T-cell receptor.

Embodiment A100. The method of any one of embodiments A93-A98, wherein the method further comprises, after the contacting step, introducing into the immune cell a nucleic acid encoding a chimeric antigen-receptor or a recombinant T-cell receptor.

Embodiment A101. The method of any one of embodiments A93-A100, wherein the method further comprises administering the immune cell to a subject in need thereof.

Embodiment A102. The method of embodiment A101, wherein the subject has been identified or diagnosed as having an age-related disease or condition.

Embodiment A103. The method of embodiment A102, wherein the age-related disease or condition is selected from the group consisting of: Alzheimer's disease, aneurysm, cystic fibrosis, fibrosis in panceatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A104. The method of embodiment A101, wherein the subject has been identified or diagnosed as having a cancer.

Embodiment A105. The method of embodiment A104, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A106. The method of embodiment A101, wherein the subject has been diagnosed or identified as having an infectious disease.

Embodiment A107. The method of embodiment A106, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A108. A method of killing a cancer cell, an infected cell, or a senescent cell in a subject in need thereof, the method comprising administering to the subject a therapeutically effective amount of any of the single-chain chimeric polypeptides of embodiments A1-A59 or the composition of embodiment A60 or A61

Embodiment A109. The method of embodiment A108, wherein the subject has been identified or diagnosed as having a cancer.

Embodiment A110. The method of embodiment A109, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A111. The method of embodiment A108, wherein the subject has been identified or diagnosed as having an aging-related disease or condition.

Embodiment A112. The method of embodiment A111, wherein the aging-related disease or condition is selected from the group consisting of: Alzheimer's disease, aneurysm, cystic fibrosis, fibrosis in panceatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A113. A method of treating a subject in need thereof, the method comprising administering to the subject a therapeutically effective amount of any of the single-chain chimeric polypeptides of embodiments A1-A59 or the composition of embodiment A60 or A61

Embodiment A114. The method of embodiment A113, wherein the subject has been identified or diagnosed as having a cancer.

Embodiment A115. The method of embodiment A114, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastic and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A116. The method of embodiment A113, wherein the subject has been identified or diagnosed as having an aging-related disease or condition.

Embodiment A117. The method of embodiment A116, wherein the aging-related disease or condition is selected from the group consisting of: Alzheimer's disease, aneurysm, cystic fibrosis, fibrosis in panceatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A118. The method of embodiment A113, wherein the subject has been diagnosed or identified as having an infectious disease.

Embodiment A119. The method of embodiment A118, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A120. Nucleic acid encoding any of the single-chain chimeric polypeptides of any one of embodiments A1-A59.

Embodiment A121. A vector comprising the nucleic acid of embodiment A120.

Embodiment A122. The vector of embodiment A121, wherein the vector is an expression vector.

Embodiment A123. A cell comprising the nucleic acid of embodiment A120 or the vector of embodiment A121 or A122.

Embodiment A124. A method of producing a single-chain chimeric polypeptide, the method comprising:

culturing the cell of embodiment A123 in a culture medium under conditions sufficient to result in the production of the single-chain chimeric polypeptide; and recovering the single-chain chimeric polypeptide from the cell and/or the culture medium.

Embodiment A125. A single-chain chimeric polypeptide produced by the method of embodiment A124.

Embodiment A126. The single-chain chimeric polypeptide of embodiment A26, wherein the soluble human tissue factor domain comprises a sequence that is at least 80% identical to SEQ ID NO: 96.

Embodiment A127. The single-chain chimeric polypeptide of embodiment A126, wherein the soluble human tissue factor domain comprises a sequence that is at least 90% identical to SEQ ID NO: 96.

Embodiment A128. The single-chain chimeric polypeptide of embodiment A127, wherein the soluble human tissue factor domain comprises a sequence that is at least 95% identical to SEQ ID NO: 96.

Embodiment A129. The single-chain chimeric polypeptide of embodiment A128, wherein the soluble human tissue factor domain comprises a sequence that is 100% identical to SEQ ID NO: 96.

Embodiment A130. The single-chain chimeric polypeptide of embodiment A26, wherein the soluble human tissue factor domain comprises a sequence that is at least 80% identical to SEQ ID NO: 97.

Embodiment A131. The single-chain chimeric polypeptide of embodiment A130, wherein the soluble human tissue factor domain comprises a sequence that is at least 90% identical to SEQ ID NO: 97.

Embodiment A132. The single-chain chimeric polypeptide of embodiment A131, wherein the soluble human tissue factor domain comprises a sequence that is at least 95% identical to SEQ ID NO: 97.

Embodiment A133. The single-chain chimeric polypeptide of embodiment A132, wherein the soluble human tissue factor domain comprises a sequence that is 100% identical to SEQ ID NO: 97.

B. Exemplary Embodiments

Embodiment B1. A single-chain chimeric polypeptide comprising:
(i) a first target-binding domain;
(ii) a soluble tissue factor domain; and
(iii) a second target-binding domain,
wherein:
the first target-binding domain and the second target-binding domain each specifically bind to an IL-2 receptor; or
the first target-binding domain and the second target-binding domain each specifically bind to an IL-15 receptor.

Embodiment B2. The single-chain chimeric polypeptide of embodiment B1, wherein the first target-binding domain and the soluble tissue factor domain directly abut each other.

Embodiment B3. The single-chain chimeric polypeptide of embodiment B1, wherein the single-chain chimeric polypeptide further comprises a linker sequence between the first target-binding domain and the soluble tissue factor domain.

Embodiment B4. The single-chain chimeric polypeptide of any one of embodiments B1-B3, wherein the soluble tissue factor domain and the second target-binding domain directly abut each other.

Embodiment B5. The single-chain chimeric polypeptide of any one of embodiments B1-B3, wherein the single-chain chimeric polypeptide further comprises a linker sequence between the soluble tissue factor domain and the second target-binding domain.

Embodiment B6. The single-chain chimeric polypeptide of embodiment B1, wherein the first target-binding domain and the second target-binding domain directly abut each other.

Embodiment B7. The single-chain chimeric polypeptide of embodiment B1, wherein the single-chain chimeric polypeptide further comprises a linker sequence between the first target-binding domain and the second target-binding domain.

Embodiment B8. The single-chain chimeric polypeptide of embodiment B6 or B7, wherein the second target-binding domain and the soluble tissue factor domain directly abut each other.

Embodiment B9. The single-chain chimeric polypeptide of embodiment B6 or B7, wherein the single-chain chimeric polypeptide further comprises a linker sequence between the second target-binding domain and the soluble tissue factor domain.

Embodiment B10. The single-chain chimeric polypeptide of any one of embodiments B1-B9, wherein both the first target-binding domain and the second target-binding domain is a soluble interleukin protein.

Embodiment B11. The single-chain chimeric polypeptide of embodiment B10, wherein the first target-binding domain and the second target-binding domain is a soluble IL-2 protein.

Embodiment B12. The single-chain chimeric polypeptide of embodiment B11, wherein the soluble IL-2 protein is a soluble human IL-2 protein.

Embodiment B13. The single-chain chimeric polypeptide of embodiment B12, wherein the soluble human IL-2 protein comprises SEQ ID NO: 28.

Embodiment B14. The single-chain chimeric polypeptide of embodiment B10, wherein the first target-binding domain and the second target-binding domain is a soluble IL-15 protein.

Embodiment B15. The single-chain chimeric polypeptide of embodiment B14, wherein the soluble IL-15 protein is a soluble human IL-15 protein.

Embodiment B16. The single-chain chimeric polypeptide of embodiment B15, wherein the soluble human IL-15 protein comprises SEQ ID NO: 39.

Embodiment B17. The single-chain chimeric polypeptide of any one of embodiments B1-B16, wherein the soluble tissue factor domain is a soluble human tissue factor domain.

Embodiment B18. The single-chain chimeric polypeptide of embodiment B17, wherein the soluble human tissue factor domain comprises a sequence that is at least 80% identical to SEQ ID NO: 9.

Embodiment B19. The single-chain chimeric polypeptide of embodiment B18, wherein the soluble human tissue factor domain comprises a sequence that is at least 90% identical to SEQ ID NO: 9.

Embodiment B20. The single-chain chimeric polypeptide of embodiment B19, wherein the soluble human tissue factor domain comprises a sequence that is at least 95% identical to SEQ ID NO: 9.

Embodiment B21. The single-chain chimeric polypeptide of any one of embodiments B17-B20, wherein the soluble human tissue factor domain does not comprise one or more of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B22. The single-chain chimeric polypeptide of embodiment B21, wherein the soluble human tissue factor domain does not comprise any of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment B23. The single-chain chimeric polypeptide of any one of embodiments B1-B22, wherein the soluble tissue factor domain is not capable of binding Factor VIIa.

Embodiment B24. The single-chain chimeric polypeptide of any one of embodiments B1-B23, wherein the soluble tissue factor domain does not convert inactive Factor X into Factor Xa.

Embodiment B25. The single-chain chimeric polypeptide of any one of embodiments B1-B24, wherein the single-chain chimeric polypeptide does not blood stimulate coagulation in a mammal.

Embodiment B26. The single-chain chimeric polypeptide of any one of embodiments B1-B25, wherein the single-chain chimeric polypeptide further comprises one or more additional target-binding domains at its N- and/or C-terminus.

Embodiment B27. The single-chain chimeric polypeptide of embodiment B26, wherein the single-chain chimeric polypeptide comprises one or more additional target-binding domains at its N-terminus.

Embodiment B28. The single-chain chimeric polypeptide of embodiment B27, wherein one or more additional target-binding domains directly abuts the first target-binding domain, the second target-binding domain, or the soluble tissue factor domain.

Embodiment B29. The single-chain chimeric polypeptide of embodiment B28, wherein the single-chain chimeric polypeptide further comprises a linker sequence between one of the at least one additional target-binding domains and the first target-binding domain, the second target-binding domain, or the soluble tissue factor domain.

Embodiment B30. The single-chain chimeric polypeptide of embodiment B26, wherein the single-chain chimeric polypeptide comprises one or more additional target-binding domains at its C-terminus.

Embodiment B31. The single-chain chimeric polypeptide of embodiment B30, wherein one of the one or more additional target-binding domains directly abuts the first target-binding domain, the second target-binding domain, or the soluble tissue factor domain.

Embodiment B32. The single-chain chimeric polypeptide of embodiment B30, wherein the single-chain chimeric polypeptide further comprises a linker sequence between one of the at least one additional target-binding domains and the first target-binding domain, the second target-binding domain, or the soluble tissue factor domain.

Embodiment B33. The single-chain chimeric polypeptide of embodiment B26, wherein the single-chain chimeric polypeptide comprises one or more additional target binding domains at its N-terminus and the C-terminus.

Embodiment B34. The single-chain chimeric polypeptide of embodiment B33, wherein one of the one or more additional antigen binding domains at the N-terminus directly abuts the first target-binding domain, the second target-binding domain, or the soluble tissue factor domain.

Embodiment B35. The single-chain chimeric polypeptide of embodiment B33, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment B36. The single-chain chimeric polypeptide of embodiment B33, wherein one of the one or more additional antigen binding domains at the C-terminus directly abuts the first target-binding domain, the second target-binding domain, or the soluble tissue factor domain.

Embodiment B37. The single-chain chimeric polypeptide of embodiment B33, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment B38. The single-chain chimeric polypeptide of any one of embodiments B26-B37, wherein each of the first target-binding domain, the second target-binding domain, and the one or more additional target-binding domains bind specifically to an IL-2 receptor or an IL-15 receptor.

Embodiment B39. The single-chain chimeric polypeptide of embodiment B38, wherein each of the first target-binding domain, the second target-binding domain, and the one or more additional target-binding domains comprise the same amino acid sequence.

Embodiment B40. The single-chain chimeric polypeptide of any one of embodiments B26-B37, wherein the one or more additional target-binding domains is an antigen-binding domain.

Embodiment B41. The single-chain chimeric polypeptide of embodiment B40, wherein the antigen-binding domain comprises a scFv or a single domain antibody.

Embodiment B42. The single-chain chimeric polypeptide of any one of embodiments B26-B37, B40, and B41, wherein the one or more additional target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment B43. The single-chain chimeric polypeptide of any one of embodiments B6-B37, B40, and B41, wherein the one or more additional target-binding domains is a soluble interleukin or cytokine protein.

Embodiment B44. The single-chain chimeric polypeptide of embodiment B43, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment B45. The single-chain chimeric polypeptide of any one of embodiments B6-B37, B40, and B41, wherein the one or more additional target-binding domains is a soluble interleukin or cytokine receptor.

Embodiment B46. The single-chain chimeric polypeptide of embodiment B45, wherein the soluble receptor is a soluble TGF-β receptor II (TGF-βRII) and a soluble TGF-βRIII.

Embodiment B47. The single-chain chimeric polypeptide of any one of embodiments B1-B46, wherein the single-chain chimeric polypeptide further comprises a signal sequence at its N-terminal end.

Embodiment B48. The single-chain chimeric polypeptide of any one of embodiments B1-B47, wherein the single-chain chimeric polypeptide further comprises a peptide tag positioned at the N-terminal end or the C-terminal end of the single-chain chimeric polypeptide.

Embodiment B49. A composition comprising any of the single-chain chimeric polypeptides of embodiments B1-B48.

Embodiment B50. The composition of embodiment B49, wherein the composition is a pharmaceutical composition.

Embodiment B51. A kit comprising at least one dose of the composition of embodiment B49 or B50.

Embodiment B52. A method of stimulating an immune cell, the method comprising:
contacting an immune cell with an effective amount of any of the single-chain chimeric polypeptides of embodiments B1-B48 or the composition of embodiment B49 or B50.

Embodiment B53. The method of embodiment B52, wherein the immune cell is contacted in vitro.

Embodiment B54. The method of embodiment B53, wherein the immune cell was previously obtained from a subject.

Embodiment B55. The method of embodiment B54, wherein the method further comprises obtaining the immune cell from the subject prior to the contacting step.

Embodiment B56. The method of embodiment B52, wherein the immune cell is contacted in vivo.

Embodiment B57. The method of any one of embodiments B52-B56, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, and a natural killer cell.

Embodiment B58. The method of any one of embodiments B52-B57, wherein the immune cell has previously been genetically modified to express a chimeric antigen receptor or a recombinant T-cell receptor.

Embodiment B59. The method of any one of embodiments B52-B57, wherein the method further comprises, after the contacting step, introducing into the immune cell a nucleic acid encoding a chimeric antigen-receptor or a recombinant T-cell receptor.

Embodiment B60. The method of any one of embodiments B52-B59, wherein the method further comprises administering the immune cell to a subject in need thereof.

Embodiment B61. The method of embodiment B60, wherein the subject has been identified or diagnosed as having an age-related disease or condition.

Embodiment B62. The method of embodiment B61, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B63. The method of embodiment B60, wherein the subject has been identified or diagnosed as having a cancer.

Embodiment B64. The method of embodiment B63, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B65. The method of embodiment B60, wherein the subject has been diagnosed or identified as having an infectious disease.

Embodiment B66. The method of embodiment B65, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B67. A method of inducing or increasing proliferation of an immune cell, the method comprising:

contacting an immune cell with an effective amount of any of the single-chain chimeric polypeptides of embodiments B1-B48 or the composition of embodiment B49 or B50.

Embodiment B68. The method of embodiment B67, wherein the immune cell is contacted in vitro.

Embodiment B69. The method of embodiment B68, wherein the immune cell was previously obtained from a subject.

Embodiment B70. The method of embodiment B60, wherein the method further comprises obtaining the immune cell from the subject prior to the contacting step.

Embodiment B71. The method of embodiment B67, wherein the immune cell is contacted in vivo.

Embodiment B72. The method of any one of embodiments B67-B71, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment B73. The method of any one of embodiments B67-B72, wherein the immune cell has previously been genetically modified to express a chimeric antigen receptor or a recombinant T-cell receptor.

Embodiment B74. The method of any one of embodiments B67-B72, wherein the method further comprises, after the contacting step, introducing into the immune cell a nucleic acid encoding a chimeric antigen-receptor or a recombinant T-cell receptor.

Embodiment B75. The method of any one of embodiments B67-B74, wherein the method further comprises administering the immune cell to a subject in need thereof.

Embodiment B76. The method of embodiment B75, wherein the subject has been identified or diagnosed as having an age-related disease or condition.

Embodiment B77. The method of embodiment B76, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B78. The method of embodiment B75, wherein the subject has been identified or diagnosed as having a cancer.

Embodiment B79. The method of embodiment B78, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B80. The method of embodiment B75, wherein the subject has been diagnosed or identified as having an infectious disease.

Embodiment B81. The method of embodiment B75, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B82. A method of inducing differentiation of an immune cell into a memory or memory-like immune cell, the method comprising:

contacting an immune cell with an effective amount of any of the single-chain chimeric polypeptides of embodiments B1-B48 or the composition of embodiment B49 or B50.

Embodiment B83. The method of embodiment B82, wherein the immune cell is contacted in vitro.

Embodiment B84. The method of embodiment B83, wherein the immune cell was previously obtained from a subject.

Embodiment B85. The method of embodiment B84, wherein the method further comprises obtaining the immune cell from the subject prior to the contacting step.

Embodiment B86. The method of embodiment B82, wherein the immune cell is contacted in vivo.

Embodiment B87. The method of any one of embodiments B82-B86, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment B88. The method of any one of embodiments B82-B87, wherein the immune cell has previously been genetically modified to express a chimeric antigen receptor or a recombinant T-cell receptor.

Embodiment B89. The method of any one of embodiments B82-B87, wherein the method further comprises, after the contacting step, introducing into the immune cell a nucleic acid encoding a chimeric antigen-receptor or a recombinant T-cell receptor.

Embodiment B90. The method of any one of embodiments B82-B89, wherein the method further comprises administering the immune cell to a subject in need thereof.

Embodiment B91. The method of embodiment B90, wherein the subject has been identified or diagnosed as having an age-related disease or condition.

Embodiment B92. The method of embodiment B91, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B93. The method of embodiment B90, wherein the subject has been identified or diagnosed as having a cancer.

Embodiment B94. The method of embodiment B93, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B95. The method of embodiment B90, wherein the subject has been diagnosed or identified as having an infectious disease.

Embodiment B96. The method of embodiment B95, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B97. A method of killing a cancer cell, an infected cell, or a senescent cell in a subject in need thereof, the method comprising administering to the subject a therapeutically effective amount of any of the single-chain chimeric polypeptides of embodiments B1-B48 or the composition of embodiment B49 or B50.

Embodiment B98. The method of embodiment B97, wherein the subject has been identified or diagnosed as having a cancer.

Embodiment B99. The method of embodiment B98, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B100. The method of embodiment B97, wherein the subject has been identified or diagnosed as having an aging-related disease or condition.

Embodiment B101. The method of embodiment B100, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B102. A method of treating a subject in need thereof, the method comprising administering to the subject a therapeutically effective amount of any of the single-chain chimeric polypeptides of embodiments B1-B48 or the composition of embodiment B49 or B50.

Embodiment B103. The method of embodiment B102, wherein the subject has been identified or diagnosed as having a cancer.

Embodiment B104. The method of embodiment B103, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B105. The method of embodiment B102, wherein the subject has been identified or diagnosed as having an aging-related disease or condition.

Embodiment B106. The method of embodiment B105, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B107. The method of embodiment B102, wherein the subject has been diagnosed or identified as having an infectious disease.

Embodiment B108. The method of embodiment B107, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B109. A nucleic acid encoding any of the single-chain chimeric polypeptides of any one of embodiments B1-B48.

Embodiment B110. A vector comprising the nucleic acid of embodiment B109.

Embodiment B111. The vector of embodiment B110, wherein the vector is an expression vector.

Embodiment B112. A cell comprising the nucleic acid of embodiment B109 or the vector of embodiment B110 or B111.

Embodiment B113. A method of producing a single-chain chimeric polypeptide, the method comprising:
culturing the cell of embodiment B112 in a culture medium under conditions sufficient to result in the production of the single-chain chimeric polypeptide; and
recovering the single-chain chimeric polypeptide from the cell and/or the culture medium.

Embodiment B114. A single-chain chimeric polypeptide produced by the method of embodiment B113.

Embodiment B115. The single-chain chimeric polypeptide of embodiment B21, wherein the soluble human tissue factor domain comprises a sequence that is at least 80% identical to SEQ ID NO: 96.

Embodiment B116. The single-chain chimeric polypeptide of embodiment B115, wherein the soluble human tissue factor domain comprises a sequence that is at least 90% identical to SEQ ID NO: 96.

Embodiment B117. The single-chain chimeric polypeptide of embodiment B116, wherein the soluble human tissue factor domain comprises a sequence that is at least 95% identical to SEQ ID NO: 96.

Embodiment B118. The single-chain chimeric polypeptide of embodiment B117, wherein the soluble human tissue factor domain comprises a sequence that is 100% identical to SEQ ID NO: 96.

Embodiment B119. The single-chain chimeric polypeptide of embodiment B21, wherein the soluble human tissue factor domain comprises a sequence that is at least 80% identical to SEQ ID NO: 97.

Embodiment B120. The single-chain chimeric polypeptide of embodiment B119, wherein the soluble human tissue factor domain comprises a sequence that is at least 90% identical to SEQ ID NO: 97.

Embodiment B121. The single-chain chimeric polypeptide of embodiment B120, wherein the soluble human tissue factor domain comprises a sequence that is at least 95% identical to SEQ ID NO: 97.

Embodiment B122. The single-chain chimeric polypeptide of embodiment B121, wherein the soluble human tissue factor domain comprises a sequence that is 100% identical to SEQ ID NO: 97.

What is claimed is:

1. A nucleic acid encoding a single-chain chimeric polypeptide comprising:
   (i) a first target-binding domain comprising a sequence at least 80% identical to SEQ ID NO: 28;
   (ii) a soluble tissue factor domain that does not have coagulation activity, wherein the soluble tissue factor domain comprises a sequence at least 80% identical to SEQ ID NO: 9; and
   (iii) a second target-binding domain comprising a sequence at least 80% identical to SEQ ID NO: 28,
   wherein the single-chain chimeric polypeptide does not stimulate blood coagulation in a mammal.

2. The nucleic acid of claim 1, wherein the first target-binding domain and the soluble tissue factor domain directly abut each other.

3. The nucleic acid of claim 1, wherein the single-chain chimeric polypeptide further comprises a linker sequence between the first target-binding domain and the soluble tissue factor domain.

4. The nucleic acid of claim 1, wherein soluble tissue factor domain and the second target-binding domain directly abut each other.

5. The nucleic acid of claim 1, wherein the single-chain chimeric polypeptide further comprises a linker sequence between the soluble tissue factor domain and the second target-binding domain.

6. The nucleic acid of claim 1, wherein the soluble tissue factor domain is a soluble human tissue factor domain that does not have coagulation activity.

7. The nucleic acid of claim 1, wherein the soluble tissue factor domain comprises or consists of a sequence from a wildtype soluble human tissue factor.

8. The nucleic acid of claim 1, wherein the first target-binding domain and the second target-binding domain are human IL-2.

9. A vector comprising the nucleic acid of claim 1.

10. A cell comprising the nucleic acid of claim 1.

11. A method of producing a single-chain chimeric polypeptide, the method comprising:
   culturing the cell of claim 10 in a culture medium under conditions sufficient to result in the production of the single-chain chimeric polypeptide; and
   recovering the single-chain chimeric polypeptide from the cell and/or the culture medium.

12. The nucleic acid of claim 1, wherein:
   the first target-binding domain comprises a sequence at least 90% identical to SEQ ID NO: 28;
   the soluble tissue factor domain comprises a sequence at least 90% identical to SEQ ID NO: 9; and
   the second target-binding domain comprises a sequence at least 90% identical to SEQ ID NO: 28.

13. The nucleic acid of claim 1, wherein:
   the first target-binding domain comprises a sequence at least 95% identical to SEQ ID NO: 28;
   the soluble tissue factor domain comprises a sequence at least 95% identical to SEQ ID NO: 9; and
   the second target-binding domain comprises a sequence at least 95% identical to SEQ ID NO: 28.

14. The nucleic acid of claim 1, wherein:
   the first target-binding domain comprises SEQ ID NO: 28;
   the soluble tissue factor domain comprises SEQ ID NO: 9; and
   the second target-binding domain comprises SEQ ID NO: 28.

15. The nucleic acid of claim 1, wherein the single-chain chimeric polypeptide comprises a sequence that is at least 80% identical to SEQ ID NO: 108.

16. The nucleic acid of claim 1, wherein the single-chain chimeric polypeptide comprises a sequence that is at least 90% identical to SEQ ID NO: 108.

17. The nucleic acid of claim 1, wherein the single-chain chimeric polypeptide comprises a sequence that is at least 95% identical to SEQ ID NO: 108.

18. The nucleic acid of claim 1, wherein the single-chain chimeric polypeptide comprises SEQ ID NO: 108.

19. The nucleic acid of claim 18, wherein the nucleic acid comprises the sequence of SEQ ID NO: 109.

20. The nucleic acid of claim 1, wherein the single-chain chimeric polypeptide comprises a sequence that is at least 80% identical to SEQ ID NO: 110.

21. The nucleic acid of claim 1, wherein the single-chain chimeric polypeptide comprises a sequence that is at least 90% identical to SEQ ID NO: 110.

22. The nucleic acid of claim 1, wherein the single-chain chimeric polypeptide comprises a sequence that is at least 95% identical to SEQ ID NO: 110.

23. The nucleic acid of claim 1, wherein the single-chain chimeric polypeptide comprises SEQ ID NO: 110.

24. The nucleic acid of claim 22, wherein the nucleic acid comprises the sequence of SEQ ID NO: 111.

25. A composition comprising the nucleic acid of claim 1.

26. A kit comprising the nucleic acid of claim 1.

27. The vector of claim 9, wherein

SEQUENCE LISTING

```
Sequence total quantity: 117
SEQ ID NO: 1             moltype = AA  length = 696
FEATURE                  Location/Qualifiers
REGION                   1..696
                         note = source = /note="Description of Artificial Sequence:
                         SyntheticalphaCD3scFv/TF/alphaCD28scFv sequence"
source                   1..696
                         mol_type = protein
                         organism = synthetic construct
SEQUENCE: 1
QIVLTQSPAI MSASPGEKVT MTCSASSSVS YMNWYQQKSG TSPKRWIYDT SKLASGVPAH    60
FRGSGSGTSY SLTISGMEAE DAATYYCQQW SSNPFTFGSG TKLEINRGGG GSGGGGSGGG   120
GSQVQLQQSG AELARPGASV KMSCKASGYT FTRYTMHWVK QRPGQGLEWI GYINPSRGYT   180
NYNQKFKDKA TLTTDKSSST AYMQLSSLTS EDSAVYYCAR YYDDHYCLDY WGQGTTLTVS   240
SSGTTNTVAA YNLTWKSTNF KTILEWEPKP VNQVYTVQIS TKSGDWKSKC FYTTDTECDL   300
TDEIVKDVKQ TYLARVFSYP AGNVESTGSA GEPLYENSPE FTPYLETNLG QPTIQSFEQV   360
GTKVNVTVED ERTLVRRNNT FLSLRDVFGK DLIYTLYYWK SSSSGKKTAK TNTNEFLIDV   420
DKGENYCFSV QAVIPSRTVN RKSTDSPVEC MGQEKGEFRE VQLQQSGPEL VKPGASVKMS   480
CKASGYTFTS YVIQWVKQKP GQGLEWIGSI NPYNDYTKYN EKFKGKATLT SDKSSITAYM   540
EFSSLTSEDS ALYYCARWGD GNYWGRGTTL TVSSGGGGSG GGGSGGGGSD IEMTQSPAIM   600
SASLGERVTM TCTASSSVSS SYFHWYQQKP GSSPKLCIYS TSNLASGVPP RFSGSGSTSY   660
SLTISSMEAE DAATYFCHQY HRSPTFGGGT KLETKR                             696

SEQ ID NO: 2             moltype = DNA  length = 2088
FEATURE                  Location/Qualifiers
misc_feature             1..2088
                         note = source = /note="alphaCD3scFv/TF/alphaCD28scFv"
source                   1..2088
                         mol_type = genomic DNA
                         organism = Homo sapiens
SEQUENCE: 2
cagatcgtgc tgacccaaag ccccgccatc atgagcgcta gccccggtga gaaggtgacc    60
atgacatgct ccgcttccag ctccgtgtcc tacatgaact ggtatcagca gaaaagcgga   120
accagcccca aaaggtggat ctacgacacc agcaagctgg cctccggagt gcccgctcat   180
ttccggggct ctggatccgg caccagctac tctttaacca tttccggcat ggaagctgaa   240
gacgctgcca cctactattg ccagcaatgg agcagcaacc ccttcacatt cggatctggc   300
accaagctcg aaatcaatcg tggaggaggt ggcagcggcg gcggtggatc cggcggagga   360
ggaagccaag ttcaactcca gcagagcggc gctgaactgg cccggccgg cgcctccgtc   420
aagatgagct gcaaggcttc cggctataca tttactcgtt acacaatgca ttgggtcaag   480
cagaggcccg gtcaaggttt agagtggatc ggatatatca accttcccg gggctacacc   540
aactataacc aaaagttcaa ggataaagcc actttaacca ctgacaagag ctcctccacc   600
gcctacatgc agctgtcctc tttaaccagc gaggactccg ctgtttacta ctgcgctagg   660
```

```
tattacgacg accactactg tttagactat tggggacaag gtaccactt t aaccgtcagc    720
agctccggca ccaccaatac cgtgccgct  tataaccctca catggaagag caccaacttc    780
aagacaattc tggaatggga acccaagccc gtcaatcaag tttacaccgt gcagatctcc    840
accaaatccg gagactggaa gagcaagtgc ttctacacaa cagacaccga gtgtgattta    900
accgacgaaa tcgtcaagga cgtcaagcaa acctatctgg ctcgggtctt ttcctacccc    960
gctggcaatg tcgagtccac cggctccgct ggcgagcctc tctacgagaa ttcccccgaa   1020
ttcaccccctt atttagagac caatttaggc cagcctacca tccagagctt cgagcaagtt   1080
ggcaccaagg tgaacgtcac cgtcgaggat gaaaggactt tagtgcggcg gaataacaca   1140
ttttatccc tccgggatgt gttcggcaaa gacctcatct acacactgta ctattggaag   1200
tccagctcct ccggcaaaaa gaccgctaag accaacacca acgagttttt aattgacgtg   1260
gacaaaggcg agaactactg cttcagcgtg caagccgtga tcccttctcg taccgtcaac   1320
cggaagagca cagattcccc cgttgagtgc atgggccaag aaaagggcga gttccgggag   1380
gtccagctgc agcagagcgg acccgaactc gtgaaacccg gtgcttccgt gaaaatgtct   1440
tgtaaggcca gcggatacac cttcacctcc tatgtgatca gtgggtcaa acagaagcct   1500
ggacaaggtc tcgagtggat cggcagcatc aaccccttaca acgactatac caaatacaac   1560
gagaagttta agggaaaggc tactttaacc tccgacaaaa gctccatcac agcctacatg   1620
gagttcagct ctttaacatc cgaggacagc gctctgtact attgcgcccg gtggggcgac   1680
ggcaattact ggggacgggg cacaacactg accgtgacga gcggagggg aggctccggc   1740
ggaggcggat ctggcggtgg cggctccgac atcgagatga cccagtcccc cgctatcatg   1800
tccgcctctt taggcgagcg ggtcacaatg acttgtacag cctcctccag cgtcctcc   1860
tcctacttcc attggtacca acagaaaccc ggaagctccc ctaaactgtg catctacagc   1920
accagcaatc tcgccagcgg cgtgccccct aggttttccg gaagcggaag caccagctac   1980
tcttttaacca tctcctccat ggaggctgag gatgccgcca cctacttttg tcaccagtac   2040
caccggtccc ccaccttcgg aggcggcacc aaactggaga caagagg              2088

SEQ ID NO: 3           moltype = AA   length = 714
FEATURE                Location/Qualifiers
REGION                 1..714
                       note = source = /note="alphaCD3scFv/TF/alphaCD28scFv"
source                 1..714
                       mol_type = protein
                       organism = Homo sapiens
SEQUENCE: 3
MKWVTFISLL FLFSSAYSQI VLTQSPAIMS ASPGEKVTMT CSASSSVSYM NWYQQKSGTS     60
PKRWIYDTSK LASGVPAHFR GSGSGTSYSL TISGMEAEDA ATYYCQQWSS NPFTFGSGTK    120
LEINRGGGGS GGGGSGGGGS QVQLQQSGAE LARPGASVKM SCKASGYTFT RYTMHWVKQR    180
PGQGLEWIGY INPSRGYTNY NQKFKDKATL TTDKSSSTAY MQLSSLTSED SAVYYCARYY    240
DDHYCLDYWG QGTTLTVSSS GTTNTVAAYN LTWKSTNFKT ILEWEPKPVN QVYTVQISTK    300
SGDWKSKCFY TTDTECDLTD EIVKDVKQTY LARVFSYPAG NVESTGSAGE PLYENSPEFT    360
PYLETNLGQP TIQSFEQVGT KVNVTVEDER TLVRRNNTFL SLRDVFGKDL IYTLYYWKSS    420
SSGKKTAKTN TNEFLIDVDK GENYCFSVQA VIPSRTVNRK STDSPVECMG QEKGEFREVQ    480
LQQSGPELVK PGASVKMSCK ASGYTFTSYV IQWVKQKPGQ GLEWIGSINP YNDYTKYNEK    540
FKGKATLTSD KSSITAYMEF SSLTSEDSAL YYCARWGDGN YWGRGTTLTV SSGGGGSGGG    600
GSGGGGSDIE MTQSPAIMSA SLGERVTMTC TASSSVSSSY FHWYQQKPGS SPKLCIYSTS    660
NLASGVPPRF SGSGSTSYSL TISSMEAEDA ATYFCHQYHR SPTFGGGTKL ETKR          714

SEQ ID NO: 4           moltype = DNA  length = 2142
FEATURE                Location/Qualifiers
misc_feature           1..2142
                       note = source = /note="alphaCD3scFv/TF/alphaCD28scFv"
source                 1..2142
                       mol_type = genomic DNA
                       organism = Homo sapiens
SEQUENCE: 4
atgaagtggg tgaccttcat cagcttatta tttttattca gctccgccta ttcccagatc     60
gtgctgaccc aaagccccgc catcatgagc gctagcccg gtgagaaggt gaccatgaca    120
tgctccgctt ccagctccgt gtcctacatg aactggtatc agcagaaaag cggaaccagc    180
cccaaaaggt ggatctacga caccagcaag ctggcctccg gagtgccgc tcatttccgg    240
ggctctggat ccggcaccag ctactcttta accatttccg gcatggaagc tgaagacgct    300
gccacctact attgccagca aacccttca cattcggatc tggcaccaag    360
ctcgaaatca atcgtggagg aggtggcagc ggcggcggtg gatccggcgg aggaggaagc    420
caagttcaac tccagcagag cggcgctaa ctggcccggc ccggcgcctc cgtcaagatg    480
agctgcaagg cttccggcta tacattact cgttacacaa tgcattgggt caagcagagg    540
cccggtcaag gtttagagtg gatcggatat atcaactctt cccggggcta caccaactat    600
aaccaaaagt tcaaggataa agccacttta accactgaca gagctcctc caccgcctac    660
atgcagctgt cctctttaac cagcgaggac tccgctgttt actactcgc taggtattac    720
gacgaccact actgtttaga ctattgggga caaggtacca ctttaaccgt cagcagctcc    780
ggcaccacca taccgtggc cgctataac ctcacatgga agagcaccaa cttcaagaca    840
attctggaat gggaaccaa gcccgtcaat caagtttaca ccgtgcagat ctccaccaaa    900
tccggagact ggaagagcaa gtgcttctac acaacagaca ccgagtgtga tttaaccgac    960
gaaatcgtca aggacgtcaa gcaaacctat ctggctcggg tcttttccta ccccgctggc   1020
aatgtcgagt ccaccggctc cgctggcgag cctctctacg agaattcccc cgaattcacc   1080
ccttatttag agaccaattt aggccagcct accatccaga gcttcgagca agttggcacc   1140
aaggtgaacg tcacggatga aaaggactt tagtgggcggaataaa cactttta   1200
tccctcggg atgtgttcgg caaagacctc atctacacac tgtactattg gaagtccagc   1260
tcctccggca aaaagaccgc taagaccaac accaacgagt tttaattga cgtggacaaa   1320
ggcgagaact actgcttcag cgtgcaagcc gtgatccctt ctcgtaccgt caaccggaag   1380
agcacagatt ccccgttga gtgcatgggc caagaaaagg gcgagttccg ggaggtccag   1440
ctgcagcaga gcggacccga actcgtgaaa cccggtgctt ccgtgaaaat gtcttgtaag   1500
```

```
gccagcggat acaccttcac ctcctatgtg atccagtggg tcaaacagaa gcccggacaa   1560
ggtctcgagt ggatcggcag catcaaccct acaacgact ataccaaata caacgagaag   1620
tttaagggaa aggctacttt aacctccgac aaaagctcca tcacagccta catggagttc   1680
agctctttaa catccgagga cagcgctctg tactattgcg cccggtgggg cgacggcaat   1740
tactggggac ggggcacaac actgaccgtg agcagcggag gcggaggctc cggcggaggc   1800
ggatctggcg gtggcggctc cgacatcgag atgacccagt cccccgctat catgtccgcc   1860
tctttaggcg agcgggtcac aatgacttgt acagcctcct ccagcgtctc ctcctcctac   1920
ttccattggt accaacagaa acccggaagc tcccctaaac tgtgcatcta cagcaccagc   1980
aatctcgcca gcggcgtgcc ccctaggttt tccggaagcg gaagcaccag ctactcttta   2040
accatctcct ccatggaggc tgaggatgcc gccacctact tttgtcacca gtaccaccgg   2100
tcccccacct tcggaggcgg caccaaactg gagacaaaga gg                     2142

SEQ ID NO: 5               moltype = AA   length = 696
FEATURE                    Location/Qualifiers
REGION                     1..696
                           note = source = /note="alphaCD28scFv/TF/alphaCD3scFv"
source                     1..696
                           mol_type = protein
                           organism = Homo sapiens
SEQUENCE: 5
VQLQQSGPEL VKPGASVKMS CKASGYTFTS YVIQWVKQKP GQGLEWIGSI NPYNDYTKYN    60
EKFKGKATLT SDKSSITAYM EFSSLTSEDS ALYYCARWGD GNYWGRGTTL TVSSGGGGSG   120
GGGSGGGGSD IEMTQSPAIM SASLGERVTM TCTASSSVSS SYFHWYQQKP GSSPKLCIYS   180
TSNLASGVPP RFSGSGSTSY SLTISSMEAE DAATYFCHQY HRSPTFGGGT KLETKRSGTT   240
NTVAAYNLTW KSTNFKTILE WEPKPVNQVY TVQISTKSGD WKSKCFYTTD TECDLTDEIV   300
KDVKQTYLAR VFSYPAGNVE STGSAGEPLY ENSPEFTPYL ETNLGQPTIQ SFEQVGTKVN   360
VTVEDERTLV RRNNTFLSLR DVFGKDLIYT LYYWKSSSSG KKTAKTNTNE FLIDVDKGEN   420
YCFSVQAVIP SRTVNRKSTD SPVECMGQEK GEFREQIVLT QSPAIMSASP GEKVTMTCSA   480
SSSVSYMNWY QQKSGTSPKR WIYDTSKLAS GVPAHFRGSG SGTSYSLTIS GMEAEDAATY   540
YCQQWSSNPF TFGSGTKLEI NRGGGGSGGG GSGGGGSQVQ LQQSGAELAR PGASVKMSCK   600
ASGYTFTRYT MHWVKQRPGQ GLEWIGYINP SRGYTNYNQK FKDKATLTTD KSSSTAYMQL   660
SSLTSEDSAV YYCARYYDDH YCLDYWGQGT TLTVSS                              696

SEQ ID NO: 6               moltype = DNA   length = 2088
FEATURE                    Location/Qualifiers
misc_feature               1..2088
                           note = source = /note="alphaCD28scFv/TF/alphaCD3scFv"
source                     1..2088
                           mol_type = genomic DNA
                           organism = Homo sapiens
SEQUENCE: 6
gtgcagctgc agcagtccgg acccgaactg gtcaagcccg gtgcctccgt gaaaatgtct    60
tgtaaggctt ctggctacac ctttacctcc tacgtcatcc aatgggtgaa gcagaagcct   120
ggtcaaggtc tcgagtggat cggcagcatc aatccctaca cgattacac caagtataac   180
gaaaagttta agggcaaggc cactctgaca agcgacaaga gctccattac cgcctacatg   240
gagtttttcct ctttaacttc tgaggactcc gctttatact attgcgctcg ttggggcgat   300
ggcaattatt ggggccggggg aactacttta acagtgagct ccggcggcgg cggaagcgga   360
ggtggaggat ctggcggtgg aggcagcgac atcgagatga cacagtcccc cgctatcatg   420
agcgcctctt taggagaacg tgtgaccatg acttgtacag cttcctccag cgtgagcagc   480
tcctatttcc actggtacca gcagaaaccc ggctcctccc ctaaactgtg tatctactcc   540
acaagcaatt tagctagcgg cgtgcctcct cgttttagcg gctccggcag cacctcttac   600
tctttaacca ttagctctat ggaggccgaa gatgccgcca catactttgt ccatcagtac   660
caccggtccc ctacctttgg cggaggcaca aagctggaga ccaagcggag cggcaccacc   720
aacacagtgg ccgcctacaa tctgacttgg aaatccacca acttcaagac catcctcgag   780
tgggagcca agcccgttaa tcaagtttat accgtgcaga tttccaccaa gagcggcgac   840
tggaaatcca agtgcttcta taccacagac accgagtgcg atctcaccga cgagatcgtc   900
aaagacgtga agcagacata tttagctagg gtgttctcct accccgctgg aaacgtggag   960
agcaccggat ccgctggaga gccttttatac gagaactccc ccgaattcac ccctatctg   1020
gaaccaatt tagcccagcc caccatccag agcttcgaac aagttggcac aaaggtgaac   1080
gtcaccgtcg aagatgagag gactttagtg cggaggaaca atacattttt atccttacgt   1140
gacgtcttcg gcaaggattt aatctacaca ctgtattact ggaagtctag ctcctccggc   1200
aagaagaccg ccaagaccaa taccaacgaa ttttaattg acgtggacaa gggcgagaac   1260
tactgcttct ccgtgcaagc tgtgatcccc tccggacag tgaaccggaa gtccaccgac   1320
tcccccgtgg agtgcatggg ccaagagaag ggagagttc cagcagat cgtgctgacc   1380
cagtccccg ctattatgag cgctagcccc ggtgaaaagg tgactatgac atgcagcgcc   1440
agctcttccg tgagctacat gaactggtat cagcagaagt ccggcaccag ccctaaaagg   1500
tggatctacg acaccagcaa gctggccagc ggcgtccccg ctcactttcg gggctccggc   1560
tccggaacaa gctactctct gaccatcagc ggcatggaag ccgaggatgc cgctacctat   1620
tactgtcagc agtggagctc caacccctc acctttggat tcggcaccaa gctcgagatt   1680
aatcgtggag gcgaggtag cggaggaggc ggatccggcg gtggaggtag ccaagttcag   1740
ctccagcaaa gcggcgccga actgctcggg cccggcgctt ccgtgaagat gtcttgtaag   1800
gcctccggct ataccttcac ccggtacaca atgcactggg tcaagcaacg gcccggtcaa   1860
ggtttagagt ggattggcta tatcaacccc tcccggggct ataccaacta caaccagaag   1920
ttcaaggaca aagccaccct caccctcgac aagtccagca catcctacat gcagctg     1980
agctctttaa catccgagga ttccgccgtg tactactgcg ctcggtacta cgacgatcat   2040
tactgcctcg attactgggg ccaaggtacc accttaacag tctcctcc              2088

SEQ ID NO: 7               moltype = AA   length = 714
FEATURE                    Location/Qualifiers
```

```
REGION                    1..714
                          note = source = /note="alphaCD28scFv/TF/alphaCD3scFv"
source                    1..714
                          mol_type = protein
                          organism = Homo sapiens
SEQUENCE: 7
MKWVTFISLL FLFSSAYSVQ LQQSGPELVK PGASVKMSCK ASGYTFTSYV IQWVKQKPGQ    60
GLEWIGSINP YNDYTKYNEK FKGKATLTSD KSSITAYMEF SSLTSEDSAL YYCARWGDGN   120
YWGRGTTLTV SSGGGGSGGG GSGGGGSDIE MTQSPAIMSA SLGERVTMTC TASSSVSSSY   180
FHWYQQKPGS SPKLCIYSTS NLASGVPPRF SGSGSTSYSL TISSMEAEDA ATYFCHQYHR   240
SPTFGGGTKL ETKRSGTTNT VAAYNLTWKS TNFKTILEWE PKPVNQVYTV QISTKSGDWK   300
SKCFYTTDTE CDLTDEIVKD VKQTYLARVF SYPAGNVEST GSAGEPLYEN SPEFTPYLET   360
NLGQPTIQSF EQVGTKVNVT VEDERTLVRR NNTFLSLRDV FGKDLIYTLY YWKSSSSGKK   420
TAKTNTNEFL IDVDKGENYC FSVQAVIPSR TVNRKSTDSP VECMGQEKGE FREQIVLTQS   480
PAIMSASPGE KVTMTCSASS SVSYMNWYQQ KSGTSPKRWI YDTSKLASGV PAHFRGSGSG   540
TSYSLTISGM EAEDAATYYC QQWSSNPFTF GSGTKLEINR GGGGSGGGGS GGGGSQVQLQ   600
QSGAELARPG ASVKMSCKAS GYTFTRYTMH WVKQRPGQGL EWIGYINPSR GYTNYNQKFK   660
DKATLTTDKS SSTAYMQLSS LTSEDSAVYY CARYYDDHYC LDYWGQGTTL TVSS         714

SEQ ID NO: 8              moltype = DNA   length = 2142
FEATURE                   Location/Qualifiers
misc_feature              1..2142
                          note = source = /note="alphaCD28scFv/TF/alphaCD3scFv"
source                    1..2142
                          mol_type = genomic DNA
                          organism = Homo sapiens
SEQUENCE: 8
atgaaatggg tcaccttcat ctctttactg tttttattta gcagcgccta cagcgtgcag     60
ctgcagcagt ccggacccga actggtcaag cccggtgcct ccgtgaaaat gtcttgtaag    120
gcttctggct acacctttac ctcctacgtc atccaatggg tgaagcagaa gcccggtcaa    180
ggtctcgagt ggatcggcag catcaatccc tacaacgatt acaccaagta taacgaaaag    240
tttaagggca aggccactct gacaagcgac aagagctcca ttaccgccta catggagttt    300
tcctctttaa cttctgagga ctccgcttta tactattgcg ctcgttgggg cgatggcaat    360
tattgggggcc ggggaactac tttaacagtg agctccggcg gcggcggaag cggaggtgga    420
ggatctggcg gtgtggaggcg cgacatcgag atgacacagt ccccgctat catgagcgct    480
tctttaggag aacgtgtgac catgacttgt acagcttcct ccagcgtgag cagctcctat    540
ttccactggt accagcagaa accggctccc tccctaaac tgtgtatcta ctccacaagc    600
aatttagcta gcggcgtgcc tcctcgttt agcggctccg gcagcacctc ttactcttta    660
accattagct ctatggaggc cgaagatgcc gccacatact tttgccatca gtaccaccgg    720
tcccctacct ttggcggagg cacaaagctg gagaccaagc ggagcggcac caccaacaca    780
gtggccgcct acaatctgac ttggaaatcc accaacttca agaccatcct cgagtgggag    840
cccaagcccg ttaatcaagt ttataccgtg cagatttcca ccaagagcgg cgactggaaa    900
tccaagtgct tctataccac agacaccgag tgcgatctca ccgacgagat cgtcaaagac    960
gtgaagcaga catatttagc tagggtgttc tcctacccgg ctggaaacgt ggagagcacc   1020
ggatccgctg gagagccttt atacgagaac tcccccgaat tcacccccta tctgaaaacc   1080
aatttaggcc agcccaccat ccagagcttc gaacaagttg gcacaaaggt gaacgtcacc   1140
gtcgaagata gaggactttt agtgcgaagg aacaataca ttttatcctt acgtgacgtc   1200
ttcggcaagg atttaatcta cacactgtat tactggaagt ctagctcctc cggcaagaag   1260
accgccaaga ccaataccaa cgaattttta attgacgtgg acaagggcga gaactactgc   1320
ttctccgtgc aagctgtgat ccctcccgg acagtgaacc ggaagtccac cgactccccc   1380
gtggagtgca tgggccaaga aagggagag tttcgtgagc agatcgtgct gacccagtcc   1440
cccgctatta tgagcgctag ccccggtgaa aaggtgacta tgacatgcag cgccagctct   1500
tccgtgagct acatgaactg gtatcagcag aagtccggca ccagccctaa aaggtggatc   1560
tacgacacca gcaagctggc cagcggcgtc ccgctcact ttcggggctc cggctccgga   1620
acaagctact ctctgaccat cagcggcatg gaagccgatg atgccgctac ctattactgt   1680
cagcagtgga gctccaaccc cttcacctt ggatccggca ccaagctcga gattaatcgt   1740
ggaggcggag gtagcggagg aggcggatcc ggcggtggag gtagcaagt tcagctccag   1800
caaagcggcg ccgaactcgc tcggcccggc gcttccgtga agatgtcttg taaggcctcc   1860
ggctataact tcacccggta cacaatgcac tgggtcaagc aacggcccgg tcaaggttta   1920
gagtggattg gctatatcaa ccccctcccgg ggctataca actacaacca gaagttcaag   1980
gacaaagcca ccctcaccac cgacaagtcc agcagcaccg cttacatgca gctgagctct   2040
ttaacatccg aggattccgc cgtgtactac tgcgctcggt actacgacga tcattactgc   2100
ctcgattact ggggccaagg taccaccta acagtctcct cc                      2142

SEQ ID NO: 9              moltype = AA   length = 219
FEATURE                   Location/Qualifiers
REGION                    1..219
                          note = source = /note="Soluble Human Tissue Factor Domain"
source                    1..219
                          mol_type = protein
                          organism = Homo sapiens
SEQUENCE: 9
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG   120
TKVNVTVEDE RTLVRRNNTF LSLRDVFGKD LIYTLYYWKS SSSGKKTAKT NTNEFLIDVD   180
KGENYCFSVQ AVIPSRTVNR KSTDSPVECM GQEKGEFRE                          219

SEQ ID NO: 10             moltype = DNA   length = 657
FEATURE                   Location/Qualifiers
```

| | | |
|---|---|---|
| misc_feature | 1..657 | |
| | note = source = /note="Soluble Human Tissue Factor Domain" | |
| source | 1..657 | |
| | mol_type = genomic DNA | |
| | organism = Homo sapiens | |
| SEQUENCE: 10 | | |

```
agcggcacaa ccaacacagt cgctgcctat aacctcactt ggaagagcac caacttcaaa  60
accatcctcg aatgggaacc caaacccgtt aaccaagttt acaccgtgca gatcagcacc 120
aagtccggcg actggaagtc caaatgtttc tataccacg acaccgagtg cgatctcacc 180
gatgagatcg tgaaagatgt gaaacagacc tacctcgccc gggtgtttag ctaccccgcc 240
ggcaatgtgg agagcactgg ttccgctggc gagcctttat acgagaacag ccccgaattt 300
accccttacc tcgagaccaa tttaggacag cccaccatcc aaagctttga gcaagttggc 360
acaaaggtga atgtgacagt ggaggacgag cggactttag tgcggcggaa caacaccttt 420
ctcagcctcc gggatgtgtt cggcaaagat ttaatctaca cactgtatta ctggaagtcc 480
tcttcctccg gcaagaagac agctaaaacc aacacaaacg agtttttaat cgacgtggat 540
aaaggcgaaa actactgttt cagcgtgcaa gctgtgatcc cctcccggac cgtgaatagg 600
aaaagcaccg atagccccgt tgagtgcatg ggccaagaaa agggcgagtt ccgggag    657
```

| | | |
|---|---|---|
| SEQ ID NO: 11 | moltype = AA  length = 223 | |
| FEATURE | Location/Qualifiers | |
| REGION | 1..223 | |
| | note = source = /note="Soluble Mouse Tissue Factor Domain" | |
| source | 1..223 | |
| | mol_type = protein | |
| | organism = Mus musculus | |
| SEQUENCE: 11 | | |

```
AGIPEKAFNL TWISTDFKTI LEWQPKPTNY TYTVQISDRS RNWKNKCFST TDTECDLTDE  60
IVKDVTWAYE AKVLSVPRRN SVHGDGDQLV IHGEEPPFTN APKFLPYRDT NLGQPVIQQF 120
EQDGRKLNVV VKDSLTLVRK NGTFLTLRQV FGKDLGYIIT YRKGSSTGKK TNITNTNEFS 180
IDVEEGVSYC FFVQAMIFSR KTNQNSPGSS TVCTEQWKSF LGE                  223
```

| | | |
|---|---|---|
| SEQ ID NO: 12 | moltype = AA  length = 224 | |
| FEATURE | Location/Qualifiers | |
| REGION | 1..224 | |
| | note = source = /note="Soluble Rat Tissue Factor Domain" | |
| source | 1..224 | |
| | mol_type = protein | |
| | organism = Rattus rattus | |
| SEQUENCE: 12 | | |

```
AGTPPGKAFN LTWISTDFKT ILEWQPKPTN YTYTVQISDR SRNWKYKCTG TTDTECDLTD  60
EIVKDVNWTY EARVLSVPWR NSTHGKETLF GTHGEEPPFT NARKFLPYRD TKIGQPVIQK 120
YEQGGTKLKV TVKDSFTLVR KNGTFLTLRQ VFGNDLGYIL TYRKDSSTGR KTNTTHTNEF 180
LIDVEKGVSY CFFAQAVIFS RKTNHKSPES ITKCTEQWKS VLGE                 224
```

| | | |
|---|---|---|
| SEQ ID NO: 13 | moltype = AA  length = 15 | |
| FEATURE | Location/Qualifiers | |
| REGION | 1..15 | |
| | note = source = /note="Description of Artificial Sequence: SyntheticLinker sequence" | |
| source | 1..15 | |
| | mol_type = protein | |
| | organism = synthetic construct | |
| SEQUENCE: 13 | | |
| GGGGSGGGGS GGGGS | | 15 |

| | | |
|---|---|---|
| SEQ ID NO: 14 | moltype = DNA  length = 45 | |
| FEATURE | Location/Qualifiers | |
| misc_feature | 1..45 | |
| | note = source = /note="Description of Artificial Sequence: SyntheticLinker sequence" | |
| source | 1..45 | |
| | mol_type = other DNA | |
| | organism = synthetic construct | |
| SEQUENCE: 14 | | |
| ggcggtggag gatccggagg aggtggctcc ggcggcggag gatct | | 45 |

| | | |
|---|---|---|
| SEQ ID NO: 15 | moltype = AA  length = 8 | |
| FEATURE | Location/Qualifiers | |
| REGION | 1..8 | |
| | note = source = /note="Description of Artificial Sequence: SyntheticLinker sequence" | |
| source | 1..8 | |
| | mol_type = protein | |
| | organism = synthetic construct | |
| SEQUENCE: 15 | | |
| GGGSGGGS | | 8 |

| | | |
|---|---|---|
| SEQ ID NO: 16 | moltype = AA  length = 119 | |
| FEATURE | Location/Qualifiers | |

```
REGION                   1..119
                         note = source = /note="Description of Artificial Sequence:
                           SyntheticAnti-CD3 scFv heavy chain variable domain
                           sequence"
source                   1..119
                         mol_type = protein
                         organism = synthetic construct
SEQUENCE: 16
QVQLQQSGAE LARPGASVKM SCKASGYTFT RYTMHWVKQR PGQGLEWIGY INPSRGYTNY    60
NQKFKDKATL TTDKSSSTAY MQLSSLTSED SAVYYCARYY DDHYCLDYWG QGTTLTVSS    119

SEQ ID NO: 17            moltype = AA   length = 107
FEATURE                  Location/Qualifiers
REGION                   1..107
                         note = source = /note="Description of Artificial Sequence:
                           SyntheticAnti-CD3 scFv light chain variable domain
                           sequence"
source                   1..107
                         mol_type = protein
                         organism = synthetic construct
SEQUENCE: 17
QIVLTQSPAI MSASPGEKVT MTCSASSSVS YMNWYQQKSG TSPKRWIYDT SKLASGVPAH    60
FRGSGSGTSY SLTISGMEAE DAATYYCQQW SSNPFTFGSG TKLEINR                 107

SEQ ID NO: 18            moltype = DNA   length = 357
FEATURE                  Location/Qualifiers
misc_feature             1..357
                         note = source = /note="Description of Artificial Sequence:
                           SyntheticAnti-CD3 scFv heavy chain variable domain
                           sequence"
source                   1..357
                         mol_type = other DNA
                         organism = synthetic construct
SEQUENCE: 18
caagttcagc tccagcaaag cggcgccgaa ctcgctcggc ccggcgcttc cgtgaagatg    60
tcttgtaagg cctccggcta taccttcacc cggtacacaa tgcactgggt caagcaacgg   120
cccggtcaag gttagagtg gattggctat atcaacccct cccggggcta taccaactac    180
aaccagaagt tcaaggacaa agccaccctc accaccgaca gtccagcag caccgcttac    240
atgcagctga gctctttaac atccgaggat tccgccgtgt actactcgc tcggtactac    300
gacgatcatt actgcctcga ttactggggc caaggtacca ccttaacagt ctcctcc     357

SEQ ID NO: 19            moltype = DNA   length = 321
FEATURE                  Location/Qualifiers
misc_feature             1..321
                         note = source = /note="Description of Artificial Sequence:
                           SyntheticAnti-CD3 scFv light chain variable domain
                           sequence"
source                   1..321
                         mol_type = other DNA
                         organism = synthetic construct
SEQUENCE: 19
cagatcgtgc tgacccagtc ccccgctatt atgagcgcta gccccggtga aaaggtgact    60
atgacatgca gcgccagctc ttccgtgagc tacatgaact ggtatcagca gaagtccggc   120
accagcccta aaaggtggat ctacgacacc agcaagctgg ccagcggcgt ccccgctcac   180
tttcggggct ccggctccgg aacaagctac tctctgacca tcagcggcat ggaagccgag   240
gatgccgcta cctattactg tcagcagtgg agctccaacc ccttcacctt tggatccggc   300
accaagctcg agattaatcg t                                             321

SEQ ID NO: 20            moltype = AA   length = 241
FEATURE                  Location/Qualifiers
REGION                   1..241
                         note = source = /note="Description of Artificial Sequence:
                           SyntheticAnti-CD3 scFv sequence"
source                   1..241
                         mol_type = protein
                         organism = synthetic construct
SEQUENCE: 20
QIVLTQSPAI MSASPGEKVT MTCSASSSVS YMNWYQQKSG TSPKRWIYDT SKLASGVPAH    60
FRGSGSGTSY SLTISGMEAE DAATYYCQQW SSNPFTFGSG TKLEINRGGG GSGGGGSGGG   120
GSQVQLQQSG AELARPGASV KMSCKASGYT FTRYTMHWVK QRPGQGLEWI GYINPSRGYT   180
NYNQKFKDKA TLTTDKSSST AYMQLSSLTS EDSAVYYCAR YYDDHYCLDY WGQGTTLTVS   240
S                                                                  241

SEQ ID NO: 21            moltype = DNA   length = 723
FEATURE                  Location/Qualifiers
misc_feature             1..723
                         note = source = /note="Description of Artificial Sequence:
                           SyntheticAnti-CD3 scFv sequence"
source                   1..723
```

-continued

```
                        mol_type = other DNA
                        organism = synthetic construct
SEQUENCE: 21
cagatcgtgc tgacccagtc ccccgctatt atgagcgcta gccccggtga aaaggtgact    60
atgacatgca gcgccagctc ttccgtgagc tacatgaact ggtatcagca gaagtccggc   120
accagcccta aaaggtggat ctacgacacc agcaagctgg ccagcggcgt ccccgctcac   180
tttcggggct ccggctccgg aacaagctac tctctgacca tcagcggcat ggaagccgag   240
gatgccgcta cctattactg tcagcagtgg agctccaacc ccttcacctt tggatccggc   300
accaagctcg agattaatcg tggaggcgga ggtagcggag gaggcggatc cggcggtgga   360
ggtagccaag ttcagctcca gcaaagcggc gccgaactcg ctcggcccgg cgcttccgtg   420
aagatgtctt gtaaggcctc cggctatacc ttcacccggt acacaatgca ctgggtcaag   480
caacggcccg gtcaaggttt agagtggatt ggctatatca ccccctcccg gggctatacc   540
aactacaacc agaagttcaa ggacaaagcc accctcacca ccgacaagtc cagcagcacc   600
gcttacatgc agctgagctc tttaacatcc gaggattccg ccgtgtacta ctgcgctcgg   660
tactacgacg atcattactg cctcgattac tggggccaag gtaccacctt aacagtctcc   720
tcc                                                                 723

SEQ ID NO: 22           moltype = AA  length = 107
FEATURE                 Location/Qualifiers
REGION                  1..107
                        note = source = /note="Description of Artificial Sequence:
                         SyntheticAnti-CD28 scFv heavy chain variable domain
                         sequence"
source                  1..107
                        mol_type = protein
                        organism = synthetic construct
SEQUENCE: 22
DIEMTQSPAI MSASLGERVT MTCTASSSVS SSYFHWYQQK PGSSPKLCIY STSNLASGVP    60
PRFSGSGSTS YSLTISSMEA EDAATYFCHQ YHRSPTFGGG TKLETKR                 107

SEQ ID NO: 23           moltype = AA  length = 114
FEATURE                 Location/Qualifiers
REGION                  1..114
                        note = source = /note="Description of Artificial Sequence:
                         SyntheticAnti-CD28 scFv light chain variable domain
                         sequence"
source                  1..114
                        mol_type = protein
                        organism = synthetic construct
SEQUENCE: 23
VQLQQSGPEL VKPGASVKMS CKASGYTFTS YVIQWVKQKP GQGLEWIGSI NPYNDYTKYN    60
EKFKGKATLT SDKSSITAYM EFSSLTSEDS ALYYCARWGD GNYWGRGTTL TVSS         114

SEQ ID NO: 24           moltype = DNA  length = 321
FEATURE                 Location/Qualifiers
misc_feature            1..321
                        note = source = /note="Description of Artificial Sequence:
                         SyntheticAnti-CD28 scFv heavy chain variable domain
                         sequence"
source                  1..321
                        mol_type = other DNA
                        organism = synthetic construct
SEQUENCE: 24
gacatcgaga tgacacagtc ccccgctatc atgagcgcct ctttaggaga acgtgtgacc    60
atgacttgta cagcttcctc cagcgtgagc agctcctatt tccactggta ccagcagaaa   120
cccggctcct cccctaaact gtgtatctac tccacaagca atttagctag cggcgtgcct   180
cctcgtttta gcggctccgg cagcacctct tactctttaa ccattagctc tatgaaggcc   240
gaagatgccg ccacatactt ttgccatcag taccaccggt cccctacctt tggcggaggc   300
acaaagctgg agaccaagcg g                                             321

SEQ ID NO: 25           moltype = DNA  length = 342
FEATURE                 Location/Qualifiers
misc_feature            1..342
                        note = source = /note="Description of Artificial Sequence:
                         SyntheticAnti-CD28 scFv light chain variable domain
                         sequence"
source                  1..342
                        mol_type = other DNA
                        organism = synthetic construct
SEQUENCE: 25
gtgcagctgc agcagtccgg acccgaactg gtcaagcccg gtgcctccgt gaaaatgtct    60
tgtaaggctt ctggctacac ctttacctcc tacgtcatcc aatgggtgaa gcagaagccc   120
ggtcaaggtc tcgagtggat cggcagcatc aatccctaca cgattacaca agtataac    180
gaaaagttta agggcaaggc cactctgaca agcgacaagt cctccattac cgcctacatg   240
gagtttttcct ctttaacttc tgaggactcc gctttatact attgcgctcg ttggggcgat   300
ggcaattatt ggggccgggg aactacttta acagtgagct cc                     342

SEQ ID NO: 26           moltype = AA  length = 236
FEATURE                 Location/Qualifiers
```

```
REGION                  1..236
                        note = source = /note="Description of Artificial Sequence:
                         SyntheticAnti-CD28 scFv sequence"
source                  1..236
                        mol_type = protein
                        organism = synthetic construct
SEQUENCE: 26
VQLQQSGPEL VKPGASVKMS CKASGYTFTS YVIQWVKQKP GQGLEWIGSI NPYNDYTKYN    60
EKFKGKATLT SDKSSITAYM EFSSLTSEDS ALYYCARWGD GNYWGRGTTL TVSSGGGGSG   120
GGGSGGGGSD IEMTQSPAIM SASLGERVTM TCTASSSVSS SYFHWYQQKP GSSPKLCIYS   180
TSNLASGVPP RFSGSGSTSY SLTISSMEAE DAATYFCHQY HRSPTFGGGT KLETKR       236

SEQ ID NO: 27           moltype = DNA  length = 708
FEATURE                 Location/Qualifiers
misc_feature            1..708
                        note = source = /note="Description of Artificial Sequence:
                         SyntheticAnti-CD28 scFv sequence"
source                  1..708
                        mol_type = other DNA
                        organism = synthetic construct
SEQUENCE: 27
gtgcagctgc agcagtccgg acccgaactg gtcaagcccg gtgcctccgt gaaaatgtct    60
tgtaaggctt ctggctacac ctttacctcc tacgtcatcc aatgggtgaa gcagaagccc   120
ggtcaaggtc tcgagtggat cggcagcatc aatccctaca acgattacac caagtataac   180
gaaaagttta agggcaaggc cactctgaca agcgacaaga gctccattac cgcctacatg   240
gagtttttcct ctttaacttc tgaggactcc gctttatact attgcgctcg ttggggcgat   300
ggcaattatt ggggccgggg aactactttta acagtgagct ccggcggcgg cggaagcgga   360
ggtggaggat ctggcggtgg aggcagcgac atcgagatga cacagtcccc cgctatcatg   420
agcgcctctt taggagaacg tgtgaccatg acttgtacag cttcctccag cgtgagcagc   480
tcctatttcc actggtacca gcagaaaccc ggctcctccc ctaaactgtg tatctactcc   540
acaagcaatt tagctagcgg cgtgcctcct cgttttagcg gctccggcag cacctcttac   600
tctttaacca ttagctctat ggaggccgaa gatgccgcca catactttg ccatcagtac   660
caccggtccc ctacctttgg cggaggcaca aagctggaga ccaagcgg              708

SEQ ID NO: 28           moltype = AA  length = 133
FEATURE                 Location/Qualifiers
REGION                  1..133
                        note = source = /note="Human Soluble IL-2"
source                  1..133
                        mol_type = protein
                        organism = Homo sapiens
SEQUENCE: 28
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 29           moltype = AA  length = 133
FEATURE                 Location/Qualifiers
REGION                  1..133
                        note = source = /note="Human Soluble IL-3"
source                  1..133
                        mol_type = protein
                        organism = Homo sapiens
SEQUENCE: 29
APMTQTTPLK TSWVNCSNMI DEIITHLKQP PLPLLDFNNL NGEDQDILME NNLRRPNLEA    60
FNRAVKSLQN ASAIESILKN LLPCLPLATA APTRHPIHIK DGDWNEFRRK LTFYLKTLEN   120
AQAQQTTLSL AIF                                                      133

SEQ ID NO: 30           moltype = AA  length = 152
FEATURE                 Location/Qualifiers
REGION                  1..152
                        note = source = /note="Human Soluble IL-7"
source                  1..152
                        mol_type = protein
                        organism = Homo sapiens
SEQUENCE: 30
DCDIEGKDGK QYESVLMVSI DQLLDSMKEI GSNCLNNEFN FFKRHICDAN KEGMFLFRAA    60
RKLRQFLKMN STGDFDLHLL KVSEGTTILL NCTGQVKGRK PAALGEAQPT KSLEENKSLK   120
EQKKLNDLCF LKRLLQEIKT CWNKILMGTK EH                                 152

SEQ ID NO: 31           moltype = AA  length = 79
FEATURE                 Location/Qualifiers
REGION                  1..79
                        note = source = /note="Human Soluble IL-8"
source                  1..79
                        mol_type = protein
                        organism = Homo sapiens
SEQUENCE: 31
EGAVLPRSAK ELRCQCIKTY SKPFHPKFIK ELRVIESGPH CANTEIIVKL SDGRELCLDP    60
```

```
KENWVQRVVE KFLKRAENS                                                    79

SEQ ID NO: 32           moltype = AA  length = 160
FEATURE                 Location/Qualifiers
REGION                  1..160
                        note = source = /note="Human Soluble IL-10"
source                  1..160
                        mol_type = protein
                        organism = Homo sapiens
SEQUENCE: 32
SPGQGTQSEN SCTHFPGNLP NMLRDLRDAF SRVKTFFQMK DQLDNLLLKE SLLEDFKGYL      60
GCQALSEMIQ FYLEEVMPQA ENQDPDIKAH VNSLGENLKT LRLRLRRCHR FLPCENKSKA    120
VEQVKNAFNK LQEKGIYKAM SEFDIFINYI EAYMTMKIRN                          160

SEQ ID NO: 33           moltype = AA  length = 306
FEATURE                 Location/Qualifiers
REGION                  1..306
                        note = source = /note="Human Soluble IL-12beta (p40)"
source                  1..306
                        mol_type = protein
                        organism = Homo sapiens
SEQUENCE: 33
IWELKKDVYV VELDWYPDAP GEMVVLTCDT PEEDGITWTL DQSSEVLGSG KTLTIQVKEF      60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCS                                                               306

SEQ ID NO: 34           moltype = DNA  length = 918
FEATURE                 Location/Qualifiers
misc_feature            1..918
                        note = source = /note="Human Soluble IL-12beta (p40)"
source                  1..918
                        mol_type = genomic DNA
                        organism = Homo sapiens
SEQUENCE: 34
atttgggaac tgaagaagga cgtctacgtg gtcgaactgg actggtatcc cgatgctccc      60
ggcgaaatgg tggtgctcac ttgtgacacc cccgaagacg gcatcac ttggaccctc      120
gatcagagca gcgaggtgct gggctccgga aagaccctca caatccaagt taaggagttc    180
ggagacgctg gccaatacac atgccacaag ggaggcgagg tgctcagcca ttccttatta    240
ttattacaca agaaggaaga cggaatctgg tccaccgaca ttttaaaaga tcagaaggag    300
cccaagaata gaccttttt aaggtgtgag gccaaaaact acagcggtcg tttcacttgt    360
tggtggctga ccaccatttc caccgattta accttctccg tgaaaagcag ccggggaagc    420
tccgaccctc aaggtgtgac atgtggagcc gctaccctca gcgctgagag ggttcgtggc    480
gataacaagg aatacgagta cagcgtggag tgccaagaag atagcgcttg tcccgctgcc    540
gaagaatctt tacccattga ggtgatggtg gacgccgtgc acaaactgaa gtacgagaac    600
tacacctcct ccttctttat ccgggacatc attaagcccg atcctcctaa gaatttacag    660
ctgaagcctc tcaaaaatag ccggcaagtt gaggtctctt gggaatatcc cgacacttgg    720
agcacacccc acagctactt ctctttaacc ttttgtgtgc aagttcaagg taaaagcaag    780
cgggagaaga aagaccgggt gtttaccgac aaaaccagcg ccaccgtcat ctgtcggaag    840
aacgcctcca tcagcgtgag ggctcaagat cgttattact ccagcagctg gtccgagtgg    900
gccagcgtgc cttgttcc                                                  918

SEQ ID NO: 35           moltype = AA  length = 197
FEATURE                 Location/Qualifiers
REGION                  1..197
                        note = source = /note="Human Soluble IL-12alpha (p35)"
source                  1..197
                        mol_type = protein
                        organism = Homo sapiens
SEQUENCE: 35
RNLPVATPDP GMFPCLHHSQ NLLRAVSNML QKARQTLEFY PCTSEEIDHE DITKDKTSTV      60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNAS                                                   197

SEQ ID NO: 36           moltype = DNA  length = 591
FEATURE                 Location/Qualifiers
misc_feature            1..591
                        note = source = /note="Human Soluble IL-12alpha (p35)"
source                  1..591
                        mol_type = genomic DNA
                        organism = Homo sapiens
SEQUENCE: 36
cgtaacctcc ccgtggctac ccccgatccc ggaatgttcc cttgtttaca ccacagccag      60
aatttactga gggccgtgag caacatgctg cagaaagcta ggcagacttt agaattttac    120
ccttgcacca cgcgaggaga tcgaccatga agatatcacc aggacaagac atccaccgtg    180
gaggcttgtt tacctctgga gctgacaaag aacgagtctt gtctcaactc tcgtgaaacc    240
```

```
agcttcatca caaatggctc ttgtttagct tcccggaaga cctccttat gatggcttta   300
tgcctcagct ccatctacga ggatttaaag atgtaccaag tggagttcaa gaccatgaac   360
gccaagctgc tcatggaccc taaacggcag atctttttag accagaacat gctggctgtg   420
attgatgagc tgatgcaagc tttaaacttc aactccgaga ccgtccctca gaagtcctcc   480
ctcgaggagc ccgattttta caagacaaag atcaaactgt gcatttact ccacgccttt     540
aggatccggg ccgtgaccat tgaccgggtc atgagctatt taaacgccag c             591

SEQ ID NO: 37            moltype = AA  length = 518
FEATURE                  Location/Qualifiers
REGION                   1..518
                         note = source = /note="Human Soluble IL-12"
source                   1..518
                         mol_type = protein
                         organism = Homo sapiens
SEQUENCE: 37
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRNLPVATPD PGMFPCLHHS QNLLRAVSNM LQKARQTLEF   360
YPCTSEEIDH EDITKDKTST VEACLPLELT KNESCLNSRE TSFITNGSCL ASRKTSFMMA   420
LCLSSIYEDL KMYQVEFKTM NAKLLMDPKR QIFLDQNMLA VIDELMQALN FNSETVPQKS   480
SLEEPDFYKT KIKLCILLHA FRIRAVTIDR VMSYLNAS                            518

SEQ ID NO: 38            moltype = DNA  length = 1554
FEATURE                  Location/Qualifiers
misc_feature             1..1554
                         note = source = /note="Human Soluble IL-12"
source                   1..1554
                         mol_type = genomic DNA
                         organism = Homo sapiens
SEQUENCE: 38
atttgggaac tgaagaagga cgtctacgtg gtcgaactgg actggtatcc cgatgctccc    60
ggcgaaatgg tggtgctcac ttgtgacacc cccgaagagg acggcatcac ttggaccctc   120
gatcagagca gcgaggtgct gggctccgga aagaccctca aatccaagt taaggagttc    180
ggagacgctg gccaatacac atgccacaag ggaggcgagg tgctcagcca ttccttatta   240
ttattacaca agaaggaaga cggaatctgg tccaccgaca ttttaaaaga tcagaaggag   300
cccaagaata agacctttt aaggtgtgag gccaaaaact acagcggtcg ttcacttgt    360
tggtggctga ccaccatttc caccgattta accttctccg tgaaaagcag ccggggaagc   420
tccgaccctc aaggtgtgac atgtggagcc gctaccctca gcgctgagag ggttcgtggc   480
gataacaagg aatacgagta cagcgtggag tgccaagaag atagcgcttg tcccgctgcc   540
gaagaatctt taccccattga ggtgatggtg gacgccgtgc acaaactgaa gtacgagaac   600
tacacctcct ccttctttat ccgggacatc attaagcccg atcctcctaa gaatttacag   660
ctgaagcctc tcaaaaatag ccggcaagtt gaggtctctt gggaatatcc cgacacttgg   720
agcacacccc acagctactt ctcttaacc tttttgtgtgc aagttcaagg taaaagcaag   780
cgggagaaga aagacccggt gttaccgac aaaaaccgga ccaccgtcat ctgtcggaag   840
aacgcctcca tcagcgtgag ggctcaagat cgttattact ccagcagctg gtccgagtgg   900
gccagcgtgc cttgttccgg cggtggagga tccggaggag gtggctccgg cggcggagga   960
tctcgtaacc tccccgtggc tacccccgat cccggaatgt tcccttgttt acaccacagc  1020
cagaatttac tgagggccgt gagcaacatg ctgcagaaag ctaggcagac tttagaattt  1080
tacccttgca ccagcgagga gatcgaccat gaagatatca ccaaggacaa gacatcccac  1140
gtggaggctt gtttacctct ggagctgaca aagaacgagt cttgtctcaa ctctcgtgaa  1200
accagcttca ttacaaatgg ctcttgttta gcttcccgga gacctccttt tatgatggct  1260
ttatgcctca gctccatcta cgaggattta aagatgtac aagtggagtt caagaccatg  1320
aacgccaagc tgctcatgga ccctaaacgg cagatctttt tagaccagaa catgctggct  1380
gtgattgatg agctgatgca agctttaaac ttcaactccg agaccgtccc tcagaagtcc  1440
tccctcgagg agcccgattt ttacaagaca aagatcaaac tgtgcatttt actccacgcc  1500
tttaggatcc gggccgtgac cattgaccgg gtcatgagct atttaaacgc cagc         1554

SEQ ID NO: 39            moltype = AA  length = 114
FEATURE                  Location/Qualifiers
REGION                   1..114
                         note = source = /note="Human Soluble IL-15"
source                   1..114
                         mol_type = protein
                         organism = Homo sapiens
SEQUENCE: 39
NWVNVISDLK KIEDLIQSMH IDATLYTESD VHPSCKVTAM KCFLLELQVI SLESGDASIH    60
DTVENLIILA NNSLSSNGNV TESGCKECEE LEEKNIKEFL QSFVHIVQMF INTS          114

SEQ ID NO: 40            moltype = AA  length = 132
FEATURE                  Location/Qualifiers
REGION                   1..132
                         note = source = /note="Human Soluble IL-17"
source                   1..132
                         mol_type = protein
                         organism = Homo sapiens
SEQUENCE: 40
```

```
GITIPRNPGC PNSEDKNFPR TVMVNLNIHN RNTNTNPKRS SDYYNRSTSP WNLHRNEDPE    60
RYPSVIWEAK CRHLGCINAD GNVDYHMNSV PIQQEILVLR REPPHCPNSF RLEKILVSVG   120
CTCVTPIVHH VA                                                      132

SEQ ID NO: 41           moltype = AA  length = 157
FEATURE                 Location/Qualifiers
REGION                  1..157
                        note = source = /note="Human Soluble IL-18"
source                  1..157
                        mol_type = protein
                        organism = Homo sapiens
SEQUENCE: 41
YFGKLESKLS VIRNLNDQVL FIDQGNRPLF EDMTDSDCRD NAPRTIFIIS MYKDSQPRGM    60
AVTISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 42           moltype = DNA  length = 471
FEATURE                 Location/Qualifiers
misc_feature            1..471
                        note = source = /note="Human Soluble IL-18"
source                  1..471
                        mol_type = genomic DNA
                        organism = Homo sapiens
SEQUENCE: 42
tacttcggca aactggaatc caagctgagc gtgatccgga atttaaacga ccaagttctg    60
tttatcgatc aaggtaaccg gcctctgttc gaggacatga cgactccga ttgccgggac   120
aatgccccc ggaccatctt cattatctcc atgtacaagg acagccagcc ccggggcatg   180
gctgtgacaa ttagcgtgaa gtgtgagaaa atcagcactt tatccttgtga gaacaagatc   240
atctccttta aggaaatgaa cccccccgat aacatcaagg acaccaagtc cgatatcatc   300
ttcttccagc ggtccgtgcc cggtcacgat aacaagatgc agttcgaatc ctcctcctac   360
gagggctact ttttagcttg tgaaaaggag agggatttat tcaagctgat cctcaagaag   420
gaggacgagc tgggcgatcg ttccatcatg ttcaccgtcc aaaacgagga t            471

SEQ ID NO: 43           moltype = AA  length = 133
FEATURE                 Location/Qualifiers
REGION                  1..133
                        note = source = /note="Human Soluble IL-21"
source                  1..133
                        mol_type = protein
                        organism = Homo sapiens
SEQUENCE: 43
QGQDRHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                     133

SEQ ID NO: 44           moltype = DNA  length = 399
FEATURE                 Location/Qualifiers
misc_feature            1..399
                        note = source = /note="Human Soluble IL-21"
source                  1..399
                        mol_type = genomic DNA
                        organism = Homo sapiens
SEQUENCE: 44
cagggccagg acaggcacat gatccggatg aggcagctca tcgacatcgt cgaccagctg    60
aagaactacg tgaacgacct ggtgcccgag tttctgcctg cccccgagga cgtggagacc   120
aactgcgagt ggtccgcctt ctcctgcttt cagaaggccc agctgaagtc cgccaacacc   180
ggcaacaacg agcggatcat caacgtgagc atcaagaagc tgaagcggaa gcctccctcc   240
acaaacgccg gcaggaggca gaagcacagg ctgacctgcc ccagctgtga ctcctacgag   300
aagaagcccc caaggagtt cctggagagg ttcaagtccc tgctgcagaa gatgatccat   360
cagcacctgt cctccaggac ccacggctcc gaggactcc                          399

SEQ ID NO: 45           moltype = AA  length = 352
FEATURE                 Location/Qualifiers
REGION                  1..352
                        note = source = /note="Human Soluble PDGF-D"
source                  1..352
                        mol_type = protein
                        organism = Homo sapiens
SEQUENCE: 45
RDTSATPQSA SIKALRNANL RRDESNHLTD LYRRDETIQV KGNGYVQSPR FPNSYPRNLL    60
LTWRLHSQEN TRIQLVFDNQ FGLEEAENDI CRYDFVEVED ISETSTIIRG RWCGHKEVPP   120
RIKSRTNQIK ITFKSDDYFV AKPGFKIYYS LLEDFQPAAA SETNWESVTS SISGVSYNSP   180
SVTDPTLIAD ALDKKIAEFD TVEDLLKYFN PESWQEDLEN MYLDTPRYRG RSYHDRKSKV   240
DLDRLNDDAK RYSCTPRNYS VNIREELKLA NVVFFPRCLL VQRCGGNCGC GTVNWRSCTC   300
NSGKTVKKYH EVLQFEPGHI KRRGRAKTMA LVDIQLDHHE RCDCICSSRP PR           352

SEQ ID NO: 46           moltype = AA  length = 248
FEATURE                 Location/Qualifiers
REGION                  1..248
```

```
                        note = source = /note="Human Soluble SCF"
source                  1..248
                        mol_type = protein
                        organism = Homo sapiens
SEQUENCE: 46
EGICRNRVTN NVKDVTKLVA NLPKDYMITL KYVPGMDVLP SHCWISEMVV QLSDSLTDLL    60
DKFSNISEGL SNYSIIDKLV NIVDDLVECV KENSSKDLKK SFKSPEPRLF TPEEFFRIFN   120
RSIDAFKDFV VASETSDCVV SSTLSPEKDS RVSVTKPFML PPVAASSLRN DSSSSNRKAK   180
NPPGDSSLHW AAMALPALFS LIIGFAFGAL YWKKRQPSLT RAVENIQINE EDNEISMLQE   240
KEREFQEV                                                            248

SEQ ID NO: 47           moltype = AA  length = 209
FEATURE                 Location/Qualifiers
REGION                  1..209
                        note = source = /note="Human Soluble FLT3L"
source                  1..209
                        mol_type = protein
                        organism = Homo sapiens
SEQUENCE: 47
TQDCSFQHSP ISSDFAVKIR ELSDYLLQDY PVTVASNLQD EELCGGLWRL VLAQRWMERL    60
KTVAGSKMQG LLERVNTEIH FVTKCAFQPP PSCLRFVQTN ISRLLQETSE QLVALKPWIT   120
RQNFSRCLEL QCQPDSSTLP PPWSPRPLEA TAPTAPQPPL LLLLLLPVGL LLLAAAWCLH   180
WQRTRRRTPR PGEQVPPVPS PQDLLLVEH                                     209

SEQ ID NO: 48           moltype = AA  length = 360
FEATURE                 Location/Qualifiers
REGION                  1..360
                        note = source = /note="Human Soluble MICA"
source                  1..360
                        mol_type = protein
                        organism = Homo sapiens
SEQUENCE: 48
EPHSLRYNLT VLSWDGSVQS GFLTEVHLDG QPFLRCDRQK CRAKPQGQWA EDVLGNKTWD    60
RETRDLTGNG KDLRMTLAHI KDQKEGLHSL QEIRVCEIHE DNSTRSSQHF YYDGELFLSQ   120
NLETKEWTMP QSSRAQTLAM NVRNFLKEDA MKTKTHYHAM HADCLQELRR YLKSGVVLRR   180
TVPPMVNVTR SEASEGNITV TCRASGFYPW NITLSWRQDG VSLSHDTQQW GDVLPDGNGT   240
YQTWVATRIC QGEEQRFTCY MEHSGNHSTH PVPSGKVLVL QSHWQTFHVS AVAAAAIFVI   300
IIFYVRCCKK KTSAAEGPEL VSLQVLDQHP VGTSDHRDAT QLGFQPLMSD LGSTGSTEGA   360

SEQ ID NO: 49           moltype = AA  length = 361
FEATURE                 Location/Qualifiers
REGION                  1..361
                        note = source = /note="Human Soluble MICB"
source                  1..361
                        mol_type = protein
                        organism = Homo sapiens
SEQUENCE: 49
AEPHSLRYNL MVLSQDESVQ SGFLAEGHLD GQPFLRYDRQ KRRAKPQGQW AEDVLGAKTW    60
DTETEDLTEN GQDLRRTLTH IKDQKGGLHS LQEIRVCEIH EDSSTRGSRH FYYDGELFLS   120
QNLETQESTV PQSSRAQTLA MNVTNFWKED AMKTKTHYRA MQADCLQKLQ RYLKSGVAIR   180
RTVPPMVNVT CSEVSEGNIT VTCRASSFYP RNITLTWRQD GVSLSHNTQQ WGDVLPDGNG   240
TYQTWVATRI RQGEEQRFTC YMEHSGNHGT HPVPSGKVLV LQSQRTDFPY VSAAMPCFVI   300
IIILCVPCCK KKTSAAEGPE LVSLQVLDQH PVGTGDHRDA AQLGFQPLMS ATGSTGSTEG   360
A                                                                   361

SEQ ID NO: 50           moltype = AA  length = 190
FEATURE                 Location/Qualifiers
REGION                  1..190
                        note = source = /note="Human Soluble ULBP1"
source                  1..190
                        mol_type = protein
                        organism = Homo sapiens
SEQUENCE: 50
WVDTHCLCYD FIITPKSRPE PQWCEVQGLV DERPFLHYDC VNHKAKAFAS LGKKVNVTKT    60
WEEQTETLRD VVDFLKGQLL DIQVENLIPI EPLTLQARMS CEHEAHGHGR GSWQFLFNGQ   120
KFLLFDSNNR KWTALHPGAK KMTEKWEKNR DVTMFFQKIS LGDCKMWLEE FLMYWEQMLD   180
PTKPPSLAPG                                                          190

SEQ ID NO: 51           moltype = AA  length = 191
FEATURE                 Location/Qualifiers
REGION                  1..191
                        note = source = /note="Human Soluble ULBP2"
source                  1..191
                        mol_type = protein
                        organism = Homo sapiens
SEQUENCE: 51
GRADPHSLCY DITVIPKFRP GPRWCAVQGQ VDEKTFLHYD CGNKTVTPVS PLGKKLNVTT    60
AWKAQNPVLR EVVDILTEQL RDIQLENYTP KEPLTLQARM SCEQKAEGHS SGSWQFSFDG   120
QIFLLFDSEK RMWTTVHPGA RKMKEKWEND KVVAMSFHYF SMGDCIGWLE DFLMGMDSTL   180
```

```
EPSAGAPLAM S                                                                191

SEQ ID NO: 52           moltype = AA  length = 188
FEATURE                 Location/Qualifiers
REGION                  1..188
                        note = source = /note="Human Soluble ULBP3"
source                  1..188
                        mol_type = protein
                        organism = Homo sapiens
SEQUENCE: 52
DAHSLWYNFT IIHLPRHGQQ WCEVQSQVDQ KNFLSYDCGS DKVLSMGHLE EQLYATDAWG    60
KQLEMLREVG QRLRLELADT ELEDFTPSGP LTLQVRMSCE CEADGYIRGS WQFSFDGRKF   120
LLFDSNNRKW TVVHAGARRM KEKWEKDSGL TTFFKMVSMR DCKSWLRDFL MHRKKRLEPT   180
APPTMAPG                                                            188

SEQ ID NO: 53           moltype = AA  length = 233
FEATURE                 Location/Qualifiers
REGION                  1..233
                        note = source = /note="Human Soluble ULBP4"
source                  1..233
                        mol_type = protein
                        organism = Homo sapiens
SEQUENCE: 53
HSLCFNFTIK SLSRPGQPWC EAQVFLNKNL FLQYNSDNNM VKPLGLLGKK VYATSTWGEL    60
TQTLGEVGRD LRMLLCDIKP QIKTSDPSTL QVEMFCQREA ERCTGASWQF ATNGEKSLLF   120
DAMNMTWTVI NHEASKIKET WKKDRGLEKY FRKLSKGDCD HWLREFLGHW EAMPEPTVSP   180
VNASDIHWSS SSLPDRWIIL GAFILLVLMG IVLICVWWQN GEWQAGLWPL RTS          233

SEQ ID NO: 54           moltype = AA  length = 193
FEATURE                 Location/Qualifiers
REGION                  1..193
                        note = source = /note="Human Soluble ULBP5"
source                  1..193
                        mol_type = protein
                        organism = Homo sapiens
SEQUENCE: 54
GLADPHSLCY DITVIPKFRP GPRWCAVQGQ VDEKTFLHYD CGSKTVTPVS PLGKKLNVTT    60
AWKAQNPVLR EVVDILTEQL LDIQLENYIP KEPLTLQARM SCEQKAEGHG SGSWQLSFDG   120
QIFLLFDSEN RMWTTVHPGA RKMKEKWEND KDMTMSFHYI SMGDCTGWLE DFLMGMDSTL   180
EPSAGAPPTM SSG                                                      193

SEQ ID NO: 55           moltype = AA  length = 193
FEATURE                 Location/Qualifiers
REGION                  1..193
                        note = source = /note="Human Soluble ULBP6"
source                  1..193
                        mol_type = protein
                        organism = Homo sapiens
SEQUENCE: 55
RRDDPHSLCY DITVIPKFRP GPRWCAVQGQ VDEKTFLHYD CGNKTVTPVS PLGKKLNVTM    60
AWKAQNPVLR EVVDILTEQL LDIQLENYTP KEPLTLQARM SCEQKAEGHS SGSWQFSIDG   120
QTFLLFDSEK RMWTTVHPGA RKMKEKWEND KDVAMSFHYI SMGDCIGWLE DFLMGMDSTL   180
EPSAGAPLAM SSG                                                      193

SEQ ID NO: 56           moltype = AA  length = 136
FEATURE                 Location/Qualifiers
REGION                  1..136
                        note = source = /note="Soluble TGFbetaRII receptor, first
                         sequence"
source                  1..136
                        mol_type = protein
                        organism = Homo sapiens
SEQUENCE: 56
IPPHVQKSVN NDMIVTDNNG AVKFPQLCKF CDVRFSTCDN QKSCMSNCSI TSICEKPQEV    60
CVAVWRKNDE NITLETVCHD PKLPYHDFIL EDAASPKCIM KEKKKPGETF FMCSCSSDEC   120
NDNIIFSEEY NTSNPD                                                   136

SEQ ID NO: 57           moltype = DNA  length = 408
FEATURE                 Location/Qualifiers
misc_feature            1..408
                        note = source = /note="Soluble TGFbetaRII receptor, first
                         sequence"
source                  1..408
                        mol_type = genomic DNA
                        organism = Homo sapiens
SEQUENCE: 57
atcccccccc atgtgcaaaa gagcgtgaac aacgatatga tcgtgaccga caacaacggc    60
gccgtgaagt tccccagct ctgcaagttc tgcgatgtca ggttcagcac ctgcgataat   120
cagaagtcct gcatgtccaa ctgcacgatc acctccatct gcgagaagcc ccaagaagtg   180
```

```
tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca accctgat               408

SEQ ID NO: 58           moltype =    length =
SEQUENCE: 58
000

SEQ ID NO: 59           moltype =    length =
SEQUENCE: 59
000

SEQ ID NO: 60           moltype = AA   length = 287
FEATURE                 Location/Qualifiers
REGION                  1..287
                        note = source = /note="Soluble TGFbetaRII receptor"
source                  1..287
                        mol_type = protein
                        organism = Homo sapiens
SEQUENCE: 60
IPPHVQKSVN NDMIVTDNNG AVKFPQLCKF CDVRFSTCDN QKSCMSNCSI TSICEKPQEV    60
CVAVWRKNDE NITLETVCHD PKLPYHDFIL EDAASPKCIM KEKKKPGETF FMCSCSSDEC   120
NDNIIFSEEY NTSNPDGGGG SGGGGSGGGG SIPPHVQKSV NNDMIVTDNN GAVKFPQLCK   180
FCDVRFSTCD NQKSCMSNCS ITSICEKPQE VCVAVWRKND ENITLETVCH DPKLPYHDFI   240
LEDAASPKCI MKEKKKPGET FFMCSCSSDE CNDNIIFSEE YNTSNPD                287

SEQ ID NO: 61           moltype = DNA   length = 861
FEATURE                 Location/Qualifiers
misc_feature            1..861
                        note = source = /note="Soluble TGFbetaRII receptor"
source                  1..861
                        mol_type = genomic DNA
                        organism = Homo sapiens
SEQUENCE: 61
atccccccc atgtgcaaaa gagcgtgaac aacgatatga tcgtgaccga caacaacggc    60
gccgtgaagt tcccccagct ctgcaagttc tgcgatgtca ggttcagcac ctgcgataat   120
cagaagtcct gcatgtccaa ctgcacgatc acctccatct gcgagaagcc caagaagtg   180
tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca accctgatgg aggtggcgga   420
tccggaggtg gaggttctgg tggaggtggg agtattcctc cccacgtgca gaagagcgtg   480
aataatgaca tgatcgtgac cgataacaat ggcgccgtga atttcccca gctgtgcaaa   540
ttctgcgatg tgaggttttc cacctgcgac aaccagaagt cctgtatgag caactgcaca   600
atcacctcca tctgtgagaa gcctcaggag gtgtgcgtgg ctgtctggcg gaagaatgac   660
gagaatatca ccctggaaac cgtctgccac gatcccaact gccttacca cgatttcatc   720
ctggaagacg ccgccagccc taagtgcatc atgaaagaga aaaagaagcc tggcgagacc   780
ttttttcatgt gctcctgcag cagcgacgaa tgcaacgaca atatcatctt tagcgaggaa   840
tacaatacca gcaaccccga c                                             861

SEQ ID NO: 62           moltype = AA   length = 18
FEATURE                 Location/Qualifiers
REGION                  1..18
                        note = source = /note="Description of Artificial Sequence:
                        SyntheticSignal sequence"
source                  1..18
                        mol_type = protein
                        organism = synthetic construct
SEQUENCE: 62
MKWVTFISLL FLFSSAYS                                                  18

SEQ ID NO: 63           moltype = DNA   length = 54
FEATURE                 Location/Qualifiers
misc_feature            1..54
                        note = source = /note="Description of Artificial Sequence:
                        SyntheticSignal sequence"
source                  1..54
                        mol_type = other DNA
                        organism = synthetic construct
SEQUENCE: 63
atgaaatggg tgacctttat ttctttactg ttcctctttta gcagcgccta ctcc         54

SEQ ID NO: 64           moltype = DNA   length = 54
FEATURE                 Location/Qualifiers
misc_feature            1..54
                        note = source = /note="Description of Artificial Sequence:
                        SyntheticSignal sequence"
source                  1..54
```

```
                            mol_type = other DNA
                            organism = synthetic construct
SEQUENCE: 64
atgaagtggg tcacatttat ctctttactg ttcctcttct ccagcgccta cagc          54

SEQ ID NO: 65              moltype = DNA  length = 54
FEATURE                    Location/Qualifiers
misc_feature               1..54
                           note = source = /note="Description of Artificial Sequence:
                             SyntheticSignal sequence"
source                     1..54
                           mol_type = other DNA
                           organism = synthetic construct
SEQUENCE: 65
atgaaatggg tgacctttat ttctttactg ttcctcttta gcagcgccta ctcc          54

SEQ ID NO: 66              moltype = AA  length = 16
FEATURE                    Location/Qualifiers
REGION                     1..16
                           note = source = /note="Description of Artificial Sequence:
                             SyntheticSignal sequence"
source                     1..16
                           mol_type = protein
                           organism = synthetic construct
SEQUENCE: 66
MKCLLYLAFL FLGVNC                                                    16

SEQ ID NO: 67              moltype = AA  length = 58
FEATURE                    Location/Qualifiers
REGION                     1..58
                           note = source = /note="Description of Artificial Sequence:
                             SyntheticSignal sequence"
source                     1..58
                           mol_type = protein
                           organism = synthetic construct
SEQUENCE: 67
MGQIVTMFEA LPHIIDEVIN IVIIVLIIIT SIKAVYNFAT CGILALVSFL FLAGRSCG      58

SEQ ID NO: 68              moltype = AA  length = 97
FEATURE                    Location/Qualifiers
REGION                     1..97
                           note = source = /note="Description of Artificial Sequence:
                             SyntheticSignal sequence"
source                     1..97
                           mol_type = protein
                           organism = synthetic construct
SEQUENCE: 68
MPNHQSGSPT GSSDLLLSGK KQRPHLALRR KRRREMRKIN RKVRRMNLAP IKEKTAWQHL    60
QALISEAEEV LKTSQTPQNS LTLFLALLSV LGPPVTG                             97

SEQ ID NO: 69              moltype = AA  length = 30
FEATURE                    Location/Qualifiers
REGION                     1..30
                           note = source = /note="Description of Artificial Sequence:
                             SyntheticSignal sequence"
source                     1..30
                           mol_type = protein
                           organism = synthetic construct
SEQUENCE: 69
MDSKGSSQKG SRLLLLLVVS NLLLCQGVVS                                     30

SEQ ID NO: 70              moltype = AA  length = 15
FEATURE                    Location/Qualifiers
REGION                     1..15
                           note = source = /note="Description of Artificial Sequence:
                             SyntheticAviTag sequence"
source                     1..15
                           mol_type = protein
                           organism = synthetic construct
SEQUENCE: 70
GLNDIFEAQK IEWHE                                                     15

SEQ ID NO: 71              moltype = AA  length = 26
FEATURE                    Location/Qualifiers
REGION                     1..26
                           note = source = /note="Description of Artificial Sequence:
                             SyntheticCalmodulin-tag sequence"
source                     1..26
                           mol_type = protein
```

```
                        organism = synthetic construct
SEQUENCE: 71
KRRWKKNFIA VSAANRFKKI SSSGAL                                        26

SEQ ID NO: 72           moltype = AA   length = 6
FEATURE                 Location/Qualifiers
REGION                  1..6
                        note = source = /note="Description of Artificial Sequence:
                         SyntheticPolyglutamate tag sequence"
source                  1..6
                        mol_type = protein
                        organism = synthetic construct
SEQUENCE: 72
EEEEEE                                                              6

SEQ ID NO: 73           moltype = AA   length = 13
FEATURE                 Location/Qualifiers
REGION                  1..13
                        note = source = /note="Description of Artificial Sequence:
                         SyntheticE-tag sequence"
source                  1..13
                        mol_type = protein
                        organism = synthetic construct
SEQUENCE: 73
GAPVPYPDPL EPR                                                      13

SEQ ID NO: 74           moltype = AA   length = 8
FEATURE                 Location/Qualifiers
REGION                  1..8
                        note = source = /note="Description of Artificial Sequence:
                         SyntheticFLAG-tag sequence"
source                  1..8
                        mol_type = protein
                        organism = synthetic construct
SEQUENCE: 74
DYKDDDDK                                                            8

SEQ ID NO: 75           moltype = AA   length = 9
FEATURE                 Location/Qualifiers
REGION                  1..9
                        note = source = /note="Description of Artificial Sequence:
                         SyntheticHA-tag sequence"
source                  1..9
                        mol_type = protein
                        organism = synthetic construct
SEQUENCE: 75
YPYDVPDYA                                                           9

SEQ ID NO: 76           moltype = AA   length = 5
FEATURE                 Location/Qualifiers
REGION                  1..5
                        note = source = /note="Description of Artificial Sequence:
                         SyntheticHis-tag sequence"
source                  1..5
                        mol_type = protein
                        organism = synthetic construct
SEQUENCE: 76
HHHHH                                                               5

SEQ ID NO: 77           moltype = AA   length = 6
FEATURE                 Location/Qualifiers
REGION                  1..6
                        note = source = /note="Description of Artificial Sequence:
                         SyntheticHis-tag sequence"
source                  1..6
                        mol_type = protein
                        organism = synthetic construct
SEQUENCE: 77
HHHHHH                                                              6

SEQ ID NO: 78           moltype = AA   length = 7
FEATURE                 Location/Qualifiers
REGION                  1..7
                        note = source = /note="Description of Artificial Sequence:
                         SyntheticHis-tag sequence"
source                  1..7
                        mol_type = protein
                        organism = synthetic construct
SEQUENCE: 78
```

```
                                    -continued
HHHHHHH                                                             7

SEQ ID NO: 79          moltype = AA  length = 8
FEATURE                Location/Qualifiers
REGION                 1..8
                       note = source = /note="Description of Artificial Sequence:
                        SyntheticHis-tag sequence"
source                 1..8
                       mol_type = protein
                       organism = synthetic construct
SEQUENCE: 79
HHHHHHHH                                                            8

SEQ ID NO: 80          moltype = AA  length = 9
FEATURE                Location/Qualifiers
REGION                 1..9
                       note = source = /note="Description of Artificial Sequence:
                        SyntheticHis-tag sequence"
source                 1..9
                       mol_type = protein
                       organism = synthetic construct
SEQUENCE: 80
HHHHHHHHH                                                           9

SEQ ID NO: 81          moltype = AA  length = 10
FEATURE                Location/Qualifiers
REGION                 1..10
                       note = source = /note="Description of Artificial Sequence:
                        SyntheticHis-tag sequence"
source                 1..10
                       mol_type = protein
                       organism = synthetic construct
SEQUENCE: 81
HHHHHHHHHH                                                          10

SEQ ID NO: 82          moltype = AA  length = 10
FEATURE                Location/Qualifiers
REGION                 1..10
                       note = source = /note="Description of Artificial Sequence:
                        SyntheticMyc-tag sequence"
source                 1..10
                       mol_type = protein
                       organism = synthetic construct
SEQUENCE: 82
EQKLISEEDL                                                          10

SEQ ID NO: 83          moltype = AA  length = 18
FEATURE                Location/Qualifiers
REGION                 1..18
                       note = source = /note="Description of Artificial Sequence:
                        SyntheticNE-tag sequence"
source                 1..18
                       mol_type = protein
                       organism = synthetic construct
SEQUENCE: 83
TKENPRSNQE ESYDDNES                                                 18

SEQ ID NO: 84          moltype = AA  length = 15
FEATURE                Location/Qualifiers
REGION                 1..15
                       note = source = /note="Description of Artificial Sequence:
                        SyntheticS-tag sequence"
source                 1..15
                       mol_type = protein
                       organism = synthetic construct
SEQUENCE: 84
KETAAAKFER QHMDS                                                    15

SEQ ID NO: 85          moltype = AA  length = 38
FEATURE                Location/Qualifiers
REGION                 1..38
                       note = source = /note="Description of Artificial Sequence:
                        SyntheticSBP-tag sequence"
source                 1..38
                       mol_type = protein
                       organism = synthetic construct
SEQUENCE: 85
MDEKTTGWRG GHVVEGLAGE LEQLRARLEH HPQGQREP                            38
```

| | | |
|---|---|---|
| SEQ ID NO: 86 | moltype = AA length = 13 | |
| FEATURE | Location/Qualifiers | |
| REGION | 1..13<br>note = source = /note="Description of Artificial Sequence: SyntheticSoftag 1 sequence" | |
| source | 1..13<br>mol_type = protein<br>organism = synthetic construct | |
| SEQUENCE: 86 | | |
| SLAELLNAGL GGS | | 13 |
| SEQ ID NO: 87 | moltype = AA length = 8 | |
| FEATURE | Location/Qualifiers | |
| REGION | 1..8<br>note = source = /note="Description of Artificial Sequence: SyntheticSoftag 3 sequence" | |
| source | 1..8<br>mol_type = protein<br>organism = synthetic construct | |
| SEQUENCE: 87 | | |
| TQDPSRVG | | 8 |
| SEQ ID NO: 88 | moltype = AA length = 12 | |
| FEATURE | Location/Qualifiers | |
| REGION | 1..12<br>note = source = /note="Description of Artificial Sequence: SyntheticSpot-tag sequence" | |
| source | 1..12<br>mol_type = protein<br>organism = synthetic construct | |
| SEQUENCE: 88 | | |
| PDRVRAVSHW SS | | 12 |
| SEQ ID NO: 89 | moltype = AA length = 8 | |
| FEATURE | Location/Qualifiers | |
| REGION | 1..8<br>note = source = /note="Description of Artificial Sequence: SyntheticStrep-tag sequence" | |
| source | 1..8<br>mol_type = protein<br>organism = synthetic construct | |
| SEQUENCE: 89 | | |
| WSHPQFEK | | 8 |
| SEQ ID NO: 90 | moltype = AA length = 6 | |
| FEATURE | Location/Qualifiers | |
| REGION | 1..6<br>note = source = /note="Description of Artificial Sequence: SyntheticTC tag sequence" | |
| source | 1..6<br>mol_type = protein<br>organism = synthetic construct | |
| SEQUENCE: 90 | | |
| CCPGCC | | 6 |
| SEQ ID NO: 91 | moltype = AA length = 10 | |
| FEATURE | Location/Qualifiers | |
| REGION | 1..10<br>note = source = /note="Description of Artificial Sequence: SyntheticTy tag sequence" | |
| source | 1..10<br>mol_type = protein<br>organism = synthetic construct | |
| SEQUENCE: 91 | | |
| EVHTNQDPLD | | 10 |
| SEQ ID NO: 92 | moltype = AA length = 14 | |
| FEATURE | Location/Qualifiers | |
| REGION | 1..14<br>note = source = /note="Description of Artificial Sequence: SyntheticV5 tag sequence" | |
| source | 1..14<br>mol_type = protein<br>organism = synthetic construct | |
| SEQUENCE: 92 | | |
| GKPIPNPLLG LDST | | 14 |
| SEQ ID NO: 93 | moltype = AA length = 11 | |
| FEATURE | Location/Qualifiers | |

| | |
|---|---|
| REGION | 1..11<br>note = source = /note="Description of Artificial Sequence: SyntheticVSV-tag sequence" |
| source | 1..11<br>mol_type = protein<br>organism = synthetic construct |

SEQUENCE: 93
YTDIEMNRLG K                                                                                          11

| | |
|---|---|
| SEQ ID NO: 94 | moltype = AA  length = 8 |
| FEATURE | Location/Qualifiers |
| REGION | 1..8<br>note = source = /note="Description of Artificial Sequence: SyntheticXpress tag sequence" |
| source | 1..8<br>mol_type = protein<br>organism = synthetic construct |

SEQUENCE: 94
DLYDDDDK                                                                                              8

| | |
|---|---|
| SEQ ID NO: 95<br>SEQUENCE: 95<br>000 | moltype =   length = |

| | |
|---|---|
| SEQ ID NO: 96 | moltype = AA  length = 219 |
| FEATURE | Location/Qualifiers |
| REGION | 1..219<br>note = source = /note="Mutant Soluble Human Tissue Factor Domain" |
| source | 1..219<br>mol_type = protein<br>organism = Homo sapiens |

SEQUENCE: 96
SGTTNTVAAY NLTWKSTNFA TALEWEPKPV NQVYTVQIST KSGDWKSKCF YTTDTECALT     60
DEIVKDVKQT YLARVFSYPA GNVESTGSAG EPLYENSPEF TPYLETNLGQ PTIQSFEQVG    120
TKVNVTVEDE RTLVARNNTA LSLRDVFGKD LIYTLYYWKS SSSGKKTAKT NTNEFLIDVD    180
KGENYCFSVQ AVIPSRTVNR KSTDSPVECM GQEKGEFRE                           219

| | |
|---|---|
| SEQ ID NO: 97 | moltype = AA  length = 219 |
| FEATURE | Location/Qualifiers |
| REGION | 1..219<br>note = source = /note="Mutant Soluble Human Tissue Factor Domain" |
| source | 1..219<br>mol_type = protein<br>organism = Homo sapiens |

SEQUENCE: 97
SGTTNTVAAY NLTWKSTNFA TALEWEPKPV NQVYTVQIST KSGDAKSKCF YTTDTECALT     60
DEIVKDVKQT YLARVFSYPA GNVESTGSAG EPLAENSPEF TPYLETNLGQ PTIQSFEQVG    120
TKVNVTVEDE RTLVARNNTA LSLRDVFGKD LIYTLYYWKS SSSGKKTAKT NTNEFLIDVD    180
KGENYCFSVQ AVIPSRTVNR KSTDSPVECM GQEKGEFRE                           219

| | |
|---|---|
| SEQ ID NO: 98<br>SEQUENCE: 98<br>000 | moltype =   length = |

| | |
|---|---|
| SEQ ID NO: 99 | moltype = DNA  length = 723 |
| FEATURE | Location/Qualifiers |
| misc_feature | 1..723<br>note = source = /note="Anti-CD3 scFv" |
| source | 1..723<br>mol_type = genomic DNA<br>organism = Homo sapiens |

SEQUENCE: 99
cagatcgtgc tgacccaaag ccccgccatc atgagcgcta gccccggtga aaggtgacc     60
atgacatgct ccgcttccag ctccgtgtcc tacatgaact ggtatcagca gaaaagcgga    120
accagcccca aaggtggat ctacgacacc agcaagctgg cctccggagt gcccgctcat    180
ttccggggct ctggatccgg caccagctac tctttaacca tttccggcat ggaagctgaa    240
gacgctgcca cctactattg ccagcaatgg agcagcaacc ccttcacatt cggagtgtc    300
accaagctcg aaatcaatcg tggaggaggt ggcagcggcg gcgtgggatc cggcggagga    360
ggaagccaag ttcaactcca gcagagcggc gctgaactgg cccggccggg cgcctccgtc    420
aagatgagct gcaaggcttc cggctataca tttactcgtt acacaatgca ttgggtcaag    480
cagaggcccg gtcaaggttt agagtggatc ggatatatca acccttcccg gggctacacc    540
aactataacc aaaagttcaa ggataaagcc actttaacca ctgacaagag ctcctccacc    600
gcctacatgc agctgtcctc tttaaccagc gaggactccg ctgtttacta ctgcgctagg    660
tattacgacg accactactg tttagactat tggggacaag gtaccacttt aaccgtcagc    720
agc                                                                 723

| | |
|---|---|
| SEQ ID NO: 100 | moltype = AA  length = 236 |

```
FEATURE                 Location/Qualifiers
REGION                  1..236
                        note = source = /note="Anti-CD28 scFv"
source                  1..236
                        mol_type = protein
                        organism = Homo sapiens
SEQUENCE: 100
VQLQQSGPEL VKPGASVKMS CKASGYTFTS YVIQWVKQKP GQGLEWIGSI NPYNDYTKYN    60
EKFKGKATLT SDKSSITAYM EFSSLTSEDS ALYYCARWGD GNYWGRGTTL TVSSGGGGSG   120
GGGSGGGGSD IEMTQSPAIM SASLGERVTM TCTASSSVSS SYFHWYQQKP GSSPKLCIYS   180
TSNLASGVPP RFSGSGSTSY SLTISSMEAE DAATYFCHQY HRSPTFGGGT KLETKR       236

SEQ ID NO: 101          moltype = DNA  length = 708
FEATURE                 Location/Qualifiers
misc_feature            1..708
                        note = source = /note="Anti-CD28 scFv"
source                  1..708
                        mol_type = genomic DNA
                        organism = Homo sapiens
SEQUENCE: 101
gtccagctgc agcagagcgg acccgaactc gtgaaacccg gtgcttccgt gaaaatgtct    60
tgtaaggcca gcggatacac cttcacctcc tatgtgatca gtgggtcaa acagaagccc   120
ggacaaggtc tcgagtggat cggcagcatc aaccettaca cgactatac caaatacaac   180
gagaagttta agggaaaggc tactttaacc tccgacaaaa gctccatcac agcctacatg   240
gagttcagct ctttaacatc cgaggacagc gctctgtact attgcgcccg gtggggcgac   300
ggcaattact ggggacgggg cacaaacactg accgtgagcc gcggaggcgg aggctccggc   360
ggaggcggat ctggcggtgg cggctccgac atcgagatga cccagtcccc cgctatcatg   420
tccgcctctt taggcgagcg ggtcacaatg acttgtacag cctcctccag cgtctcctcc   480
tcctacttcc attggtacca acagaaaccc ggaagctccc ctaaactgtg catctacagc   540
accagcaatc tcgccagcgg cgtgcccct aggttttccg gaagcggaag caccagctac   600
tcttttaacca tctcctccat ggaggctgag gatgccgcca cctactttg tcaccagtac   660
caccggtccc ccaccttcgg aggcggcacc aaactggaga caaagagg             708

SEQ ID NO: 102          moltype =      length =
SEQUENCE: 102
000

SEQ ID NO: 103          moltype =      length =
SEQUENCE: 103
000

SEQ ID NO: 104          moltype =      length =
SEQUENCE: 104
000

SEQ ID NO: 105          moltype =      length =
SEQUENCE: 105
000

SEQ ID NO: 106          moltype = DNA  length = 399
FEATURE                 Location/Qualifiers
misc_feature            1..399
                        note = source = /note="IL-2"
source                  1..399
                        mol_type = genomic DNA
                        organism = Homo sapiens
SEQUENCE: 106
gcacctactt caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga acatcttca gtgtctagaa   180
gaagaactca aacctctgga ggaagtgcta aatttagctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt ctgaacaga   360
tggattacct tttgtcaaag catcatctca acactaact                         399

SEQ ID NO: 107          moltype = DNA  length = 399
FEATURE                 Location/Qualifiers
misc_feature            1..399
                        note = source = /note="IL-2"
source                  1..399
                        mol_type = genomic DNA
                        organism = Homo sapiens
SEQUENCE: 107
gcccccacct cctcctccac caagaagacc cagctgcagc tggagcattt actgctggat    60
ttacagatga ttttaaacgg catcaacaac tacaagaacc ccaagctgac tcgtatgctg   120
accttcaagt tctacatgcc caagaaggcc accgagctga gcatttaca gtgtttagag   180
gaggagctga agccctcga ggaggtgctg aatttagccc agtccaagaa tttccattta   240
aggccccggg atttaatcag caacatcaac gtgatcgttt tagagctgaa gggctccgag   300
accaccttca tgtgcgagta cgccgacgag accgccacca tcgtggagtt tttaaatcgt   360
```

```
SEQ ID NO: 108            moltype = AA  length = 485
FEATURE                   Location/Qualifiers
REGION                    1..485
                          note = source = /note="IL-2/TF/IL-2"
source                    1..485
                          mol_type = protein
                          organism = Homo sapiens
SEQUENCE: 108
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGTTNTV AAYNLTWKST NFKTILEWEP KPVNQVYTVQ ISTKSGDWKS   180
KCFYTTDTEC DLTDEIVKDV KQTYLARVFS YPAGNVESTG SAGEPLYENS PEFTPYLETN   240
LGQPTIQSFE QVGTKVNVTV EDERTLVRRN NTFLSLRDVF GKDLIYTLYY WKSSSSGKKT   300
AKTNTNEFLI DVDKGENYCF SVQAVIPSRT VNRKSTDSPV ECMGQEKGEF REAPTSSSTK   360
KTQLQLEHLL LDLQMILNGI NNYKNPKLTR MLTFKFYMPK KATELKHLQC LEEELKPLEE   420
VLNLAQSKNF HLRPRDLISN INVIVLELKG SETTFMCEYA DETATIVEFL NRWITFCQSI   480
ISTLT                                                               485

SEQ ID NO: 109            moltype = DNA  length = 1455
FEATURE                   Location/Qualifiers
misc_feature              1..1455
                          note = source = /note="IL-2/TF/IL-2"
source                    1..1455
                          mol_type = genomic DNA
                          organism = Homo sapiens
SEQUENCE: 109
gcccccacct cctcctccac caagaagacc cagctgcagc tggagcattt actgctggat     60
ttacagatga ttttaaacgg catcaacaac tacaagaacc ccaagctgac tcgtatgctg    120
accttcaagt tctacatgcc caagaaggcc accgagctga agcatttaca gtgtttagag    180
gaggagctga agcccctcga ggaggtgctg aatttagccc agtccaagaa tttccattta    240
aggcccgggg atttaatcag caacatcaac gtgatcgttt tagagctgaa gggctccgag    300
accaccttca tgtgcgagta cgccgacgag accgccacca tcgtggagtt tttaaatcgt    360
tggatcacct tctgccagtc catcatctcc actttaacca gcggcacaac caacacagtg    420
gctgcctata acctcacttg gaagagcacc aacttcaaaa ccatcctcga atgggaaccc    480
aaacccgtta accaagttta caccgtgcag atcagcacca gtccggcga ctggaagtcc    540
aaatgttttc tataccaccga caccgagtgc gatctcaccg atgagatcgt gaaagatgtg    600
aaacagacct acctcgcccg ggtgtttagc taccccgccg gcaatgtgga gagcactggt    660
tccgctggcg agcctttata cgagaacagc cccgaattta cccttacct cgagaccaat    720
ttaggacagc ccaccatcca aagctttgag caagttggca caaggtgaa tgtgacagtg    780
gaggacgagc ggacttagt gcggcggaac aacacctttc tcagcctccg ggatgtgttc    840
ggcaaagatt taatctacac actgtattac tggaagtact cttcctccgg caagaagaca    900
gctaaaacca acacaaacga gttttttaatc gacgtggata aaggcgaaaa ctactgtttc    960
agcgtgcaag ctgtgatccc ctcccggacc gtgaatagga aaagcaccga tagccccgtt   1020
gagtgcatgg gccaagaaaa gggcgagttc cgggaggcac ctactttcaag ttctacaaag  1080
aaaacacagc tacaactgga gcatttactg ctggatttac agatgattttt gaatggaatt   1140
aataattaca gaatcccaa actcaccagg atgctcacat ttaagtttta catgcccaag   1200
aaggccacag aactgaaaca tcttcagtgt ctagaagaag aactcaaacc tctggaggaa   1260
gtgctaaatt tagctcaaag caaaaacttt cacttaagac ccagggactt aatcagcaat   1320
atcaacgtaa tagttctgga actaaaggga tctgaaacaa cattcatgtg tgaatatgct   1380
gatgagacag caaccattgt agaatttctg aacagatgga ttaccttttg tcaaagcatc   1440
atctcaacac taact                                                   1455

SEQ ID NO: 110            moltype = AA  length = 503
FEATURE                   Location/Qualifiers
REGION                    1..503
                          note = source = /note="IL-2/TF/IL-2 with signal sequence"
source                    1..503
                          mol_type = protein
                          organism = Homo sapiens
SEQUENCE: 110
MKWVTFISLL FLFSSAYSAP TSSSTKKTQL QLEHLLLDLQ MILNGINNYK NPKLTRMLTF    60
KFYMPKKATE LKHLQCLEEE LKPLEEVLNL AQSKNFHLRP RDLISNINVI VLELKGSETT   120
FMCEYADETA TIVEFLNRWI TFCQSIISTL TSGTTNTVAA YNLTWKSTNF KTILEWEPKP   180
VNQVYTVQIS TKSGDWKSKC FYTTDTECDL TDEIVKDVKQ TYLARVFSYP AGNVESTGSA   240
GEPLYENSPE FTPYLETNLG QPTIQSFEQV GTKVNVTVED ERTLVRRNNT FLSLRDVFGK   300
DLIYTLYYWK SSSSGKKTAK TNTNEFLIDV DKGENYCFSV QAVIPSRTVN RKSTDSPVEC   360
MGQEKGEFRE APTSSSTKKT QLQLEHLLLD LQMILNGINN YKNPKLTRML TFKFYMPKKA   420
TELKHLQCLE EELKPLEEVL NLAQSKNFHL RPRDLISNIN VIVLELKGSE TTFMCEYADE   480
TATIVEFLNR WITFCQSIIS TLT                                           503

SEQ ID NO: 111            moltype = DNA  length = 1509
FEATURE                   Location/Qualifiers
misc_feature              1..1509
                          note = source = /note="IL-2/TF/IL-2 with signal sequence"
source                    1..1509
                          mol_type = genomic DNA
                          organism = Homo sapiens
```

-continued

```
SEQUENCE: 111
atgaagtggg tgaccttcat cagcctgctg ttcctgttct ccagcgccta ctccgccccc    60
acctcctcct ccaccaagaa gacccagctg cagctggagc atttactgct ggatttacag   120
atgattttaa acggcatcaa caactacaag aaccccaagc tgactcgtat gctgaccttc   180
aagttctaca tgcccaagaa ggccaccgag ctgaagcatt tacagtgttt agaggaggag   240
ctgaagcccc tcgaggaggt gctgaattta gcccagtcca gaatttccat tttaaggccc   300
cgggatttaa tcagcaacat caacgtgatc gttttagagc tgaagggctc cgagaccacc   360
ttcatgtgcg agtacgccga cgagaccgcc accatcgtgg agtttttaaa tcgttggatc   420
accttctgcc agtccatcat ctccacttta accagcggca caaccaacac agtcgctgcc   480
tataacctca cttggaagag caccaacttc aaaaccatcc tcgaatggga acccaaaccc   540
gttaaccaag tttacaccgt gcagatcagc accaagtccg gcgactggaa gtccaaatgt   600
ttctatacca ccgacaccga gtgcgatctc accgatgaga tcgtgaaaga tgtgaaacag   660
acctacctcg cccgggtgtt tagctacccc gccggcaatg tggagagcac tggttccgct   720
ggcgagcctt tatacgagaa cagccccgaa tttacccctt acctcgagac caatttagga   780
cagcccacca tccaaagctt tgagcaagtt ggcacaaagg tgaatgtgac agtggaggac   840
gagcggactt tagtgcggcg gaacaacacc tttctcagcc tccgggatgt gttcggcaaa   900
gatttaatct acacactgta ttactggaag tcctcttcct ccggcaagaa gacagctaaa   960
accaacacaa acgagtttt aatcgacgtg gataaggcg aaaactactg tttcagcgtg  1020
caagctgtga tccctcccg gaccgtgaat aggaaaagcc ccgatagccc cgttgagtgc  1080
atgggccaag aaaagggcga gttccggag gcacctactt caagttctac aaagaaaaca  1140
cagctacaac tggagcattt actgctggat ttacagatga ttttgaatgg aattaataat  1200
tacaagaatc ccaaactcac caggatgctc acatttaagt tttacatgcc caagaaggcc  1260
acagaactga acatcttca gtgtctagaa gaagaactca aacctctgga ggaagtgcta  1320
aatttagctc aaagcaaaaa ctttcactta gacccaggg acttaatcag caatatcaac  1380
gtaatagttc tggaactaaa gggatctgaa acaacattca tgtgtgaata tgctgatgag  1440
acagcaacca ttgtagaatt tctgaacaga tggattacct tttgtcaaag catcatctca  1500
acactaact                                                          1509

SEQ ID NO: 112           moltype = DNA  length = 342
FEATURE                  Location/Qualifiers
misc_feature             1..342
                         note = source = /note="IL-15"
source                   1..342
                         mol_type = genomic DNA
                         organism = Homo sapiens
SEQUENCE: 112
aactgggtga acgtgatcag cgatttaaag aagatcgagg atttaatcca gagcatgcac    60
atcgacgcca ctctgtacac tgagagcgac gtgcacccta gctgcaaggt gactgccatg   120
aagtgctttt tactggagct gcaagttatc tctttagaga gcggcgatgc cagcatccac   180
gacactgtgg agaatttaat catttttagcc aacaactctt taagcagcaa cggcaacgtg   240
acagagagcg gctgcaagga gtgcgaggag ctggaggaga gaacatcaa ggagtttttta  300
cagagcttcg tgcacatcgt gcagatgttc atcaacacta gc                      342

SEQ ID NO: 113           moltype = DNA  length = 342
FEATURE                  Location/Qualifiers
misc_feature             1..342
                         note = source = /note="IL-15"
source                   1..342
                         mol_type = genomic DNA
                         organism = Homo sapiens
SEQUENCE: 113
aactgggtga acgtcatcag cgatttaaag aagatcgaag atttaattca gtccatgcat    60
atcgacgcca ctttatacac agaatccgac gtgcacccct cttgtaaggt gaccgccatg   120
aaatgttttt tactggagct gcaagttatc tctttagaga gcggagacgc tagcatccac   180
gacaccgtgg agaatttaat catttttagcc aataactctt tatccagcaa cggcaacgtg   240
acagagtccg gctgcaagga gtgcgaagga ctggaggaga gaacatcaa ggagtttctg   300
caatcctttg tgcacattgt ccagatgttc atcaatacct cc                       342

SEQ ID NO: 114           moltype = AA  length = 447
FEATURE                  Location/Qualifiers
REGION                   1..447
                         note = source = /note="IL-15/TF/IL-15"
source                   1..447
                         mol_type = protein
                         organism = Homo sapiens
SEQUENCE: 114
NWVNVISDLK KIEDLIQSMH IDATLYTESD VHPSCKVTAM KCFLLELQVI SLESGDASIH    60
DTVENLIILA NNSLSSNGNV TESGCKECEE LEEKNIKEFL QSFVHIVQMF INTSSGTTNT   120
VAAYNLTWKS TNFKTILEWE PKPVNQVYTV QISTKSGDWK SKCFYTTDTE CDLTDEIVKD   180
VKQTYLARVF SYPAGNVEST GSAGEPLYEN SPEFTPYLET NLGQPTIQSF EQVGTKVNVT   240
VEDERTLVRR NNTFLSLRDV FGKDLIYTLY YWKSSSSGKK TAKTNTNEFL IDVDKGENYC   300
FSVQAVIPSR TVNRKSTDSP VECMGQEKGE FRENWVNVIS DLKKIEDLIQ SMHIDATLYT   360
ESDVHPSCKV TAMKCFLLEL QVISLESGDA SIHDTVENLI ILANNSLSSN GNVTESGCKE   420
CEELEEKNIK EFLQSFVHIV QMFINTS                                       447

SEQ ID NO: 115           moltype = DNA  length = 1341
FEATURE                  Location/Qualifiers
misc_feature             1..1341
                         note = source = /note="IL-15/TF/IL-15"
```

```
source                  1..1341
                        mol_type = genomic DNA
                        organism = Homo sapiens
SEQUENCE: 115
aactgggtga acgtgatcag cgatttaaag aagatcgagg atttaatcca gagcatgcac  60
atcgacgcca ctctgtacac tgagagcgac gtgcaccct a gctgcaaggt gactgccatg 120
aagtgctttt tactggagct gcaagttatc tctttagaga gcggcgatgc cagcatccac 180
gacactgtgg agaatttaat cattttagcc aacaactctt taagcagcaa cggcaacgtg 240
acagagagcg gctgcaagga gtgcgaggag ctggaggaga agaacatcaa ggagttttta 300
cagagcttcg tgcacatcgt gcagatgttc atcaacacta gcagcggcac aaccaacaca 360
gtcgctgcct ataacctcac ttggaagagc accaacttca aaaccatcct gaatgggaa  420
cccaaacccg ttaaccaagt ttacaccgtg cagatcagca ccaagtccgg cgactggaag 480
tccaaatgtt tctataccac cgacaccgag tgcgatctca ccgatgagat cgtgaaagat 540
gtgaaacaga cctacccgc ccgggtgttt agctacccgg ccgcaatgt ggagagcact 600
ggttccgctg gcgagccttt atacgagaac agccccgaat tacccctta cctcgagacc 660
aatttaggac agcccaccat ccaaagcttt gagcaagttg gcacaaggt gaatgtgaca 720
gtggaggacg agcggacttt agtgcggcgg aacaaccct ttctcagcct ccgggatgtg 780
ttcggcaaag atttaatcta cactgtat tactggaagt cctcttcctc cggcaagaag 840
acagctaaaa ccaacacaaa cgagttttta atcgacgtgg ataaaggcga aaactactgt 900
ttcagcgtgc aagctgtgat ccctcccgg accgtgaata ggaaaagcac cgatagcccc 960
gttgagtgca tgggccaaga aaagggcgag ttccgggaga actgggtgaa cgtcatcagc 1020
gatttaaaga agatcgaaga tttaattcag tccatgcata tcgacgccac tttatacaca 1080
gaatccgacg tgcacccctc ttgtaaggtg accgccatga aatgttttt actggagctg 1140
caagttatct ctttagagag cggagacgct agcatccacg acaccgtgga aatttaatc 1200
attttagcca ataactcttt atccagcaac ggcaacgtga cagagtccgg ctgcaaggag 1260
tgcgaagagc tggaggagaa gaacatcaag gagtttctgc aatcctttgt gcacattgtc 1320
cagatgttca tcaatacctc c                                           1341

SEQ ID NO: 116          moltype = AA  length = 465
FEATURE                 Location/Qualifiers
REGION                  1..465
                        note = source = /note="IL-15/TF/IL-15 with signal sequence"
source                  1..465
                        mol_type = protein
                        organism = Homo sapiens
SEQUENCE: 116
MKWVTFISLL FLFSSAYSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS 120
FVHIVQMFIN TSSGTTNTVA AYNLTWKSTN FKTILEWEPK PVNQVYTVQI STKSGDWKSK 180
CFYTTDTECD LTDEIVKDVK QTYLARVFSY PAGNVESTGS AGEPLYENSP EFTPYLETNL 240
GQPTIQSFEQ VGTKVNVTVE DERTLVRRNN TFLSLRDVFG KDLIYTLYYW KSSSSGKKTA 300
KTNTNEFLID VDKGENYCFS VQAVIPSRTV NRKSTDSPVE CMGQEKGEFR ENWVNVISDL 360
KKIEDLIQSM HIDATLYTES DVHPSCKVTA MKCFLLELQV ISLESGDASI HDTVENLIIL 420
ANNSLSSNGN VTESGCKECE ELEEKNIKEF LQSFVHIVQM FINTS                  465

SEQ ID NO: 117          moltype = DNA  length = 1395
FEATURE                 Location/Qualifiers
misc_feature            1..1395
                        note = source = /note="IL-15/TF/IL-15 with signal sequence"
source                  1..1395
                        mol_type = genomic DNA
                        organism = Homo sapiens
SEQUENCE: 117
atgaagtggg tgaccttcat cagcctgctg ttcctgttct ccagcgccta ctccaactgg  60
gtgaacgtga tcagcgattt aaagaagatc gaggatttaa tccagagcat gcacatcgac 120
gccactctgt acactgagag cgacgtgcac cctagctgca aggtgactgc catgaagtgc 180
tttttactgg agctgcaagt tatctcttta gagagcggcg atgccagcat ccacgacact 240
gtggagaatt taatcatttt agccaacaac tctttaagca gcaacggcaa cgtgacagag 300
agcggctgca aggagtgcga ggagctggag gagaagaaca tcaaggagtt tttacagagc 360
ttcgtgcaca tcgtgcagat gttcatcaac actagcagcg gcacaaccaa cacagtcgct 420
gcctataacc tcacttggaa gagcaccaac ttcaaaacca tcctcgaatg gaacccaaa  480
cccgttaacc aagtttacac cgtgcagatc agcaccaagt ccggcgactg gaagtccaaa 540
tgtttctata ccaccgacac cgagtgcgat ctcaccgatg agatcgtgaa agatgtgaaa 600
cagacctacc tcgcccggt gtttagctac ccgccggca atgtggagag cactggttcc 660
gctggcgagc ctttatacga gaacagcccc gaatttaccc cttacctcga gaccaattta 720
ggacagccca tccaaag ctttgagcaa gttggcacaa aggtgaatgt gacagtggag 780
gacgagcgga ctttagtgcg gcggaacaac ccttt ctca gcctccggga tgtgttcggc 840
aaagatttaa tctacacact gtattactgg aagtcctctt cctccggcaa gaagacagct 900
aaaaccaaca aaacgagtt tttaatcgac gtggataaag gcgaaaacta ctgtttcagc 960
gtgcaagctg tgatccctc cggaccgtg aataggaaaa gcaccgatag ccccgttgag 1020
tgcatggc aagaaaaggg cgagttccgg gagaactggg tgaacgtcat cagcgattta 1080
aagaagatcg aagatttaat tcagtccatg catatcgacg ccactttata cacagaatcc 1140
gacgtgcacc cctcttgtaa ggtgaccgcc atgaaatgtt ttttactgga gctgcaagtt 1200
atctctttag agagcggaga cgctagcatc cacgacaccg tggagaattt aatcatttta 1260
gccaataact ctttatccag caacggcaac gtgacagagt ccggctgcaa ggagtgcgaa 1320
gagctggagg agaagaacat caaggagttt ctgcaatcct ttgtgcacat tgtccagatg 1380
ttcatcaata cctcc                                                  1395
```